US012503461B2

(12) United States Patent
Sikervar et al.

(10) Patent No.: US 12,503,461 B2
(45) Date of Patent: Dec. 23, 2025

(54) PESTICIDALLY ACTIVE HETEROCYCLIC DERIVATIVES WITH SULFUR AND SULFOXIMINE CONTAINING SUBSTITUENTS

(71) Applicant: SYNGENTA CROP PROTECTION AG, Basel (CH)

(72) Inventors: Vikas Sikervar, Goa (IN); Indira Sen, Goa (IN); Michel Muehlebach, Stein (CH); Sebastian Rendler, Basel (CH); André Stoller, Stein (CH); Daniel Emery, Stein (CH); Anke Buchholz, Stein (CH); Benedikt Kurtz, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 929 days.

(21) Appl. No.: 17/761,829

(22) PCT Filed: Sep. 17, 2020

(86) PCT No.: PCT/EP2020/076038

§ 371 (c)(1),
(2) Date: Mar. 18, 2022

(87) PCT Pub. No.: WO2021/053110

PCT Pub. Date: Mar. 25, 2021

(65) Prior Publication Data

US 2022/0372026 A1 Nov. 24, 2022

(30) Foreign Application Priority Data

Sep. 20, 2019 (IN) ............................. 201911038070
Jul. 20, 2020 (IN) ............................. 202011030926

(51) Int. Cl.

| | |
|---|---|
| ***C07D 413/04*** | (2006.01) |
| ***C07D 401/04*** | (2006.01) |
| ***C07D 413/14*** | (2006.01) |
| ***C07D 471/04*** | (2006.01) |
| *C07D 401/14* | (2006.01) |

(52) U.S. Cl.

CPC ......... *C07D 413/04* (2013.01); *C07D 401/04* (2013.01); *C07D 413/14* (2013.01); *C07D 471/04* (2013.01); *C07D 401/14* (2013.01)

(58) Field of Classification Search

CPC .. C07D 413/04; C07D 401/04; C07D 413/14; C07D 471/04; C07D 401/14
See application file for complete search history.

(56) References Cited

U.S. PATENT DOCUMENTS

2016/0272638 A1* 9/2016 Muehlebach .......... A01N 43/90
2017/0000127 A1 1/2017 Muehlebach et al.

FOREIGN PATENT DOCUMENTS

JP 2019006686 A 1/2019
WO 2016116338 A1 7/2016

OTHER PUBLICATIONS

English Machine Translation of JP 2019 006686 obtained from Espacenet (Year: 2019).*
Written Opinion of the International Searching Authority and International Search Report for International Application No. PCT/EP2020/076038 mailed Nov. 12, 2020.

* cited by examiner

*Primary Examiner* — Joseph K Mckane
*Assistant Examiner* — Jalisa Holmes Ferguson
(74) *Attorney, Agent, or Firm* — BakerHostetler; Toni-Junell Herbert

(57) ABSTRACT

Compounds of the formula (I), wherein the substituents are as defined in claim 1. Furthermore, the present invention relates to agrochemical compositions which comprise compounds of formula (I), to preparation of these compositions, and to the use of the compounds or compositions in agriculture or horticulture for combating, preventing or controlling animal pests, including arthropods and in particular insects or representatives of the order *Acarina*.

(I)

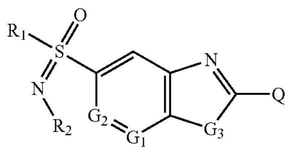

29 Claims, No Drawings

PESTICIDALLY ACTIVE HETEROCYCLIC DERIVATIVES WITH SULFUR AND SULFOXIMINE CONTAINING SUBSTITUENTS

CROSS-REFERENCE TO RELATED APPLICATIONS

This application is a 371 National Stage application of International Application No. PCT/EP2020/076038 filed Sep. 17, 2020, which claims the benefit of IN 201911038070, filed Sep. 20, 2019, and IN 2020111030926, filed Jul. 20, 2020, the entire contents of these applications are hereby incorporated by reference.

The present invention relates to pesticidally active, in particular insecticidally active heterocyclic derivatives containing sulfur substituents, to processes for their preparation, to compositions comprising those compounds, and to their use for controlling animal pests, including arthropods and in particular insects or representatives of the order *Acarina*.

Heterocyclic compounds with pesticidal action are known and described, for example, in WO2014/104407, WO2016/107831, WO2016/107831, WO2013/018928, WO2014/119672, WO2014/119494, WO2014/119679, and WO2014/119670.

It has now surprisingly been found that certain novel pesticidally active derivatives with sulfur and sulfoximine containing substituents have favourable properties as pesticides.

The present invention therefore provides compounds of formula I,

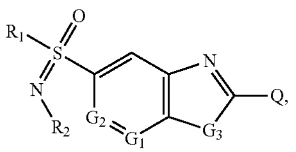

(I)

wherein $G_1$ and $G_2$ are, independently from each other, CH or N;

$G_3$ is $NCH_3$ or O;

$R_1$ is $C_1$-$C_6$alkyl or $C_1$-$C_6$haloalkyl;

$R_2$ is H, $C_1$-$C_6$alkyl, $C_1$-$C_6$cycloalkyl, $C_1$-$C_6$haloalkyl, —C(O)$R_3$ or CN;

$R_3$ is $C_1$-$C_6$alkyl;

Q is a radical selected from the group consisting of formula Qa and Qb

Qa

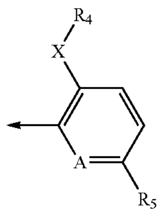

-continued

Qb

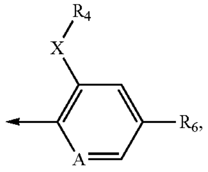

wherein the arrow denotes the point of attachment to the carbon atom of the bicyclic ring;

and wherein

A is CH or N;

X is S, SO or $SO_2$;

$R_4$ is $C_1$-$C_4$alkyl;

$R_5$ is hydrogen or halogen; or $R_5$ is a five- to six-membered aromatic ring system, linked via a ring carbon atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system can contain 1, 2 or 3 ring heteroatoms selected from the group consisting of nitrogen, oxygen and sulphur, where said ring system may not contain more than one ring oxygen atom and may not contain more than one ring sulfur atom; or $R_5$ is a five-membered aromatic ring system linked via a ring nitrogen atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system contains 1, 2 or 3 ring heteroatoms selected from the group consisting of nitrogen, oxygen and sulphur, where said ring system contains at least one ring nitrogen atom and may not contain more than one ring oxygen atom and may not contain more than one ring sulfur atom;

$R_6$ is halogen, $C_1$-$C_6$haloalkyl, $C_3$-$C_6$cycloalkyl, $C_3$-$C_6$cycloalkyl monosubstituted by cyano, $C_3$-$C_6$alkyl monosubstituted by cyano, $C_1$-$C_6$alkoxy, $C_1$-$C_6$haloalkoxy, $C_1$-$C_6$alkoxy monosubstituted by cyano, —N═S(O)$R_7R_8$, —N($R_9$)C(═O)$R_{10}$, —N($R_{11}$)$R_{12}$, or 2-pyridyloxy; or $R_6$ is a five- to six-membered aromatic ring system, linked via a ring carbon atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system can contain 1, 2 or 3 ring heteroatoms selected from the group consisting of nitrogen, oxygen and sulphur, where said ring system may not contain more than one ring oxygen atom and may not contain more than one ring sulfur atom; or $R_6$ is a five-membered aromatic ring system linked via a ring nitrogen atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system contains at least 1 ring nitrogen atom and can contain 2 or 3 additional ring heteroatoms selected from the group consisting of nitrogen, oxygen and sulphur, where said ring system may not contain more than one ring oxygen atom and may not contain more than one ring sulfur atom;

$R_7$ and $R_8$ are, independently from each other, $C_1$-$C_6$alkyl;

$R_9$ is H or $C_1$-$C_6$alkyl;

$R_{10}$ is $C_1$-$C_6$alkyl or $C_3$-$C_6$cycloalkyl;

$R_{11}$ and $R_{12}$ are, independently from each other, H or $C_1$-$C_6$alkyl.

or an agrochemically acceptable salt, stereoisomer, enantiomer, tautomer or N-oxides of a compound of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as mor-pholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$-fluoroalkyl" would refer to a $C_1$-$C_2$-alkyl radical which carries 1,2,3,4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "$C_1$-$C_n$alkoxy" as used herein refers to a straight-chain or branched saturated alkyl radical having 1 to n carbon atoms (as mentioned above) which is attached via an oxygen atom, i.e., for example, any one of methoxy, ethoxy, n-propoxy, 1-methylethoxy, n-butoxy, 1-methylpropoxy, 2-methylpropoxy or 1,1-dimethylethoxy.

The term "$C_1$-$C_n$haloalkoxy" as used herein refers to a $C_1$-$C_n$alkoxy radical as mentioned above which is partially or fully substituted by fluorine, chlorine, bromine and/or iodine, i.e., for example, any one of chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroeth-oxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, or 4-bromobutoxy.

The term "$C_1$-$C_n$-alkylsulfanyl" as used herein refers to a straight chain or branched saturated alkyl radical having 1 to n carbon atoms (as mentioned above) which is attached via a sulfur atom, i.e., for example, any one of methylthio, ethylthio, n-propylthio, 1-methylethylthio, butylthio, 1-methylpropylthio, 2-methylpropylthio or 1,1-dimethylethylthio.

The term "$C_1$-$C_n$alkylsulfinyl" as used herein refers to a straight chain or branched saturated alkyl radical having 1 to n carbon atoms (as mentioned above) which is attached via the sulfur atom of the sulfinyl group, i.e., for example, any one of methylsulfinyl, ethylsulfinyl, n-propylsulfinyl, 1-methylethyl-sulfinyl, n-butylsulfinyl, 1-methylpropylsulfinyl, 2-methylpropylsulfinyl, 1,1-dimethyl-ethylsulfinyl, n-pentylsulfinyl, 1-methylbutylsulfinyl, 2-methylbutylsulfinyl, 3-methyl-butylsulfinyl, 1,1-dimethylpropylsulfinyl, 1,2-dimethylpropylsulfinyl, 2,2-dimethylpropylsulfinyl or 1-ethylpropylsulfinyl.

The term "$C_1$-$C_n$alkylsulfonyl" as used herein refers to a straight chain or branched saturated alkyl radical having 1 to n carbon atoms (as mentioned above) which is attached via the sulfur atom of the sulfonyl group, i.e., for example, any one of methylsulfonyl, ethylsulfonyl, n-propylsulfonyl, isopropylsulfonyl, n-butylsulfonyl, 1-methylpropylsulfonyl, 2-methylpropylsulfonyl ort-butylsulphonyl.

The term "$C_1$-$C_n$alkyl monosubstituted by cyano" as used herein refers to a straight chain or branched saturated alkyl radicals having 1 to n carbon atoms (as mentioned above) which is substituted by a cyano group, for example cyanomethylene, cyanoethylene, 1,1-dimethylcyanomethyl, cyanomethyl, cyanoethyl, and 1-dimethylcyanomethyl.

The term "$C_1$-$C_n$alkoxy monosubstituted by cyano" as used herein refers to a straight chain or branched saturated alkyoxy radicals having 1 to n carbon atoms (as mentioned above) which is substituted by a cyano group, for example cyanomethoxy, cyanoethyoxy, 1,1-dimethylcyanomethoxy, and 1-dimethylcyanomethoxy.

The term "$C_3$-$C_6$cycloalkyl" as used herein refers to 3-6 membered cycloylkyl groups such as cyclopropane, cyclobutane, cyclopropane, cyclopentane and cyclohexane.

Halogen is generally fluorine, chlorine, bromine or iodine. This also applies, correspondingly, to halogen in combination with other meanings, such as haloalkyl.

In the context of this invention "mono- or polysubstituted" in the definition of the substituents, means typically, depending on the chemical structure of the substituents, monosubstituted to five-times substituted, more preferably mono-, double- or triple-substituted.

In the context of this invention, examples of a "five- to six-membered aromatic ring system, linked via a ring carbon atom . . . and said ring system can contain 1, 2 or 3 ring heteroatoms" are, but not limited to, phenyl, pyridinyl and pyrimidinyl; preferably phenyl, 2-pyridyl, 3-pyridyl, 4-pyridyl, pyrimidin-2-yl, pyrimidin-4-yl, and pyrimidin-5-yl.

In the context of this invention, examples of a "five-membered aromatic ring system linked via a ring nitrogen atom . . . and said ring system contains 1, 2 or 3 ring heteroatoms" are, but not limited to, pyrazolyl, pyrrolyl, imidazolyl and triazolyl; preferably pyrrol-1-yl, pyrazol-1-yl, triazol-2-yl, 1,2,4-triazol-1-yl, triazol-1-yl, and imidazol-1-yl.

Certain embodiments according to the invention are provided as set out below.

Embodiment 1 provides compounds of formula I, or an agrochemically acceptable salt, stereoisomer, enantiomer, tautomer or N-oxide thereof, wherein $G_1$, $G_2$, $G_3$, $R_1$, $R_2$, $R_3$, A, X, Q, $R_4$, $R_5$, $R_6$, $R_7$, $R_8$, $R_9$, $R_{10}$, $R_{11}$, and $R_{12}$ are as defined under formula I above.

Embodiment 2 provides compounds, or an agrochemically acceptable salt, stereoisomer, enantiomer, tautomer or N-oxide thereof, according to embodiment 1 wherein Q is Qa.

Embodiment 3 provides compounds, or an agrochemically acceptable salt, stereoisomer, enantiomer, tautomer or N-oxide thereof, according to embodiment 1 wherein Q is Qb.

With respect to embodiments 1-3, preferred values of $G_1$, $G_2$, $G_3$, $R_1$, $R_2$, $R_3$, A, X, $R_4$, $R_5$, $R_6$, $R_7$, $R_8$, $R_9$, $R_{10}$, $R_{11}$, and $R_{12}$ are, in any combination thereof, as set out below:

Preferably both $G_1$ and $G_2$ are N.

Also preferred is when $G_1$ is CH and $G_2$ is N.

Also preferred is when $G_1$ is N and $G_2$ is CH.

Most preferably both $G_1$ and $G_2$ are CH.

Preferably $G_3$ is O.

Preferably $R_1$ is methy or trifluoromethyl; most preferably trifluoromethyl.

Preferably $R_2$ is H, $C_1$-$C_4$alkyl, cyclopropyl, $C_1$-$C_4$haloalkyl, —C(O)$R_3$ or cyano.

More preferably $R_2$ is H, cyano, $COCH_3$, cyclopropyl, methyl, ethyl, trifluoroethyl, or trifluoromethyl.

Most preferably $R_2$ is H, cyano, methyl, ethyl, cyclopropyl, or 2,2,2-trifluoroethyl.

Preferably $R_3$ is $C_1$-$C_4$alkyl; most preferably $R_3$ is methyl.

Preferably X is S or $SO_2$; most preferably, X is $SO_2$.

Preferably $R_4$ is $C_1$-$C_2$alkyl; most preferably $R_4$ is ethyl.

Preferably $R_5$ is hydrogen; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system can contain 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

More preferably $R_5$ is hydrogen; or $R_5$ is a six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 2 or 3 ring nitrogen atoms.

More preferably $R_5$ is hydrogen; or $R_5$ is a six-membered aromatic ring system selected from pyridyl and pyrimidinyl (preferably pyrimidinyl) which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl (preferably pyrazolyl and triazolyl) which is linked via a ring nitrogen atom to the ring which contains the substituent A, said ring system is unsubstituted or is mono-substituted by substituents selected from the group consisting of halogen and $C_1$-$C_4$haloalkyl.

More preferably $R_5$ is hydrogen, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl.

Most preferably $R_5$ is hydrogen, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, or 3-trifluoromethyl-1,2,4-triazol-1-yl.

Preferably $R_6$ is $C_3$-$C_6$cycloalkyl, $C_3$-$C_6$cycloalkyl mono-substituted by cyano, $C_1$-$C_6$haloalkoxy, $C_1$-$C_6$alkoxy mono-substituted with cyano, —N═S(O)$R_7R_8$, in which $R_7$ and $R_8$ are, independently from each other, $C_1$-$C_4$alkyl, —N($R_9$)$COR_{10}$, in which $R_9$ and $R_{10}$ are, independently from each other, $C_1$-$C_4$alkyl, or $R_6$ is 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system can contain 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

More preferably $R_6$ is, cyclopropyl, cyanocyclopropyl, trifluoroethoxy, difluoropropyoxy, cyanoisopropoxy, —N=S(O)$(CH_3)_2$, —N($CH_3$)$COCH_3$, or 2-pyridyloxy; or $R_6$ is a six-membered aromatic ring system selected from pyridyl and pyrimidinyl (preferably pyrimidinyl) which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl (preferably pyrazolyl and triazolyl) which is linked via a ring nitrogen atom to the ring which contains the substituent A, said ring system is unsubstituted or is mono-substituted by substituents selected from the group consisting of halogen and $C_1$-$C_4$haloalkyl.

Most preferably $R_6$ is cyclopropyl, 1-cyanocyclopropyl, 2,2,2-trifluoroethoxy, 2,2-difluoropropoxy, 1-cyano-1-methyl-ethoxy, —N=S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, 3-trifluoromethyl-pyrazol-1-yl.

Preferably $R_7$ and $R_8$ are, independently from each other, $C_1$-$C_4$alkyl.

Most preferably $R_7$ and $R_8$ are methyl.

Preferably $R_9$ is H or $C_1$-$C_4$alkyl.

More preferably $R_9$ is H or methyl; most preferably $R_9$ is methyl.

Preferably $R_{10}$ is $C_1$-$C_6$alkyl; more preferably $R_{10}$ is $C_1$-$C_4$alkyl; most preferably $R_{10}$ is methyl.

Preferably $R_{11}$ and $R_{12}$ are, independently from each other, H or $C_1$-$C_4$alkyl; most preferably $R_{11}$ and $R_{12}$ are methyl.

One group of compounds according to the invention are those of formula I-1

(I-1)

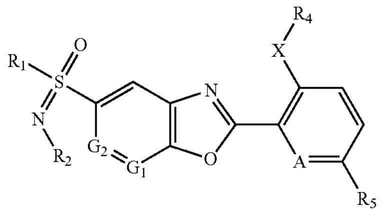

wherein $G_1$, $G_2$, $R_1$, $R_2$, $R_3$, A, X, $R_4$, and $R_5$, are as defined under formula I above, or an agrochemically acceptable salt, stereoisomer, enantiomer, tautomer or N-oxide thereof; and wherein:

$R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-1, $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-1, $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

One preferred group of compounds according to this embodiment are compounds of formula (I-1a) which are compounds of formula (I-1) or of any of the preferred embodiments of the compounds of formula (I-1) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-1 b) which are compounds of formula (I-1) or of any of the preferred embodiments of the compounds of formula (I-1) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-1c) which are compounds of formula (I-1) or of any of the preferred embodiments of the compounds of formula (I-1) wherein X is S or $SO_2$, preferably $SO_2$.

A further preferred group of compounds according to this embodiment are compounds of formula (I-1d) which are compounds of formula (I-1) or of any of the preferred embodiments of the compounds of formula (I-1) wherein $R_4$ is $C_1$-$C_2$alkyl; preferably $R_4$ is ethyl.

One preferred group of compounds according to this embodiment are compounds of formula (I-1e) which are compounds of formula (I-1) or of any of the preferred embodiments of the compounds of formula (I-1) wherein A is N.

Another preferred group of compounds according to this embodiment are compounds of formula (I-1f) which are compounds of formula (I-1) or of any of the preferred embodiments of the compounds of formula (I-1) wherein A is CH.

One preferred group of compounds according to this embodiment are compounds of formula (I-1g) which are compounds of formula (I-1) or of any of the preferred embodiments of the compounds of formula (I-1) wherein $G_2$ is N and $G_1$ is CH.

Another preferred group of compounds according to this embodiment are compounds of formula (I-1 h) which are compounds of formula (I-1) or of any of the preferred embodiments of the compounds of formula (I-1) wherein $G_2$ and $G_1$ are both CH.

Another preferred group of compounds according to this embodiment are compounds of formula (I-1i) which are compounds of formula (I-1) or of any of the preferred embodiments of the compounds of formula (I-1) wherein $G_2$ is CH and $G_1$ is N.

Another group of compounds according to the invention are those of formula I-2

(I-2)

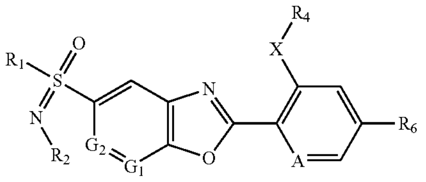

wherein $G_1$, $G_2$, $R_1$, $R_2$, $R_3$, A, X, $R_4$, $R_6$, $R_7$, $R_8$, $R_9$, $R_{10}$, $R_{11}$, and $R_{12}$ are as defined under formula I above, or an agrochemically acceptable salt, stereoisomer, enantiomer, tautomer or N-oxide thereof; and wherein:

$R_6$ is preferably $C_3$-$C_6$cycloalkyl, $C_3$-$C_6$cycloalkyl mono-substituted by cyano, $C_1$-$C_6$haloalkoxy, $C_1$-$C_6$alkoxy substituted with cyano, —N═S(O)$R_7R_8$, —N($R_9$)CO$R_{10}$, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-2, $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$ or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$ or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-2, $R_6$ is preferably cyclopropyl, cyanocyclopropyl, trifluoroethoxy, difluoropropyoxy, cyanoisopropoxy, —N═S(O)$(CH_3)_2$, —N($CH_3$)$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

One preferred group of compounds according to this embodiment are compounds of formula (I-2a) which are compounds of formula (I-2) or of any of the preferred embodiments of the compounds of formula (I-2) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-2b) which are compounds of formula (I-2) or of any of the preferred embodiments of the compounds of formula (I-2) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-2c) which are compounds of formula (I-2) or of any of the preferred embodiments of the compounds of formula (I-2) wherein X is S or $SO_2$, preferably $SO_2$.

A further preferred group of compounds according to this embodiment are compounds of formula (I-2d) which are compounds of formula (I-2) or of any of the preferred embodiments of the compounds of formula (I-2) wherein $R_4$ is $C_1$-$C_2$alkyl; preferably $R_4$ is ethyl.

One preferred group of compounds according to this embodiment are compounds of formula (I-2e) which are compounds of formula (I-2) or of any of the preferred embodiments of the compounds of formula (I-2) wherein A is N.

Another preferred group of compounds according to this embodiment are compounds of formula (I-20 which are compounds of formula (I-2) or of any of the preferred embodiments of the compounds of formula (I-2) wherein A is CH.

One preferred group of compounds according to this embodiment are compounds of formula (I-2g) which are compounds of formula (I-2) or of any of the preferred embodiments of the compounds of formula (I-2) wherein $G_2$ is N and $G_1$ is CH.

Another preferred group of compounds according to this embodiment are compounds of formula (I-2h) which are compounds of formula (I-2) or of any of the preferred embodiments of the compounds of formula (I-2) wherein $G_2$ and $G_1$ are both CH.

Another preferred group of compounds according to this embodiment are compounds of formula (I-2i) which are compounds of formula (I-2) or of any of the preferred embodiments of the compounds of formula (I-2) wherein $G_2$ is CH and $G_1$ is N.

Another group of compounds according to the invention are those of formula I-3

(I-3)

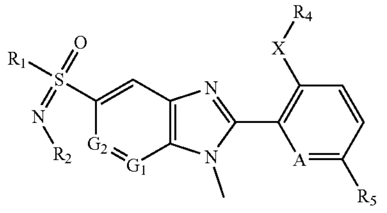

wherein $G_1$, $G_2$, $R_1$, $R_2$, $R_3$, A, X, $R_4$, and $R_5$, are as defined under formula I above, or an agrochemically acceptable salt, stereoisomer, enantiomer, tautomer or N-oxide thereof; and wherein:

$R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-3, $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-3, $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

One preferred group of compounds according to this embodiment are compounds of formula (I-3a) which are compounds of formula (I-3) or of any of the preferred embodiments of the compounds of formula (I-3) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-3b) which are compounds of formula (I-3) or of any of the preferred embodiments of the compounds of formula (I-3) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-3c) which are compounds of formula (I-3) or of any of the preferred embodiments of the compounds of formula (I-3) wherein X is S or $SO_2$, preferably $SO_2$.

A further preferred group of compounds according to this embodiment are compounds of formula (I-3d) which are compounds of formula (I-3) or of any of the preferred embodiments of the compounds of formula (I-3) wherein $R_4$ is $C_1$-$C_2$alkyl; preferably $R_4$ is ethyl.

One preferred group of compounds according to this embodiment are compounds of formula (I-3e) which are compounds of formula (I-3) or of any of the preferred embodiments of the compounds of formula (I-3) wherein A is N.

Another preferred group of compounds according to this embodiment are compounds of formula (I-3f which are compounds of formula (I-3) or of any of the preferred embodiments of the compounds of formula (I-3) wherein A is CH.

One preferred group of compounds according to this embodiment are compounds of formula (I-3g) which are compounds of formula (I-3) or of any of the preferred embodiments of the compounds of formula (I-3) wherein $G_2$ is N and $G_1$ is CH.

Another preferred group of compounds according to this embodiment are compounds of formula (I-3h) which are compounds of formula (I-3) or of any of the preferred embodiments of the compounds of formula (I-3) wherein $G_2$ and $G_1$ are both CH.

Another preferred group of compounds according to this embodiment are compounds of formula (I-3i) which are compounds of formula (I-3) or of any of the preferred embodiments of the compounds of formula (I-3) wherein $G_2$ is CH and $G_1$ is N.

Another group of compounds according to the invention are those of formula I-4

(I-4)

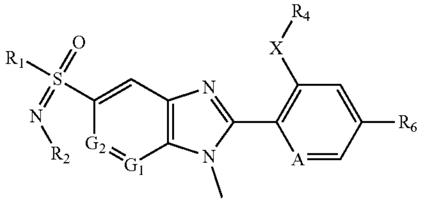

wherein $G_1$, $G_2$, $R_1$, $R_2$, $R_3$, A, X, $R_4$, $R_6$, $R_7$, $R_8$, $R_9$, $R_{10}$, $R_{11}$, and $R_{12}$ are as defined under formula I above, or an agrochemically acceptable salt, stereoisomer, enantiomer, tautomer or N-oxide thereof, and wherein:

$R_6$ is preferably $C_3$-$C_6$cycloalkyl, $C_3$-$C_6$cycloalkyl monosubstituted by cyano, $C_1$-$C_6$haloalkoxy, $C_1$-$C_6$alkoxy substituted with cyano, —N═S(O)$R_7R_8$, —N($R_9$)$COR_{10}$, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-4, $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$ or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$ or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-4, $R_6$ is preferably cyclopropyl, cyanocyclopropyl, trifluoroethoxy, difluoropropyoxy, cyanoisopropoxy, —N═S(O)$(CH_3)_2$, —N($CH_3$)$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

One preferred group of compounds according to this embodiment are compounds of formula (I-4a) which are compounds of formula (I-4) or of any of the preferred embodiments of the compounds of formula (I-4) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-4b) which are compounds of formula (I-4) or of any of the preferred embodiments of the compounds of formula (I-4) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-4c) which are compounds of formula (I-4) or of any of the preferred embodiments of the compounds of formula (I-4) wherein X is S or $SO_2$, preferably $SO_2$.

A further preferred group of compounds according to this embodiment are compounds of formula (I-4d) which are compounds of formula (I-2) or of any of the preferred embodiments of the compounds of formula (I-4) wherein $R_4$ is $C_1$-$C_2$alkyl; preferably $R_4$ is ethyl.

One preferred group of compounds according to this embodiment are compounds of formula (I-4e) which are compounds of formula (I-4) or of any of the preferred embodiments of the compounds of formula (I-4) wherein A is N.

Another preferred group of compounds according to this embodiment are compounds of formula (I-40 which are compounds of formula (I-4) or of any of the preferred embodiments of the compounds of formula (I-4) wherein A is CH.

One preferred group of compounds according to this embodiment are compounds of formula (I-4g) which are compounds of formula (I-4) or of any of the preferred embodiments of the compounds of formula (I-4) wherein $G_2$ is N and $G_1$ is CH.

Another preferred group of compounds according to this embodiment are compounds of formula (I-4h) which are compounds of formula (I-4) or of any of the preferred embodiments of the compounds of formula (I-4) wherein $G_2$ and $G_1$ are both CH.

Another preferred group of compounds according to this embodiment are compounds of formula (I-4i) which are compounds of formula (I-4) or of any of the preferred embodiments of the compounds of formula (I-4) wherein $G_2$ is CH and $G_1$ is N.

Another group of compounds according to the invention are those of formula I-5

(I-5)

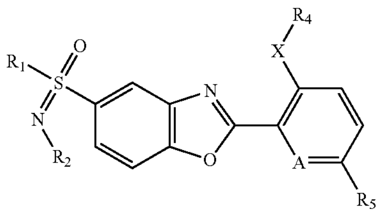

wherein $R_1$, $R_2$, $R_3$, A, X, $R_4$, and $R_5$, are as defined under formula I above, or an agrochemically acceptable salt, stereoisomer, enantiomer, tautomer or N-oxide thereof; and wherein: $R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-5, $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-5, $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

One preferred group of compounds according to this embodiment are compounds of formula (I-5a) which are compounds of formula (I-5) or of any of the preferred embodiments of the compounds of formula (I-5) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-5b) which are compounds of formula (I-5) or of any of the preferred embodiments of the compounds of formula (I-5) wherein: $R_2$ is H, $C_1$-$C_4$alkyl, cyclopropyl, $C_1$-$C_4$haloalkyl, $C(O)R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-5c) which are compounds of formula (I-5) or of any of the preferred embodiments of the compounds of formula (I-5) wherein X is S or $SO_2$, preferably $SO_2$.

A further preferred group of compounds according to this embodiment are compounds of formula (I-5d) which are compounds of formula (I-5) or of any of the preferred embodiments of the compounds of formula (I-5) wherein $R_4$ is $C_1$-$C_2$alkyl; preferably $R_4$ is ethyl.

One preferred group of compounds according to this embodiment are compounds of formula (I-5e) which are compounds of formula (I-5) or of any of the preferred embodiments of the compounds of formula (I-5) wherein A is N.

Another preferred group of compounds according to this embodiment are compounds of formula (I-5) which are compounds of formula (I-5) or of any of the preferred embodiments of the compounds of formula (I-5) wherein A is CH.

Another group of compounds according to the invention are those of formula I-6

(I-6)

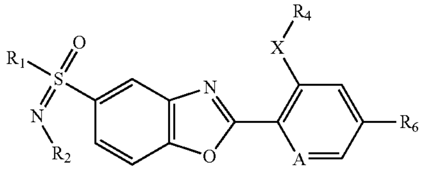

wherein $R_1$, $R_2$, $R_3$, A, X, $R_4$, $R_6$, $R_7$, $R_8$, $R_9$, $R_{10}$, $R_{11}$, and $R_{12}$ are as defined under formula I above, or an agrochemically acceptable salt, stereoisomer, enantiomer, tautomer or N-oxide thereof; and wherein:

$R_6$ is preferably $C_3$-$C_6$cycloalkyl, $C_3$-$C_6$cycloalkyl mono-substituted by cyano, $C_1$-$C_6$haloalkoxy, $C_1$-$C_6$alkoxy substituted with cyano, —N═S(O)$R_7R_8$, —N($R_9$)$COR_{10}$, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-6, $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$, or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$, or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-6, $R_6$ is preferably cyclopropyl, cyanocyclopropyl, trifluoroethoxy, difluoropropyoxy, cyanoisopropoxy, —N═S(O)$(CH_3)_2$, —$N(CH_3)COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —$N(CH_3)COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

One preferred group of compounds according to this embodiment are compounds of formula (I-6a) which are compounds of formula (I-6) or of any of the preferred embodiments of the compounds of formula (I-6) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-6b) which are compounds of formula (I-6) or of any of the preferred embodiments of the compounds of formula (I-6) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-6c) which are compounds of formula (I-6) or of any of the preferred embodiments of the compounds of formula (I-6) wherein X is S or $SO_2$, preferably $SO_2$.

A further preferred group of compounds according to this embodiment are compounds of formula (I-6d) which are compounds of formula (I-6) or of any of the preferred embodiments of the compounds of formula (I-6) wherein $R_4$ is $C_1$-$C_2$alkyl; preferably $R_4$ is ethyl.

One preferred group of compounds according to this embodiment are compounds of formula (I-6e) which are compounds of formula (I-6) or of any of the preferred embodiments of the compounds of formula (I-6) wherein A is N.

Another preferred group of compounds according to this embodiment are compounds of formula (I-60 which are compounds of formula (I-6) or of any of the preferred embodiments of the compounds of formula (I-6) wherein A is CH.

Another group of compounds according to the invention are those of formula I-7

(I-7)

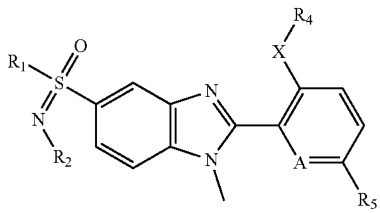

wherein $R_1$, $R_2$, $R_3$, A, X, $R_4$, and $R_5$, are as defined under formula I above, or an agrochemically acceptable salt, stereoisomer, enantiomer, tautomer or N-oxide thereof; and wherein: $R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-7, $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-7, $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

One preferred group of compounds according to this embodiment are compounds of formula (I-7a) which are compounds of formula (I-7) or of any of the preferred embodiments of the compounds of formula (I-7) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-7b) which are compounds of formula (I-7) or of any of the preferred embodiments of the compounds of formula (I-7) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-7c) which are compounds of formula (I-7) or of any of the preferred embodiments of the compounds of formula (I-7) wherein X is S or $SO_2$, preferably $SO_2$.

A further preferred group of compounds according to this embodiment are compounds of formula (I-7d) which are compounds of formula (I-7) or of any of the preferred embodiments of the compounds of formula (I-7) wherein $R_4$ is $C_1$-$C_2$alkyl; preferably $R_4$ is ethyl.

One preferred group of compounds according to this embodiment are compounds of formula (I-7e) which are compounds of formula (I-7) or of any of the preferred embodiments of the compounds of formula (I-7) wherein A is N.

Another preferred group of compounds according to this embodiment are compounds of formula (I-70 which are compounds of formula (I-7) or of any of the preferred embodiments of the compounds of formula (I-7) wherein A is CH.

Another group of compounds according to the invention are those of formula I-8

(I-8)

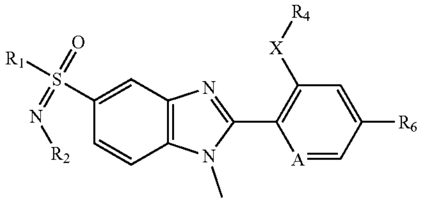

wherein $R_1$, $R_2$, $R_3$, A, X, $R_4$, $R_6$, $R_7$, $R_8$, $R_9$, $R_{10}$, $R_{11}$, and $R_{12}$ are as defined under formula I above, or an agrochemically acceptable salt, stereoisomer, enantiomer, tautomer or N-oxide thereof; and wherein:

$R_6$ is preferably $C_3$-$C_6$cycloalkyl, $C_3$-$C_6$cycloalkyl mono-substituted by cyano, $C_1$-$C_6$haloalkoxy, $C_1$-$C_6$alkoxy substituted with cyano, —N═S(O)$R_7R_8$, —N($R_9$)CO$R_{10}$, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-8, $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$, or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$, or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-8, $R_6$ is preferably cyclopropyl, cyanocyclopropyl, trifluoroethoxy, difluoropropyoxy, cyanoisopropoxy, —N═S(O)$(CH_3)_2$, —N($CH_3$)$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

One preferred group of compounds according to this embodiment are compounds of formula (I-8a) which are compounds of formula (I-8) or of any of the preferred embodiments of the compounds of formula (I-8) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-8b) which are compounds of formula (I-8) or of any of the preferred embodiments of the compounds of formula (I-8) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl.

Another preferred group of compounds according to this embodiment are compounds of formula (I-8c) which are compounds of formula (I-8) or of any of the preferred embodiments of the compounds of formula (I-8) wherein X is S or $SO_2$, preferably $SO_2$.

A further preferred group of compounds according to this embodiment are compounds of formula (I-8d) which are compounds of formula (I-8) or of any of the preferred embodiments of the compounds of formula (I-8) wherein $R_4$ is $C_1$-$C_2$alkyl; preferably $R_4$ is ethyl.

One preferred group of compounds according to this embodiment are compounds of formula (I-8e) which are compounds of formula (I-8) or of any of the preferred embodiments of the compounds of formula (I-8) wherein A is N.

Another preferred group of compounds according to this embodiment are compounds of formula (I-8f) which are compounds of formula (I-8) or of any of the preferred embodiments of the compounds of formula (I-8) wherein A is CH.

An outstanding group of compounds according to the invention are those of formula (I-9)

(I-9)

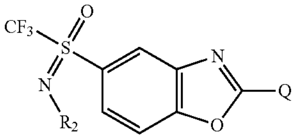

wherein $R_2$ is as defined under formula I above and Q is a radical selected from the group consisting of formula Qa1 and Qb1

Qa1

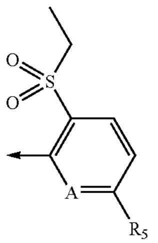

Qb1

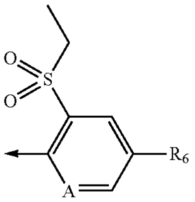

wherein the arrow denotes the point of attachment to the carbon atom of the bicyclic ring; and wherein A, $R_5$ and $R_6$ are as defined under formula I above, or an agrochemically acceptable salt, stereoisomer, enantiomer, tautomer or N-oxide thereof; and wherein:

$R_2$ is preferably H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl.

In one preferred group of compounds of formula I-9, A is N.

In another preferred group of compounds of formula I-9, $R_2$ is H, cyano, $COCH_3$, cyclopropyl, methyl, ethyl, trifluoroethyl, or trifluoromethyl; more preferably $R_2$ is H, cyano, methyl, ethyl, cyclopropyl, or 2,2,2-trifluoroethyl; even more preferably $R_2$ is H, methyl, ethyl, cyclopropyl, or 2,2,2-trifluoroethyl.

In a particularly preferred group of compounds of formula I-9, $R_2$ is H, ethyl, cyclopropyl, or 2,2,2-trifluoroethyl; even more preferably $R_2$ is H or ethyl.

One preferred group of compounds according to this embodiment are compounds of formula (I-9a) which are compounds of formula (I-9) or of any of the preferred embodiments of the compounds of formula (I-9) wherein Q is Qa1.

Another preferred group of compounds according to this embodiment are compounds of formula (I-9b) which are compounds of formula (I-9) or of any of the preferred embodiments of the compounds of formula (I-9) wherein Q is Qb1.

In a preferred group of compounds of formula (I-9a), $R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a more preferred group of compounds of formula (I-9a), $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a particularly preferred group of compounds of formula (I-9a), $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

In an outstanding group of compounds of formula (I-9a), $R_5$ is preferably H, unsubstituted C-linked pyrimidinyl or N-linked triazolyl which is unsubstituted or can be mono-substituted by chloro, or trifluoromethyl; more preferably $R_5$ is selected from the group consisting of H, pyrimidin-2-yl, 1,2,4-triazol-1-yl, 3-chloro-1,2,4-triazol-1-yl, and 3-trifluoromethyl-1,2,4-triazol-1-yl; even more preferably $R_5$ is selected from the group consisting of H, pyrimidin-2-yl and 1,2,4-triazol-1-yl.

In a preferred group of compounds of formula (I-9b), $R_6$ is preferably $C_3$-$C_6$cycloalkyl, $C_3$-$C_6$cycloalkyl monosubstituted by cyano, $C_1$-$C_5$haloalkoxy, $C_1$-$C_5$alkoxy substituted with cyano, —N═S(O)$R_7R_8$ in which $R_7$ and $R_8$ are, independently from each other, $C_1$-$C_4$alkyl, —N($R_9$)$COR_{10}$ in which $R_5$ and $R_{10}$ are, independently from each other, $C_1$-$C_4$alkyl, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a more preferred group of compounds of formula (I-9b), $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$, or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$, or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a particularly preferred group of compounds of formula (I-9b), $R_6$ is preferably cyclopropyl, cyanocyclopropyl, trifluoroethoxy, difluoropropyoxy, cyanoisopropoxy, —N═S(O)$(CH_3)_2$, —N$(CH_3)$$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N$(CH_3)$$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

In another particularly preferred group of compounds of formula (I-9b), $R_6$ is preferably cyclopropyl, cyanocyclopropyl, trifluoroethoxy, difluoropropyoxy, —N═S(O)$(CH_3)_2$, —N$(CH_3)$$COCH_3$, 2-pyridyloxy, N-linked pyrazolyl which is unsubstituted or can be mono-substituted by chloro or trifluoromethyl, or C-linked pyrimidinyl which is unsubstituted or can be mono-substituted by chloro, cyano or trifluoromethyl; more preferably $R_6$ is selected from the group consisting of cyclopropyl, 1-cyanocyclopropyl, 2,2,2-trifluoroethoxy, 2,2-difluoropropoxy, —N═S(O)$(CH_3)_2$, —N$(CH_3)$$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl; even more preferably $R_6$ is selected from the group consisting of cyclopropyl, 1-cyanocyclopropyl, 2,2,2-trifluoroethoxy, 2,2-difluoropropoxy, —N═S(O)$(CH_3)_2$, —N$(CH_3)$$COCH_3$, 2-pyridyloxy, pyrimidin-2-yl, 4-trifluoromethyl-pyrimidin-2-yl, 5-chloro-pyrimidin-2-yl, 3-chloro-pyrazol-1-yl, and 3-trifluoromethyl-pyrazol-1-yl.

One preferred group of compounds according to this embodiment are compounds of formula (I-9c) which are compounds of formula (I-9) or of any of the preferred embodiments of the compounds of formula (I-9) wherein A is N.

Another preferred group of compounds according to this embodiment are compounds of formula (I-9e) which are compounds of formula (I-9) or of any of the preferred embodiments of the compounds of formula (I-9) wherein A is CH.

Another group of compounds according to the invention are those of formula I-10

(I-10)

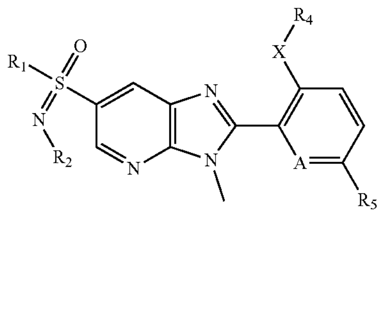

wherein $R_1$, $R_2$, $R_3$, A, X, $R_4$, and $R_5$, are as defined under formula I above, or an agrochemically acceptable salt, stereoisomer, enantiomer, tautomer or N-oxide thereof; and wherein: $R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-10, $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-10, $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

One preferred group of compounds according to this embodiment are compounds of formula (I-10a) which are compounds of formula (I-10) or of any of the preferred embodiments of the compounds of formula (I-10) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-10b) which are compounds of formula (I-10) or of any of the preferred embodiments of the compounds of formula (I-10) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl Another preferred group of compounds according to this embodiment are compounds of formula (I-10c) which are compounds of formula (I-10) or of any of the preferred embodiments of the compounds of formula (I-10) wherein X is S or $SO_2$, preferably $SO_2$.

A further preferred group of compounds according to this embodiment are compounds of formula (I-10d) which are compounds of formula (I-10) or of any of the preferred embodiments of the compounds of formula (I-10) wherein $R_4$ is $C_1$-$C_2$alkyl; preferably $R_4$ is ethyl.

One preferred group of compounds according to this embodiment are compounds of formula (I-10e) which are compounds of formula (I-10) or of any of the preferred embodiments of the compounds of formula (I-10) wherein A is N.

Another preferred group of compounds according to this embodiment are compounds of formula (I-10f) which are compounds of formula (I-10) or of any of the preferred embodiments of the compounds of formula (I-10) wherein A is CH.

Another group of compounds according to the invention are those of formula I-11

(I-11)

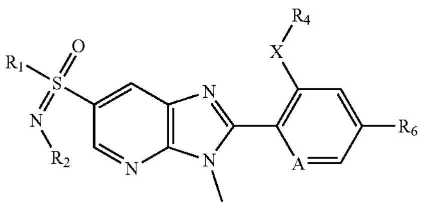

wherein $R_1$, $R_2$, $R_3$, A, X, $R_4$, $R_6$, $R_7$, $R_8$, $R_9$, $R_{10}$, $R_{11}$, and $R_{12}$ are as defined under formula I above, or an agrochemically acceptable salt, stereoisomer, enantiomer, tautomer or N-oxide thereof; and wherein:

$R_6$ is preferably $C_3$-$C_6$cycloalkyl, $C_3$-$C_6$cycloalkyl mono-substituted by cyano, $C_1$-$C_6$haloalkoxy, $C_1$-$C_6$alkoxy substituted with cyano, —N═S(O)$R_7R_8$, —N($R_9$)COR$_{10}$, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a preferred group of compounds of formula I-11, $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$, or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$, or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a more preferred group of compounds of formula I-11, $R_6$ is preferably cyclopropyl, cyanocyclopropyl, trifluoroethoxy, difluoropropyoxy, cyanoisopropoxy, —N═S(O)$(CH_3)_2$, —N($CH_3$)$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

One preferred group of compounds according to this embodiment are compounds of formula (I-11a) which are compounds of formula (I-11) or of any of the preferred embodiments of the compounds of formula (I-11) wherein $R_1$ is $C_1$-$C_4$alkyl or $C_1$-$C_4$haloalkyl; preferably $R_1$ is $CH_3$ or $CF_3$; more preferably $R_1$ is $CF_3$.

Another preferred group of compounds according to this embodiment are compounds of formula (I-11b) which are compounds of formula (I-11) or of any of the preferred embodiments of the compounds of formula (I-11) wherein: $R_2$ is H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl;

More preferably $R_2$ is H, cyano, $COCH_3$, cyclopropyl, methyl, ethyl, trifluoroethyl, or trifluoromethyl;

more preferably $R_2$ is H, cyano, methyl, ethyl, cyclopropyl, or 2,2,2-trifluoroethyl.

Another preferred group of compounds according to this embodiment are compounds of formula (I-11c) which are compounds of formula (I-11) or of any of the preferred embodiments of the compounds of formula (I-11) wherein X is S or $SO_2$, preferably $SO_2$.

A further preferred group of compounds according to this embodiment are compounds of formula (I-11d) which are compounds of formula (I-11) or of any of the preferred embodiments of the compounds of formula (I-11) wherein $R_4$ is $C_1$-$C_2$alkyl; preferably $R_4$ is ethyl.

One preferred group of compounds according to this embodiment are compounds of formula (I-11e) which are compounds of formula (I-11) or of any of the preferred embodiments of the compounds of formula (I-11) wherein A is N.

Another preferred group of compounds according to this embodiment are compounds of formula (I-11f) which are compounds of formula (I-11) or of any of the preferred embodiments of the compounds of formula (I-11) wherein A is CH.

An outstanding group of compounds according to the invention are those of formula (I-12)

(I-12)

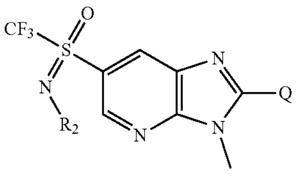

wherein $R_2$ is as defined under formula I above and Q is a radical selected from the group consisting of formula Qa1 and Qb1

Qa1

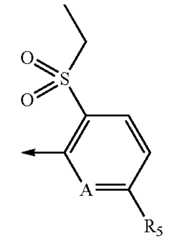

Qb1

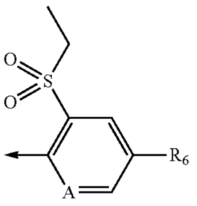

wherein the arrow denotes the point of attachment to the carbon atom of the bicyclic ring;

and wherein A, $R_5$ and $R_6$ are as defined under formula I above, or an agrochemically acceptable salt, stereoisomer, enantiomer, tautomer or N-oxide thereof; and wherein:

$R_2$ is preferably H, $C_1$-$C_4$alkyl, cyclopropyl, $C_1$-$C_4$haloalkyl, $C(O)R_3$ or cyano; and wherein $R_3$ is $C_1$-$C_4$alkyl; preferably $R_3$ is methyl.

In one preferred group of compounds of formula I-12, A is N.

In another preferred group of compounds of formula I-12, $R_2$ is H, cyano, $COCH_3$, cyclopropyl, methyl, ethyl, trifluoroethyl, or trifluoromethyl; more preferably $R_2$ is H, cyano, methyl, ethyl, cyclopropyl, or 2,2,2-trifluoroethyl; even more preferably $R_2$ is H, methyl, ethyl, cyclopropyl, or 2,2,2-trifluoroethyl.

In a particularly preferred group of compounds of formula I-12, $R_2$ is H, ethyl, cyclopropyl, or 2,2,2-trifluoroethyl; even more preferably $R_2$ is H or ethyl.

One preferred group of compounds according to this embodiment are compounds of formula (I-12a) which are compounds of formula (I-12) or of any of the preferred embodiments of the compounds of formula (I-12) wherein Q is Qa1.

Another preferred group of compounds according to this embodiment are compounds of formula (I-12b) which are compounds of formula (I-12) or of any of the preferred embodiments of the compounds of formula (I-12) wherein Q is Qb1.

In a preferred group of compounds of formula (I-12a), $R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a more preferred group of compounds of formula (I-12a), $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a particularly preferred group of compounds of formula (I-12a), $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

In an outstanding group of compounds of formula (I-12a), $R_5$ is preferably H, unsubstituted C-linked pyrimidinyl or N-linked triazolyl which is unsubstituted or can be mono-substituted by chloro, or trifluoromethyl; more preferably $R_5$ is selected from the group consisting of H, pyrimidin-2-yl, 1,2,4-triazol-1-yl, 3-chloro-1,2,4-triazol-1-yl, and 3-trifluoromethyl-1,2,4-triazol-1-yl; even more preferably $R_5$ is selected from the group consisting of H, pyrimidin-2-yl and 1,2,4-triazol-1-yl; even further preferred is when $R_5$ is H.

In a preferred group of compounds of formula (I-12b), $R_6$ is preferably $C_3$-$C_6$cycloalkyl, $C_3$-$C_6$cycloalkyl monosubstituted by cyano, $C_1$-$C_5$haloalkoxy, $C_1$-$C_5$alkoxy substituted with cyano, $-N{=}S(O)R_7R_8$ in which $R_7$ and $R_8$ are, independently from each other, $C_1$-$C_4$alkyl, $-N(R_9)COR_{10}$ in which $R_5$ and $R_{10}$ are, independently from each other, $C_1$-$C_4$alkyl, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a more preferred group of compounds of formula (I-12b), $R_6$ is preferably cyclopropyl, cyanocyclopropyl, $C_1$-$C_4$haloalkoxy, $C_1$-$C_4$alkoxy substituted with cyano, $-N{=}S(O)(CH_3)_2$, $-N(CH_3)COCH_3$, or 2-pyridyloxy; most preferably $R_6$ is cyclopropyl, cyanocyclopropyl, $-OCH_2CF_3$, $-OCH_2CF_2CH_3$, $C_1$-$C_3$alkoxy monosubstituted by cyano, $-N{=}S(O)(CH_3)_2$, $-N(CH_3)COCH_3$, or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a particularly preferred group of compounds of formula (I-12b), $R_6$ is preferably cyclopropyl, cyanocyclopropyl, trifluoroethoxy, difluoropropyoxy, cyanoisopropoxy, —N═S(O)($CH_3$)$_2$, —N($CH_3$)$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)($CH_3$)$_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

In another particularly preferred group of compounds of formula (I-12b), $R_6$ is preferably cyclopropyl, cyanocyclopropyl, trifluoroethoxy, difluoropropyoxy, —N═S(O)($CH_3$)$_2$, —N($CH_3$)$COCH_3$, 2-pyridyloxy, N-linked pyrazolyl which is unsubstituted or can be mono-substituted by chloro or trifluoromethyl, or C-linked pyrimidinyl which is unsubstituted or can be mono-substituted by chloro, cyano or trifluoromethyl; more preferably $R_6$ is selected from the group consisting of cyclopropyl, 1-cyanocyclopropyl, 2,2,2-trifluoroethoxy, 2,2-difluoropropoxy, —N═S(O)($CH_3$)$_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl; even more preferably $R_6$ is selected from the group consisting of cyclopropyl, 1-cyanocyclopropyl, 2,2,2-trifluoroethoxy, 2,2-difluoropropoxy, —N═S(O)($CH_3$)$_2$, —N($CH_3$)$COCH_3$, 2-pyridyloxy, pyrimidin-2-yl, 4-trifluoromethyl-pyrimidin-2-yl, 5-chloro-pyrimidin-2-yl, 3-chloro-pyrazol-1-yl, and 3-trifluoromethyl-pyrazol-1-yl.

In a further particularly preferred group of compounds of formula (I-12b), $R_6$ is preferably cyanocyclopropyl; more preferably $R_6$ is 1-cyanocyclopropyl.

One preferred group of compounds according to this embodiment are compounds of formula (I-12c) which are compounds of formula (I-12) or of any of the preferred embodiments of the compounds of formula (I-12) wherein A is N.

Another preferred group of compounds according to this embodiment are compounds of formula (I-12e) which are compounds of formula (I-12) or of any of the preferred embodiments of the compounds of formula (I-12) wherein A is CH.

Another outstanding group of compounds according to the invention are those of formula (I-13)

(I-13)

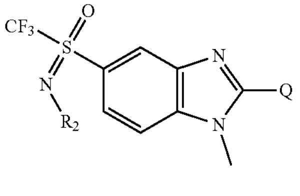

wherein $R_2$ is as defined under formula I above and Q is a radical selected from the group consisting of formula Qa1 and Qb1

Qa1

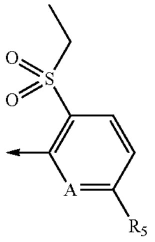

Qb1

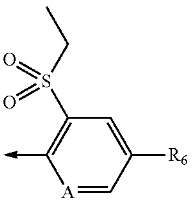

wherein the arrow denotes the point of attachment to the carbon atom of the bicyclic ring; and wherein A, $R_5$ and $R_6$ are as defined under formula I above, or an agrochemically acceptable salt, stereoisomer, enantiomer, tautomer or N-oxide thereof; and wherein:

$R_2$ is preferably H, $C_1$-$C_4$alkyl, cyclopropyl, $C_1$-$C_4$haloalkyl, C(O)$R_3$ or cyano; and wherein $R_3$ is $C_1$-$C_4$alkyl; preferably $R_3$ is methyl.

In a preferred group of compounds of formula I-13, A is N.

In another preferred group of compounds of formula I-13, $R_2$ is H, cyano, $COCH_3$, cyclopropyl, methyl, ethyl, trifluoroethyl, or trifluoromethyl; more preferably $R_2$ is H, cyano, methyl, ethyl, cyclopropyl, or 2,2,2-trifluoroethyl; even more preferably $R_2$ is H, methyl, ethyl, cyclopropyl, or 2,2,2-trifluoroethyl.

In a particularly preferred group of compounds of formula I-13, $R_2$ is H, ethyl, cyclopropyl, or 2,2,2-trifluoroethyl; even more preferably $R_2$ is H or ethyl.

One preferred group of compounds according to this embodiment are compounds of formula (I-13a) which are compounds of formula (I-13) or of any of the preferred embodiments of the compounds of formula (I-13) wherein Q is Qa1.

Another preferred group of compounds according to this embodiment are compounds of formula (I-13b) which are compounds of formula (I-13) or of any of the preferred embodiments of the compounds of formula (I-13) wherein Q is Qb1.

In a preferred group of compounds of formula (I-13a), $R_5$ is preferably H; or $R_5$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_5$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a more preferred group of compounds of formula (I-13a), $R_5$ is preferably H; or $R_5$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen and $C_1$-$C_4$haloalkyl; or $R_5$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a particularly preferred group of compounds of formula (I-13a), $R_5$ is preferably H, N-linked pyrazolyl which is unsubstituted or can be mono-substituted by chloro, or trifluoromethyl, C-linked pyrimidinyl which is unsubstituted or can be mono-substituted by chloro, or trifluoromethyl, or N-linked triazolyl which is unsubstituted or can be mono-substituted by chloro, or trifluoromethyl; even more preferably $R_5$ is selected from the group consisting of H, 3-chloro-pyrazol-1-yl, 3-trifluoromethyl-pyrazol-1-yl, pyrimidin-2-yl, 1,2,4-triazol-1-yl, 3-chloro-1,2,4-triazol-1-yl, and 3-trifluoromethyl-1,2,4-triazol-1-yl.

In an outstanding group of compounds of formula (I-13a), $R_5$ is preferably H, unsubstituted C-linked pyrimidinyl or N-linked triazolyl which is unsubstituted or can be mono-substituted by chloro, or trifluoromethyl; more preferably $R_5$ is selected from the group consisting of H, pyrimidin-2-yl, 1,2,4-triazol-1-yl, 3-chloro-1,2,4-triazol-1-yl, and 3-trifluoromethyl-1,2,4-triazol-1-yl; even more preferably $R_5$ is selected from the group consisting of H, pyrimidin-2-yl and 1,2,4-triazol-1-yl.

In a further outstanding group of compounds of formula (I-13a), $R_5$ is preferably H or N-linked triazolyl which is unsubstituted or can be mono-substituted by chloro, or trifluoromethyl; more preferably $R_5$ is selected from the group consisting of H, 1,2,4-triazol-1-yl, 3-chloro-1,2,4-triazol-1-yl, and 3-trifluoromethyl-1,2,4-triazol-1-yl.

In a preferred group of compounds of formula (I-13b), $R_6$ is preferably $C_3$-$C_6$cycloalkyl, $C_3$-$C_6$cycloalkyl monosubstituted by cyano, $C_1$-$C_6$haloalkoxy, $C_1$-$C_6$alkoxy substituted with cyano, —N═S(O)$R_7R_8$ in which $R_7$ and $R_8$ are, independently from each other, $C_1$-$C_4$alkyl, —N($R_9$)COR$_{10}$ in which $R_5$ and $R_{10}$ are, independently from each other, $C_1$-$C_4$alkyl, or 2-pyridyloxy; or $R_6$ is a five- to six-membered aromatic ring system linked via a ring carbon atom to the ring which contains the substituent A, said ring system is unsubstituted or is mono-substituted by a substituent selected from the group consisting of halogen, cyano and $C_1$-$C_4$haloalkyl; and said ring system contains 1 or 2 ring nitrogen atoms; or $R_6$ is a five-membered aromatic ring system linked via a ring nitrogen atom to the ring which contains the substituent A, said ring system is unsubstituted or is mono-substituted by a substituent selected from the group consisting of halogen, cyano and $C_1$-$C_4$haloalkyl; and said ring system contains 1, 2 or 3 ring nitrogen atoms.

In a more preferred group of compounds of formula (I-13b), $R_6$ is preferably cyclopropyl, cyanocyclopropyl, $C_1$-$C_4$haloalkoxy, $C_1$-$C_4$alkoxy substituted with cyano, —N═S(O)$(CH_3)_2$, —N($CH_3$)$COCH_3$, or 2-pyridyloxy; most preferably $R_6$ is cyclopropyl, cyanocyclopropyl, —$OCH_2CF_3$, —$OCH_2CF_2CH_3$, $C_1$-$C_3$alkoxy monosubstituted by cyano, —N═S(O)$(CH_3)_2$, —N($CH_3$)$COCH_3$, or 2-pyridyloxy; or $R_6$ is a six-membered aromatic ring system selected from pyridyl and pyrimidinyl which is linked via a ring carbon atom to the ring which contains the substituent A, said ring system is unsubstituted or is mono-substituted by substituents selected from the group consisting of halogen, cyano and $C_1$-$C_4$haloalkyl; or $R_6$ is a five-membered aromatic ring system selected from pyrazolyl, imidazolyl and triazolyl which is linked via a ring nitrogen atom to the ring which contains the substituent A, said ring system is unsubstituted or is mono-substituted by substituents selected from the group consisting of halogen and $C_1$-$C_4$haloalkyl.

In a particularly preferred group of compounds of formula (I-13b), $R_6$ is preferably cyclopropyl, cyanocyclopropyl, trifluoroethoxy, difluoropropyoxy, cyanoisopropoxy, —N═S(O)$(CH_3)_2$, —N($CH_3$)$COCH_3$, 2-pyridyloxy, N-linked pyrazolyl which is unsubstituted or can be mono-substituted by chloro, cyano or trifluoromethyl, or C-linked pyrimidinyl which is unsubstituted or can be mono-substituted by chloro, cyano or trifluoromethyl; even more preferably $R_6$ is selected from the group consisting of cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl.

In another particularly preferred group of compounds of formula (I-13b), $R_6$ is preferably cyclopropyl, cyanocyclopropyl, trifluoroethoxy, difluoropropyoxy, —N═S(O)$(CH_3)_2$, —N($CH_3$)$COCH_3$, 2-pyridyloxy, N-linked pyrazolyl which is unsubstituted or can be mono-substituted by chloro or trifluoromethyl, or C-linked pyrimidinyl which is unsubstituted or can be mono-substituted by chloro, cyano or trifluoromethyl; more preferably $R_6$ is selected from the group consisting of cyclopropyl, 1-cyanocyclopropyl, 2,2,2-trifluoroethoxy, 2,2-difluoropropoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, and 3-trifluoromethyl-pyrazol-1-yl; even more preferably $R_6$ is selected from the group consisting of cyclopropyl, 1-cyanocyclopropyl, 2,2,2-trifluoroethoxy, 2,2-difluoropropoxy, —N═S(O)$(CH_3)_2$, —N($CH_3$)$COCH_3$, 2-pyridyloxy, pyrimidin-2-yl, 4-trifluoromethyl-pyrimidin-2-yl, 5-chloro-pyrimidin-2-yl, 3-chloro-pyrazol-1-yl, and 3-trifluoromethyl-pyrazol-1-yl.

In a further particularly preferred group of compounds of formula (I-13b), $R_6$ is preferably cyanocyclopropyl, 2-pyridyloxy, or C-linked pyrimidinyl which can be mono-substituted by cyano; more preferably $R_6$ is 1-cyanocyclopropyl, 2-pyridyloxy, or 5-cyano-pyrimidin-2-yl.

One preferred group of compounds according to this embodiment are compounds of formula (I-13c) which are compounds of formula (I-13) or of any of the preferred embodiments of the compounds of formula (I-13) wherein A is N.

Another preferred group of compounds according to this embodiment are compounds of formula (I-13e) which are compounds of formula (I-13) or of any of the preferred embodiments of the compounds of formula (I-13) wherein A is CH.

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile, improved physico-chemical properties, or increased biodegradability or environmental profile). In particular, it has been surprisingly found that certain compounds of formula (I) may show an advantageous safety profile with respect to non-target arthropods, in particular pollinators such as honey bees, solitary bees, and bumble bees. Most particularly, *Apis mellifera.*

In another aspect the present invention provides a composition comprising an insecticidally, acaricidally, nematicidally or molluscicidally effective amount of a compound of formula (I), or an agrochemically acceptable salt, stereoisomer, enantiomer, tautomer or N-oxide thereof, as defined in any of embodiments 1, 2 or 3 (above) or any of the embodiments under compounds of formulae (I-1), (I-2), (I-3), (I-4), (I-5), (I-6), (I-7), (I-8), (I-9), (I-10), (I-11), (I-12) or (I-13) and, optionally, an auxiliary or diluent.

In a further aspect the present invention provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in any of embodiments 1, 2 or 3 (above) or any of the embodiments under compounds of formula (I-1), (I-2), (I-3), (I-4), (I-5), (I-6), (I-7), (I-8), (I-9), (I-10), (I-11), (I-12) or (I-13) (above) or a composition as defined above.

In a yet further aspect the present invention provides a method for the protection of plant propagation material from the attack by insects, acarines, nematodes or molluscs, which comprises treating the propagation material or the site, where the propagation material is planted, with a composition as defined above.

The process according to the invention for preparing compounds of formula I is carried out by methods known to those skilled in the art. Compounds of formula I-a3, wherein X is $SO_2$ and $R_1$, $R_2$, $R_4$, $R_5$, $G_1$, $G_2$, $G_3$ and A are defined as under formula I above, may be prepared by oxidation of compounds of formula I-a2, wherein X is SO and $R_1$, $R_2$, $R_4$, $R_5$, $G_1$, $G_2$, $G_3$ and A are defined as under formula I above. The reaction can be performed with reagents such as a peracid, for example peracetic acid or m-chloroperbenzoic acid, or a hydroperoxide, as for example, hydrogen peroxide or tert-butyl-hydroperoxide, or an inorganic oxidant, such as a monoperoxo-disulfate salt or potassium permanganate. In a similar way, compounds of formula I-a2, wherein X is SO and $R_1$, $R_2$, $R_4$, $R_5$, $G_1$, $G_2$, $G_3$ and A are defined as under formula I above, may be prepared by oxidation of compounds of formula I-a1, wherein X is S and $R_1$, $R_2$, $R_4$, $R_5$, $G_1$, $G_2$, $G_3$ and A are defined as under formula I above, under analogous conditions described above. These reactions can be performed in various organic or aqueous solvents compatible to these conditions, at temperatures from below 0° C. up to the boiling point of the solvent system. Examples of the solvent to be used in the reaction include aliphatic halogenated hydrocarbons such as dichloromethane and chloroform, alcohols such as methanol and ethanol, acetic acid, water; and mixtures thereof. Compounds of formula I-a1 can also be directly oxidized into compounds of formula I-a3 under similar conditions as described above. The transformation of compounds of the formula I-a1 into compounds of the formula I-a2 and I-a3 is represented in Scheme 1.

Scheme 1

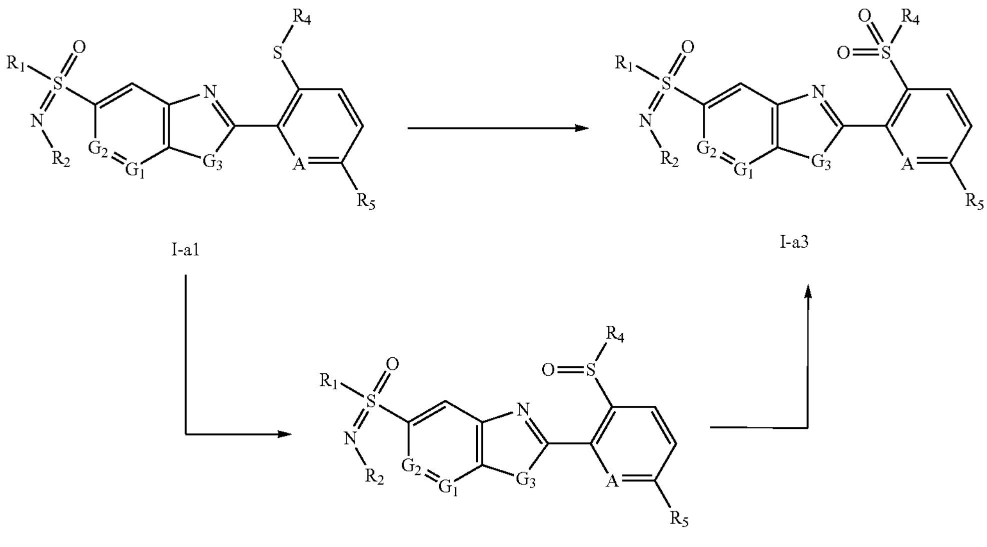

I-a1

I-a3

I-a2

Compounds of formula I-aa3 (scheme 2), wherein X is $SO_2$ and $R_1$, $R_2$, $R_4$, $R_6$, $G_1$, $G_2$, $G_3$ and A are defined as under formula I above, may be prepared from compounds of formula I-aa2, respectively compounds of formula I-aa1, wherein X is $SO_2$ and $R_1$, $R_2$, $R_4$, $R_6$, $G_1$, $G_2$, $G_3$ and A are defined as under formula I above, by analogous procedures as described in scheme 1 for the synthesis of compounds of formula I-a3.

Scheme 2

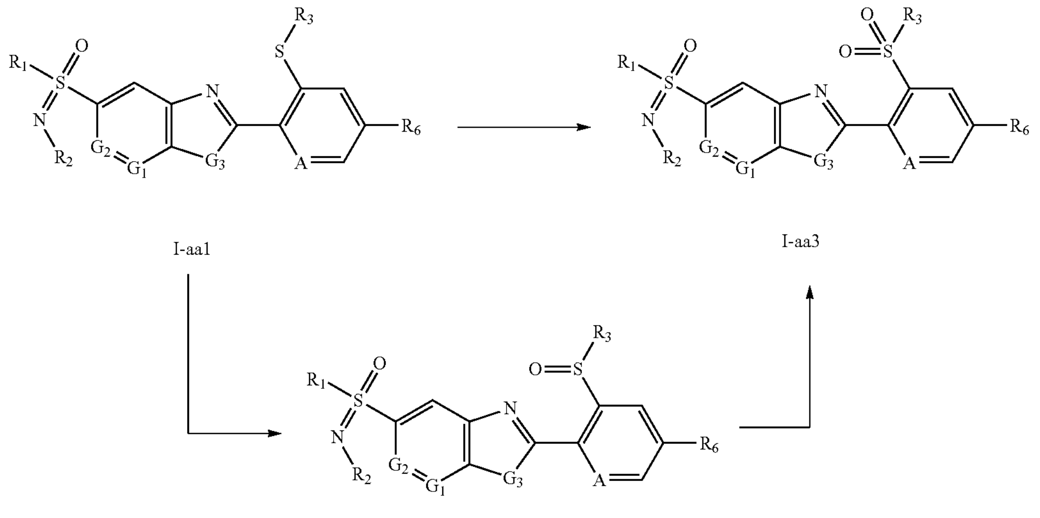

I-aa1

I-aa3

I-aa2

Alternatively compounds of formula I-a5, wherein $R_1$, $G_1$, $G_2$, $G_3$ and Q are defined as under formula I above, and in which $R_2$ is H, can be prepared (scheme 3) by reacting sulfide compounds of formula II, wherein $R_1$, $G_1$, $G_2$, $G_3$ and Q are defined as under formula I above, Scheme 3

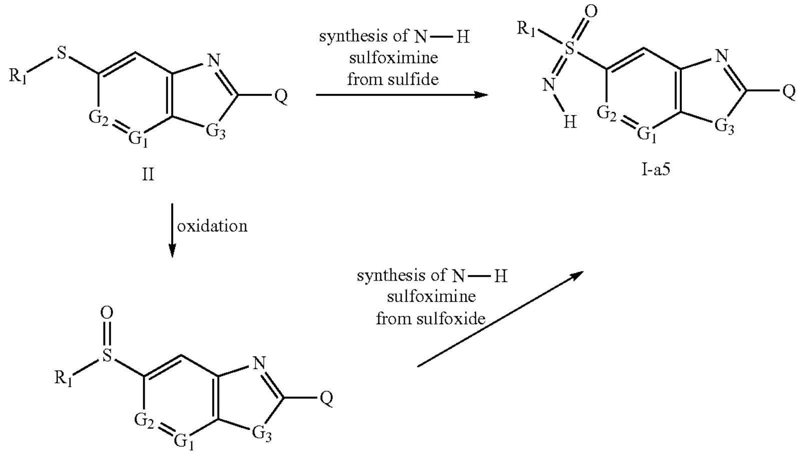

II

I-a5

III with a suitable nitrogen source such as, for example, ammonia, ammonium carbamate or ammonium acetate (preferably ammonium carbamate), in the presence of hypervalent iodine reagents, such as diacetoxyiodobenzene PhI $(OAc)_2$, in solvents such as toluene, acetonitrile or alcohols (preferably methanol, 2,2,2-trifluoroethanol or 2,2,3,3,4,4,5,5-octafluorpentan-1-ol, amongst others), at temperatures between 0 and 100° C., preferably around room temperature, in analogy to descriptions found, for example, in Chem. Commun. 2017, 53, 348-351 (and references cited therein). Alternatively sulfoxide compounds of formula III, wherein $R_1$, $G_1$, $G_2$, $G_3$ and Q are defined as under formula I above, can react with sodium azide or trimethylsilyl azide in the presence of an acid catalyst such as sulfuric acid, trifluoroacetic acid, methanesulfonic acid, Eaton's reagent amongst others, at temperatures between 0° C. and 100° C. and in solvents such as toluene, dichloromethane, chloroform amongst other halogenated solvents, to form compounds of formula I-a5, wherein $R_1$, $G_1$, $G_2$, $G_3$ and Q are defined as under formula I above, and in which $R_2$ is H. Such reactions are described for example in Org. Process Res. Dev. 2015, 19(8), 1062-1067, and WO16/180695.

Sulfoxide compounds of formula III, wherein $R_1$, $G_1$, $G_2$, $G_3$ and Q are defined as under formula I above, may be prepared by oxidation of sulfide compounds of formula II, wherein $R_1$, $G_1$, $G_2$, $G_3$ and Q are defined as under formula I above, under conditions already described above in schemes 1 and 2.

Alternatively compounds of formula I-a5, wherein $R_1$, $G_1$, $G_2$, $G_3$ and Q are defined as under formula I above, and in which $R_2$ is H, Scheme 4

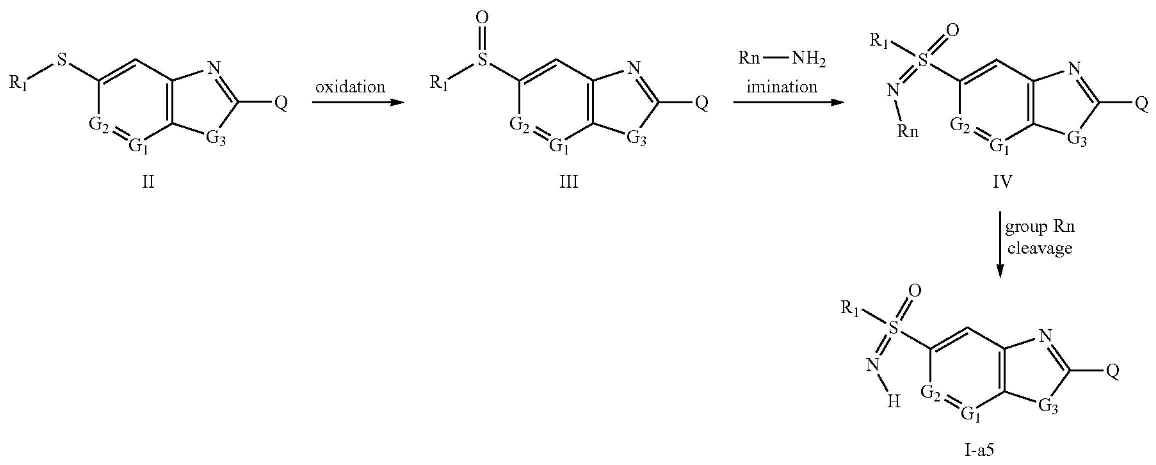

II III IV I-a5 can be prepared (scheme 4) from compounds of formula IV, wherein $R_1$, $G_1$, $G_2$, $G_3$ and Q are defined as under formula I above, and wherein Rn is CN, —C═O($C_1$-$C_6$alkyl), —C═O($C_1$-$C_6$haloalkyl), or $SO_2$-aryl by a deprotection reaction of the sulfoximine N-linked functional group Rn. For example compounds of the formula IV, wherein $R_1$, $G_1$, $G_2$, $G_3$ and Q are defined as under formula I above, and wherein Rn is CN, may be transformed into a compound of the formula IV wherein Rn is $C(O)CF_3$, by treatment with trifluoroacetic anhydride in a solvent such as dichloromethane as described, for example, in O. G. Mancheno, C. Bolm, Org. Lett. 2007, 9, 3809-3811. A compound of the formula IV, wherein $R_1$, $G_1$, $G_2$, $G_3$ and Q are defined as under formula I above, and wherein Rn is $C(O)CF_3$, may be transformed into a compound of the formula I-a5, by treatment with a base such as sodium or potassium carbonate in a polar protic solvent such as methanol or ethanol as described, for example, in H. Okamura, C. Bolm, Org. Lett. 2004, 6, 1305-1307.

Compounds of the formula IV, wherein $R_1$, $G_1$, $G_2$, $G_3$ and Q are defined as under formula I above, and wherein Rn is CN, —C═O($C_1$-$C_6$alkyl), —C═O($C_1$-$C_6$haloalkyl), or $SO_2$-aryl can be prepared by submitting compound of the formula III, wherein $R_1$, $G_1$, $G_2$, $G_3$ and Q are defined as under formula I above, to imination reaction conditions, in the presence of a reagent of the formula $RnNH_2$, wherein Rn is as defined above, and as described for example in H. Okamura, C. Bolm, Org. Lett. 2004, 6, 1305-1307; H. Okamura, C. Bolm, Chem. Lett. 2004, 33, 482-487; D. Leca, K. Song, M. Amatore, L. Fensterbank, E. Lacôte, M. Malacria, Chem. Eur. J. 2004, 10, 906-916; or M. Reggelin, C. Zur, Synthesis, 2000, 1-64. Alternative imination reagents/conditions may be defined as $NaN_3/H_2SO_4$, O-mesitylenesulfonyl-hydroxylamine (MSH), or metal-catalyzed methods [see O. G. Mancheno, C. Bolm, Chem. Eur. J. 2007, 13, 6674-6681] such as $R_n$—$N_3/FeCl_2$, $R_n$—$NH_2$/Fe(acac)$_3$/PhI═O, PhI═N—$R_n$/Fe(OTf)$_2$, PhI═N—$R_n$/CuOTf, PhI═N—$R_n$/Cu(OTf$_2$, PhI═N—$R_n$/$CuPF_6$, PhI(OAc)$_2$/$R_n$—$NH_2$/MgO/$Rh_2(OAc)_4$ or oxaziridines (e.g. 3-(4-cyano-phenyl)-oxaziridine-2-carboxylic acid tert-butyl ester).

Of particular interest are metal-free imination methods involving Rn-$NH_2$ and an oxidant, for example, PhI(OAc)$_2$/Rn-$NH_2$ as described in G. Y. Cho, C. Bolm, Tetrahedron Lett. 2005, 46, 8007-8008; or N-bromosuccinimide (NBS)/Rn-$NH_2$ and a base such as sodium or potassium ter-butoxide as described in C. Bolm et al., Synthesis 2010, No 17, 2922-2925. Oxidants such as N-iodosuccinimide (NIS) or iodine may be also used alternatively as described, for example, in O. G. Mancheno, C. Bolm, Org. Lett. 2007, 9, 3809-3811. An example of hypochlorite salts being used as oxidant, such as sodium hypochlorite NaOCl or calcium hypochlorite Ca(OCl)$_2$, was described in WO2008/1060.

Compounds of the formula III, wherein $R_1$, $G_1$, $G_2$, $G_3$ and Q are defined as under formula I above, can be prepared from compounds of formula II wherein $R_1$, $G_1$, $G_2$, $G_3$ and Q are defined as under formula I above, as described in scheme 3.

Conversely, the order of the two oxidation/imination steps may be reverted as shown in scheme 5.

Scheme 5

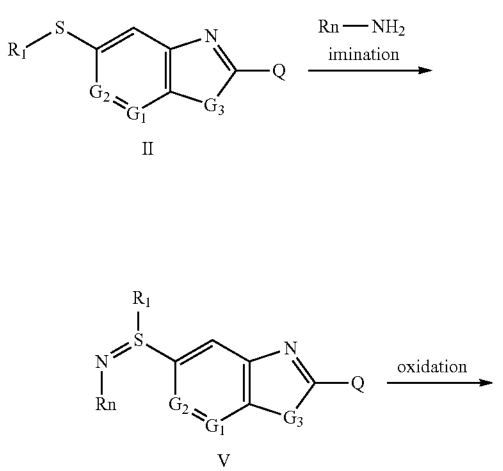

II V

-continued

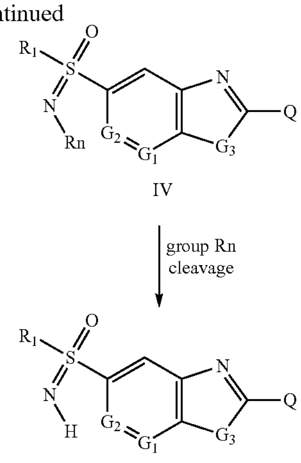

IV

I-a5

Hence, compounds of formula IV may be prepared from compounds of formula V by oxidation; and compounds of formula V from compounds of formula II by imination by involving the same chemistry as described above in scheme 4.

Alternatively compounds of formula I-a6, wherein $R_1$, $R_2$, $G_1$, $G_2$, $G_3$ and Q are defined as under formula I above, may be prepared by the alkylation or metal catalyzed coupling of Scheme 6

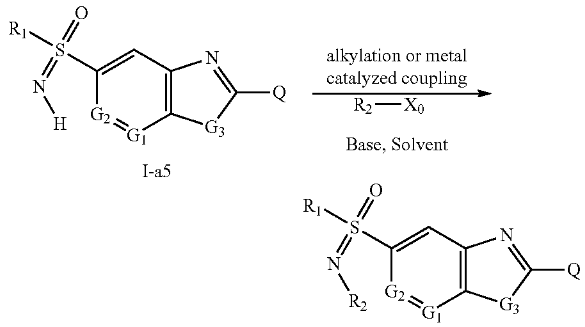

I-a5

I-a6 compounds of formula I-a5, wherein $R_1$, $G_1$, $G_2$, $G_3$ and Q are defined as under formula I above, and in which $R_2$ is H, with a reagent $R_2$—$X_0$, wherein $R_2$ is as defined in formula I above, and $X_0$ is a leaving group, for example halides such as chloro, bromo or iodo, or an aryl- or alkylsulfonate such as trifluoromethanesulfonate (scheme 6). Alkylation reaction can be performed in the presence of base such as sodium hydroxide, potassium hydroxide, potassium carbonate, sodium carbonate, cesium carbonate, triethylamine amongst other and in the presence of solvent such as dichloromethane, dichloroethane, DMF, DMSO, ethanol, methanol amongst others and at temperature between 0° C. to the boiling point of solvent. Metal catalyzed coupling for the preparation of compounds of formula I-a6 from compounds of formula I-a5 can be performed in the presence of a base, such as potassium carbonate, cesium carbonate, sodium hydroxide, in an inert solvent, such as toluene, dimethylformamide DMF, N-methyl pyrrolidine NMP, dimethyl sulfoxide DMSO, dioxane, tetrahydrofuran THF, and the like, optionally in the presence of a catalyst, for example palladium(II)acetate, bis(dibenzylideneacetone)palladium(0) (Pd $(dba)_2$) or tris(dibenzylideneacetone)dipalladium(0) ($Pd_2$ $(dba)_3$, optionally in form of a chloroform adduct), or a palladium pre-catalyst such as for example tert-BuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd G3 [(2-dicyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation.

A compound of the formula I-a6, wherein $R_1$, $G_1$, $G_2$, $G_3$ and Q are defined as under formula I above, and in which $R_2$ is —C(O)$R_3$ and $R_3$ is $C_1$-$C_6$alkyl, may be prepared from a compound of the formula I-a5, wherein $R_1$, $G_1$, $G_2$, $G_3$ and Q are defined as under formula I above, by treatment with a reagent of formula $LG_1$-C(O)$R_3$ or an anhydride reagent of formula $R_3$C(O)—O—C(O)$R_3$, wherein $R_3$ is $C_1$-$C_6$alkyl and $LG_1$ is a leaving group such as a halogen (especially chlorine), optionally in presence of an acylating catalyst, such as 4-dimethylaminopyridine (DMAP), preferably in presence of a base, such as triethylamine, diisopropylethylamine or pyridine, in an inert solvent at temperatures between 0 and 50° C. Examples of solvent to be used include ethers such as tetrahydrofuran, ethylene glycol dimethyl ether, tert-butylmethyl ether, and 1,4-dioxane, aromatic hydrocarbons such as toluene and xylene, halogenated hydrocarbons such as dichloromethane and chloroform, nitriles such as acetonitrile or polar aprotic solvents such as N,N-dimethylformamide, N,N-dimethylacetamide, N-methyl-2-pyrrolidone or dimethyl sulfoxide. The reaction may be carried out in the presence of an excess of base, which then may also act as a solvent or diluent. Such conditions have been described in, for example, WO15/071180.

Compounds of formula II wherein $R_1$, $G_1$, $G_2$, $G_3$ and Q are defined as under formula I above may be prepared (scheme 7) by cyclizing compounds of the formula (VI), Scheme 7

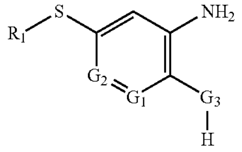

(VII)

+

-continued

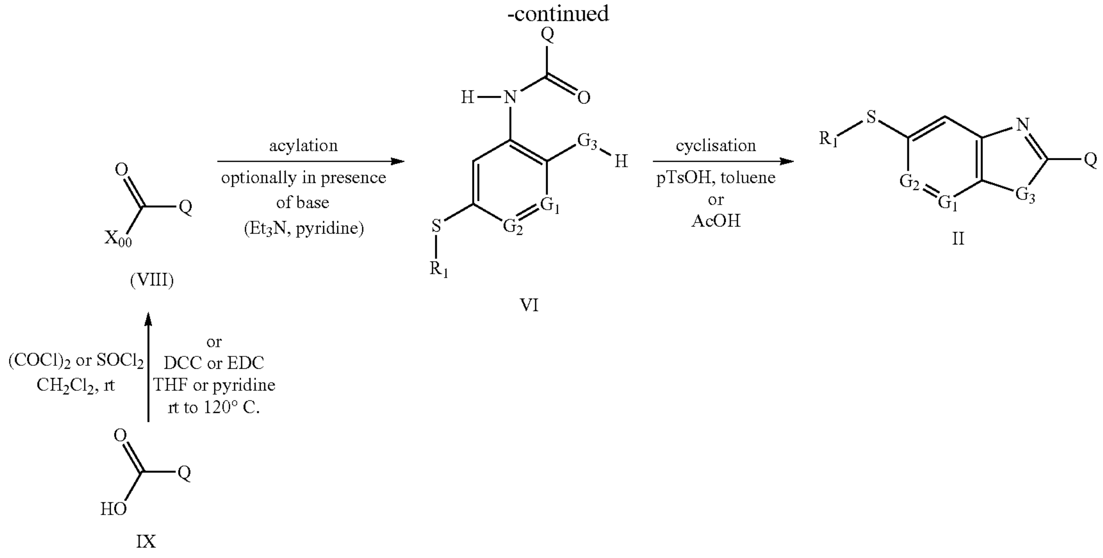

$X_{00}$ = Cl,

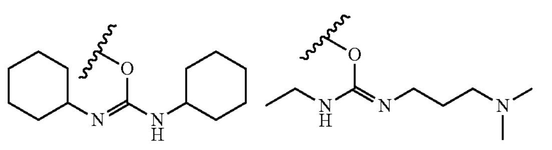

$X_{01}$ $X_{02}$ (X)

wherein $R_1$, $G_1$, $G_2$, $G_3$ and Q are defined as under formula I above, for example through heating in acetic acid or trifluoroacetic acid (preferably when $G_3$ is NMe, at temperatures between 0 and 180° C., preferably between 20 and 150° C., optionally under microwave irradiation. Cyclization of compounds of formula (VI), wherein $R_1$, $G_1$, $G_2$, $G_3$ and Q are defined are as defined in formula I, may also be achieved in the presence of an acid catalyst, for example methanesulfonic acid, or para-toluenesulfonic acid p-TsOH, in an inert solvent such as N-methyl pyrrolidone, toluene or xylene, at temperatures between 25-180° C., preferably 100-170° C. Such processes have been described previously, for example, in WO 2010/125985. Alternatively, compounds of formula (VI) may be converted into compounds of formula II (preferably when $G_3$ is O) using triphenylphosphine, diisopropyl azodicarboxylate (or di-ethyl azodicarboxylate) in an inert solvent such as tetrahydrofuran THE at temperatures between 20-50° C. Such Mitsunobu conditions have been previously described for these transformations (see WO 2009/131237).

Compounds of the formula (VI), wherein $R_1$, $G_1$, $G_2$, $G_3$ and Q are defined are as defined in formula I, may be prepared via acylation by i) Activation of compounds of formula (IX), wherein Q is as defined in formula I, by methods known to those skilled in the art and described in, for example, Tetrahedron, 2005, 61 (46), 10827-10852, to form an activated species (VIII), wherein Q is as defined in formula I, and wherein $X_{00}$ is halogen, preferably chlorine. For example, compounds (VIII) where $X_{00}$ is halogen, preferably chlorine, are formed by treatment of (IX) with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THE at temperatures between 20 to 100° C., preferably 25° C. Alternatively, treatment of compounds of formula (IX) with, for example, 1-ethyl-3-(3-dimethylaminopropyl)carbodiimide EDC or dicyclohexyl carbodiimide DCC will generate an activated species (VIII), wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by ii) Treatment of the activated species (VIII), with compounds of the formula (VII), wherein $R_1$, $G_1$, $G_2$ and $G_3$ are as defined in formula I, in the presence of a base, such as triethylamine, N,N-diisopropyl-ethyl-amine or pyridine, in an inert solvents such as dichloromethane, tetrahydrofuran, dioxane, N,N-dimethylformamide, N,N-dimethylacetamide, acetonitrile, ethyl acetate or toluene, at temperatures between 0 and 50° C., to form the compounds of formula (VI).

Compounds of the formula (VII), wherein $R_1$, $G_1$, $G_2$ and $G_3$ are as defined in formula I, are either known, commercially available or may be prepared by methods known to a person skilled in the art.

Alternatively, compounds of formula I-a6, wherein $R_1$, $R_2$, $G_1$, $G_2$, $G_3$ and Q are as defined in formula I above, may be prepared following scheme 8 which is analogous to procedure as described in scheme 7. All substituent definitions mentioned previously remain valid.

Scheme 8

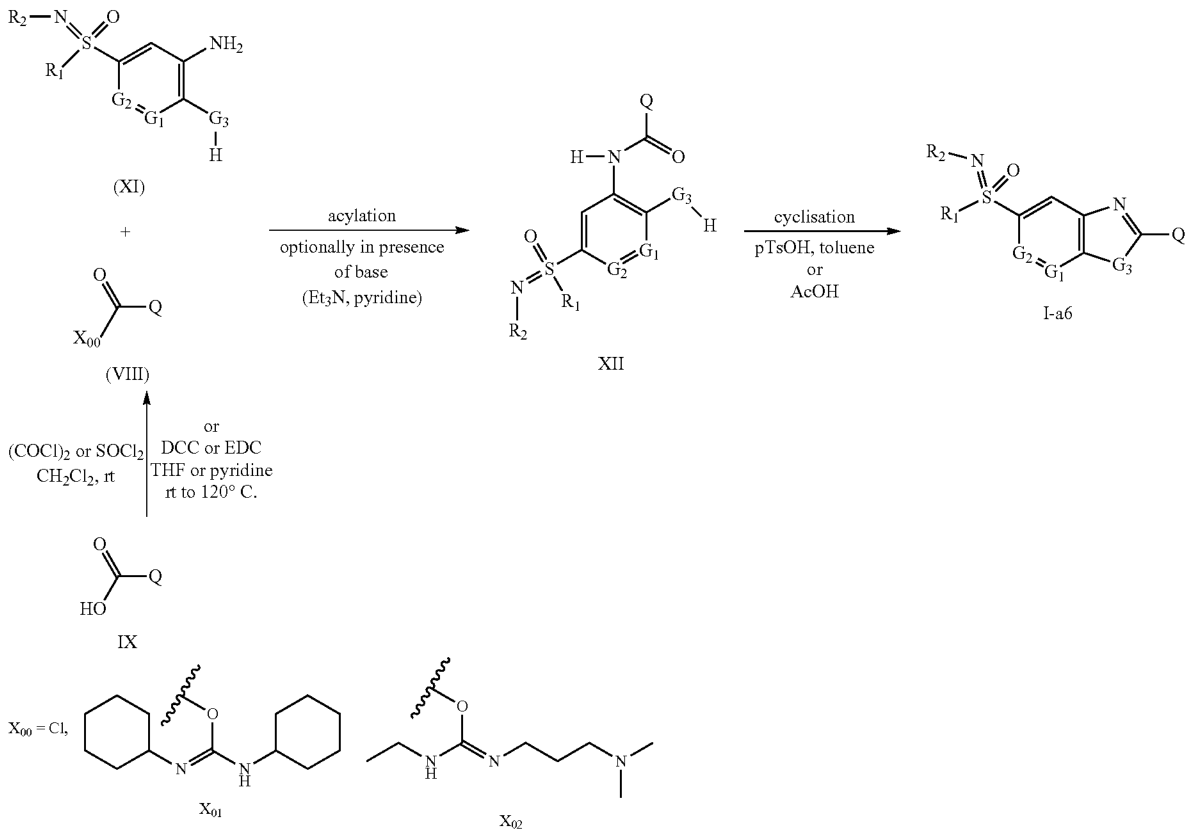

(XI)

+

(VIII)

IX

XII

I-a6

$X_{00}$ = Cl, $X_{01}$ $X_{02}$ (X)

Compounds of formula XI, wherein $R_1$, $R_2$, $G_1$, $G_2$, and $G_3$ are as defined in formula I above, Scheme 9

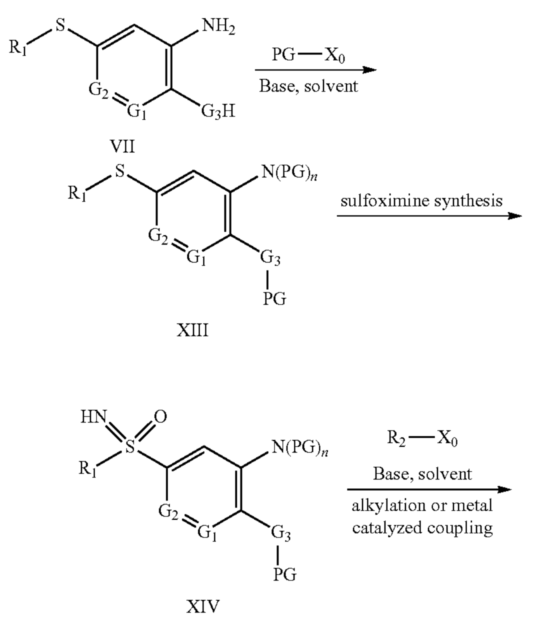

VII

XIII

XIV

-continued

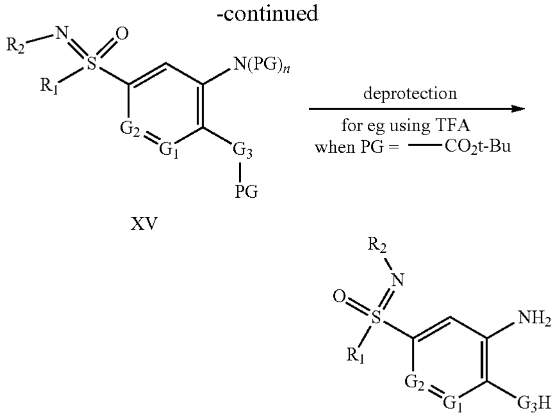

XV

XI may be prepared following scheme 9. Compounds of formula VII, wherein $R_1$, $G_1$, $G_2$, and $G_3$ are as defined in formula I above, can react with PG-$X_0$, wherein PG is benzyl, para-methoxybenzyl, benzoyl, acetyl or tert-butyloxycarbonyl, or similar other suitable protecting groups for NH or OH functional groups known to a person skilled in the art, and wherein $X_0$ is a leaving group, for example halides such as chloro, bromo or iodo or an aryl- or alkylsulfonate such as trifluoromethanesulfonate, to form compounds of formula XIII, wherein $R_1$, $G_1$, $G_2$, and $G_3$ are as defined in formula I, and wherein PG is benzyl, para-methoxybenzyl, benzoyl, acetyl or tert-butyloxycarbonyl, or similar other suitable protecting groups for NH or OH functional groups, and in which n is 1 or 2. Compounds of formula XIII can be converted to compounds of formula XV, wherein $R_1$, $R_2$, $G_1$, $G_2$, and $G_3$ are as defined in formula I, and wherein PG is benzyl, para-methoxybenzyl, benzoyl, acetyl or tert-butyloxycarbonyl, or similar other suitable protecting groups for NH or OH functional groups, and in which n is 1 or 2, by applying chemistry and conditions described in schemes 3 & 4, and scheme 6. Compounds of formula XV can be converted to compounds of formula XI, wherein $R_1$, $R_2$, $G_1$, $G_2$ and $G_3$ are as defined in formula I above, by deprotection reaction of amino or alcohol functional groups. As an example, when PG is a —$CO_2$t-Bu group in compounds of formula XV, it can be deprotected using acids such as trifluoroacetic acid, hydrochloric acid, sulfuric acid amongst others to form compounds of formula XI.

Certain compounds of formula IX, wherein Q is as defined in formula I above, are commercially available. Other compounds of formula IX, wherein Q is as defined in formula I above, are known in the literature (for example compounds Q-1 to Q-10 below) and described, for example, in WO18/108726 for the synthesis of Q-1 (X is S), and in WO16/046071 for the synthesis of Q-2, and in WO17/146226 for the synthesis of Q-3.

Q-1

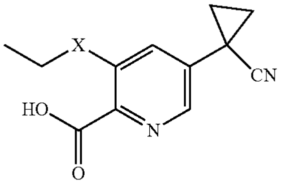

X is S CAS 2225113-77-7
X is $SO_2$ CAS 1879106-82-7

Q-2

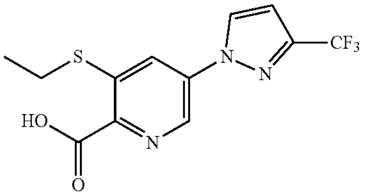

CAS 1889393-25-2

Q-3

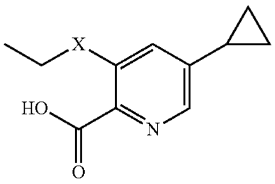

X is S CAS 1975148-58-3
X is $SO_2$ CAS 2173047-84-0

Q-4

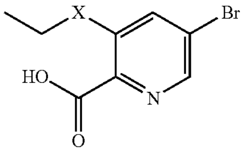

X is S CAS 1857366-13-2
X is $SO_2$ CAS 2098699-89-7

-continued

Q-5

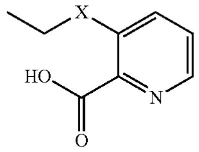

X is S CAS 14440-97-2
X is $SO_2$ CAS 1421953-17-4

Q-6

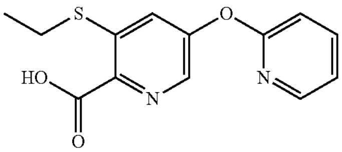

CAS 2448153-73-7

Yet other compounds of formula IX may be prepared by a person skilled in the art in analogy to the methods described for the synthesis of compounds Q-1 to Q-10 ("CAS" means the Chemical Abstracts Registry number).

Q-7

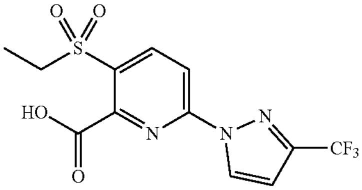

CAS 1970134-16-7

Q-8

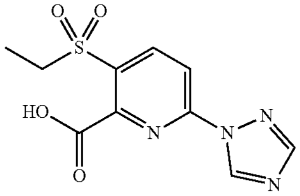

CAS 2016034-28-7

Q-9

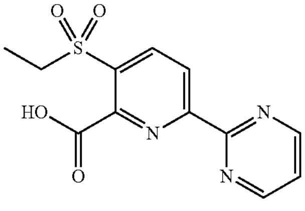

CAS 1970134-19-0

Q-10

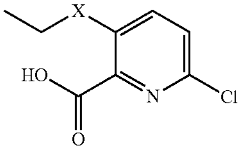

X is S CAS 2059118-28-2
X is $SO_2$ CAS 1848219-28-2

The subgroup of compounds of formula I, wherein $R_1$, $R_2$, $G_1$, $G_2$, $G_3$ are as defined in formula I above and wherein Q is defined as Qb, in which A, X, $R_4$, and $R_6$ are as defined in formula I, may be defined as compounds of formula I-Qb (scheme 10).

In the particular situation within scheme 10 when $R_6$ is an optionally substituted triazole linked via a ring nitrogen atom to the ring which contains the group A, then compounds of formula I-Qb, wherein X is SO or $SO_2$, may be prepared from compounds of formula XVIb, wherein $R_1$, $R_2$, $G_1$, $G_2$, $G_3$, A and $R_4$ are as defined in formula I above and in which X is SO or $SO_2$, and wherein $X_b$ is a leaving formation) with an optionally substituted triazole $R_6$—H (which contains an appropriate NH functionality) (XVIIaa), wherein $R_6$ is N-linked triazolyl, in solvents such as alcohols (eg. methanol, ethanol, isopropanol, or higher boiling linear or branched alcohols), pyridine or acetic acid, optionally in the presence of an additional base, such as potassium carbonate $K_2CO_3$ or cesium carbonate $Cs_2CO_3$, optionally in the presence of a copper catalyst, for example copper(I) iodide, at temperatures between 30-180° C., optionally under microwave irradiation.

Scheme 10

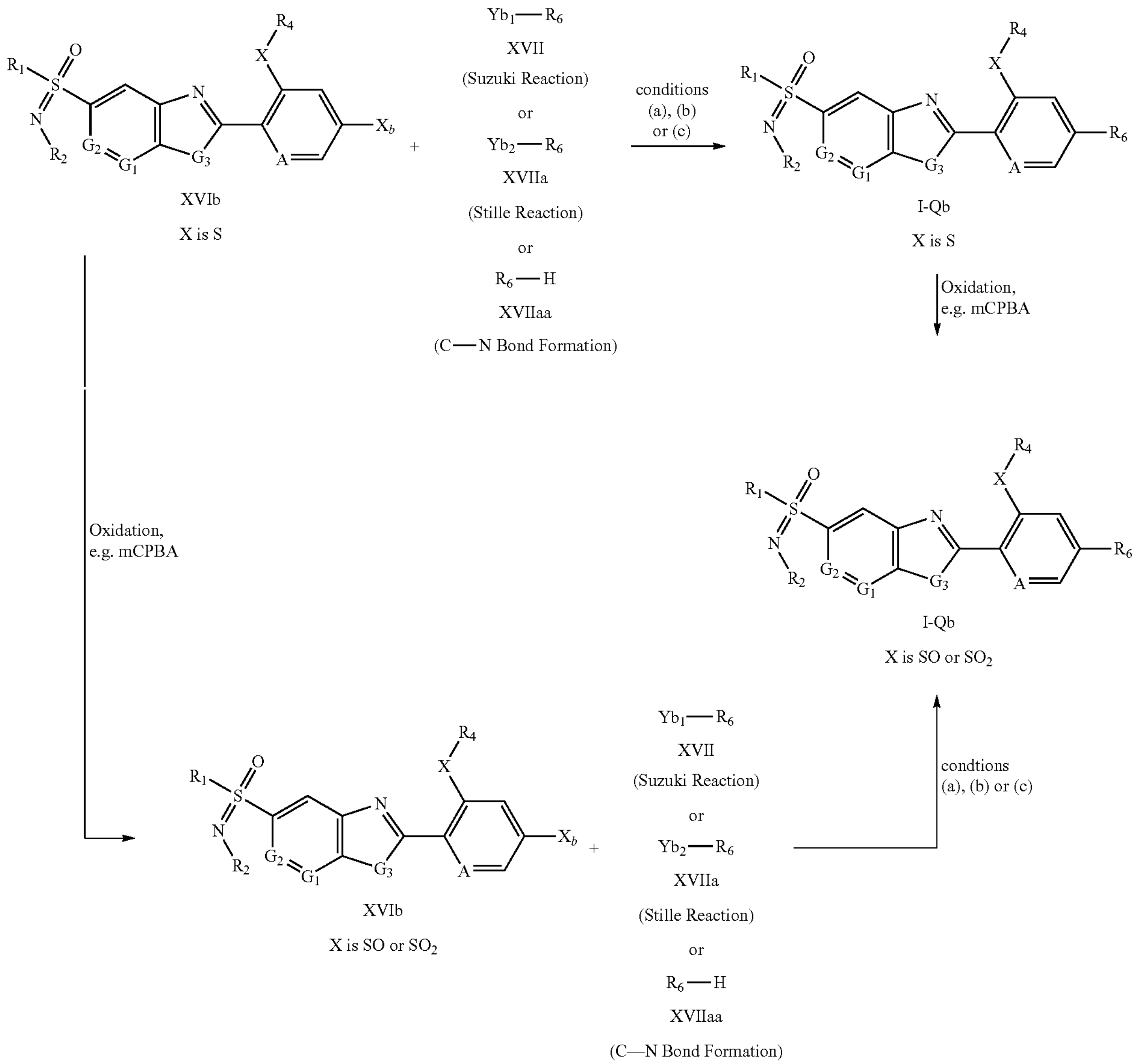

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° C.
(c) C—N bond formation: Optional base (e.g. $K_2CO_3$ or $Cs_2CO_3$), optional presence of copper or palladium catalyst, optional additive (such as N,N'-dimethylethlenediamine), optional ligand (such as Xantphos), solvent (e.g. dioxane, pyridine or N,N-dimethylformamide DMF), 25-180° C.

group like, for example, chlorine, bromine or iodine (preferably chlorine or bromine), or an aryl- or alkylsulfonate such as trifluoromethanesulfonate, by reaction (C—N bond Alternatively, compounds of formula I-Qb, wherein X is SO or $SO_2$, may be prepared by a Suzuki reaction, which involves for example, reacting compounds of formula XVIb, wherein $R_1$, $R_2$, $G_1$, $G_2$, $G_3$, A and $R_4$ are as defined in formula I above and in which X is SO or $SO_2$, and wherein Xb is a leaving group like, for example, chlorine, bromine or iodine (preferably chlorine or bromine), or an aryl- or alkylsulfonate such as trifluoromethanesulfonate, with compounds of formula (XVII), wherein $R_6$ is as defined in formula I, and wherein $Y_{b1}$ can be a boron-derived functional group, such as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction may be catalyzed by a palladium based catalyst, for example tetrakis(triphenyl-phosphine)palladium(0), (1,1' bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Orgmet. Chem. 576, 1999, 147-168.

Alternatively compounds of formula I-Qb, wherein X is SO or $SO_2$, may be prepared by a Stille reaction between compounds of formula (XVIIa), wherein $R_6$ is as defined above, and wherein $Y_{b2}$ is a trialkyl tin derivative, preferably tri-n-butyl tin or tri-methyl-tin, and compounds of formula XVIb, wherein $R_1$, $R_2$, $G_1$, $G_2$, $G_3$, A and $R_4$ are as defined in formula I above and in which X is SO or $SO_2$, and wherein Xb is a leaving group like, for example, chlorine, bromine or iodine (preferably chlorine or bromine), or an aryl- or alkylsulfonate such as trifluoromethanesulfonate. Such Stille reactions are usually carried out in the presence of a palladium catalyst, for example tetrakis(triphenylphosphine) palladium(0), or bis(triphenylphosphine)palladium (II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example J. Org. Chem., 2005, 70, 8601-8604, J. Org. Chem., 2009, 74, 5599-5602, and Angew. Chem. Int. Ed., 2004, 43, 1132-1136.

When $R_6$ is a five-membered aromatic ring system linked via a ring nitrogen atom to the ring which contains the substituent A, then compounds of formula I-Qb, wherein X is SO or $SO_2$, may be prepared from compounds of formula XVIb, wherein $R_1$, $R_2$, $G_1$, $G_2$, $G_3$, A and $R_4$ are as defined in formula I above and in which X is SO or $SO_2$, and wherein Xb is a leaving group like, for example, chlorine, bromine or iodine (preferably chlorine or bromine), or an aryl- or alkylsulfonate such as trifluoromethanesulfonate, by reaction with a heterocycle $R_6$—H (which contains an appropriate NH functionality) (XVIIaa), wherein $R_6$ is as defined above, in the presence of a base, such as potassium carbonate $K_2CO_3$ or cesium carbonate $Cs_2CO_3$, optionally in the presence of a copper catalyst, for example copper(I) iodide, with or without an additive such as L-proline, N,N'-dimethylcyclohexane-1,2-diamine or N,N'-dimethylethylene-diamine, in an inert solvent such as N-methylpyrrolidone NMP or N,N-dimethylformamide DMF at temperatures between 30-150° C., optionally under microwave irradiation.

In the particular situation within scheme 10 when $R_6$ is —$N(R_9)C(=O)R_{10}$, wherein $R_9$ and $R_{10}$ are as defined in formula I, then compounds of formula I-Qb, wherein X is SO or $SO_2$, may be prepared from compounds of formula XVIb, wherein $R_1$, $R_2$, $G_1$, $G_2$, $G_3$, A and $R_4$ are as defined in formula I above and in which X is SO or $SO_2$, and, and wherein Xb is a leaving group like, for example, chlorine, bromine or iodine (preferably chlorine or bromine), or an aryl- or alkylsulfonate such as trifluoromethanesulfonate, by reaction (C—N bond formation) with a reagent $R_6$—H (XVIIaa) equivalent to $HN(R_9)COR_{10}$, wherein $R_9$ and $R_{10}$ are as defined in formula I. Such a reaction is performed in the presence of a base, such as potassium carbonate, cesium carbonate, sodium hydroxide, in an inert solvent, such as toluene, dimethylformamide DMF, N-methyl pyrrolidine NMP, dimethyl sulfoxide DMSO, dioxane, tetrahydrofuran THF, and the like, optionally in the presence of a catalyst, for example palladium(II)acetate, bis(dibenzylideneacetone) palladium(0) ($Pd(dba)_2$) or tris(dibenzylideneacetone)dipalladium(0) ($Pd_2(dba)_3$, optionally in form of a chloroform adduct), or a palladium pre-catalyst such as for example tert-BuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation.

In the particular situation within scheme 10 when $R_6$ is $N(R_{11})R_{12}$, wherein Rn, $R_{12}$ are as defined in formula I, then compounds of formula I-Qb, wherein X is SO or $SO_2$, may be prepared from compounds of formula XVIb, wherein $R_1$, $R_2$, $G_1$, $G_2$, $G_3$, A and $R_4$ are as defined in formula I above and in which X is SO or $SO_2$, and wherein Xb is a leaving group like, for example, chlorine, bromine or iodine (preferably chlorine or bromine), or an aryl- or alkylsulfonate such as trifluoromethanesulfonate, by reaction (C—N bond formation) with a reagent $R_6$—H (XVIIaa) equivalent to $HN(R_{11})R_{12}$, or a salt thereof (such as a hydrohalide salt, preferably a hydrochloride or a hydrobromide salt, or a trifluoroacetic acid salt, or any other equivalent salt), wherein Rn, $R_{12}$ are as defined in formula I. Such a reaction is commonly performed in an inert solvent such as alcohols, amides, esters, ethers, nitriles and water, particularly preferred are methanol, ethanol, 2,2,2-trifluoroethanol, propanol, isopropanol, N,N-dimethylformamide, N,N-dimethylacetamide, dioxane, tetrahydrofuran, dimethoxyethane, acetonitrile, ethyl acetate, toluene, water or mixtures thereof, at temperatures between 0-150° C., optionally under microwave irradiation or pressurized conditions using an autoclave, optionally in the presence of a copper catalyst, such as copper powder, copper(I) iodide or copper sulfate (optionally in form of a hydrate), or mixtures thereof, optionaly in presence a ligand, for example diamine ligands (e.g. N,N'-dimethylethylenediamine or trans-cyclohexyldiamine) or dibenzylideneacetone (dba), or 1,10-phenanthroline, and optionally in presence of a base such as potassium phosphate.

Reagents $HN(R_{11})R_{12}$ and $HN(R_9)C(=O)R_{10}$, wherein $R_9$, $R_{10}$, $R_{11}$, and $R_{12}$ are as defined in formula I, are either known, commercially available or may be prepared by methods known to a person skilled in the art.

In the particular situation within scheme 10 when $R_6$ is —N═S(O)$R_7R_8$, wherein $R_7$ and $R_8$ are as defined in formula I, then compounds of formula I-Qb, wherein X is SO or $SO_2$, may be prepared from compounds of formula XVIb, wherein $R_1$, $R_2$, $G_1$, $G_2$, $G_3$, A and $R_4$ are as defined in formula I above and in which X is SO or $SO_2$, and, and wherein Xb is a leaving group like, for example, chlorine, bromine or iodine (preferably chlorine or bromine), or an aryl- or alkylsulfonate such as trifluoromethanesulfonate, by reaction (C—N bond formation) with a reagent $R_6$—H (XVIIaa) equivalent to HN═S(O)$R_7R_8$, wherein $R_7$ and $R_8$ are as defined in formula I. Such a reaction may be performed in analogy to descriptions found, for example, in WO18099812.

Reagents HN═S(O)$R_7R_8$, wherein $R_7$ and $R_8$ are as defined in formula I, are either known, commercially available or may be prepared by methods known to a person skilled in the art.

Oxidation of compounds of formula XVIb, wherein $R_1$, $R_2$, $G_1$, $G_2$, $G_3$, A and $R_4$ are as defined in formula I above and in which X is S, and wherein Xb is a leaving group like, for example, chlorine, bromine or iodine (preferably chlorine or bromine), or an aryl- or alkylsulfonate such as trifluoromethanesulfonate, with a suitable oxidizing agent, into compounds of formula XVIb, wherein X is SO or $SO_2$ may be achieved under conditions already described above.

A large number of compounds of the formula (XVII), (XVIIa) and (XVIIaa) are commercially available or can be prepared by those skilled in the art.

Alternatively, compounds of formula I-Qb, wherein X is SO or $SO_2$, may be prepared from compounds of formula XVIb, wherein X is S (sulfide) by involving the same chemistry as described above, but by changing the order of the steps (i.e. by running the sequence XVIb (X is S) to I-Qb (X is S) via Suzuki, Stille or C—N bond formation, followed by an oxidation step to form I-Qb (X is SO or $SO_2$).

Compounds of formula XVIb, wherein $R_1$, $R_2$, $G_1$, $G_2$, $G_3$, A and $R_4$ are as defined in formula I above and in which X is S, SO or $SO_2$, and wherein $X_b$ is a leaving group like, for example, chlorine, bromine or iodine (preferably chlorine or bromine), or an aryl- or alkylsulfonate such as trifluoromethanesulfonate, may be prepared (scheme 10a) from compounds of compounds of formula XVIIIb, wherein $R_1$, $G_1$, $G_2$, $G_3$, A and $R_4$ are as defined in formula I above and in which X is S, SO or $SO_2$, and wherein $X_b$ is a leaving group like, for example, chlorine, bromine or iodine (preferably chlorine or bromine), or an aryl- or alkylsulfonate such as trifluoromethanesulfonate, according to chemistry already disclosed in scheme 6.

Scheme 10a
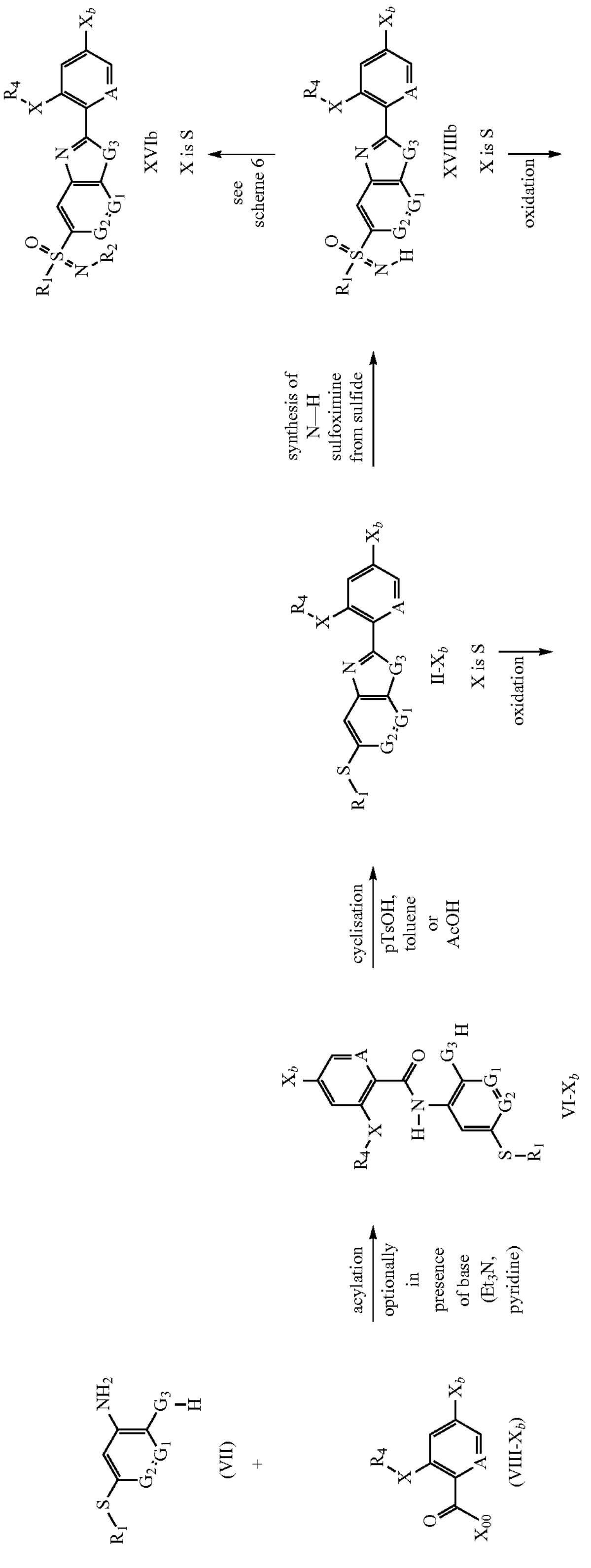

-continued
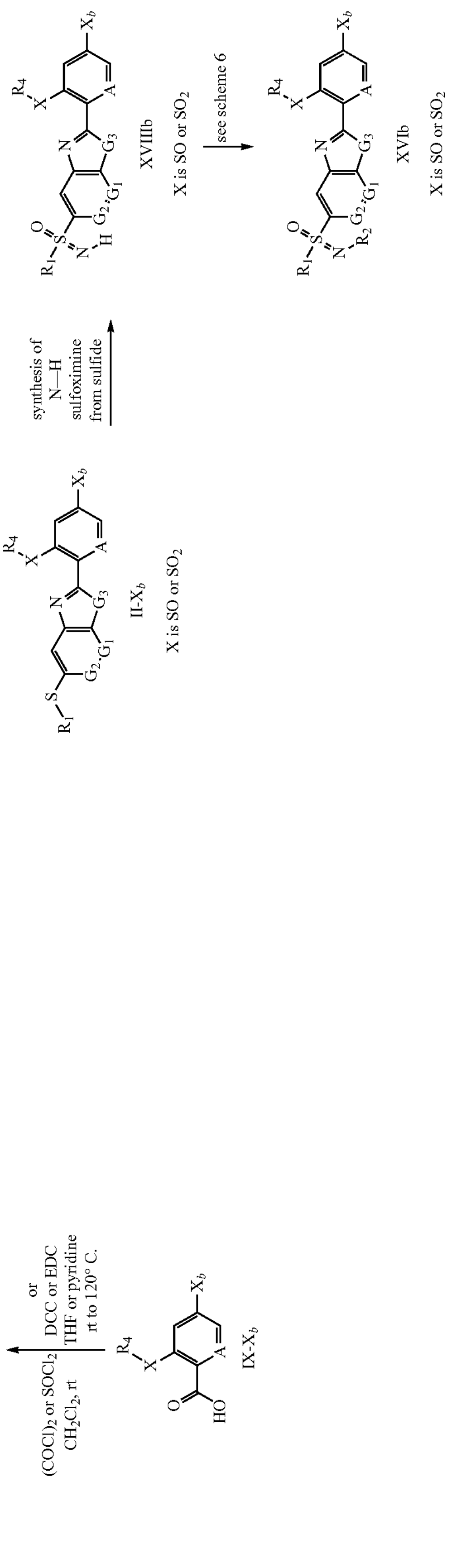

Compounds of compounds of formula XVIIIb, wherein $R_1$, $G_1$, $G_2$, $G_3$, A and $R_4$ are as defined in formula I above and in which X is S, SO or $SO_2$, and wherein $X_b$ is a leaving group like, for example, chlorine, bromine or iodine (preferably chlorine or bromine), or an aryl- or alkylsulfonate such as trifluoromethanesulfonate, may be prepared from compounds of compounds of formula II-$X_b$, wherein $R_1$, $G_1$, $G_2$, $G_3$, A and $R_4$ are as defined in formula I above and in which X is S, and wherein $X_b$ is a leaving group as defined above, by applying chemistry already disclosed in scheme 3 and oxidation conditions described above.

Compounds of compounds of formula II-$X_b$, wherein $R_1$, $G_1$, $G_2$, $G_3$, A and $R_4$ are as defined in formula I above and in which X is S, and wherein $X_b$ is a leaving group as defined above, may be prepared from compounds of formula IX-$X_b$, wherein A and $R_4$ are as defined in formula I above and in which X is S, and wherein $X_b$ is a leaving group as defined above, and compounds of formula VII, wherein $R_1$, $G_1$, $G_2$, and $G_3$ are as defined in formula I above, via intermediates of formula VI-$X_b$, wherein $R_1$, $G_1$, $G_2$, $G_3$, A and $R_4$ are as defined in formula I above and in which X is S, and wherein $X_b$ is a leaving group as defined above, by following chemistry already disclosed in scheme 7.

Compounds of formula IX-$X_b$, wherein A and $R_4$ are as defined in formula I above and in which X is S, and wherein $X_b$ is a leaving group like, for example, chlorine, bromine or iodine (preferably chlorine or bromine), are either known (see for example Q-4 discussed above), commercially available or may be prepared by methods known to a person skilled in the art.

The subgroup of compounds of formula I, wherein $R_1$, $R_2$, $G_1$, $G_2$, $G_3$ are as defined in formula I above and wherein Q is defined as Qa, in which A, X, $R_4$, and $R_5$ are as defined in formula I, may be defined as compounds of formula I-Qa (scheme 11).

Scheme 11

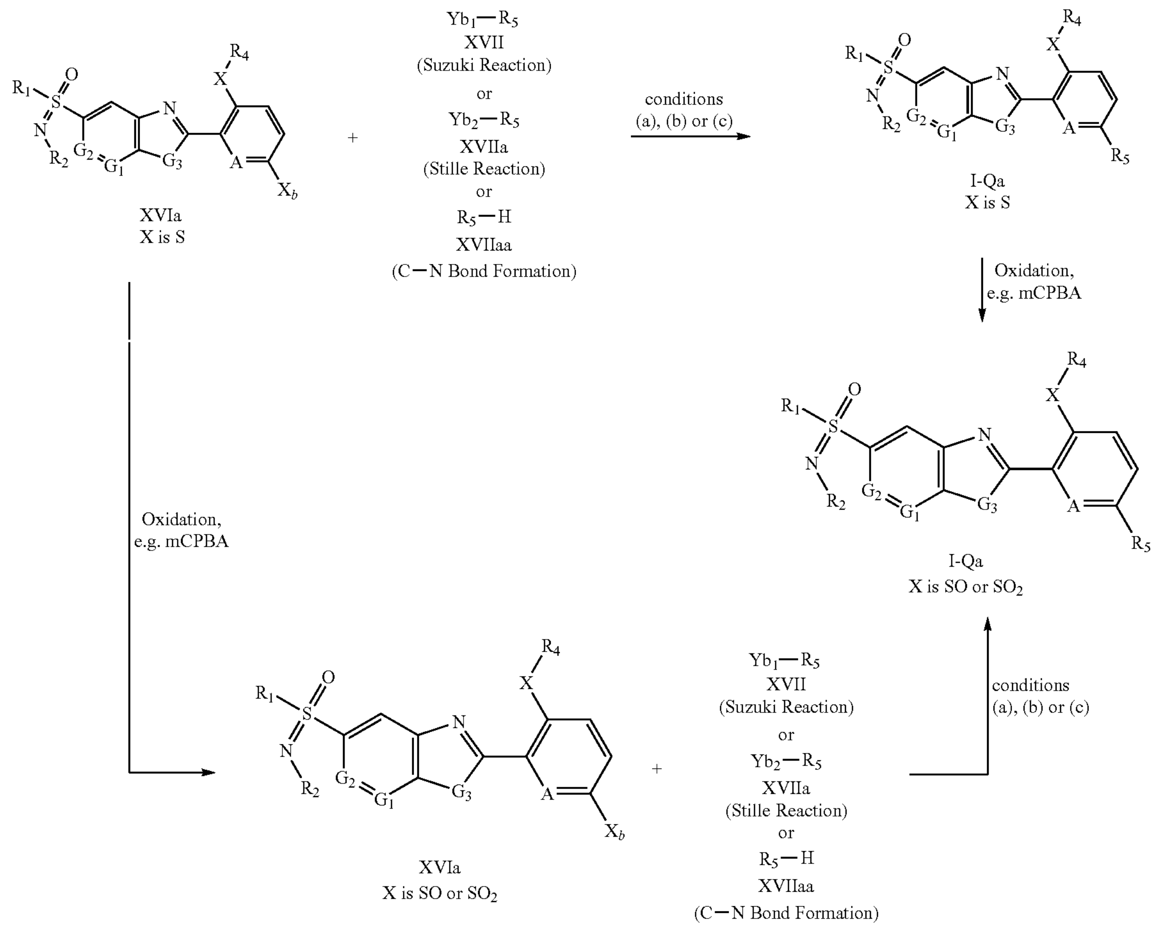

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.

(b) Stille reaction: Pd cat. (e.g. $Pd(PPh_3)_4$ or $Pd(PPh_3)Cl_2$), solvent (e.g. toluene), 25-180° C.

(c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

The chemistry described previously in scheme 10 to access compounds of formula I-Qb from compounds of formula XVIb, can be applied analogously (scheme 11) for the preparation of compounds of formula I-Qa from compounds of formula XVIa, wherein all substituent definitions mentioned previously remain valid.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an) other substituent(s) according to the invention, and by post modification of compounds of with reactions such as oxidation, alkylation, reduction, acylation and other methods known by those skilled in the art.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables A-1 to A-96, C-1 to C-96, E-1 to E-96, F-1 to F-96, G-1 to G-96 and H-1 to H-96 below can be prepared according to the methods described above. The examples which follow are intended to illustrate the invention and show preferred compounds of formula I.

The tables A-1 to A-96 below illustrate specific compounds of the invention.

"cPr" represents cyclopropyl.

(I-1-Qb)

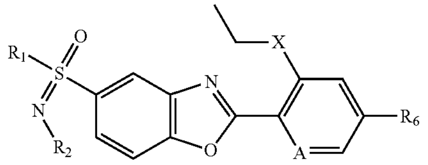

Table A-1 provides 14 compounds A-1.001 to A-1.014 of formula I-1-Qb wherein $R_1$ is Me, $R_2$ is H, A is N, X is S and $R_6$ is as defined in table B.

TABLE B

| Substituent definitions of $R_6$ | |
|---|---|
| Index | $R_6$ |
| 1 | 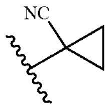 [SMILES: *C1(C#N)CC1] |
| 2 | 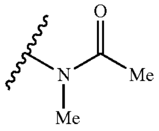 [SMILES: *N(C)C(C)=O] |
| 3 | 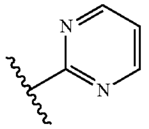 [SMILES: *c1ncccn1] |
| 4 | 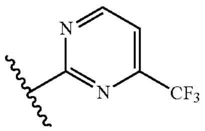 [SMILES: *c1nccc(C(F)(F)F)n1] |
| 5 | 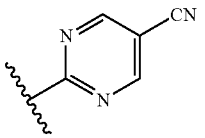 [SMILES: *c1ncc(C#N)cn1] |

TABLE B-continued

| Substituent definitions of $R_6$ | |
|---|---|
| Index | $R_6$ |
| 6 | 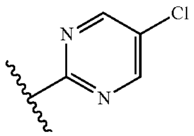 [SMILES: *c1ncc(Cl)cn1] |
| 7 | $OCH_2CF_3$ |
| 8 | 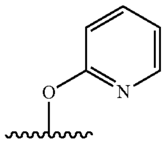 [SMILES: *Oc1ccccn1] |
| 9 | 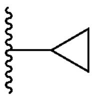 [SMILES: *C1CC1] |
| 10 | 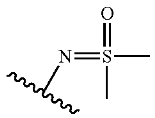 [SMILES: *N=S(C)(C)=O] |
| 11 | 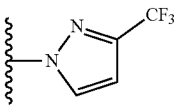 [SMILES: *n1ccc(C(F)(F)F)n1] |
| 12 | $—OCH_2CF_2Me$ |
| 13 | 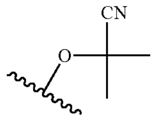 [SMILES: *OC(C)(C)C#N] |
| 14 | 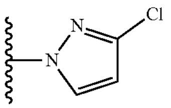 |

Table A-2 provides 14 compounds A-2.001 to A-2.014 of formula I-1-Qb wherein $R_1$ is Me, $R_2$ is H, A is N, X is SO and $R_6$ is as defined in table B.

Table A-3 provides 14 compounds A-3.001 to A-3.014 of formula I-1-Qb wherein $R_1$ is Me, $R_2$ is H, A is N, X is $SO_2$ and $R_6$ is as defined in table B.

Table A-4 provides 14 compounds A-4.001 to A-4.014 of formula I-1-Qb wherein $R_1$ is Me, $R_2$ is H, A is OH, X is S and $R_6$ is as defined in table B.

Table A-5 provides 14 compounds A-5.001 to A-5.014 of formula I-1-Qb wherein $R_1$ is Me, $R_2$ is H, A is OH, X is SO and $R_6$ is as defined in table B.

Table A-6 provides 14 compounds A-6.001 to A-6.014 of formula I-1-Qb wherein $R_1$ is Me, $R_2$ is H, A is OH, X is $SO_2$ and $R_6$ is as defined in table B.

Table A-7 provides 14 compounds A-7.001 to A-7.014 of formula I-1-Qb wherein $R_1$ is Me, $R_2$ is CN, A is N, X is S and $R_6$ is as defined in table B.

Table A-8 provides 14 compounds A-8.001 to A-8.014 of formula I-1-Qb wherein $R_1$ is Me, $R_2$ is CN, A is N, X is SO and $R_6$ is as defined in table B.

Table A-9 provides 14 compounds A-9.001 to A-9.014 of formula I-1-Qb wherein $R_1$ is Me, $R_2$ is CN, A is N, X is $SO_2$ and $R_6$ is as defined in table B.

Table A-10 provides 14 compounds A-10.001 to A-10.014 of formula I-1-Qb wherein $R_1$ is Me, $R_2$ is CN, A is CH, X is S and $R_6$ is as defined in table B.

Table A-11 provides 14 compounds A-11.001 to A-11.014 of formula I-1-Qb wherein $R_1$ is Me, $R_2$ is CN, A is CH, X is SO and $R_6$ is as defined in table B.

Table A-12 provides 14 compounds A-12.001 to A-12.014 of formula I-1-Qb wherein $R_1$ is Me, $R_2$ is CN, A is CH, X is $SO_2$ and $R_6$ is as defined in table B.

Table A-13 provides 14 compounds A-13.001 to A-13.014 of formula I-1-Qb wherein $R_1$ is Me, $R_2$ is $COCH_3$, A is N, X is S and $R_6$ is as defined in table B.

Table A-14 provides 14 compounds A-14.001 to A-14.014 of formula I-1-Qb wherein $R_1$ is Me, $R_2$ is $COCH_3$, A is N, X is SO and $R_6$ is as defined in table B.

Table A-15 provides 14 compounds A-15.001 to A-15.014 of formula I-1-Qb wherein $R_1$ is Me, $R_2$ is $COCH_3$, A is N, X is $SO_2$ and $R_6$ is as defined in table B.

Table A-16 provides 14 compounds A-16.001 to A-16.014 of formula I-1-Qb wherein $R_1$ is Me, $R_2$ is $COCH_3$, A is CH, X is S and $R_6$ is as defined in table B.

Table A-17 provides 14 compounds A-17.001 to A-17.014 of formula I-1-Qb wherein $R_1$ is Me, $R_2$ is $COCH_3$, A is CH, X is SO and $R_6$ is as defined in table B.

Table A-18 provides 14 compounds A-18.001 to A-18.014 of formula I-1-Qb wherein $R_1$ is Me, $R_2$ is $COCH_3$, A is CH, X is $SO_2$ and $R_6$ is as defined in table B.

Table A-19 provides 14 compounds A-19.001 to A-19.014 of formula I-1-Qb wherein $R_1$ is Me, $R_2$ is cPr, A is N, X is S and $R_6$ is as defined in table B.

Table A-20 provides 14 compounds A-20.001 to A-20.014 of formula I-1-Qb wherein $R_1$ is Me, $R_2$ is cPr, A is N, X is SO and $R_6$ is as defined in table B.

Table A-21 provides 14 compounds A-21.001 to A-21.014 of formula I-1-Qb wherein $R_1$ is Me, $R_2$ is cPr, A is N, X is $SO_2$ and $R_6$ is as defined in table B.

Table A-22 provides 14 compounds A-22.001 to A-22.014 of formula I-1-Qb wherein $R_1$ is Me, $R_2$ is cPr, A is CH, X is S and $R_6$ is as defined in table B.

Table A-23 provides 14 compounds A-23.001 to A-23.014 of formula I-1-Qb wherein $R_1$ is Me, $R_2$ is cPr, A is CH, X is SO and $R_6$ is as defined in table B.

Table A-24 provides 14 compounds A-24.001 to A-24.014 of formula I-1-Qb wherein $R_1$ is Me, $R_2$ is cPr, A is CH, X is $SO_2$ and $R_6$ is as defined in table B.

Table A-25 provides 14 compounds A-25.001 to A-25.014 of formula I-1-Qb wherein $R_1$ is Me, $R_2$ is Me, A is N, X is S and $R_6$ is as defined in table B.

Table A-26 provides 14 compounds A-26.001 to A-26.014 of formula I-1-Qb wherein $R_1$ is Me, $R_2$ is Me, A is N, X is SO and $R_6$ is as defined in table B.

Table A-27 provides 14 compounds A-27.001 to A-27.014 of formula I-1-Qb wherein $R_1$ is Me, $R_2$ is Me, A is N, X is $SO_2$ and $R_6$ is as defined in table B.

Table A-28 provides 14 compounds A-28.001 to A-28.014 of formula I-1-Qb wherein $R_1$ is Me, $R_2$ is Me, A is CH, X is S and $R_6$ is as defined in table B.

Table A-29 provides 14 compounds A-29.001 to A-29.014 of formula I-1-Qb wherein $R_1$ is Me, $R_2$ is Me, A is CH, X is SO and $R_6$ is as defined in table B.

Table A-30 provides 14 compounds A-30.001 to A-30.014 of formula I-1-Qb wherein $R_1$ is Me, $R_2$ is Me, A is CH, X is $SO_2$ and $R_6$ is as defined in table B.

Table A-31 provides 14 compounds A-31.001 to A-31.014 of formula I-1-Qb wherein $R_1$ is Me, $R_2$ is Et, A is N, X is S and $R_6$ is as defined in table B.

Table A-32 provides 14 compounds A-32.001 to A-32.014 of formula I-1-Qb wherein $R_1$ is Me, $R_2$ is Et, A is N, X is SO and $R_6$ is as defined in table B.

Table A-33 provides 14 compounds A-33.001 to A-33.014 of formula I-1-Qb wherein $R_1$ is Me, $R_2$ is Et, A is N, X is $SO_2$ and $R_6$ is as defined in table B.

Table A-34 provides 14 compounds A-34.001 to A-34.014 of formula I-1-Qb wherein $R_1$ is Me, $R_2$ is Et, A is CH, X is S and $R_6$ is as defined in table B.

Table A-35 provides 14 compounds A-35.001 to A-35.014 of formula I-1-Qb wherein $R_1$ is Me, $R_2$ is Et, A is CH, X is SO and $R_6$ is as defined in table B.

Table A-36 provides 14 compounds A-36.001 to A-36.014 of formula I-1-Qb wherein $R_1$ is Me, $R_2$ is Et, A is CH, X is $SO_2$ and $R_6$ is as defined in table B.

Table A-37 provides 14 compounds A-37.001 to A-37.014 of formula I-1-Qb wherein $R_1$ is Me, $R_2$ is $CH_2CF_3$, A is N, X is S and $R_6$ is as defined in table B.

Table A-38 provides 14 compounds A-38.001 to A-38.014 of formula I-1-Qb wherein $R_1$ is Me, $R_2$ is $CH_2CF_3$, A is N, X is SO and $R_6$ is as defined in table B.

Table A-39 provides 14 compounds A-39.001 to A-39.014 of formula I-1-Qb wherein $R_1$ is Me, $R_2$ is $CH_2CF_3$, A is N, X is $SO_2$ and $R_6$ is as defined in table B.

Table A-40 provides 14 compounds A-40.001 to A-40.014 of formula I-1-Qb wherein $R_1$ is Me, $R_2$ is $CH_2CF_3$, A is CH, X is S and $R_6$ is as defined in table B.

Table A-41 provides 14 compounds A-41.001 to A-41.014 of formula I-1-Qb wherein $R_1$ is Me, $R_2$ is $CH_2CF_3$, A is CH, X is SO and $R_6$ is as defined in table B.

Table A-42 provides 14 compounds A-42.001 to A-42.014 of formula I-1-Qb wherein $R_1$ is Me, $R_2$ is $CH_2CF_3$, A is CH, X is $SO_2$ and $R_6$ is as defined in table B.

Table A-43 provides 14 compounds A-43.001 to A-43.014 of formula I-1-Qb wherein $R_1$ is Me, $R_2$ is $CF_3$, A is N, X is S and $R_6$ is as defined in table B.

Table A-44 provides 14 compounds A-44.001 to A-44.014 of formula I-1-Qb wherein $R_1$ is Me, $R_2$ is $CF_3$, A is N, X is SO and $R_6$ is as defined in table B.

Table A-45 provides 14 compounds A-45.001 to A-45.014 of formula I-1-Qb wherein $R_1$ is Me, $R_2$ is $CF_3$, A is N, X is $SO_2$ and $R_6$ is as defined in table B.

Table A-46 provides 14 compounds A-46.001 to A-46.014 of formula I-1-Qb wherein $R_1$ is Me, $R_2$ is $CF_3$, A is CH, X is S and $R_6$ is as defined in table B.

Table A-47 provides 14 compounds A-47.001 to A-47.014 of formula I-1-Qb wherein $R_1$ is Me, $R_2$ is $CF_3$, A is CH, X is SO and $R_6$ is as defined in table B.

Table A-48 provides 14 compounds A-48.001 to A-48.014 of formula I-1-Qb wherein $R_1$ is Me, $R_2$ is $CF_3$, A is CH, X is $SO_2$ and $R_6$ is as defined in table B.

Table A-49 provides 14 compounds A-49.001 to A-49.014 of formula I-1-Qb wherein $R_1$ is $CF_3$, $R_2$ is H, A is N, X is S and $R_6$ is as defined in table B.

Table A-50 provides 14 compounds A-50.001 to A-50.014 of formula I-1-Qb wherein $R_1$ is $CF_3$, $R_2$ is H, A is N, X is SO and $R_6$ is as defined in table B.

Table A-51 provides 14 compounds A-51.001 to A-51.014 of formula I-1-Qb wherein $R_1$ is $CF_3$, $R_2$ is H, A is N, X is $SO_2$ and $R_6$ is as defined in table B.

Table A-52 provides 14 compounds A-52.001 to A-52.014 of formula I-1-Qb wherein $R_1$ is $CF_3$, $R_2$ is H, A is CH, X is S and $R_6$ is as defined in table B.

Table A-53 provides 14 compounds A-53.001 to A-53.014 of formula I-1-Qb wherein $R_1$ is $CF_3$, $R_2$ is H, A is CH, X is SO and $R_6$ is as defined in table B.

Table A-54 provides 14 compounds A-54.001 to A-54.014 of formula I-1-Qb wherein $R_1$ is $CF_3$, $R_2$ is H, A is CH, X is $SO_2$ and $R_6$ is as defined in table B.

Table A-55 provides 14 compounds A-55.001 to A-55.014 of formula I-1-Qb wherein $R_1$ is $CF_3$, $R_2$ is CN, A is N, X is S and $R_6$ is as defined in table B.

Table A-56 provides 14 compounds A-56.001 to A-56.014 of formula I-1-Qb wherein $R_1$ is $CF_3$, $R_2$ is CN, A is N, X is SO and $R_6$ is as defined in table B.

Table A-57 provides 14 compounds A-57.001 to A-57.014 of formula I-1-Qb wherein $R_1$ is $CF_3$, $R_2$ is CN, A is N, X is $SO_2$ and $R_6$ is as defined in table B.

Table A-58 provides 14 compounds A-58.001 to A-58.014 of formula I-1-Qb wherein $R_1$ is $CF_3$, $R_2$ is CN, A is CH, X is S and $R_6$ is as defined in table B.

Table A-59 provides 14 compounds A-59.001 to A-59.014 of formula I-1-Qb wherein $R_1$ is $CF_3$, $R_2$ is CN, A is CH, X is SO and $R_6$ is as defined in table B.

Table A-60 provides 14 compounds A-60.001 to A-60.014 of formula I-1-Qb wherein $R_1$ is $CF_3$, $R_2$ is CN, A is CH, X is $SO_2$ and $R_6$ is as defined in table B.

Table A-61 provides 14 compounds A-61.001 to A-61.014 of formula I-1-Qb wherein $R_1$ is $CF_3$, $R_2$ is $COCH_3$, A is N, X is S and $R_6$ is as defined in table B.

Table A-62 provides 14 compounds A-62.001 to A-62.014 of formula I-1-Qb wherein $R_1$ is $CF_3$, $R_2$ is $COCH_3$, A is N, X is SO and $R_6$ is as defined in table B.

Table A-63 provides 14 compounds A-63.001 to A-63.014 of formula I-1-Qb wherein $R_1$ is $CF_3$, $R_2$ is $COCH_3$, A is N, X is $SO_2$ and $R_6$ is as defined in table B.

Table A-64 provides 14 compounds A-64.001 to A-64.014 of formula I-1-Qb wherein $R_1$ is $CF_3$, $R_2$ is $COCH_3$, A is CH, X is S and $R_6$ is as defined in table B.

Table A-65 provides 14 compounds A-65.001 to A-65.014 of formula I-1-Qb wherein $R_1$ is $CF_3$, $R_2$ is $COCH_3$, A is CH, X is SO and $R_6$ is as defined in table B.

Table A-66 provides 14 compounds A-66.001 to A-66.014 of formula I-1-Qb wherein $R_1$ is $CF_3$, $R_2$ is $COCH_3$, A is CH, X is $SO_2$ and $R_6$ is as defined in table B.

Table A-67 provides 14 compounds A-67.001 to A-67.014 of formula I-1-Qb wherein $R_1$ is $CF_3$, $R_2$ is cPr, A is N, X is S and $R_6$ is as defined in table B.

Table A-68 provides 14 compounds A-68.001 to A-68.014 of formula I-1-Qb wherein $R_1$ is $CF_3$, $R_2$ is cPr, A is N, X is SO and $R_6$ is as defined in table B.

Table A-69 provides 14 compounds A-69.001 to A-69.014 of formula I-1-Qb wherein $R_1$ is $CF_3$, $R_2$ is cPr, A is N, X is $SO_2$ and $R_6$ is as defined in table B.

Table A-70 provides 14 compounds A-70.001 to A-70.014 of formula I-1-Qb wherein $R_1$ is $CF_3$, $R_2$ is cPr, A is CH, X is S and $R_6$ is as defined in table B.

Table A-71 provides 14 compounds A-71.001 to A-71.014 of formula I-1-Qb wherein $R_1$ is $CF_3$, $R_2$ is cPr, A is CH, X is SO and $R_6$ is as defined in table B.

Table A-72 provides 14 compounds A-72.001 to A-72.014 of formula I-1-Qb wherein $R_1$ is $CF_3$, $R_2$ is cPr, A is CH, X is $SO_2$ and $R_6$ is as defined in table B.

Table A-73 provides 14 compounds A-73.001 to A-73.014 of formula I-1-Qb wherein $R_1$ is $CF_3$, $R_2$ is Me, A is N, X is S and $R_6$ is as defined in table B.

Table A-74 provides 14 compounds A-74.001 to A-74.014 of formula I-1-Qb wherein $R_1$ is $CF_3$, $R_2$ is Me, A is N, X is SO and $R_6$ is as defined in table B.

Table A-75 provides 14 compounds A-75.001 to A-75.014 of formula I-1-Qb wherein $R_1$ is $CF_3$, $R_2$ is Me, A is N, X is $SO_2$ and $R_6$ is as defined in table B.

Table A-76 provides 14 compounds A-76.001 to A-76.014 of formula I-1-Qb wherein $R_1$ is $CF_3$, $R_2$ is Me, A is CH, X is S and $R_6$ is as defined in table B.

Table A-77 provides 14 compounds A-77.001 to A-77.014 of formula I-1-Qb wherein $R_1$ is $CF_3$, $R_2$ is Me, A is CH, X is SO and $R_6$ is as defined in table B.

Table A-78 provides 14 compounds A-78.001 to A-78.014 of formula I-1-Qb wherein $R_1$ is $CF_3$, $R_2$ is Me, A is CH, X is $SO_2$ and $R_6$ is as defined in table B.

Table A-79 provides 14 compounds A-79.001 to A-79.014 of formula I-1-Qb wherein $R_1$ is $CF_3$, $R_2$ is Et, A is N, X is S and $R_6$ is as defined in table B.

Table A-80 provides 14 compounds A-80.001 to A-80.014 of formula I-1-Qb wherein $R_1$ is $CF_3$, $R_2$ is Et, A is N, X is SO and $R_6$ is as defined in table B.

Table A-81 provides 14 compounds A-81.001 to A-81.014 of formula I-1-Qb wherein $R_1$ is $CF_3$, $R_2$ is Et, A is N, X is $SO_2$ and $R_6$ is as defined in table B.

Table A-82 provides 14 compounds A-82.001 to A-82.014 of formula I-1-Qb wherein $R_1$ is $CF_3$, $R_2$ is Et, A is CH, X is S and $R_6$ is as defined in table B.

Table A-83 provides 14 compounds A-83.001 to A-83.014 of formula I-1-Qb wherein $R_1$ is $CF_3$, $R_2$ is Et, A is CH, X is SO and $R_6$ is as defined in table B.

Table A-84 provides 14 compounds A-84.001 to A-84.014 of formula I-1-Qb wherein $R_1$ is $CF_3$, $R_2$ is Et, A is CH, X is $SO_2$ and $R_6$ is as defined in table B.

Table A-85 provides 14 compounds A-85.001 to A-85.014 of formula I-1-Qb wherein $R_1$ is $CF_3$, $R_2$ is $CH_2CF_3$, A is N, X is S and $R_6$ is as defined in table B.

Table A-86 provides 14 compounds A-86.001 to A-86.014 of formula I-1-Qb wherein $R_1$ is $CF_3$, $R_2$ is $CH_2CF_3$, A is N, X is SO and $R_6$ is as defined in table B.

Table A-87 provides 14 compounds A-87.001 to A-87.014 of formula I-1-Qb wherein $R_1$ is $CF_3$, $R_2$ is $CH_2CF_3$, A is N, X is $SO_2$ and $R_6$ is as defined in table B.

Table A-88 provides 14 compounds A-88.001 to A-88.014 of formula I-1-Qb wherein $R_1$ is $CF_3$, $R_2$ is $CH_2CF_3$, A is CH, X is S and $R_6$ is as defined in table B.

Table A-89 provides 14 compounds A-89.001 to A-89.014 of formula I-1-Qb wherein $R_1$ is $CF_3$, $R_2$ is $CH_2CF_3$, A is CH, X is SO and $R_6$ is as defined in table B.

Table A-90 provides 14 compounds A-90.001 to A-90.014 of formula I-1-Qb wherein $R_1$ is $CF_3$, $R_2$ is $CH_2CF_3$, A is CH, X is $SO_2$ and $R_6$ is as defined in table B.

Table A-91 provides 14 compounds A-91.001 to A-91.014 of formula I-1-Qb wherein $R_1$ is $CF_3$, $R_2$ is $CF_3$, A is N, X is S and $R_6$ is as defined in table B.

Table A-92 provides 14 compounds A-92.001 to A-92.014 of formula I-1-Qb wherein $R_1$ is $CF_3$, $R_2$ is $CF_3$, A is N, X is SO and $R_6$ is as defined in table B.

Table A-93 provides 14 compounds A-93.001 to A-93.014 of formula I-1-Qb wherein $R_1$ is $CF_3$, $R_2$ is $CF_3$, A is N, X is $SO_2$ and $R_6$ is as defined in table B.

Table A-94 provides 14 compounds A-94.001 to A-94.014 of formula I-1-Qb wherein $R_1$ is $CF_3$, $R_2$ is $CF_3$, A is CH, X is S and $R_6$ is as defined in table B.

Table A-95 provides 14 compounds A-95.001 to A-95.014 of formula I-1-Qb wherein $R_1$ is $CF_3$, $R_2$ is $CF_3$, A is CH, X is SO and $R_6$ is as defined in table B.

Table A-96 provides 14 compounds A-96.001 to A-96.014 of formula I-1-Qb wherein $R_1$ is $CF_3$, $R_2$ is $CF_3$, A is CH, X is $SO_2$ and $R_6$ is as defined in table B.

The tables C-1 to C-96 below further illustrate specific compounds of the invention.

"cPr" represents cyclopropyl.

(I-1-Qa)

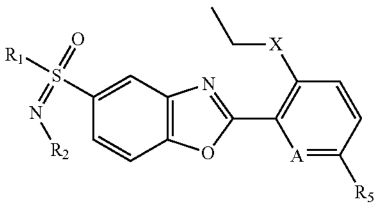

Table C-1 provides 7 compounds C-1.001 to C-1.007 of formula I-1-Qa wherein A is N, X is S, $R_1$ is $CF_3$, $R_2$ is H and $R_5$ is as defined in table D.

TABLE D

| Substituent definitions of $R_5$ | |
|---|---|
| Index | $R_5$ |
| 1 | 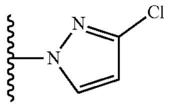 |
| 2 | 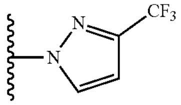 [SMILES: *n1ccc(C(F)(F)F)n1] |
| 3 | 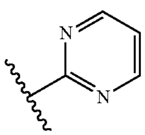 [SMILES: *c1ncccn1] |
| 4 | 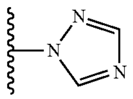 [SMILES: *n1cncn1] |
| 5 | 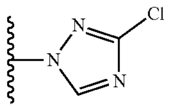 |
| 6 | 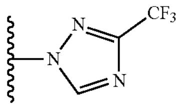 [SMILES: *n1cnc(C(F)(F)F)n1] |
| 7 | H |

Table C-2 provides 7 compounds C-2.001 to C-2.007 of formula I-1-Qa wherein A is N, X is S, $R_1$ is $CF_3$, $R_2$ is CN and $R_5$ is as defined in table D.

Table C-3 provides 7 compounds C-3.001 to C-3.007 of formula I-1-Qa wherein A is N, X is S, $R_1$ is $CF_3$, $R_2$ is $COCH_3$ and $R_5$ is as defined in table D.

Table C-4 provides 7 compounds C-4.001 to C-4.007 of formula I-1-Qa wherein A is N, X is S, $R_1$ is $CF_3$, $R_2$ is cPr and $R_5$ is as defined in table D.

Table C-5 provides 7 compounds C-5.001 to C-5.007 of formula I-1-Qa wherein A is N, X is S, $R_1$ is $CF_3$, $R_2$ is Me and $R_5$ is as defined in table D.

Table C-6 provides 7 compounds C-6.001 to C-6.007 of formula I-1-Qa wherein A is N, X is S, $R_1$ is $CF_3$, $R_2$ is Et and $R_5$ is as defined in table D.

Table C-7 provides 7 compounds C-7.001 to C-7.007 of formula I-1-Qa wherein A is N, X is S, $R_1$ is $CF_3$, $R_2$ is $CH_2CF_3$ and $R_5$ is as defined in table D.

Table C-8 provides 7 compounds C-8.001 to C-8.007 of formula I-1-Qa wherein A is N, X is S, $R_1$ is $CF_3$, $R_2$ is $CF_3$ and $R_5$ is as defined in table D.

Table C-9 provides 7 compounds C-9.001 to C-9.007 of formula I-1-Qa wherein A is N, X is S, $R_1$ is $CH_3$, $R_2$ is H and $R_5$ is as defined in table D.

Table C-10 provides 7 compounds C-10.001 to C-10.007 of formula I-1-Qa wherein A is N, X is S, $R_1$ is $CH_3$, $R_2$ is CN and $R_5$ is as defined in table D.

Table C-11 provides 7 compounds C-11.001 to C-11.007 of formula I-1-Qa wherein A is N, X is S, $R_1$ is $CH_3$, $R_2$ is $COCH_3$ and $R_5$ is as defined in table D.

Table C-12 provides 7 compounds C-12.001 to C-12.007 of formula I-1-Qa wherein A is N, X is S, $R_1$ is $CH_3$, $R_2$ is cPr and $R_5$ is as defined in table D.

Table C-13 provides 7 compounds C-13.001 to C-13.007 of formula I-1-Qa wherein A is N, X is S, $R_1$ is $CH_3$, $R_2$ is Me and $R_5$ is as defined in table D.

Table C-14 provides 7 compounds C-14.001 to C-14.007 of formula I-1-Qa wherein A is N, X is S, $R_1$ is $CH_3$, $R_2$ is Et and $R_5$ is as defined in table D.

Table C-15 provides 7 compounds C-15.001 to C-15.007 of formula I-1-Qa wherein A is N, X is S, $R_1$ is $CH_3$, $R_2$ is $CH_2CF_3$ and $R_5$ is as defined in table D.

Table C-16 provides 7 compounds C-16.001 to C-16.007 of formula I-1-Qa wherein A is N, X is S, $R_1$ is $CH_3$, $R_2$ is $CF_3$ and $R_5$ is as defined in table D.

Table C-17 provides 7 compounds C-17.001 to C-17.007 of formula I-1-Qa wherein A is N, X is SO, $R_1$ is $CF_3$, $R_2$ is H and $R_5$ is as defined in table D.

Table C-18 provides 7 compounds C-18.001 to C-18.007 of formula I-1-Qa wherein A is N, X is SO, $R_1$ is $CF_3$, $R_2$ is CN and $R_5$ is as defined in table D.

Table C-19 provides 7 compounds C-19.001 to C-19.007 of formula I-1-Qa wherein A is N, X is SO, $R_1$ is $CF_3$, $R_2$ is $COCH_3$ and $R_5$ is as defined in table D.

Table C-20 provides 7 compounds C-20.001 to C-20.007 of formula I-1-Qa wherein A is N, X is SO, $R_1$ is $CF_3$, $R_2$ is cPr and $R_5$ is as defined in table D.

Table C-21 provides 7 compounds C-21.001 to C-21.007 of formula I-1-Qa wherein A is N, X is SO, $R_1$ is $CF_3$, $R_2$ is Me and $R_5$ is as defined in table D.

Table C-22 provides 7 compounds C-22.001 to C-22.007 of formula I-1-Qa wherein A is N, X is SO, $R_1$ is $CF_3$, $R_2$ is Et and $R_5$ is as defined in table D.

Table C-23 provides 7 compounds C-23.001 to C-23.007 of formula I-1-Qa wherein A is N, X is SO, $R_1$ is $CF_3$, $R_2$ is $CH_2CF_3$ and $R_5$ is as defined in table D.

Table C-24 provides 7 compounds C-24.001 to C-24.007 of formula I-1-Qa wherein A is N, X is SO, $R_1$ is $CF_3$, $R_2$ is $CF_3$ and $R_5$ is as defined in table D.

Table C-25 provides 7 compounds C-25.001 to C-25.007 of formula I-1-Qa wherein A is N, X is SO, $R_1$ is $CH_3$, $R_2$ is H and $R_5$ is as defined in table D.

Table C-26 provides 7 compounds C-26.001 to C-26.007 of formula I-1-Qa wherein A is N, X is SO, $R_1$ is $CH_3$, $R_2$ is CN and $R_5$ is as defined in table D.

Table C-27 provides 7 compounds C-27.001 to C-27.007 of formula I-1-Qa wherein A is N, X is SO, $R_1$ is $CH_3$, $R_2$ is $COCH_3$ and $R_5$ is as defined in table D.

Table C-28 provides 7 compounds C-28.001 to C-28.007 of formula I-1-Qa wherein A is N, X is SO, $R_1$ is $CH_3$, $R_2$ is cPr and $R_5$ is as defined in table D.

Table C-29 provides 7 compounds C-29.001 to C-29.007 of formula I-1-Qa wherein A is N, X is SO, $R_1$ is $CH_3$, $R_2$ is Me and $R_5$ is as defined in table D.

Table C-30 provides 7 compounds C-30.001 to C-30.007 of formula I-1-Qa wherein A is N, X is SO, $R_1$ is $CH_3$, $R_2$ is Et and $R_5$ is as defined in table D.

Table C-31 provides 7 compounds C-31.001 to C-31.007 of formula I-1-Qa wherein A is N, X is SO, $R_1$ is $CH_3$, $R_2$ is $CH_2CF_3$ and $R_5$ is as defined in table D.

Table C-32 provides 7 compounds C-32.001 to C-32.007 of formula I-1-Qa wherein A is N, X is SO, $R_1$ is $CH_3$, $R_2$ is $CF_3$ and $R_5$ is as defined in table D.

Table C-33 provides 7 compounds C-33.001 to C-33.007 of formula I-1-Qa wherein A is N, X is $SO_2$, $R_1$ is $CF_3$, $R_2$ is H and $R_5$ is as defined in table D.

Table C-34 provides 7 compounds C-34.001 to C-34.007 of formula I-1-Qa wherein A is N, X is $SO_2$, $R_1$ is $CF_3$, $R_2$ is CN and $R_5$ is as defined in table D.

Table C-35 provides 7 compounds C-35.001 to C-35.007 of formula I-1-Qa wherein A is N, X is $SO_2$, $R_1$ is $CF_3$, $R_2$ is $COCH_3$ and $R_5$ is as defined in table D.

Table C-36 provides 7 compounds C-36.001 to C-36.007 of formula I-1-Qa wherein A is N, X is $SO_2$, $R_1$ is $CF_3$, $R_2$ is cPr and $R_5$ is as defined in table D.

Table C-37 provides 7 compounds C-37.001 to C-37.007 of formula I-1-Qa wherein A is N, X is $SO_2$, $R_1$ is $CF_3$, $R_2$ is Me and $R_5$ is as defined in table D.

Table C-38 provides 7 compounds C-38.001 to C-38.007 of formula I-1-Qa wherein A is N, X is $SO_2$, $R_1$ is $CF_3$, $R_2$ is Et and $R_5$ is as defined in table D.

Table C-39 provides 7 compounds C-39.001 to C-39.007 of formula I-1-Qa wherein A is N, X is $SO_2$, $R_1$ is $CF_3$, $R_2$ is $CH_2CF_3$ and $R_5$ is as defined in table D.

Table C-40 provides 7 compounds C-40.001 to C-40.007 of formula I-1-Qa wherein A is N, X is $SO_2$, $R_1$ is $CF_3$, $R_2$ is $CF_3$ and $R_5$ is as defined in table D.

Table C-41 provides 7 compounds C-41.001 to C-41.007 of formula I-1-Qa wherein A is N, X is $SO_2$, $R_1$ is $CH_3$, $R_2$ is H and $R_5$ is as defined in table D.

Table C-42 provides 7 compounds C-42.001 to C-42.007 of formula I-1-Qa wherein A is N, X is $SO_2$, $R_1$ is $CH_3$, $R_2$ is CN and $R_5$ is as defined in table D.

Table C-43 provides 7 compounds C-43.001 to C-43.007 of formula I-1-Qa wherein A is N, X is $SO_2$, $R_1$ is $CH_3$, $R_2$ is $COCH_3$ and $R_5$ is as defined in table D.

Table C-44 provides 7 compounds C-44.001 to C-44.007 of formula I-1-Qa wherein A is N, X is $SO_2$, $R_1$ is $CH_3$, $R_2$ is cPr and $R_5$ is as defined in table D.

Table C-45 provides 7 compounds C-45.001 to C-45.007 of formula I-1-Qa wherein A is N, X is $SO_2$, $R_1$ is $CH_3$, $R_2$ is Me and $R_5$ is as defined in table D.

Table C-46 provides 7 compounds C-46.001 to C-46.007 of formula I-1-Qa wherein A is N, X is $SO_2$, $R_1$ is $CH_3$, $R_2$ is Et and $R_5$ is as defined in table D.

Table C-47 provides 7 compounds C-47.001 to C-47.007 of formula I-1-Qa wherein A is N, X is $SO_2$, $R_1$ is $CH_3$, $R_2$ is $CH_2CF_3$ and $R_5$ is as defined in table D.

Table C-48 provides 7 compounds C-48.001 to C-48.007 of formula I-1-Qa wherein A is N, X is $SO_2$, $R_1$ is $CH_3$, $R_2$ is $CF_3$ and $R_5$ is as defined in table D.

Table C-49 provides 7 compounds C-49.001 to C-49.007 of formula I-1-Qa wherein A is CH, X is S, $R_1$ is $CF_3$, $R_2$ is H and $R_5$ is as defined in table D.

Table C-50 provides 7 compounds C-50.001 to C-50.007 of formula I-1-Qa wherein A is CH, X is S, $R_1$ is $CF_3$, $R_2$ is CN and $R_5$ is as defined in table D.

Table C-51 provides 7 compounds C-51.001 to C-51.007 of formula I-1-Qa wherein A is CH, X is S, $R_1$ is $CF_3$, $R_2$ is $COCH_3$ and $R_5$ is as defined in table D.

Table C-52 provides 7 compounds C-52.001 to C-52.007 of formula I-1-Qa wherein A is CH, X is S, $R_1$ is $CF_3$, $R_2$ is cPr and $R_5$ is as defined in table D.

Table C-53 provides 7 compounds C-53.001 to C-53.007 of formula I-1-Qa wherein A is CH, X is S, $R_1$ is $CF_3$, $R_2$ is Me and $R_5$ is as defined in table D.

Table C-54 provides 7 compounds C-54.001 to C-54.007 of formula I-1-Qa wherein A is CH, X is S, $R_1$ is $CF_3$, $R_2$ is Et and $R_5$ is as defined in table D.

Table C-55 provides 7 compounds C-55.001 to C-55.007 of formula I-1-Qa wherein A is CH, X is S, $R_1$ is $CF_3$, $R_2$ is $CH_2CF_3$ and $R_5$ is as defined in table D.

Table C-56 provides 7 compounds C-56.001 to C-56.007 of formula I-1-Qa wherein A is CH, X is S, $R_1$ is $CF_3$, $R_2$ is $CF_3$ and $R_5$ is as defined in table D.

Table C-57 provides 7 compounds C-57.001 to C-57.007 of formula I-1-Qa wherein A is CH, X is S, $R_1$ is $CH_3$, $R_2$ is H and $R_5$ is as defined in table D.

Table C-58 provides 7 compounds C-58.001 to C-58.007 of formula I-1-Qa wherein A is CH, X is S, $R_1$ is $CH_3$, $R_2$ is CN and $R_5$ is as defined in table D.

Table C-59 provides 7 compounds C-59.001 to C-59.007 of formula I-1-Qa wherein A is CH, X is S, $R_1$ is $CH_3$, $R_2$ is $COCH_3$ and $R_5$ is as defined in table D.

Table C-60 provides 7 compounds C-60.001 to C-60.007 of formula I-1-Qa wherein A is CH, X is S, $R_1$ is $CH_3$, $R_2$ is cPr and $R_5$ is as defined in table D.

Table C-61 provides 7 compounds C-61.001 to C-61.007 of formula I-1-Qa wherein A is CH, X is S, $R_1$ is $CH_3$, $R_2$ is Me and $R_5$ is as defined in table D.

Table C-62 provides 7 compounds C-62.001 to C-62.007 of formula I-1-Qa wherein A is CH, X is S, $R_1$ is $CH_3$, $R_2$ is Et and $R_5$ is as defined in table D.

Table C-63 provides 7 compounds C-63.001 to C-63.007 of formula I-1-Qa wherein A is CH, X is S, $R_1$ is $CH_3$, $R_2$ is $CH_2CF_3$ and $R_5$ is as defined in table D.

Table C-64 provides 7 compounds C-64.001 to C-64.007 of formula I-1-Qa wherein A is CH, X is S, $R_1$ is $CH_3$, $R_2$ is $CF_3$ and $R_5$ is as defined in table D.

Table C-65 provides 7 compounds C-65.001 to C-65.007 of formula I-1-Qa wherein A is CH, X is SO, $R_1$ is $CF_3$, $R_2$ is H and $R_5$ is as defined in table D.

Table C-66 provides 7 compounds C-66.001 to C-66.007 of formula I-1-Qa wherein A is CH, X is SO, $R_1$ is $CF_3$, $R_2$ is CN and $R_5$ is as defined in table D.

Table C-67 provides 7 compounds C-67.001 to C-67.007 of formula I-1-Qa wherein A is CH, X is SO, $R_1$ is $CF_3$, $R_2$ is $COCH_3$ and $R_5$ is as defined in table D.

Table C-68 provides 7 compounds C-68.001 to C-68.007 of formula I-1-Qa wherein A is CH, X is SO, $R_1$ is $CF_3$, $R_2$ is cPr and $R_5$ is as defined in table D.

Table C-69 provides 7 compounds C-69.001 to C-69.007 of formula I-1-Qa wherein A is CH, X is SO, $R_1$ is $CF_3$, $R_2$ is Me and $R_5$ is as defined in table D.

Table C-70 provides 7 compounds C-70.001 to C-70.007 of formula I-1-Qa wherein A is CH, X is SO, $R_1$ is $CF_3$, $R_2$ is Et and $R_5$ is as defined in table D.

Table C-71 provides 7 compounds C-71.001 to C-71.007 of formula I-1-Qa wherein A is CH, X is SO, $R_1$ is $CF_3$, $R_2$ is $CH_2CF_3$ and $R_5$ is as defined in table D.

Table C-72 provides 7 compounds C-72.001 to C-72.007 of formula I-1-Qa wherein A is CH, X is SO, $R_1$ is $CF_3$, $R_2$ is $CF_3$ and $R_5$ is as defined in table D.

Table C-73 provides 7 compounds C-73.001 to C-73.007 of formula I-1-Qa wherein A is CH, X is SO, $R_1$ is $CH_3$, $R_2$ is H and $R_5$ is as defined in table D.

Table C-74 provides 7 compounds C-74.001 to C-74.007 of formula I-1-Qa wherein A is CH, X is SO, $R_1$ is $CH_3$, $R_2$ is CN and $R_5$ is as defined in table D.

Table C-75 provides 7 compounds C-75.001 to C-75.007 of formula I-1-Qa wherein A is CH, X is SO, $R_1$ is $CH_3$, $R_2$ is $COCH_3$ and $R_5$ is as defined in table D.

Table C-76 provides 7 compounds C-76.001 to C-76.007 of formula I-1-Qa wherein A is CH, X is SO, $R_1$ is $CH_3$, $R_2$ is cPr and $R_5$ is as defined in table D.

Table C-77 provides 7 compounds C-77.001 to C-77.007 of formula I-1-Qa wherein A is CH, X is SO, $R_1$ is $CH_3$, $R_2$ is Me and $R_5$ is as defined in table D.

Table C-78 provides 7 compounds C-78.001 to C-78.007 of formula I-1-Qa wherein A is CH, X is SO, $R_1$ is $CH_3$, $R_2$ is Et and $R_5$ is as defined in table D.

Table C-79 provides 7 compounds C-79.001 to C-79.007 of formula I-1-Qa wherein A is CH, X is SO, $R_1$ is $CH_3$, $R_2$ is $CH_2CF_3$ and $R_5$ is as defined in table D.

Table C-80 provides 7 compounds C-80.001 to C-80.007 of formula I-1-Qa wherein A is CH, X is SO, $R_1$ is $CH_3$, $R_2$ is $CF_3$ and $R_5$ is as defined in table D.

Table C-81 provides 7 compounds C-81.001 to C-81.007 of formula I-1-Qa wherein A is CH, X is $SO_2$, $R_1$ is $CF_3$, $R_2$ is H and $R_5$ is as defined in table D.

Table C-82 provides 7 compounds C-82.001 to C-82.007 of formula I-1-Qa wherein A is CH, X is $SO_2$, $R_1$ is $CF_3$, $R_2$ is CN and $R_5$ is as defined in table D.

Table C-83 provides 7 compounds C-83.001 to C-83.007 of formula I-1-Qa wherein A is CH, X is $SO_2$, $R_1$ is $CF_3$, $R_2$ is $COCH_3$ and $R_5$ is as defined in table D.

Table C-84 provides 7 compounds C-84.001 to C-84.007 of formula I-1-Qa wherein A is CH, X is $SO_2$, $R_1$ is $CF_3$, $R_2$ is cPr and $R_5$ is as defined in table D.

Table C-85 provides 7 compounds C-85.001 to C-85.007 of formula I-1-Qa wherein A is CH, X is $SO_2$, $R_1$ is $CF_3$, $R_2$ is Me and $R_5$ is as defined in table D.

Table C-86 provides 7 compounds C-86.001 to C-86.007 of formula I-1-Qa wherein A is CH, X is $SO_2$, $R_1$ is $CF_3$, $R_2$ is Et and $R_5$ is as defined in table D.

Table C-87 provides 7 compounds C-87.001 to C-87.007 of formula I-1-Qa wherein A is CH, X is $SO_2$, $R_1$ is $CF_3$, $R_2$ is $CH_2CF_3$ and $R_5$ is as defined in table D.

Table C-88 provides 7 compounds C-88.001 to C-88.007 of formula I-1-Qa wherein A is CH, X is $SO_2$, $R_1$ is $CF_3$, $R_2$ is $CF_3$ and $R_5$ is as defined in table D.

Table C-89 provides 7 compounds C-89.001 to C-89.007 of formula I-1-Qa wherein A is CH, X is $SO_2$, $R_1$ is $CH_3$, $R_2$ is H and $R_5$ is as defined in table D.

Table C-90 provides 7 compounds C-90.001 to C-90.007 of formula I-1-Qa wherein A is CH, X is $SO_2$, $R_1$ is $CH_3$, $R_2$ is CN and $R_5$ is as defined in table D.

Table C-91 provides 7 compounds C-91.001 to C-91.007 of formula I-1-Qa wherein A is CH, X is $SO_2$, $R_1$ is $CH_3$, $R_2$ is $COCH_3$ and $R_5$ is as defined in table D.

Table C-92 provides 7 compounds C-92.001 to C-92.007 of formula I-1-Qa wherein A is CH, X is $SO_2$, $R_1$ is $CH_3$, $R_2$ is cPr and $R_5$ is as defined in table D.

Table C-93 provides 7 compounds C-93.001 to C-93.007 of formula I-1-Qa wherein A is CH, X is $SO_2$, $R_1$ is $CH_3$, $R_2$ is Me and $R_5$ is as defined in table D.

Table C-94 provides 7 compounds C-94.001 to C-94.007 of formula I-1-Qa wherein A is CH, X is $SO_2$, $R_1$ is $CH_3$, $R_2$ is Et and $R_5$ is as defined in table D.

Table C-95 provides 7 compounds C-95.001 to C-95.007 of formula I-1-Qa wherein A is CH, X is $SO_2$, $R_1$ is $CH_3$, $R_2$ is $CH_2CF_3$ and $R_5$ is as defined in table D.

Table C-96 provides 7 compounds C-96.001 to C-96.007 of formula I-1-Qa wherein A is CH, X is $SO_2$, $R_1$ is $CH_3$, $R_2$ is $CF_3$ and $R_5$ is as defined in table D.

The tables E-1 to E-96 below further illustrate specific compounds of the invention.

"cPr" represents cyclopropyl.

(I-2-Qb)

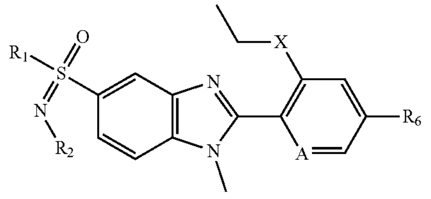

Table E-1 provides 14 compounds E-1.001 to E-1.014 of formula I-2-Qb wherein $R_1$ is Me, $R_2$ is H, A is N, X is S and $R_6$ is as defined in Table B.

Table E-2 provides 14 compounds E-2.001 to E-2.014 of formula I-2-Qb wherein $R_1$ is Me, $R_2$ is H, A is N, X is SO and $R_6$ is as defined in Table B.

Table E-3 provides 14 compounds E-3.001 to E-3.014 of formula I-2-Qb wherein $R_1$ is Me, $R_2$ is H, A is N, X is $SO_2$ and $R_6$ is as defined in Table B.

Table E-4 provides 14 compounds E-4.001 to E-4.014 of formula I-2-Qb wherein $R_1$ is Me, $R_2$ is H, A is CH, X is S and $R_6$ is as defined in Table B.

Table E-5 provides 14 compounds E-5.001 to E-5.014 of formula I-2-Qb wherein $R_1$ is Me, $R_2$ is H, A is CH, X is SO and $R_6$ is as defined in Table B.

Table E-6 provides 14 compounds E-6.001 to E-6.014 of formula I-2-Qb wherein $R_1$ is Me, $R_2$ is H, A is CH, X is $SO_2$ and $R_6$ is as defined in Table B.

Table E-7 provides 14 compounds E-7.001 to E-7.014 of formula I-2-Qb wherein $R_1$ is Me, $R_2$ is CN, A is N, X is S and $R_6$ is as defined in Table B.

Table E-8 provides 14 compounds E-8.001 to E-8.014 of formula I-2-Qb wherein $R_1$ is Me, $R_2$ is CN, A is N, X is SO and $R_6$ is as defined in Table B.

Table E-9 provides 14 compounds E-9.001 to E-9.014 of formula I-2-Qb wherein $R_1$ is Me, $R_2$ is CN, A is N, X is $SO_2$ and $R_6$ is as defined in Table B.

Table E-10 provides 14 compounds E-10.001 to E-10.014 of formula I-2-Qb wherein $R_1$ is Me, $R_2$ is CN, A is CH, X is S and $R_6$ is as defined in Table B.

Table E-11 provides 14 compounds E-11.001 to E-11.014 of formula I-2-Qb wherein $R_1$ is Me, $R_2$ is CN, A is CH, X is SO and $R_6$ is as defined in Table B.

Table E-12 provides 14 compounds E-12.001 to E-12.014 of formula I-2-Qb wherein $R_1$ is Me, $R_2$ is CN, A is CH, X is $SO_2$ and $R_6$ is as defined in Table B.

Table E-13 provides 14 compounds E-13.001 to E-13.014 of formula I-2-Qb wherein $R_1$ is Me, $R_2$ is $COCH_3$, A is N, X is S and $R_6$ is as defined in Table B.

Table E-14 provides 14 compounds E-14.001 to E-14.014 of formula I-2-Qb wherein $R_1$ is Me, $R_2$ is $COCH_3$, A is N, X is SO and $R_6$ is as defined in Table B.

Table E-15 provides 14 compounds E-15.001 to E-15.014 of formula I-2-Qb wherein $R_1$ is Me, $R_2$ is $COCH_3$, A is N, X is $SO_2$ and $R_6$ is as defined in Table B.

Table E-16 provides 14 compounds E-16.001 to E-16.014 of formula I-2-Qb wherein $R_1$ is Me, $R_2$ is $COCH_3$, A is CH, X is S and $R_6$ is as defined in Table B.

Table E-17 provides 14 compounds E-17.001 to E-17.014 of formula I-2-Qb wherein $R_1$ is Me, $R_2$ is $COCH_3$, A is CH, X is SO and $R_6$ is as defined in Table B.

Table E-18 provides 14 compounds E-18.001 to E-18.014 of formula I-2-Qb wherein $R_1$ is Me, $R_2$ is $COCH_3$, A is CH, X is $SO_2$ and $R_6$ is as defined in Table B.

Table E-19 provides 14 compounds E-19.001 to E-19.014 of formula I-2-Qb wherein $R_1$ is Me, $R_2$ is cPr, A is N, X is S and $R_6$ is as defined in Table B.

Table E-20 provides 14 compounds E-20.001 to E-20.014 of formula I-2-Qb wherein $R_1$ is Me, $R_2$ is cPr, A is N, X is SO and $R_6$ is as defined in Table B.

Table E-21 provides 14 compounds E-21.001 to E-21.014 of formula I-2-Qb wherein $R_1$ is Me, $R_2$ is cPr, A is N, X is $SO_2$ and $R_6$ is as defined in Table B.

Table E-22 provides 14 compounds E-22.001 to E-22.014 of formula I-2-Qb wherein $R_1$ is Me, $R_2$ is cPr, A is CH, X is S and $R_6$ is as defined in Table B.

Table E-23 provides 14 compounds E-23.001 to E-23.014 of formula I-2-Qb wherein $R_1$ is Me, $R_2$ is cPr, A is CH, X is SO and $R_6$ is as defined in Table B.

Table E-24 provides 14 compounds E-24.001 to E-24.014 of formula I-2-Qb wherein $R_1$ is Me, $R_2$ is cPr, A is CH, X is $SO_2$ and $R_6$ is as defined in Table B.

Table E-25 provides 14 compounds E-25.001 to E-25.014 of formula I-2-Qb wherein $R_1$ is Me, $R_2$ is Me, A is N, X is S and $R_6$ is as defined in Table B.

Table E-26 provides 14 compounds E-26.001 to E-26.014 of formula I-2-Qb wherein $R_1$ is Me, $R_2$ is Me, A is N, X is SO and $R_6$ is as defined in Table B.

Table E-27 provides 14 compounds E-27.001 to E-27.014 of formula I-2-Qb wherein $R_1$ is Me, $R_2$ is Me, A is N, X is $SO_2$ and $R_6$ is as defined in Table B.

Table E-28 provides 14 compounds E-28.001 to E-28.014 of formula I-2-Qb wherein $R_1$ is Me, $R_2$ is Me, A is CH, X is S and $R_6$ is as defined in Table B.

Table E-29 provides 14 compounds E-29.001 to E-29.014 of formula I-2-Qb wherein $R_1$ is Me, $R_2$ is Me, A is CH, X is SO and $R_6$ is as defined in Table B.

Table E-30 provides 14 compounds E-30.001 to E-30.014 of formula I-2-Qb wherein $R_1$ is Me, $R_2$ is Me, A is CH, X is $SO_2$ and $R_6$ is as defined in Table B.

Table E-31 provides 14 compounds E-31.001 to E-31.014 of formula I-2-Qb wherein $R_1$ is Me, $R_2$ is Et, A is N, X is S and $R_6$ is as defined in Table B.

Table E-32 provides 14 compounds E-32.001 to E-32.014 of formula I-2-Qb wherein $R_1$ is Me, $R_2$ is Et, A is N, X is SO and $R_6$ is as defined in Table B.

Table E-33 provides 14 compounds E-33.001 to E-33.014 of formula I-2-Qb wherein $R_1$ is Me, $R_2$ is Et, A is N, X is $SO_2$ and $R_6$ is as defined in Table B.

Table E-34 provides 14 compounds E-34.001 to E-34.014 of formula I-2-Qb wherein $R_1$ is Me, $R_2$ is Et, A is CH, X is S and $R_6$ is as defined in Table B.

Table E-35 provides 14 compounds E-35.001 to E-35.014 of formula I-2-Qb wherein $R_1$ is Me, $R_2$ is Et, A is CH, X is SO and $R_6$ is as defined in Table B.

Table E-36 provides 14 compounds E-36.001 to E-36.014 of formula I-2-Qb wherein $R_1$ is Me, $R_2$ is Et, A is CH, X is $SO_2$ and $R_6$ is as defined in Table B.

Table E-37 provides 14 compounds E-37.001 to E-37.014 of formula I-2-Qb wherein $R_1$ is Me, $R_2$ is $CH_2CF_3$, A is N, X is S and $R_6$ is as defined in Table B.

Table E-38 provides 14 compounds E-38.001 to E-38.014 of formula I-2-Qb wherein $R_1$ is Me, $R_2$ is $CH_2CF_3$, A is N, X is SO and $R_6$ is as defined in Table B.

Table E-39 provides 14 compounds E-39.001 to E-39.014 of formula I-2-Qb wherein $R_1$ is Me, $R_2$ is $CH_2CF_3$, A is N, X is $SO_2$ and $R_6$ is as defined in Table B.

Table E-40 provides 14 compounds E-40.001 to E-40.014 of formula I-2-Qb wherein $R_1$ is Me, $R_2$ is $CH_2CF_3$, A is CH, X is S and $R_6$ is as defined in Table B.

Table E-41 provides 14 compounds E-41.001 to E-41.014 of formula I-2-Qb wherein $R_1$ is Me, $R_2$ is $CH_2CF_3$, A is CH, X is SO and $R_6$ is as defined in Table B.

Table E-42 provides 14 compounds E-42.001 to E-42.014 of formula I-2-Qb wherein $R_1$ is Me, $R_2$ is $CH_2CF_3$, A is CH, X is $SO_2$ and $R_6$ is as defined in Table B.

Table E-43 provides 14 compounds E-43.001 to E-43.014 of formula I-2-Qb wherein $R_1$ is Me, $R_2$ is $CF_3$, A is N, X is S and $R_6$ is as defined in Table B.

Table E-44 provides 14 compounds E-44.001 to E-44.014 of formula I-2-Qb wherein $R_1$ is Me, $R_2$ is $CF_3$, A is N, X is SO and $R_6$ is as defined in Table B.

Table E-45 provides 14 compounds E-45.001 to E-45.014 of formula I-2-Qb wherein $R_1$ is Me, $R_2$ is $CF_3$, A is N, X is $SO_2$ and $R_6$ is as defined in Table B.

Table E-46 provides 14 compounds E-46.001 to E-46.014 of formula I-2-Qb wherein $R_1$ is Me, $R_2$ is $CF_3$, A is CH, X is S and $R_6$ is as defined in Table B.

Table E-47 provides 14 compounds E-47.001 to E-47.014 of formula I-2-Qb wherein $R_1$ is Me, $R_2$ is $CF_3$, A is CH, X is SO and $R_6$ is as defined in Table B.

Table E-48 provides 14 compounds E-48.001 to E-48.014 of formula I-2-Qb wherein $R_1$ is Me, $R_2$ is $CF_3$, A is CH, X is $SO_2$ and $R_6$ is as defined in Table B.

Table E-49 provides 14 compounds E-49.001 to E-49.014 of formula I-2-Qb wherein $R_1$ is $CF_3$, $R_2$ is H, A is N, X is S and $R_6$ is as defined in Table B.

Table E-50 provides 14 compounds E-50.001 to E-50.014 of formula I-2-Qb wherein $R_1$ is $CF_3$, $R_2$ is H, A is N, X is SO and $R_6$ is as defined in Table B.

Table E-51 provides 14 compounds E-51.001 to E-51.014 of formula I-2-Qb wherein $R_1$ is $CF_3$, $R_2$ is H, A is N, X is $SO_2$ and $R_6$ is as defined in Table B.

Table E-52 provides 14 compounds E-52.001 to E-52.014 of formula I-2-Qb wherein $R_1$ is $CF_3$, $R_2$ is H, A is CH, X is S and $R_6$ is as defined in Table B.

Table E-53 provides 14 compounds E-53.001 to E-53.014 of formula I-2-Qb wherein $R_1$ is $CF_3$, $R_2$ is H, A is CH, X is SO and $R_6$ is as defined in Table B.

Table E-54 provides 14 compounds E-54.001 to E-54.014 of formula I-2-Qb wherein $R_1$ is $CF_3$, $R_2$ is H, A is CH, X is $SO_2$ and $R_6$ is as defined in Table B.

Table E-55 provides 14 compounds E-55.001 to E-55.014 of formula I-2-Qb wherein $R_1$ is $CF_3$, $R_2$ is CN, A is N, X is S and $R_6$ is as defined in Table B.

Table E-56 provides 14 compounds E-56.001 to E-56.014 of formula I-2-Qb wherein $R_1$ is $CF_3$, $R_2$ is CN, A is N, X is SO and $R_6$ is as defined in Table B.

Table E-57 provides 14 compounds E-57.001 to E-57.014 of formula I-2-Qb wherein $R_1$ is $CF_3$, $R_2$ is CN, A is N, X is $SO_2$ and $R_6$ is as defined in Table B.

Table E-58 provides 14 compounds E-58.001 to E-58.014 of formula I-2-Qb wherein $R_1$ is $CF_3$, $R_2$ is CN, A is CH, X is S and $R_6$ is as defined in Table B.

Table E-59 provides 14 compounds E-59.001 to E-59.014 of formula I-2-Qb wherein $R_1$ is $CF_3$, $R_2$ is CN, A is CH, X is SO and $R_6$ is as defined in Table B.

Table E-60 provides 14 compounds E-60.001 to E-60.014 of formula I-2-Qb wherein $R_1$ is $CF_3$, $R_2$ is CN, A is CH, X is $SO_2$ and $R_6$ is as defined in Table B.

Table E-61 provides 14 compounds E-61.001 to E-61.014 of formula I-2-Qb wherein $R_1$ is $CF_3$, $R_2$ is $COCH_3$, A is N, X is S and $R_6$ is as defined in Table B.

Table E-62 provides 14 compounds E-62.001 to E-62.014 of formula I-2-Qb wherein $R_1$ is $CF_3$, $R_2$ is $COCH_3$, A is N, X is SO and $R_6$ is as defined in Table B.

Table E-63 provides 14 compounds E-63.001 to E-63.014 of formula I-2-Qb wherein $R_1$ is $CF_3$, $R_2$ is $COCH_3$, A is N, X is $SO_2$ and $R_6$ is as defined in Table B.

Table E-64 provides 14 compounds E-64.001 to E-64.014 of formula I-2-Qb wherein $R_1$ is $CF_3$, $R_2$ is $COCH_3$, A is CH, X is S and $R_6$ is as defined in Table B.

Table E-65 provides 14 compounds E-65.001 to E-65.014 of formula I-2-Qb wherein $R_1$ is $CF_3$, $R_2$ is $COCH_3$, A is CH, X is SO and $R_6$ is as defined in Table B.

Table E-66 provides 14 compounds E-66.001 to E-66.014 of formula I-2-Qb wherein $R_1$ is $CF_3$, $R_2$ is $COCH_3$, A is CH, X is $SO_2$ and $R_6$ is as defined in Table B.

Table E-67 provides 14 compounds E-67.001 to E-67.014 of formula I-2-Qb wherein $R_1$ is $CF_3$, $R_2$ is cPr, A is N, X is S and $R_6$ is as defined in Table B.

Table E-68 provides 14 compounds E-68.001 to E-68.014 of formula I-2-Qb wherein $R_1$ is $CF_3$, $R_2$ is cPr, A is N, X is SO and $R_6$ is as defined in Table B.

Table E-69 provides 14 compounds E-69.001 to E-69.014 of formula I-2-Qb wherein $R_1$ is $CF_3$, $R_2$ is cPr, A is N, X is $SO_2$ and $R_6$ is as defined in Table B.

Table E-70 provides 14 compounds E-70.001 to E-70.014 of formula I-2-Qb wherein $R_1$ is $CF_3$, $R_2$ is cPr, A is CH, X is S and $R_6$ is as defined in Table B.

Table E-71 provides 14 compounds E-71.001 to E-71.014 of formula I-2-Qb wherein $R_1$ is $CF_3$, $R_2$ is cPr, A is CH, X is SO and $R_6$ is as defined in Table B.

Table E-72 provides 14 compounds E-72.001 to E-72.014 of formula I-2-Qb wherein $R_1$ is $CF_3$, $R_2$ is cPr, A is CH, X is $SO_2$ and $R_6$ is as defined in Table B.

Table E-73 provides 14 compounds E-73.001 to E-73.014 of formula I-2-Qb wherein $R_1$ is $CF_3$, $R_2$ is Me, A is N, X is S and $R_6$ is as defined in Table B.

Table E-74 provides 14 compounds E-74.001 to E-74.014 of formula I-2-Qb wherein $R_1$ is $CF_3$, $R_2$ is Me, A is N, X is SO and $R_6$ is as defined in Table B.

Table E-75 provides 14 compounds E-75.001 to E-75.014 of formula I-2-Qb wherein $R_1$ is $CF_3$, $R_2$ is Me, A is N, X is $SO_2$ and $R_6$ is as defined in Table B.

Table E-76 provides 14 compounds E-76.001 to E-76.014 of formula I-2-Qb wherein $R_1$ is $CF_3$, $R_2$ is Me, A is CH, X is S and $R_6$ is as defined in Table B.

Table E-77 provides 14 compounds E-77.001 to E-77.014 of formula I-2-Qb wherein $R_1$ is $CF_3$, $R_2$ is Me, A is CH, X is SO and $R_6$ is as defined in Table B.

Table E-78 provides 14 compounds E-78.001 to E-78.014 of formula I-2-Qb wherein $R_1$ is $CF_3$, $R_2$ is Me, A is CH, X is $SO_2$ and $R_6$ is as defined in Table B.

Table E-79 provides 14 compounds E-79.001 to E-79.014 of formula I-2-Qb wherein $R_1$ is $CF_3$, $R_2$ is Et, A is N, X is S and $R_6$ is as defined in Table B.

Table E-80 provides 14 compounds E-80.001 to E-80.014 of formula I-2-Qb wherein $R_1$ is $CF_3$, $R_2$ is Et, A is N, X is SO and $R_6$ is as defined in Table B.

Table E-81 provides 14 compounds E-81.001 to E-81.014 of formula I-2-Qb wherein $R_1$ is $CF_3$, $R_2$ is Et, A is N, X is $SO_2$ and $R_6$ is as defined in Table B.

Table E-82 provides 14 compounds E-82.001 to E-82.014 of formula I-2-Qb wherein $R_1$ is $CF_3$, $R_2$ is Et, A is CH, X is S and $R_6$ is as defined in Table B.

Table E-83 provides 14 compounds E-83.001 to E-83.014 of formula I-2-Qb wherein $R_1$ is $CF_3$, $R_2$ is Et, A is CH, X is SO and $R_6$ is as defined in Table B.

Table E-84 provides 14 compounds E-84.001 to E-84.014 of formula I-2-Qb wherein $R_1$ is $CF_3$, $R_2$ is Et, A is CH, X is $SO_2$ and $R_6$ is as defined in Table B.

Table E-85 provides 14 compounds E-85.001 to E-85.014 of formula I-2-Qb wherein $R_1$ is $CF_3$, $R_2$ is $CH_2CF_3$, A is N, X is S and $R_6$ is as defined in Table B.

Table E-86 provides 14 compounds E-86.001 to E-86.014 of formula I-2-Qb wherein $R_1$ is $CF_3$, $R_2$ is $CH_2CF_3$, A is N, X is SO and $R_6$ is as defined in Table B.

Table E-87 provides 14 compounds E-87.001 to E-87.014 of formula I-2-Qb wherein $R_1$ is $CF_3$, $R_2$ is $CH_2CF_3$, A is N, X is $SO_2$ and $R_6$ is as defined in Table B.

Table E-88 provides 14 compounds E-88.001 to E-88.014 of formula I-2-Qb wherein $R_1$ is $CF_3$, $R_2$ is $CH_2CF_3$, A is CH, X is S and $R_6$ is as defined in Table B.

Table E-89 provides 14 compounds E-89.001 to E-89.014 of formula I-2-Qb wherein $R_1$ is $CF_3$, $R_2$ is $CH_2CF_3$, A is CH, X is SO and $R_6$ is as defined in Table B.

Table E-90 provides 14 compounds E-90.001 to E-90.014 of formula I-2-Qb wherein $R_1$ is $CF_3$, $R_2$ is $CH_2CF_3$, A is CH, X is $SO_2$ and $R_6$ is as defined in Table B.

Table E-91 provides 14 compounds E-91.001 to E-91.014 of formula I-2-Qb wherein $R_1$ is $CF_3$, $R_2$ is $CF_3$, A is N, X is S and $R_6$ is as defined in Table B.

Table E-92 provides 14 compounds E-92.001 to E-92.014 of formula I-2-Qb wherein $R_1$ is $CF_3$, $R_2$ is $CF_3$, A is N, X is SO and $R_6$ is as defined in Table B.

Table E-93 provides 14 compounds E-93.001 to E-93.014 of formula I-2-Qb wherein $R_1$ is $CF_3$, $R_2$ is $CF_3$, A is N, X is $SO_2$ and $R_6$ is as defined in Table B.

Table E-94 provides 14 compounds E-94.001 to E-94.014 of formula I-2-Qb wherein $R_1$ is $CF_3$, $R_2$ is $CF_3$, A is CH, X is S and $R_6$ is as defined in Table B.

Table E-95 provides 14 compounds E-95.001 to E-95.014 of formula I-2-Qb wherein $R_1$ is $CF_3$, $R_2$ is $CF_3$, A is CH, X is SO and $R_6$ is as defined in Table B.

Table E-96 provides 14 compounds E-96.001 to E-96.014 of formula I-2-Qb wherein $R_1$ is $CF_3$, $R_2$ is $CF_3$, A is CH, X is $SO_2$ and $R_6$ is as defined in Table B.

The tables F-1 to F-96 below further illustrate specific compounds of the invention.

"cPr" represents cyclopropyl.

(I-2-Qa)

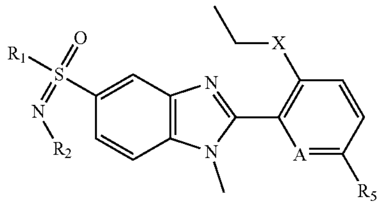

Table F-1 provides 7 compounds F-1.001 to F-1.007 of formula I-2-Qa wherein A is N, X is S, $R_1$ is $CF_3$, $R_2$ is H and $R_5$ is as defined in table D.

Table F-2 provides 7 compounds F-2.001 to F-2.007 of formula I-2-Qa wherein A is N, X is S, $R_1$ is $CF_3$, $R_2$ is CN and $R_5$ is as defined in table D.

Table F-3 provides 7 compounds F-3.001 to F-3.007 of formula I-2-Qa wherein A is N, X is S, $R_1$ is $CF_3$, $R_2$ is $COCH_3$ and $R_5$ is as defined in table D.

Table F-4 provides 7 compounds F-4.001 to F-4.007 of formula I-2-Qa wherein A is N, X is S, $R_1$ is $CF_3$, $R_2$ is cPr and $R_5$ is as defined in table D.

Table F-5 provides 7 compounds F-5.001 to F-5.007 of formula I-2-Qa wherein A is N, X is S, $R_1$ is $CF_3$, $R_2$ is Me and $R_5$ is as defined in table D.

Table F-6 provides 7 compounds F-6.001 to F-6.007 of formula I-2-Qa wherein A is N, X is S, $R_1$ is $CF_3$, $R_2$ is Et and $R_5$ is as defined in table D.

Table F-7 provides 7 compounds F-7.001 to F-7.007 of formula I-2-Qa wherein A is N, X is S, $R_1$ is $CF_3$, $R_2$ is $CH_2CF_3$ and $R_5$ is as defined in table D.

Table F-8 provides 7 compounds F-8.001 to F-8.007 of formula I-2-Qa wherein A is N, X is S, $R_1$ is $CF_3$, $R_2$ is $CF_3$ and $R_5$ is as defined in table D.

Table F-9 provides 7 compounds F-9.001 to F-9.007 of formula I-2-Qa wherein A is N, X is S, $R_1$ is $CH_3$, $R_2$ is H and $R_5$ is as defined in table D.

Table F-10 provides 7 compounds F-10.001 to F-10.007 of formula I-2-Qa wherein A is N, X is S, $R_1$ is $CH_3$, $R_2$ is CN and $R_5$ is as defined in table D.

Table F-11 provides 7 compounds F-11.001 to F-11.007 of formula I-2-Qa wherein A is N, X is S, $R_1$ is $CH_3$, $R_2$ is $COCH_3$ and $R_5$ is as defined in table D.

Table F-12 provides 7 compounds F-12.001 to F-12.007 of formula I-2-Qa wherein A is N, X is S, $R_1$ is $CH_3$, $R_2$ is cPr and $R_5$ is as defined in table D.

Table F-13 provides 7 compounds F-13.001 to F-13.007 of formula I-2-Qa wherein A is N, X is S, $R_1$ is $CH_3$, $R_2$ is Me and $R_5$ is as defined in table D.

Table F-14 provides 7 compounds F-14.001 to F-14.007 of formula I-2-Qa wherein A is N, X is S, $R_1$ is $CH_3$, $R_2$ is Et and $R_5$ is as defined in table D.

Table F-15 provides 7 compounds F-15.001 to F-15.007 of formula I-2-Qa wherein A is N, X is S, $R_1$ is $CH_3$, $R_2$ is $CH_2CF_3$ and $R_5$ is as defined in table D.

Table F-16 provides 7 compounds F-16.001 to F-16.007 of formula I-2-Qa wherein A is N, X is S, $R_1$ is $CH_3$, $R_2$ is $CF_3$ and $R_5$ is as defined in table D.

Table F-17 provides 7 compounds F-17.001 to F-17.007 of formula I-2-Qa wherein A is N, X is SO, $R_1$ is $CF_3$, $R_2$ is H and $R_5$ is as defined in table D.

Table F-18 provides 7 compounds F-18.001 to F-18.007 of formula I-2-Qa wherein A is N, X is SO, $R_1$ is $CF_3$, $R_2$ is CN and $R_5$ is as defined in table D.

Table F-19 provides 7 compounds F-19.001 to F-19.007 of formula I-2-Qa wherein A is N, X is SO, $R_1$ is $CF_3$, $R_2$ is $COCH_3$ and $R_5$ is as defined in table D.

Table F-20 provides 7 compounds F-20.001 to F-20.007 of formula I-2-Qa wherein A is N, X is SO, $R_1$ is $CF_3$, $R_2$ is cPr and $R_5$ is as defined in table D.

Table F-21 provides 7 compounds F-21.001 to F-21.007 of formula I-2-Qa wherein A is N, X is SO, $R_1$ is $CF_3$, $R_2$ is Me and $R_5$ is as defined in table D.

Table F-22 provides 7 compounds F-22.001 to F-22.007 of formula I-2-Qa wherein A is N, X is SO, $R_1$ is $CF_3$, $R_2$ is Et and $R_5$ is as defined in table D.

Table F-23 provides 7 compounds F-23.001 to F-23.007 of formula I-2-Qa wherein A is N, X is SO, $R_1$ is $CF_3$, $R_2$ is $CH_2CF_3$ and $R_5$ is as defined in table D.

Table F-24 provides 7 compounds F-24.001 to F-24.007 of formula I-2-Qa wherein A is N, X is SO, $R_1$ is $CF_3$, $R_2$ is $CF_3$ and $R_5$ is as defined in table D.

Table F-25 provides 7 compounds F-25.001 to F-25.007 of formula I-2-Qa wherein A is N, X is SO, $R_1$ is $CH_3$, $R_2$ is H and $R_5$ is as defined in table D.

Table F-26 provides 7 compounds F-26.001 to F-26.007 of formula I-2-Qa wherein A is N, X is SO, $R_1$ is $CH_3$, $R_2$ is CN and $R_5$ is as defined in table D.

Table F-27 provides 7 compounds F-27.001 to F-27.007 of formula I-2-Qa wherein A is N, X is SO, $R_1$ is $CH_3$, $R_2$ is $COCH_3$ and $R_5$ is as defined in table D.

Table F-28 provides 7 compounds F-28.001 to F-28.007 of formula I-2-Qa wherein A is N, X is SO, $R_1$ is $CH_3$, $R_2$ is cPr and $R_5$ is as defined in table D.

Table F-29 provides 7 compounds F-29.001 to F-29.007 of formula I-2-Qa wherein A is N, X is SO, $R_1$ is $CH_3$, $R_2$ is Me and $R_5$ is as defined in table D.

Table F-30 provides 7 compounds F-30.001 to F-30.007 of formula I-2-Qa wherein A is N, X is SO, $R_1$ is $CH_3$, $R_2$ is Et and $R_5$ is as defined in table D.

Table F-31 provides 7 compounds F-31.001 to F-31.007 of formula I-2-Qa wherein A is N, X is SO, $R_1$ is $CH_3$, $R_2$ is $CH_2CF_3$ and $R_5$ is as defined in table D.

Table F-32 provides 7 compounds F-32.001 to F-32.007 of formula I-2-Qa wherein A is N, X is SO, $R_1$ is $CH_3$, $R_2$ is $CF_3$ and $R_5$ is as defined in table D.

Table F-33 provides 7 compounds F-33.001 to F-33.007 of formula I-2-Qa wherein A is N, X is $SO_2$, $R_1$ is $CF_3$, $R_2$ is H and $R_5$ is as defined in table D.

Table F-34 provides 7 compounds F-34.001 to F-34.007 of formula I-2-Qa wherein A is N, X is $SO_2$, $R_1$ is $CF_3$, $R_2$ is CN and $R_5$ is as defined in table D.

Table F-35 provides 7 compounds F-35.001 to F-35.007 of formula I-2-Qa wherein A is N, X is $SO_2$, $R_1$ is $CF_3$, $R_2$ is $COCH_3$ and $R_5$ is as defined in table D.

Table F-36 provides 7 compounds F-36.001 to F-36.007 of formula I-2-Qa wherein A is N, X is $SO_2$, $R_1$ is $CF_3$, $R_2$ is cPr and $R_5$ is as defined in table D.

Table F-37 provides 7 compounds F-37.001 to F-37.007 of formula I-2-Qa wherein A is N, X is $SO_2$, $R_1$ is $CF_3$, $R_2$ is Me and $R_5$ is as defined in table D.

Table F-38 provides 7 compounds F-38.001 to F-38.007 of formula I-2-Qa wherein A is N, X is $SO_2$, $R_1$ is $CF_3$, $R_2$ is Et and $R_5$ is as defined in table D.

Table F-39 provides 7 compounds F-39.001 to F-39.007 of formula I-2-Qa wherein A is N, X is $SO_2$, $R_1$ is $CF_3$, $R_2$ is $CH_2CF_3$ and $R_5$ is as defined in table D.

Table F-40 provides 7 compounds F-40.001 to F-40.007 of formula I-2-Qa wherein A is N, X is $SO_2$, $R_1$ is $CF_3$, $R_2$ is $CF_3$ and $R_5$ is as defined in table D.

Table F-41 provides 7 compounds F-41.001 to F-41.007 of formula I-2-Qa wherein A is N, X is $SO_2$, $R_1$ is $CH_3$, $R_2$ is H and $R_5$ is as defined in table D.

Table F-42 provides 7 compounds F-42.001 to F-42.007 of formula I-2-Qa wherein A is N, X is $SO_2$, $R_1$ is $CH_3$, $R_2$ is CN and $R_5$ is as defined in table D.

Table F-43 provides 7 compounds F-43.001 to F-43.007 of formula I-2-Qa wherein A is N, X is $SO_2$, $R_1$ is $CH_3$, $R_2$ is $COCH_3$ and $R_5$ is as defined in table D.

Table F-44 provides 7 compounds F-44.001 to F-44.007 of formula I-2-Qa wherein A is N, X is $SO_2$, $R_1$ is $CH_3$, $R_2$ is cPr and $R_5$ is as defined in table D.

Table F-45 provides 7 compounds F-45.001 to F-45.007 of formula I-2-Qa wherein A is N, X is $SO_2$, $R_1$ is $CH_3$, $R_2$ is Me and $R_5$ is as defined in table D.

Table F-46 provides 7 compounds F-46.001 to F-46.007 of formula I-2-Qa wherein A is N, X is $SO_2$, $R_1$ is $CH_3$, $R_2$ is Et and $R_5$ is as defined in table D.

Table F-47 provides 7 compounds F-47.001 to F-47.007 of formula I-2-Qa wherein A is N, X is $SO_2$, $R_1$ is $CH_3$, $R_2$ is $CH_2CF_3$ and $R_5$ is as defined in table D.

Table F-48 provides 7 compounds F-48.001 to F-48.007 of formula I-2-Qa wherein A is N, X is $SO_2$, $R_1$ is $CH_3$, $R_2$ is $CF_3$ and $R_5$ is as defined in table D.

Table F-49 provides 7 compounds F-49.001 to F-49.007 of formula I-2-Qa wherein A is CH, X is S, $R_1$ is $CF_3$, $R_2$ is H and $R_5$ is as defined in table D.

Table F-50 provides 7 compounds F-50.001 to F-50.007 of formula I-2-Qa wherein A is CH, X is S, $R_1$ is $CF_3$, $R_2$ is CN and $R_5$ is as defined in table D.

Table F-51 provides 7 compounds F-51.001 to F-51.007 of formula I-2-Qa wherein A is CH, X is S, $R_1$ is $CF_3$, $R_2$ is $COCH_3$ and $R_5$ is as defined in table D.

Table F-52 provides 7 compounds F-52.001 to F-52.007 of formula I-2-Qa wherein A is CH, X is S, $R_1$ is $CF_3$, $R_2$ is cPr and $R_5$ is as defined in table D.

Table F-53 provides 7 compounds F-53.001 to F-53.007 of formula I-2-Qa wherein A is CH, X is S, $R_1$ is $CF_3$, $R_2$ is Me and $R_5$ is as defined in table D.

Table F-54 provides 7 compounds F-54.001 to F-54.007 of formula I-2-Qa wherein A is CH, X is S, $R_1$ is $CF_3$, $R_2$ is Et and $R_5$ is as defined in table D.

Table F-55 provides 7 compounds F-55.001 to F-55.007 of formula I-2-Qa wherein A is CH, X is S, $R_1$ is $CF_3$, $R_2$ is $CH_2CF_3$ and $R_5$ is as defined in table D.

Table F-56 provides 7 compounds F-56.001 to F-56.007 of formula I-2-Qa wherein A is CH, X is S, $R_1$ is $CF_3$, $R_2$ is $CF_3$ and $R_5$ is as defined in table D.

Table F-57 provides 7 compounds F-57.001 to F-57.007 of formula I-2-Qa wherein A is CH, X is S, $R_1$ is $CH_3$, $R_2$ is H and $R_5$ is as defined in table D.

Table F-58 provides 7 compounds F-58.001 to F-58.007 of formula I-2-Qa wherein A is CH, X is S, $R_1$ is $CH_3$, $R_2$ is CN and $R_5$ is as defined in table D.

Table F-59 provides 7 compounds F-59.001 to F-59.007 of formula I-2-Qa wherein A is CH, X is S, $R_1$ is $CH_3$, $R_2$ is $COCH_3$ and $R_5$ is as defined in table D.

Table F-60 provides 7 compounds F-60.001 to F-60.007 of formula I-2-Qa wherein A is CH, X is S, $R_1$ is $CH_3$, $R_2$ is cPr and $R_5$ is as defined in table D.

Table F-61 provides 7 compounds F-61.001 to F-61.007 of formula I-2-Qa wherein A is CH, X is S, $R_1$ is $CH_3$, $R_2$ is Me and $R_5$ is as defined in table D.

Table F-62 provides 7 compounds F-62.001 to F-62.007 of formula I-2-Qa wherein A is CH, X is S, $R_1$ is $CH_3$, $R_2$ is Et and $R_5$ is as defined in table D.

Table F-63 provides 7 compounds F-63.001 to F-63.007 of formula I-2-Qa wherein A is CH, X is S, $R_1$ is $CH_3$, $R_2$ is $CH_2CF_3$ and $R_5$ is as defined in table D.

Table F-64 provides 7 compounds F-64.001 to F-64.007 of formula I-2-Qa wherein A is CH, X is S, $R_1$ is $CH_3$, $R_2$ is $CF_3$ and $R_5$ is as defined in table D.

Table F-65 provides 7 compounds F-65.001 to F-65.007 of formula I-2-Qa wherein A is CH, X is SO, $R_1$ is $CF_3$, $R_2$ is H and $R_5$ is as defined in table D.

Table F-66 provides 7 compounds F-66.001 to F-66.007 of formula I-2-Qa wherein A is CH, X is SO, $R_1$ is $CF_3$, $R_2$ is CN and $R_5$ is as defined in table D.

Table F-67 provides 7 compounds F-67.001 to F-67.007 of formula I-2-Qa wherein A is CH, X is SO, $R_1$ is $CF_3$, $R_2$ is $COCH_3$ and $R_5$ is as defined in table D.

Table F-68 provides 7 compounds F-68.001 to F-68.007 of formula I-2-Qa wherein A is CH, X is SO, $R_1$ is $CF_3$, $R_2$ is cPr and $R_5$ is as defined in table D.

Table F-69 provides 7 compounds F-69.001 to F-69.007 of formula I-2-Qa wherein A is CH, X is SO, $R_1$ is $CF_3$, $R_2$ is Me and $R_5$ is as defined in table D.

Table F-70 provides 7 compounds F-70.001 to F-70.007 of formula I-2-Qa wherein A is CH, X is SO, $R_1$ is $CF_3$, $R_2$ is Et and $R_5$ is as defined in table D.

Table F-71 provides 7 compounds F-71.001 to F-71.007 of formula I-2-Qa wherein A is CH, X is SO, $R_1$ is $CF_3$, $R_2$ is $CH_2CF_3$ and $R_5$ is as defined in table D.

Table F-72 provides 7 compounds F-72.001 to F-72.007 of formula I-2-Qa wherein A is CH, X is SO, $R_1$ is $CF_3$, $R_2$ is $CF_3$ and $R_5$ is as defined in table D.

Table F-73 provides 7 compounds F-73.001 to F-73.007 of formula I-2-Qa wherein A is CH, X is SO, $R_1$ is $CH_3$, $R_2$ is H and $R_5$ is as defined in table D.

Table F-74 provides 7 compounds F-74.001 to F-74.007 of formula I-2-Qa wherein A is CH, X is SO, $R_1$ is $CH_3$, $R_2$ is CN and $R_5$ is as defined in table D.

Table F-75 provides 7 compounds F-75.001 to F-75.007 of formula I-2-Qa wherein A is CH, X is SO, $R_1$ is $CH_3$, $R_2$ is $COCH_3$ and $R_5$ is as defined in table D.

Table F-76 provides 7 compounds F-76.001 to F-76.007 of formula I-2-Qa wherein A is CH, X is SO, $R_1$ is $CH_3$, $R_2$ is cPr and $R_5$ is as defined in table D.

Table F-77 provides 7 compounds F-77.001 to F-77.007 of formula I-2-Qa wherein A is CH, X is SO, $R_1$ is $CH_3$, $R_2$ is Me and $R_5$ is as defined in table D.

Table F-78 provides 7 compounds F-78.001 to F-78.007 of formula I-2-Qa wherein A is CH, X is SO, $R_1$ is $CH_3$, $R_2$ is Et and $R_5$ is as defined in table D.

Table F-79 provides 7 compounds F-79.001 to F-79.007 of formula I-2-Qa wherein A is CH, X is SO, $R_1$ is $CH_3$, $R_2$ is $CH_2CF_3$ and $R_5$ is as defined in table D.

Table F-80 provides 7 compounds F-80.001 to F-80.007 of formula I-2-Qa wherein A is CH, X is SO, $R_1$ is $CH_3$, $R_2$ is $CF_3$ and $R_5$ is as defined in table D.

Table F-81 provides 7 compounds F-81.001 to F-81.007 of formula I-2-Qa wherein A is CH, X is $SO_2$, $R_1$ is $CF_3$, $R_2$ is H and $R_5$ is as defined in table D.

Table F-82 provides 7 compounds F-82.001 to F-82.007 of formula I-2-Qa wherein A is CH, X is $SO_2$, $R_1$ is $CF_3$, $R_2$ is CN and $R_5$ is as defined in table D.

Table F-83 provides 7 compounds F-83.001 to F-83.007 of formula I-2-Qa wherein A is CH, X is $SO_2$, $R_1$ is $CF_3$, $R_2$ is $COCH_3$ and $R_5$ is as defined in table D.

Table F-84 provides 7 compounds F-84.001 to F-84.007 of formula I-2-Qa wherein A is CH, X is $SO_2$, $R_1$ is $CF_3$, $R_2$ is cPr and $R_5$ is as defined in table D.

Table F-85 provides 7 compounds F-85.001 to F-85.007 of formula I-2-Qa wherein A is CH, X is $SO_2$, $R_1$ is $CF_3$, $R_2$ is Me and $R_5$ is as defined in table D.

Table F-86 provides 7 compounds F-86.001 to F-86.007 of formula I-2-Qa wherein A is CH, X is $SO_2$, $R_1$ is $CF_3$, $R_2$ is Et and $R_5$ is as defined in table D.

Table F-87 provides 7 compounds F-87.001 to F-87.007 of formula I-2-Qa wherein A is CH, X is $SO_2$, $R_1$ is $CF_3$, $R_2$ is $CH_2CF_3$ and $R_5$ is as defined in table D.

Table F-88 provides 7 compounds F-88.001 to F-88.007 of formula I-2-Qa wherein A is CH, X is $SO_2$, $R_1$ is $CF_3$, $R_2$ is $CF_3$ and $R_5$ is as defined in table D.

Table F-89 provides 7 compounds F-89.001 to F-89.007 of formula I-2-Qa wherein A is CH, X is $SO_2$, $R_1$ is $CH_3$, $R_2$ is H and $R_5$ is as defined in table D.

Table F-90 provides 7 compounds F-90.001 to F-90.007 of formula I-2-Qa wherein A is CH, X is $SO_2$, $R_1$ is $CH_3$, $R_2$ is CN and $R_5$ is as defined in table D.

Table F-91 provides 7 compounds F-91.001 to F-91.007 of formula I-2-Qa wherein A is CH, X is $SO_2$, $R_1$ is $CH_3$, $R_2$ is $COCH_3$ and $R_5$ is as defined in table D.

Table F-92 provides 7 compounds F-92.001 to F-92.007 of formula I-2-Qa wherein A is CH, X is $SO_2$, $R_1$ is $CH_3$, $R_2$ is cPr and $R_5$ is as defined in table D.

Table F-93 provides 7 compounds F-93.001 to F-93.007 of formula I-2-Qa wherein A is CH, X is $SO_2$, $R_1$ is $CH_3$, $R_2$ is Me and $R_5$ is as defined in table D.

Table F-94 provides 7 compounds F-94.001 to F-94.007 of formula I-2-Qa wherein A is CH, X is $SO_2$, $R_1$ is $CH_3$, $R_2$ is Et and $R_5$ is as defined in table D.

Table F-95 provides 7 compounds F-95.001 to F-95.007 of formula I-2-Qa wherein A is CH, X is $SO_2$, $R_1$ is $CH_3$, $R_2$ is $CH_2CF_3$ and $R_5$ is as defined in table D.

Table F-96 provides 7 compounds F-96.001 to F-96.007 of formula I-2-Qa wherein A is CH, X is $SO_2$, $R_1$ is $CH_3$, $R_2$ is $CF_3$ and $R_5$ is as defined in table D.

The tables G-1 to G-96 below further illustrate specific compounds of the invention.

"cPr" represents cyclopropyl.

(I-3-Qb)

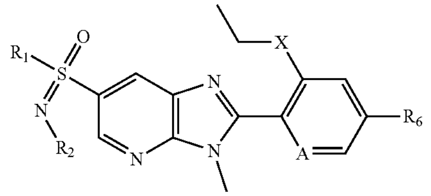

Table G-1 provides 14 compounds G-1.001 to G-1.014 of formula I-3-Qb wherein $R_1$ is Me, $R_2$ is H, A is N, X is S and $R_6$ is as defined in table B.

Table G-2 provides 14 compounds G-2.001 to G-2.014 of formula I-3-Qb wherein $R_1$ is Me, $R_2$ is H, A is N, X is SO and $R_6$ is as defined in table B.

Table G-3 provides 14 compounds G-3.001 to G-3.014 of formula I-3-Qb wherein $R_1$ is Me, $R_2$ is H, A is N, X is $SO_2$ and $R_6$ is as defined in table B.

Table G-4 provides 14 compounds G-4.001 to G-4.014 of formula I-3-Qb wherein $R_1$ is Me, $R_2$ is H, A is CH, X is S and $R_6$ is as defined in table B.

Table G-5 provides 14 compounds G-5.001 to G-5.014 of formula I-3-Qb wherein $R_1$ is Me, $R_2$ is H, A is CH, X is SO and $R_6$ is as defined in table B.

Table G-6 provides 14 compounds G-6.001 to G-6.014 of formula I-3-Qb wherein $R_1$ is Me, $R_2$ is H, A is CH, X is $SO_2$ and $R_6$ is as defined in table B.

Table G-7 provides 14 compounds G-7.001 to G-7.014 of formula I-3-Qb wherein $R_1$ is Me, $R_2$ is CN, A is N, X is S and $R_6$ is as defined in table B.

Table G-8 provides 14 compounds G-8.001 to G-8.014 of formula I-3-Qb wherein $R_1$ is Me, $R_2$ is CN, A is N, X is SO and $R_6$ is as defined in table B.

Table G-9 provides 14 compounds G-9.001 to G-9.014 of formula I-3-Qb wherein $R_1$ is Me, $R_2$ is CN, A is N, X is $SO_2$ and $R_6$ is as defined in table B.

Table G-10 provides 14 compounds G-10.001 to G-10.014 of formula I-3-Qb wherein $R_1$ is Me, $R_2$ is CN, A is CH, X is S and $R_6$ is as defined in table B.

Table G-11 provides 14 compounds G-11.001 to G-11.014 of formula I-3-Qb wherein $R_1$ is Me, $R_2$ is CN, A is CH, X is SO and $R_6$ is as defined in table B.

Table G-12 provides 14 compounds G-12.001 to G-12.014 of formula I-3-Qb wherein $R_1$ is Me, $R_2$ is CN, A is CH, X is $SO_2$ and $R_6$ is as defined in table B.

Table G-13 provides 14 compounds G-13.001 to G-13.014 of formula I-3-Qb wherein $R_1$ is Me, $R_2$ is $COCH_3$, A is N, X is S and $R_6$ is as defined in table B.

Table G-14 provides 14 compounds G-14.001 to G-14.014 of formula I-3-Qb wherein $R_1$ is Me, $R_2$ is $COCH_3$, A is N, X is SO and $R_6$ is as defined in table B.

Table G-15 provides 14 compounds G-15.001 to G-15.014 of formula I-3-Qb wherein $R_1$ is Me, $R_2$ is $COCH_3$, A is N, X is $SO_2$ and $R_6$ is as defined in table B.

Table G-16 provides 14 compounds G-16.001 to G-16.014 of formula I-3-Qb wherein $R_1$ is Me, $R_2$ is $COCH_3$, A is CH, X is S and $R_6$ is as defined in table B.

Table G-17 provides 14 compounds G-17.001 to G-17.014 of formula I-3-Qb wherein $R_1$ is Me, $R_2$ is $COCH_3$, A is CH, X is SO and $R_6$ is as defined in table B.

Table G-18 provides 14 compounds G-18.001 to G-18.014 of formula I-3-Qb wherein $R_1$ is Me, $R_2$ is $COCH_3$, A is CH, X is $SO_2$ and $R_6$ is as defined in table B.

Table G-19 provides 14 compounds G-19.001 to G-19.014 of formula I-3-Qb wherein $R_1$ is Me, $R_2$ is cPr, A is N, X is S and $R_6$ is as defined in table B.

Table G-20 provides 14 compounds G-20.001 to G-20.014 of formula I-3-Qb wherein $R_1$ is Me, $R_2$ is cPr, A is N, X is SO and $R_6$ is as defined in table B.

Table G-21 provides 14 compounds G-21.001 to G-21.014 of formula I-3-Qb wherein $R_1$ is Me, $R_2$ is cPr, A is N, X is $SO_2$ and $R_6$ is as defined in table B.

Table G-22 provides 14 compounds G-22.001 to G-22.014 of formula I-3-Qb wherein $R_1$ is Me, $R_2$ is cPr, A is CH, X is S and $R_6$ is as defined in table B.

Table G-23 provides 14 compounds G-23.001 to G-23.014 of formula I-3-Qb wherein $R_1$ is Me, $R_2$ is cPr, A is CH, X is SO and $R_6$ is as defined in table B.

Table G-24 provides 14 compounds G-24.001 to G-24.014 of formula I-3-Qb wherein $R_1$ is Me, $R_2$ is cPr, A is CH, X is $SO_2$ and $R_6$ is as defined in table B.

Table G-25 provides 14 compounds G-25.001 to G-25.014 of formula I-3-Qb wherein $R_1$ is Me, $R_2$ is Me, A is N, X is S and $R_6$ is as defined in table B.

Table G-26 provides 14 compounds G-26.001 to G-26.014 of formula I-3-Qb wherein $R_1$ is Me, $R_2$ is Me, A is N, X is SO and $R_6$ is as defined in table B.

Table G-27 provides 14 compounds G-27.001 to G-27.014 of formula I-3-Qb wherein $R_1$ is Me, $R_2$ is Me, A is N, X is $SO_2$ and $R_6$ is as defined in table B.

Table G-28 provides 14 compounds G-28.001 to G-28.014 of formula I-3-Qb wherein $R_1$ is Me, $R_2$ is Me, A is CH, X is S and $R_6$ is as defined in table B.

Table G-29 provides 14 compounds G-29.001 to G-29.014 of formula I-3-Qb wherein $R_1$ is Me, $R_2$ is Me, A is CH, X is SO and $R_6$ is as defined in table B.

Table G-30 provides 14 compounds G-30.001 to G-30.014 of formula I-3-Qb wherein $R_1$ is Me, $R_2$ is Me, A is CH, X is $SO_2$ and $R_6$ is as defined in table B.

Table G-31 provides 14 compounds G-31.001 to G-31.014 of formula I-3-Qb wherein $R_1$ is Me, $R_2$ is Et, A is N, X is S and $R_6$ is as defined in table B.

Table G-32 provides 14 compounds G-32.001 to G-32.014 of formula I-3-Qb wherein $R_1$ is Me, $R_2$ is Et, A is N, X is SO and $R_6$ is as defined in table B.

Table G-33 provides 14 compounds G-33.001 to G-33.014 of formula I-3-Qb wherein $R_1$ is Me, $R_2$ is Et, A is N, X is $SO_2$ and $R_6$ is as defined in table B.

Table G-34 provides 14 compounds G-34.001 to G-34.014 of formula I-3-Qb wherein $R_1$ is Me, $R_2$ is Et, A is CH, X is S and $R_6$ is as defined in table B.

Table G-35 provides 14 compounds G-35.001 to G-35.014 of formula I-3-Qb wherein $R_1$ is Me, $R_2$ is Et, A is CH, X is SO and $R_6$ is as defined in table B.

Table G-36 provides 14 compounds G-36.001 to G-36.014 of formula I-3-Qb wherein $R_1$ is Me, $R_2$ is Et, A is CH, X is $SO_2$ and $R_6$ is as defined in table B.

Table G-37 provides 14 compounds G-37.001 to G-37.014 of formula I-3-Qb wherein $R_1$ is Me, $R_2$ is $CH_2CF_3$, A is N, X is S and $R_6$ is as defined in table B.

Table G-38 provides 14 compounds G-38.001 to G-38.014 of formula I-3-Qb wherein $R_1$ is Me, $R_2$ is $CH_2CF_3$, A is N, X is SO and $R_6$ is as defined in table B.

Table G-39 provides 14 compounds G-39.001 to G-39.014 of formula I-3-Qb wherein $R_1$ is Me, $R_2$ is $CH_2CF_3$, A is N, X is $SO_2$ and $R_6$ is as defined in table B.

Table G-40 provides 14 compounds G-40.001 to G-40.014 of formula I-3-Qb wherein $R_1$ is Me, $R_2$ is $CH_2CF_3$, A is CH, X is S and $R_6$ is as defined in table B.

Table G-41 provides 14 compounds G-41.001 to G-41.014 of formula I-3-Qb wherein $R_1$ is Me, $R_2$ is $CH_2CF_3$, A is CH, X is SO and $R_6$ is as defined in table B.

Table G-42 provides 14 compounds G-42.001 to G-42.014 of formula I-3-Qb wherein $R_1$ is Me, $R_2$ is $CH_2CF_3$, A is CH, X is $SO_2$ and $R_6$ is as defined in table B.

Table G-43 provides 14 compounds G-43.001 to G-43.014 of formula I-3-Qb wherein $R_1$ is Me, $R_2$ is $CF_3$, A is N, X is S and $R_6$ is as defined in table B.

Table G-44 provides 14 compounds G-44.001 to G-44.014 of formula I-3-Qb wherein $R_1$ is Me, $R_2$ is $CF_3$, A is N, X is SO and $R_6$ is as defined in table B.

Table G-45 provides 14 compounds G-45.001 to G-45.014 of formula I-3-Qb wherein $R_1$ is Me, $R_2$ is $CF_3$, A is N, X is $SO_2$ and $R_6$ is as defined in table B.

Table G-46 provides 14 compounds G-46.001 to G-46.014 of formula I-3-Qb wherein $R_1$ is Me, $R_2$ is $CF_3$, A is CH, X is S and $R_6$ is as defined in table B.

Table G-47 provides 14 compounds G-47.001 to G-47.014 of formula I-3-Qb wherein $R_1$ is Me, $R_2$ is $CF_3$, A is CH, X is SO and $R_6$ is as defined in table B.

Table G-48 provides 14 compounds G-48.001 to G-48.014 of formula I-3-Qb wherein $R_1$ is Me, $R_2$ is $CF_3$, A is CH, X is $SO_2$ and $R_6$ is as defined in table B.

Table G-49 provides 14 compounds G-49.001 to G-49.014 of formula I-3-Qb wherein $R_1$ is $CF_3$, $R_2$ is H, A is N, X is S and $R_6$ is as defined in table B.

Table G-50 provides 14 compounds G-50.001 to G-50.014 of formula I-3-Qb wherein $R_1$ is $CF_3$, $R_2$ is H, A is N, X is SO and $R_6$ is as defined in table B.

Table G-51 provides 14 compounds G-51.001 to G-51.014 of formula I-3-Qb wherein $R_1$ is $CF_3$, $R_2$ is H, A is N, X is $SO_2$ and $R_6$ is as defined in table B.

Table G-52 provides 14 compounds G-52.001 to G-52.014 of formula I-3-Qb wherein $R_1$ is $CF_3$, $R_2$ is H, A is CH, X is S and $R_6$ is as defined in table B.

Table G-53 provides 14 compounds G-53.001 to G-53.014 of formula I-3-Qb wherein $R_1$ is $CF_3$, $R_2$ is H, A is CH, X is SO and $R_6$ is as defined in table B.

Table G-54 provides 14 compounds G-54.001 to G-54.014 of formula I-3-Qb wherein $R_1$ is $CF_3$, $R_2$ is H, A is CH, X is $SO_2$ and $R_6$ is as defined in table B.

Table G-55 provides 14 compounds G-55.001 to G-55.014 of formula I-3-Qb wherein $R_1$ is $CF_3$, $R_2$ is CN, A is N, X is S and $R_6$ is as defined in table B.

Table G-56 provides 14 compounds G-56.001 to G-56.014 of formula I-3-Qb wherein $R_1$ is $CF_3$, $R_2$ is CN, A is N, X is SO and $R_6$ is as defined in table B.

Table G-57 provides 14 compounds G-57.001 to G-57.014 of formula I-3-Qb wherein $R_1$ is $CF_3$, $R_2$ is CN, A is N, X is $SO_2$ and $R_6$ is as defined in table B.

Table G-58 provides 14 compounds G-58.001 to G-58.014 of formula I-3-Qb wherein $R_1$ is $CF_3$, $R_2$ is CN, A is CH, X is S and $R_6$ is as defined in table B.

Table G-59 provides 14 compounds G-59.001 to G-59.014 of formula I-3-Qb wherein $R_1$ is $CF_3$, $R_2$ is CN, A is CH, X is SO and $R_6$ is as defined in table B.

Table G-60 provides 14 compounds G-60.001 to G-60.014 of formula I-3-Qb wherein $R_1$ is $CF_3$, $R_2$ is CN, A is CH, X is $SO_2$ and $R_6$ is as defined in table B.

Table G-61 provides 14 compounds G-61.001 to G-61.014 of formula I-3-Qb wherein $R_1$ is $CF_3$, $R_2$ is $COCH_3$, A is N, X is S and $R_6$ is as defined in table B.

Table G-62 provides 14 compounds G-62.001 to G-62.014 of formula I-3-Qb wherein $R_1$ is $CF_3$, $R_2$ is $COCH_3$, A is N, X is SO and $R_6$ is as defined in table B.

Table G-63 provides 14 compounds G-63.001 to G-63.014 of formula I-3-Qb wherein $R_1$ is $CF_3$, $R_2$ is $COCH_3$, A is N, X is $SO_2$ and $R_6$ is as defined in table B.

Table G-64 provides 14 compounds G-64.001 to G-64.014 of formula I-3-Qb wherein $R_1$ is $CF_3$, $R_2$ is $COCH_3$, A is CH, X is S and $R_6$ is as defined in table B.

Table G-65 provides 14 compounds G-65.001 to G-65.014 of formula I-3-Qb wherein $R_1$ is $CF_3$, $R_2$ is $COCH_3$, A is CH, X is SO and $R_6$ is as defined in table B.

Table G-66 provides 14 compounds G-66.001 to G-66.014 of formula I-3-Qb wherein $R_1$ is $CF_3$, $R_2$ is $COCH_3$, A is CH, X is $SO_2$ and $R_6$ is as defined in table B.

Table G-67 provides 14 compounds G-67.001 to G-67.014 of formula I-3-Qb wherein $R_1$ is $CF_3$, $R_2$ is cPr, A is N, X is S and $R_6$ is as defined in table B.

Table G-68 provides 14 compounds G-68.001 to G-68.014 of formula I-3-Qb wherein $R_1$ is $CF_3$, $R_2$ is cPr, A is N, X is SO and $R_6$ is as defined in table B.

Table G-69 provides 14 compounds G-69.001 to G-69.014 of formula I-3-Qb wherein $R_1$ is $CF_3$, $R_2$ is cPr, A is N, X is $SO_2$ and $R_6$ is as defined in table B.

Table G-70 provides 14 compounds G-70.001 to G-70.014 of formula I-3-Qb wherein $R_1$ is $CF_3$, $R_2$ is cPr, A is CH, X is S and $R_6$ is as defined in table B.

Table G-71 provides 14 compounds G-71.001 to G-71.014 of formula I-3-Qb wherein $R_1$ is $CF_3$, $R_2$ is cPr, A is CH, X is SO and $R_6$ is as defined in table B.

Table G-72 provides 14 compounds G-72.001 to G-72.014 of formula I-3-Qb wherein $R_1$ is $CF_3$, $R_2$ is cPr, A is CH, X is $SO_2$ and $R_6$ is as defined in table B.

Table G-73 provides 14 compounds G-73.001 to G-73.014 of formula I-3-Qb wherein $R_1$ is $CF_3$, $R_2$ is Me, A is N, X is S and $R_6$ is as defined in table B.

Table G-74 provides 14 compounds G-74.001 to G-74.014 of formula I-3-Qb wherein $R_1$ is $CF_3$, $R_2$ is Me, A is N, X is SO and $R_6$ is as defined in table B.

Table G-75 provides 14 compounds G-75.001 to G-75.014 of formula I-3-Qb wherein $R_1$ is $CF_3$, $R_2$ is Me, A is N, X is $SO_2$ and $R_6$ is as defined in table B.

Table G-76 provides 14 compounds G-76.001 to G-76.014 of formula I-3-Qb wherein $R_1$ is $CF_3$, $R_2$ is Me, A is CH, X is S and $R_6$ is as defined in table B.

Table G-77 provides 14 compounds G-77.001 to G-77.014 of formula I-3-Qb wherein $R_1$ is $CF_3$, $R_2$ is Me, A is CH, X is SO and $R_6$ is as defined in table B.

Table G-78 provides 14 compounds G-78.001 to G-78.014 of formula I-3-Qb wherein $R_1$ is $CF_3$, $R_2$ is Me, A is CH, X is $SO_2$ and $R_6$ is as defined in table B.

Table G-79 provides 14 compounds G-79.001 to G-79.014 of formula I-3-Qb wherein $R_1$ is $CF_3$, $R_2$ is Et, A is N, X is S and $R_6$ is as defined in table B.

Table G-80 provides 14 compounds G-80.001 to G-80.014 of formula I-3-Qb wherein $R_1$ is $CF_3$, $R_2$ is Et, A is N, X is SO and $R_6$ is as defined in table B.

Table G-81 provides 14 compounds G-81.001 to G-81.014 of formula I-3-Qb wherein $R_1$ is $CF_3$, $R_2$ is Et, A is N, X is $SO_2$ and $R_6$ is as defined in table B.

Table G-82 provides 14 compounds G-82.001 to G-82.014 of formula I-3-Qb wherein $R_1$ is $CF_3$, $R_2$ is Et, A is CH, X is S and $R_6$ is as defined in table B.

Table G-83 provides 14 compounds G-83.001 to G-83.014 of formula I-3-Qb wherein $R_1$ is $CF_3$, $R_2$ is Et, A is CH, X is SO and $R_6$ is as defined in table B.

Table G-84 provides 14 compounds G-84.001 to G-84.014 of formula I-3-Qb wherein $R_1$ is $CF_3$, $R_2$ is Et, A is CH, X is $SO_2$ and $R_6$ is as defined in table B.

Table G-85 provides 14 compounds G-85.001 to G-85.014 of formula I-3-Qb wherein $R_1$ is $CF_3$, $R_2$ is $CH_2CF_3$, A is N, X is S and $R_6$ is as defined in table B.

Table G-86 provides 14 compounds G-86.001 to G-86.014 of formula I-3-Qb wherein $R_1$ is $CF_3$, $R_2$ is $CH_2CF_3$, A is N, X is SO and $R_6$ is as defined in table B.

Table G-87 provides 14 compounds G-87.001 to G-87.014 of formula I-3-Qb wherein $R_1$ is $CF_3$, $R_2$ is $CH_2CF_3$, A is N, X is $SO_2$ and $R_6$ is as defined in table B.

Table G-88 provides 14 compounds G-88.001 to G-88.014 of formula I-3-Qb wherein $R_1$ is $CF_3$, $R_2$ is $CH_2CF_3$, A is CH, X is S and $R_6$ is as defined in table B.

Table G-89 provides 14 compounds G-89.001 to G-89.014 of formula I-3-Qb wherein $R_1$ is $CF_3$, $R_2$ is $CH_2CF_3$, A is CH, X is SO and $R_6$ is as defined in table B.

Table G-90 provides 14 compounds G-90.001 to G-90.014 of formula I-3-Qb wherein $R_1$ is $CF_3$, $R_2$ is $CH_2CF_3$, A is CH, X is $SO_2$ and $R_6$ is as defined in table B.

Table G-91 provides 14 compounds G-91.001 to G-91.014 of formula I-3-Qb wherein $R_1$ is $CF_3$, $R_2$ is $CF_3$, A is N, X is S and $R_6$ is as defined in table B.

Table G-92 provides 14 compounds G-92.001 to G-92.014 of formula I-3-Qb wherein $R_1$ is $CF_3$, $R_2$ is $CF_3$, A is N, X is SO and $R_6$ is as defined in table B.

Table G-93 provides 14 compounds G-93.001 to G-93.014 of formula I-3-Qb wherein $R_1$ is $CF_3$, $R_2$ is $CF_3$, A is N, X is $SO_2$ and $R_6$ is as defined in table B.

Table G-94 provides 14 compounds G-94.001 to G-94.014 of formula I-3-Qb wherein $R_1$ is $CF_3$, $R_2$ is $CF_3$, A is CH, X is S and $R_6$ is as defined in table B.

Table G-95 provides 14 compounds G-95.001 to G-95.014 of formula I-3-Qb wherein $R_1$ is $CF_3$, $R_2$ is $CF_3$, A is CH, X is SO and $R_6$ is as defined in table B.

Table G-96 provides 14 compounds G-96.001 to G-96.014 of formula I-3-Qb wherein $R_1$ is $CF_3$, $R_2$ is $CF_3$, A is CH, X is $SO_2$ and $R_6$ is as defined in table B.

The tables H-1 to H-96 below further illustrate specific compounds of the invention.

"cPr" represents cyclopropyl.

(I-3-Qa)

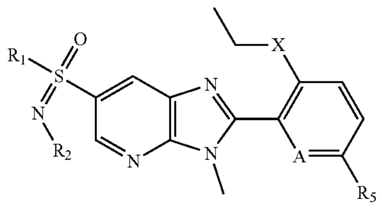

Table H-1 provides 7 compounds H-1.001 to H-1.007 of formula I-3-Qa wherein A is N, X is S, $R_1$ is $CF_3$, $R_2$ is H and $R_5$ is as defined in table D.

Table H-2 provides 7 compounds H-2.001 to H-2.007 of formula I-3-Qa wherein A is N, X is S, $R_1$ is $CF_3$, $R_2$ is CN and $R_5$ is as defined in table D.

Table H-3 provides 7 compounds H-3.001 to H-3.007 of formula I-3-Qa wherein A is N, X is S, $R_1$ is $CF_3$, $R_2$ is $COCH_3$ and $R_5$ is as defined in table D.

Table H-4 provides 7 compounds H-4.001 to H-4.007 of formula I-3-Qa wherein A is N, X is S, $R_1$ is $CF_3$, $R_2$ is cPr and $R_5$ is as defined in table D.

Table H-5 provides 7 compounds H-5.001 to H-5.007 of formula I-3-Qa wherein A is N, X is S, $R_1$ is $CF_3$, $R_2$ is Me and $R_5$ is as defined in table D.

Table H-6 provides 7 compounds H-6.001 to H-6.007 of formula I-3-Qa wherein A is N, X is S, $R_1$ is $CF_3$, $R_2$ is Et and $R_5$ is as defined in table D.

Table H-7 provides 7 compounds H-7.001 to H-7.007 of formula I-3-Qa wherein A is N, X is S, $R_1$ is $CF_3$, $R_2$ is $CH_2CF_3$ and $R_5$ is as defined in table D.

Table H-8 provides 7 compounds H-8.001 to H-8.007 of formula I-3-Qa wherein A is N, X is S, $R_1$ is $CF_3$, $R_2$ is $CF_3$ and $R_5$ is as defined in table D.

Table H-9 provides 7 compounds H-9.001 to H-9.007 of formula I-3-Qa wherein A is N, X is S, $R_1$ is $CH_3$, $R_2$ is H and $R_5$ is as defined in table D.

Table H-10 provides 7 compounds H-10.001 to H-10.007 of formula I-3-Qa wherein A is N, X is S, $R_1$ is $CH_3$, $R_2$ is CN and $R_5$ is as defined in table D.

Table H-11 provides 7 compounds H-11.001 to H-11.007 of formula I-3-Qa wherein A is N, X is S, $R_1$ is $CH_3$, $R_2$ is $COCH_3$ and $R_5$ is as defined in table D.

Table H-12 provides 7 compounds H-12.001 to H-12.007 of formula I-3-Qa wherein A is N, X is S, $R_1$ is $CH_3$, $R_2$ is cPr and $R_5$ is as defined in table D.

Table H-13 provides 7 compounds H-13.001 to H-13.007 of formula I-3-Qa wherein A is N, X is S, $R_1$ is $CH_3$, $R_2$ is Me and $R_5$ is as defined in table D.

Table H-14 provides 7 compounds H-14.001 to H-14.007 of formula I-3-Qa wherein A is N, X is S, $R_1$ is $CH_3$, $R_2$ is Et and $R_5$ is as defined in table D.

Table H-15 provides 7 compounds H-15.001 to H-15.007 of formula I-3-Qa wherein A is N, X is S, $R_1$ is $CH_3$, $R_2$ is $CH_2CF_3$ and $R_5$ is as defined in table D.

Table H-16 provides 7 compounds H-16.001 to H-16.007 of formula I-3-Qa wherein A is N, X is S, $R_1$ is $CH_3$, $R_2$ is $CF_3$ and $R_5$ is as defined in table D.

Table H-17 provides 7 compounds H-17.001 to H-17.007 of formula I-3-Qa wherein A is N, X is SO, $R_1$ is $CF_3$, $R_2$ is H and $R_5$ is as defined in table D.

Table H-18 provides 7 compounds H-18.001 to H-18.007 of formula I-3-Qa wherein A is N, X is SO, $R_1$ is $CF_3$, $R_2$ is CN and $R_5$ is as defined in table D.

Table H-19 provides 7 compounds H-19.001 to H-19.007 of formula I-3-Qa wherein A is N, X is SO, $R_1$ is $CF_3$, $R_2$ is $COCH_3$ and $R_5$ is as defined in table D.

Table H-20 provides 7 compounds H-20.001 to H-20.007 of formula I-3-Qa wherein A is N, X is SO, $R_1$ is $CF_3$, $R_2$ is cPr and $R_5$ is as defined in table D.

Table H-21 provides 7 compounds H-21.001 to H-21.007 of formula I-3-Qa wherein A is N, X is SO, $R_1$ is $CF_3$, $R_2$ is Me and $R_5$ is as defined in table D.

Table H-22 provides 7 compounds H-22.001 to H-22.007 of formula I-3-Qa wherein A is N, X is SO, $R_1$ is $CF_3$, $R_2$ is Et and $R_5$ is as defined in table D.

Table H-23 provides 7 compounds H-23.001 to H-23.007 of formula I-3-Qa wherein A is N, X is SO, $R_1$ is $CF_3$, $R_2$ is $CH_2CF_3$ and $R_5$ is as defined in table D.

Table H-24 provides 7 compounds H-24.001 to H-24.007 of formula I-3-Qa wherein A is N, X is SO, $R_1$ is $CF_3$, $R_2$ is $CF_3$ and $R_5$ is as defined in table D.

Table H-25 provides 7 compounds H-25.001 to H-25.007 of formula I-3-Qa wherein A is N, X is SO, $R_1$ is $CH_3$, $R_2$ is H and $R_5$ is as defined in table D.

Table H-26 provides 7 compounds H-26.001 to H-26.007 of formula I-3-Qa wherein A is N, X is SO, $R_1$ is $CH_3$, $R_2$ is CN and $R_5$ is as defined in table D.

Table H-27 provides 7 compounds H-27.001 to H-27.007 of formula I-3-Qa wherein A is N, X is SO, $R_1$ is $CH_3$, $R_2$ is $COCH_3$ and $R_5$ is as defined in table D.

Table H-28 provides 7 compounds H-28.001 to H-28.007 of formula I-3-Qa wherein A is N, X is SO, $R_1$ is $CH_3$, $R_2$ is cPr and $R_5$ is as defined in table D.

Table H-29 provides 7 compounds H-29.001 to H-29.007 of formula I-3-Qa wherein A is N, X is SO, $R_1$ is $CH_3$, $R_2$ is Me and $R_5$ is as defined in table D.

Table H-30 provides 7 compounds H-30.001 to H-30.007 of formula I-3-Qa wherein A is N, X is SO, $R_1$ is $CH_3$, $R_2$ is Et and $R_5$ is as defined in table D.

Table H-31 provides 7 compounds H-31.001 to H-31.007 of formula I-3-Qa wherein A is N, X is SO, $R_1$ is $CH_3$, $R_2$ is $CH_2CF_3$ and $R_5$ is as defined in table D.

Table H-32 provides 7 compounds H-32.001 to H-32.007 of formula I-3-Qa wherein A is N, X is SO, $R_1$ is $CH_3$, $R_2$ is $CF_3$ and $R_5$ is as defined in table D.

Table H-33 provides 7 compounds H-33.001 to H-33.007 of formula I-3-Qa wherein A is N, X is $SO_2$, $R_1$ is $CF_3$, $R_2$ is H and $R_5$ is as defined in table D.

Table H-34 provides 7 compounds H-34.001 to H-34.007 of formula I-3-Qa wherein A is N, X is $SO_2$, $R_1$ is $CF_3$, $R_2$ is CN and $R_5$ is as defined in table D.

Table H-35 provides 7 compounds H-35.001 to H-35.007 of formula I-3-Qa wherein A is N, X is $SO_2$, $R_1$ is $CF_3$, $R_2$ is $COCH_3$ and $R_5$ is as defined in table D.

Table H-36 provides 7 compounds H-36.001 to H-36.007 of formula I-3-Qa wherein A is N, X is $SO_2$, $R_1$ is $CF_3$, $R_2$ is cPr and $R_5$ is as defined in table D.

Table H-37 provides 7 compounds H-37.001 to H-37.007 of formula I-3-Qa wherein A is N, X is $SO_2$, $R_1$ is $CF_3$, $R_2$ is Me and $R_5$ is as defined in table D.

Table H-38 provides 7 compounds H-38.001 to H-38.007 of formula I-3-Qa wherein A is N, X is $SO_2$, $R_1$ is $CF_3$, $R_2$ is Et and $R_5$ is as defined in table D.

Table H-39 provides 7 compounds H-39.001 to H-39.007 of formula I-3-Qa wherein A is N, X is $SO_2$, $R_1$ is $CF_3$, $R_2$ is $CH_2CF_3$ and $R_5$ is as defined in table D.

Table H-40 provides 7 compounds H-40.001 to H-40.007 of formula I-3-Qa wherein A is N, X is $SO_2$, $R_1$ is $CF_3$, $R_2$ is $CF_3$ and $R_5$ is as defined in table D.

Table H-41 provides 7 compounds H-41.001 to H-41.007 of formula I-3-Qa wherein A is N, X is $SO_2$, $R_1$ is $CH_3$, $R_2$ is H and $R_5$ is as defined in table D.

Table H-42 provides 7 compounds H-42.001 to H-42.007 of formula I-3-Qa wherein A is N, X is $SO_2$, $R_1$ is $CH_3$, $R_2$ is CN and $R_5$ is as defined in table D.

Table H-43 provides 7 compounds H-43.001 to H-43.007 of formula I-3-Qa wherein A is N, X is $SO_2$, $R_1$ is $CH_3$, $R_2$ is $COCH_3$ and $R_5$ is as defined in table D.

Table H-44 provides 7 compounds H-44.001 to H-44.007 of formula I-3-Qa wherein A is N, X is $SO_2$, $R_1$ is $CH_3$, $R_2$ is cPr and $R_5$ is as defined in table D.

Table H-45 provides 7 compounds H-45.001 to H-45.007 of formula I-3-Qa wherein A is N, X is $SO_2$, $R_1$ is $CH_3$, $R_2$ is Me and $R_5$ is as defined in table D.

Table H-46 provides 7 compounds H-46.001 to H-46.007 of formula I-3-Qa wherein A is N, X is $SO_2$, $R_1$ is $CH_3$, $R_2$ is Et and $R_5$ is as defined in table D.

Table H-47 provides 7 compounds H-47.001 to H-47.007 of formula I-3-Qa wherein A is N, X is $SO_2$, $R_1$ is $CH_3$, $R_2$ is $CH_2CF_3$ and $R_5$ is as defined in table D.

Table H-48 provides 7 compounds H-48.001 to H-48.007 of formula I-3-Qa wherein A is N, X is $SO_2$, $R_1$ is $CH_3$, $R_2$ is $CF_3$ and $R_5$ is as defined in table D.

Table H-49 provides 7 compounds H-49.001 to H-49.007 of formula I-3-Qa wherein A is CH, X is S, $R_1$ is $CF_3$, $R_2$ is H and $R_5$ is as defined in table D.

Table H-50 provides 7 compounds H-50.001 to H-50.007 of formula I-3-Qa wherein A is CH, X is S, $R_1$ is $CF_3$, $R_2$ is CN and $R_5$ is as defined in table D.

Table H-51 provides 7 compounds H-51.001 to H-51.007 of formula I-3-Qa wherein A is CH, X is S, $R_1$ is $CF_3$, $R_2$ is $COCH_3$ and $R_5$ is as defined in table D.

Table H-52 provides 7 compounds H-52.001 to H-52.007 of formula I-3-Qa wherein A is CH, X is S, $R_1$ is $CF_3$, $R_2$ is cPr and $R_5$ is as defined in table D.

Table H-53 provides 7 compounds H-53.001 to H-53.007 of formula I-3-Qa wherein A is CH, X is S, $R_1$ is $CF_3$, $R_2$ is Me and $R_5$ is as defined in table D.

Table H-54 provides 7 compounds H-54.001 to H-54.007 of formula I-3-Qa wherein A is CH, X is S, $R_1$ is $CF_3$, $R_2$ is Et and $R_5$ is as defined in table D.

Table H-55 provides 7 compounds H-55.001 to H-55.007 of formula I-3-Qa wherein A is CH, X is S, $R_1$ is $CF_3$, $R_2$ is $CH_2CF_3$ and $R_5$ is as defined in table D.

Table H-56 provides 7 compounds H-56.001 to H-56.007 of formula I-3-Qa wherein A is CH, X is S, $R_1$ is $CF_3$, $R_2$ is $CF_3$ and $R_5$ is as defined in table D.

Table H-57 provides 7 compounds H-57.001 to H-57.007 of formula I-3-Qa wherein A is CH, X is S, $R_1$ is $CH_3$, $R_2$ is H and $R_5$ is as defined in table D.

Table H-58 provides 7 compounds H-58.001 to H-58.007 of formula I-3-Qa wherein A is CH, X is S, $R_1$ is $CH_3$, $R_2$ is CN and $R_5$ is as defined in table D.

Table H-59 provides 7 compounds H-59.001 to H-59.007 of formula I-3-Qa wherein A is CH, X is S, $R_1$ is $CH_3$, $R_2$ is $COCH_3$ and $R_5$ is as defined in table D.

Table H-60 provides 7 compounds H-60.001 to H-60.007 of formula I-3-Qa wherein A is CH, X is S, $R_1$ is $CH_3$, $R_2$ is cPr and $R_5$ is as defined in table D.

Table H-61 provides 7 compounds H-61.001 to H-61.007 of formula I-3-Qa wherein A is CH, X is S, $R_1$ is $CH_3$, $R_2$ is Me and $R_5$ is as defined in table D.

Table H-62 provides 7 compounds H-62.001 to H-62.007 of formula I-3-Qa wherein A is CH, X is S, $R_1$ is $CH_3$, $R_2$ is Et and $R_5$ is as defined in table D.

Table H-63 provides 7 compounds H-63.001 to H-63.007 of formula I-3-Qa wherein A is CH, X is S, $R_1$ is $CH_3$, $R_2$ is $CH_2CF_3$ and $R_5$ is as defined in table D.

Table H-64 provides 7 compounds H-64.001 to H-64.007 of formula I-3-Qa wherein A is CH, X is S, $R_1$ is $CH_3$, $R_2$ is $CF_3$ and $R_5$ is as defined in table D.

Table H-65 provides 7 compounds H-65.001 to H-65.007 of formula I-3-Qa wherein A is CH, X is SO, $R_1$ is $CF_3$, $R_2$ is H and $R_5$ is as defined in table D.

Table H-66 provides 7 compounds H-66.001 to H-66.007 of formula I-3-Qa wherein A is CH, X is SO, $R_1$ is $CF_3$, $R_2$ is CN and $R_5$ is as defined in table D.

Table H-67 provides 7 compounds H-67.001 to H-67.007 of formula I-3-Qa wherein A is CH, X is SO, $R_1$ is $CF_3$, $R_2$ is $COCH_3$ and $R_5$ is as defined in table D.

Table H-68 provides 7 compounds H-68.001 to H-68.007 of formula I-3-Qa wherein A is CH, X is SO, $R_1$ is $CF_3$, $R_2$ is cPr and $R_5$ is as defined in table D.

Table H-69 provides 7 compounds H-69.001 to H-69.007 of formula I-3-Qa wherein A is CH, X is SO, $R_1$ is $CF_3$, $R_2$ is Me and $R_5$ is as defined in table D.

Table H-70 provides 7 compounds H-70.001 to H-70.007 of formula I-3-Qa wherein A is CH, X is SO, $R_1$ is $CF_3$, $R_2$ is Et and $R_5$ is as defined in table D.

Table H-71 provides 7 compounds H-71.001 to H-71.007 of formula I-3-Qa wherein A is CH, X is SO, $R_1$ is $CF_3$, $R_2$ is $CH_2CF_3$ and $R_5$ is as defined in table D.

Table H-72 provides 7 compounds H-72.001 to H-72.007 of formula I-3-Qa wherein A is CH, X is SO, $R_1$ is $CF_3$, $R_2$ is $CF_3$ and $R_5$ is as defined in table D.

Table H-73 provides 7 compounds H-73.001 to H-73.007 of formula I-3-Qa wherein A is CH, X is SO, $R_1$ is $CH_3$, $R_2$ is H and $R_5$ is as defined in table D.

Table H-74 provides 7 compounds H-74.001 to H-74.007 of formula I-3-Qa wherein A is CH, X is SO, $R_1$ is $CH_3$, $R_2$ is CN and $R_5$ is as defined in table D.

Table H-75 provides 7 compounds H-75.001 to H-75.007 of formula I-3-Qa wherein A is CH, X is SO, $R_1$ is $CH_3$, $R_2$ is $COCH_3$ and $R_5$ is as defined in table D.

Table H-76 provides 7 compounds H-76.001 to H-76.007 of formula I-3-Qa wherein A is CH, X is SO, $R_1$ is $CH_3$, $R_2$ is cPr and $R_5$ is as defined in table D.

Table H-77 provides 7 compounds H-77.001 to H-77.007 of formula I-3-Qa wherein A is CH, X is SO, $R_1$ is $CH_3$, $R_2$ is Me and $R_5$ is as defined in table D.

Table H-78 provides 7 compounds H-78.001 to H-78.007 of formula I-3-Qa wherein A is CH, X is SO, $R_1$ is $CH_3$, $R_2$ is Et and $R_5$ is as defined in table D.

Table H-79 provides 7 compounds H-79.001 to H-79.007 of formula I-3-Qa wherein A is CH, X is SO, $R_1$ is $CH_3$, $R_2$ is $CH_2CF_3$ and $R_5$ is as defined in table D.

Table H-80 provides 7 compounds H-80.001 to H-80.007 of formula I-3-Qa wherein A is CH, X is SO, $R_1$ is $CH_3$, $R_2$ is $CF_3$ and $R_5$ is as defined in table D.

Table H-81 provides 7 compounds H-81.001 to H-81.007 of formula I-3-Qa wherein A is CH, X is $SO_2$, $R_1$ is $CF_3$, $R_2$ is H and $R_5$ is as defined in table D.

Table H-82 provides 7 compounds H-82.001 to H-82.007 of formula I-3-Qa wherein A is CH, X is $SO_2$, $R_1$ is $CF_3$, $R_2$ is CN and $R_5$ is as defined in table D.

Table H-83 provides 7 compounds H-83.001 to H-83.007 of formula I-3-Qa wherein A is CH, X is $SO_2$, $R_1$ is $CF_3$, $R_2$ is $COCH_3$ and $R_5$ is as defined in table D.

Table H-84 provides 7 compounds H-84.001 to H-84.007 of formula I-3-Qa wherein A is CH, X is $SO_2$, $R_1$ is $CF_3$, $R_2$ is cPr and $R_5$ is as defined in table D.

Table H-85 provides 7 compounds H-85.001 to H-85.007 of formula I-3-Qa wherein A is CH, X is $SO_2$, $R_1$ is $CF_3$, $R_2$ is Me and $R_5$ is as defined in table D.

Table H-86 provides 7 compounds H-86.001 to H-86.007 of formula I-3-Qa wherein A is CH, X is $SO_2$, $R_1$ is $CF_3$, $R_2$ is Et and $R_5$ is as defined in table D.

Table H-87 provides 7 compounds H-87.001 to H-87.007 of formula I-3-Qa wherein A is CH, X is $SO_2$, $R_1$ is $CF_3$, $R_2$ is $CH_2CF_3$ and $R_5$ is as defined in table D.

Table H-88 provides 7 compounds H-88.001 to H-88.007 of formula I-3-Qa wherein A is CH, X is $SO_2$, $R_1$ is $CF_3$, $R_2$ is $CF_3$ and $R_5$ is as defined in table D.

Table H-89 provides 7 compounds H-89.001 to H-89.007 of formula I-3-Qa wherein A is CH, X is $SO_2$, $R_1$ is $CH_3$, $R_2$ is H and $R_5$ is as defined in table D.

Table H-90 provides 7 compounds H-90.001 to H-90.007 of formula I-3-Qa wherein A is CH, X is $SO_2$, $R_1$ is $CH_3$, $R_2$ is CN and $R_5$ is as defined in table D.

Table H-91 provides 7 compounds H-91.001 to H-91.007 of formula I-3-Qa wherein A is CH, X is $SO_2$, $R_1$ is $CH_3$, $R_2$ is $COCH_3$ and $R_5$ is as defined in table D.

Table H-92 provides 7 compounds H-92.001 to H-92.007 of formula I-3-Qa wherein A is CH, X is $SO_2$, $R_1$ is $CH_3$, $R_2$ is cPr and $R_5$ is as defined in table D.

Table H-93 provides 7 compounds H-93.001 to H-93.007 of formula I-3-Qa wherein A is CH, X is $SO_2$, $R_1$ is $CH_3$, $R_2$ is Me and $R_5$ is as defined in table D.

Table H-94 provides 7 compounds H-94.001 to H-94.007 of formula I-3-Qa wherein A is CH, X is $SO_2$, $R_1$ is $CH_3$, $R_2$ is Et and $R_5$ is as defined in table D.

Table H-95 provides 7 compounds H-95.001 to H-95.007 of formula I-3-Qa wherein A is CH, X is $SO_2$, $R_1$ is $CH_3$, $R_2$ is $CH_2CF_3$ and $R_5$ is as defined in table D.

Table H-96 provides 7 compounds H-96.001 to H-96.007 of formula I-3-Qa wherein A is CH, X is $SO_2$, $R_1$ is $CH_3$, $R_2$ is $CF_3$ and $R_5$ is as defined in table D.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order *Acarina*. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the above mentioned animal pests are:

from the order *Acarina*, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizogly-*

*phus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order *Coleoptera*, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., Psylliodes spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order *Diptera*, for example,

*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euschistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans*, Oebalus *insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens;*

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae*, Amarasca *biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma*, Hoplo-*campa* spp., *Lasius* spp., *Monomorium pharaonis, Neodiprion* spp., *Pogonomyrmex* spp, Slenopsis *invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order *Lepidoptera*, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypi-ela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., Sylepta derogate, *Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order *Siphonaptera*, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp orjute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare,*

*Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosmarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo suppressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo suppressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, Meloidogyne *hapla*, Meloidogyne *incognita*, Meloidogyne *javanica*, Meloidogyne *arenaria* and other Meloidogyne species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, Criconema species, Criconemella species, Criconemoides species, Mesocriconema species; Stem and bulb nematodes, *Ditylenchus* destructor, *Ditylenchus dipsaci* and other *Ditylenchus* species; Awl nematodes, Dolichodorus species; Spiral nematodes, Heliocotylenchus *multicinctus* and other *Helicotylenchus* species; Sheath and sheathoid nematodes, Hemicycliophora species and Hemicriconemoides species; Hirshmanniella species; Lance nematodes, *Hoploaimus* species; false rootknot nematodes, Nacobbus species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; Scutellonema species; Stubby root nematodes, *Trichodorus primitivus* and other *Trichodorus* species, Paratrichodorus species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp. Particularly, the nematode species *Meloidogyne* spp. (*Meloidogyne incognita*), *Heterodera* spp. (*Heterodera schachtih*), *Rotylenchus* spp. and *Pratylenchus* spp. can be controlled by compounds of the invention.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1 Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and moths (*Lepidoptera*).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order *Lepidoptera* as mentioned above and from the order *Coleoptera*, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

| Examples of native woodborers of economic importance. | | |
|---|---|---|
| Family | Species | Host or Crop Infested |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |

TABLE B-continued

| Examples of native woodborers of economic importance. | | |
|---|---|---|
| Family | Species | Host or Crop Infested |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus* verstitus and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes* cynodoniensis), rhodesgrass mealybug (*Antonina graminis*), two-lined spittlebug (Propsapia *bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and Phtirus spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order *Diptera* and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fan-*

*nia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., Panstrongylus spp.

Of the order Blattarida, for example *Blatta orientalis, Periplaneta americana*, Blattelagermanica and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum*, Xestobium *rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirexjuvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
- active ingredient: 1 to 95%, preferably 60 to 90%
- surface-active agent: 1 to 30%, preferably 5 to 20%
- liquid carrier: 1 to 80%, preferably 1 to 35%

Dusts:
- active ingredient: 0.1 to 10%, preferably 0.1 to 5%
- solid carrier: 99.9 to 90%, preferably 99.9 to 99%

Suspension Concentrates:
- active ingredient: 5 to 75%, preferably 10 to 50%
- water: 94 to 24%, preferably 88 to 30%
- surface-active agent: 1 to 40%, preferably 2 to 30%

Wettable Powders:
- active ingredient: 0.5 to 90%, preferably 1 to 80%
- surface-active agent: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |

-continued

| Emulsifiable concentrate | |
|---|---|
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder dranules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$ or $(M-H)^-$.

LCMS Methods:

Method 1:

Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters:

Binary pump, heated column compartment and diode-array detector. Column: Waters UPLC HSS T3 C18, 1.8 μm, 30×2.1 mm, Temp: 40° C., DAD Wavelength range (nm): 210 to 400, Solvent Gradient: A=water+5% Acetonitrile+0.1% HCOOH, B=Acetonitrile+0.05% HCOOH: gradient: 0 min 10% B; 0-0.2 min 10-50% B; 0.2-0.7 min 50-100% B; 0.7-1.3 min 100% B; 1.3-1.4 min 100-10% B; 1.4-1.6 min 10% B; Flow (mL/min) 0.6.

Method 2:

Spectra were recorded on a Mass Spectrometer from Agilent Technologies (6410 Triple Quadrupole mass spectrometer) equipped with an equipped with an electrospray source (Polarity: positive or negative ions, MS2 Scan, Capillary: 4.00 kV, Fragmentor: 100 V, Desolvatation Temperature: 350° C., Gas Flow: 11 L/min, Nebulizer Gas: 45 psi, Mass range: 110 to 1000 Da) and a 1200 Series HPLC from Agilent: quaternary pump, heated column compartment and diode-array detector. Column: KINETEX EVO C18, 2.6 μm, 50×4.6 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 0% B, 100% A; 0.9-1.8 min 100% B; 1.8-2.2 min 100-10% B; 2.2-2.5 min 10% B; Flow (mL/min) 1.8.

Example P1: Preparation of [2-[5-[[dimethyl(oxo)-$\lambda^6$-sulfanylidene]amino]-3-ethylsulfonyl-2-pyridyl]-1,3-benzoxazol-5-yl]-imino-oxo-(trifluoromethyl)-$\lambda^6$-sulfane (compound P1

(P1)

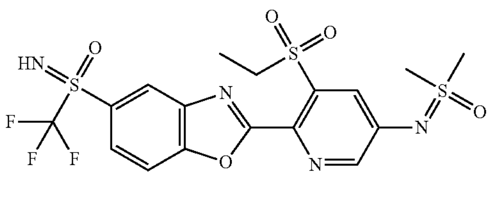

Step 1: Preparation of 5-bromo-3-ethylsulfonyl-N-[2-hydroxy-5-(trifluoromethylsulfanyl)phenyl]pyridine-2-carboxamide (Intermediate I1

(I1)

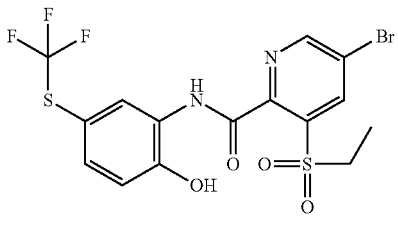

To a 0° C. cooled suspension of 5-bromo-3-ethylsulfonyl-pyridine-2-carboxylic acid (CAS 2098699-89-7, prepared as described in WO 2018215304) (5.3 g, 18 mmol) in dichloromethane (53 mL) and DMF (1.8 mL) was added oxalyl dichloride (3.2 mL, 36 mmol) dropwise via syringe. The resulting off white suspension was stirred at room temperature for 2 hours. Reaction mass was evaporated to dryness under nitrogen atmosphere to afford crude 5-bromo-3-ethylsulfonyl-pyridine-2-carbonyl chloride which was used as such for the next step.

To a 0° C. cooled solution of 2-amino-4-(trifluoromethylsulfanyl)phenol (CAS 228401-48-7, prepared as described in WO 2011040629) (4.5 g, 21 mmol) in tetrahydrofuran (20 mL) was added N,N-diisopropylethylamine (6.1 mL, 36 mmol) followed by addition of the freshly prepared solution of 5-bromo-3-ethylsulfonyl-pyridine-2-carbonyl chloride in THE (20 mL). Reaction mass was stirred for 16 hours at room temperature, then quenched with water (100 mL) and extracted with ethyl acetate (3×80 mL). Combined organic layers were washed with brine (100 mL), dried over sodium sulfate, filtered and concentrated in vacuo. The crude compound was purified using combiflash (silica-gel, 10-15% ethyl acetate in cyclohexane) to afford 5-bromo-3-ethylsulfonyl-N-[2-hydroxy-5-(trifluoromethyl-sulfanyl)phenyl] pyridine-2-carboxamide. LCMS (method 1): retention time 1.11 min, 485 $(M+H)^+$.

Step 2: Preparation of 2-(5-bromo-3-ethylsulfonyl-2-pyridyl)-5-(trifluoromethylsulfanyl)-1,3-benzoxazole (Intermediate I2

(I2)

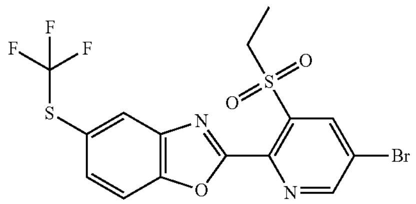

To a stirred solution of 5-bromo-3-ethylsulfonyl-N-[2-hydroxy-5-(trifluoromethylsulfanyl)phenyl]pyridine-2-carboxamide (intermediate I1 prepared as described above) (4.5 g, 9.3 mmol) in m-xylene (45 mL) was added 4-methylbenzenesulfonic acid hydrate (1.6 g, 9.3 mmol) at room temperature and reaction mass was heated at 160° C. for 9 hours. Reaction mixture was cooled to room temperature, diluted with water (50 mL) and extracted with ethyl acetate (3×50 mL). Combined organic layers were washed with brine (50 mL), dried over sodium sulfate, filtered and concentrated in vacuo. The crude compound was purification using combiflash (silica gel, 10-15% ethyl acetate in cyclohexane) to afford 2-(5-bromo-3-ethylsulfonyl-2-pyridyl)-5-(trifluoromethylsulfanyl)-1,3-benzoxazole.

LCMS (method 1): retention time 1.23 min, 476 $(M+H)^+$. 1H NMR (400 MHz, DMSO-$d_6$) δ ppm 1.28 (t, 3H), 3.91-3.98 (m, 2H), 7.91 (dd, 1H), 8.10 (d, 1H), 8.38 (d, 1H), 8.74 (d, 1H), 9.30 (d, 1H).

Step 3: Preparation of [5-ethylsulfonyl-6-[5-(trifluoromethylsulfanyl)-1,3-benzoxazol-2-yl]-3-pyridyl]imino-dimethyl-oxo-$\lambda^6$-sulfane (Intermediate I3

(I3)

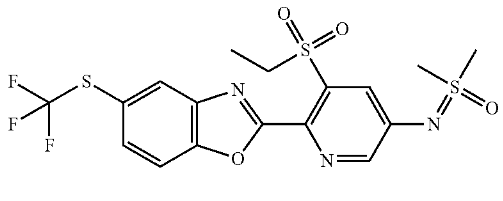

To a solution of 2-(5-bromo-3-ethylsulfonyl-2-pyridyl)-5-(trifluoromethylsulfanyl)-1,3-benzoxazole (intermediate I2 prepared as described above) (0.59 g, 1.26 mmol) in 1,4-dioxane (5.0 mL) was added (dimethanesulfinylidene) amine (0.136 g, 1.38 mmol), cesium carbonate (0.827 g, 2.52 mmol) and (5-diphenylphosphanyl-9,9-dimethyl-xanthen-4-yl)-diphenyl-phosphane (0.15 g, 0.25 mmol). The reaction mass was degassed with nitrogen for 10 min, to this was then added (1E,4E)-1,5-diphenylpenta-1,4-dien-3-one; palladium (0.11 g, 0.12 mmol). Reaction mass was refluxed at 110° C. for 3 hours under nitrogen atmosphere, then diluted with water (30 mL), extracted with ethyl acetate (3x30 mL). Combined organic layers were dried over sodium sulfate, filtered and concentrated in vacuo. The crude product was purified by combiflash (silica gel, 10% Methanol in dichloromethane) to afford [[5-ethylsulfonyl-6-[5-(trifluoromethylsulfanyl)-1,3-benzoxazol-2-yl]-3-pyridyl]imino-dimethyl-oxo-$\lambda^6$-sulfane. LCMS (method 1): retention time 1.05 min, 480 $(M+H)^+$. $^1H$ NMR (400 MHz, chloroform-d) δ ppm 1.44 (t, 3H), 3.32 (s, 6H), 4.05 (q, 2H), 7.68-7.75 (m, 2H), 8.14-8.18 (m, 2H), 8.70 (d, 1H).

Step 4: Preparation of [2-[5-[[dimethyl(oxo)-$\lambda^6$-sulfanylidene]amino]-3-ethylsulfonyl-2-pyridyl]-1,3-benzoxazol-5-yl]-imino-oxo-(trifluoromethyl)-$\lambda^6$-sulfane (compound P1

(P1)

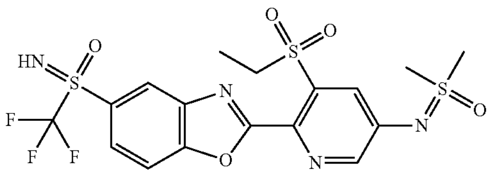

To a stirred solution of [[5-ethylsulfonyl-6-[5-(trifluoromethylsulfanyl)-1,3-benzoxazol-2-yl]-3-pyridyl]imino-dimethyl-oxo-$\lambda^6$-sulfane (intermediate I3 prepared as described above) (0.4 g, 0.83 mmol) in 2,2,3,3,4,4,5,5-octafluoropentan-1-ol (7.0 mL) was added ammonium carbamate (0.19 g, 2.5 mmol), followed by $PhI(OAc)_2$ (1.15 g, 3.5 mmol) at room temperature. The reaction mixture was stirred at room temperature for 6 hours. Reaction mass was quenched with ice cold water (20 mL), extracted with ethyl acetate (3x20 mL). Combined organic layers were washed with sodium thiosulfate solution (20 mL) and brine (20 mL), dried over sodium sulfate, filtered and concentrated in vacuo. The crude product was purified by combiflash (silica gel, 10% MeOH in dichloromethane) to afford [2-[5-[[dimethyl(oxo)-$\lambda^6$-sulfanylidene]amino]-3-ethylsulfonyl-2-pyridyl]-1,3-benzoxazol-5-yl]-imino-oxo-(trifluoromethyl)-$\lambda^6$-sulfane. LCMS (method 1): retention time 0.91 min, 511 $(M+H)^+$.

1H NMR (400 MHz, acetone-$d_6$) δ ppm 1.32-1.41 (m, 3H), 3.49 (s, 6H), 3.94 (q, 2H), 8.05 (d, 1H), 8.16 (d, 1H), 8.32 (d, 1H), 8.32 (d, 1H), 8.58-8.63 (m, 2H).

Example P2: Preparation of [2-[5-[[dimethyl(oxo)-$\lambda^6$-sulfanylidene]amino]-3-ethylsulfonyl-2-pyridyl]-1,3-benzoxazol-5-yl]-ethylimino-oxo-(trifluoromethyl)-$\lambda^6$-sulfane (compound P2

(P2)

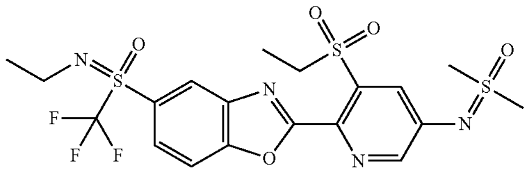

Step 1: Preparation of [2-(5-bromo-3-ethylsulfonyl-2-pyridyl)-1,3-benzoxazol-5-yl]-imino-oxo-(trifluoromethyl)-$\lambda^6$-sulfane (Intermediate I4

(I4)

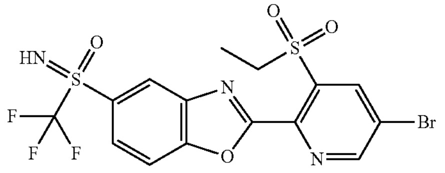

To a stirred solution of 2-(5-bromo-3-ethylsulfonyl-2-pyridyl)-5-(trifluoromethylsulfanyl)-1,3-benzoxazole (intermediate I2 prepared as described above) (0.9 g, 1.92 mmol) in 2,2,3,3,4,4,5,5-octafluoropentan-1-ol (12.0 mL) was added ammonium carbamate (0.46 g, 5.77 mmol) followed by $PhI(OAc)_2$ (2.65 g, 8.09 mmol) at room temperature. The reaction mixture was stirred at room temperature for 16 hours. Reaction mass was quenched with ice cold water (50 mL), extracted with ethyl acetate (3x50 mL). Combined organic layers were washed with sodium thiosulfate solution (50 mL) and brine (50 mL), dried over sodium sulfate, filtered and concentrated in vacuo. The crude product was purified by combiflash (silica gel, 40% ethyl acetate in cyclohexane) to afford [2-(5-bromo-3-ethylsulfonyl-2-pyridyl)-1,3-benzoxazol-5-yl]-imino-oxo-(trifluoromethyl)-$\lambda^6$-sulfane.

LCMS (method 1): retention time 1.05 min, 498 $(M+H)^+$.

Step 2: Preparation of [2-(5-bromo-3-ethylsulfonyl-2-pyridyl)-1,3-benzoxazol-5-yl]-ethylimino-oxo-(trifluoromethyl)-$\lambda^6$-sulfane (Intermediate I5

(I5)

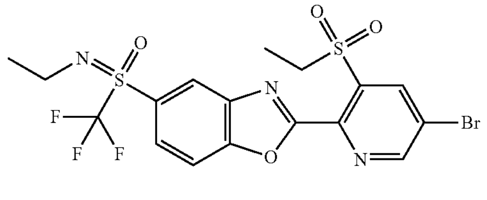

To a stirred solution of [2-(5-bromo-3-ethylsulfonyl-2-pyridyl)-1,3-benzoxazol-5-yl]-imino-oxo-(trifluoromethyl)-$\lambda^6$-sulfane (intermediate I4 prepared as described above) (1.5 g, 3.0 mmol) in N,N-dimethylformamide (15.0 mL) was added potassium carbonate (1.2 g, 9.0 mmol) followed by iodoethane (700 mg, 4.5 mmol). Reaction mass was stirred at room temperature for 4 hours, then quenched with ice cold water (80 mL), extracted with ethyl acetate (3×50 mL). Combined organic layers were dried over sodium sulfate, filtered and concentrated in vacuo. The crude product was purified by combiflash (silica gel, 40% ethyl acetate in cyclohexane) to afford [2-(5-bromo-3-ethylsulfonyl-2-pyridyl)-1,3-benzoxazol-5-yl]-ethylimino-oxo-(trifluoromethyl)-$\lambda^6$-sulfane.

LCMS (method 1): retention time 1.21 min, 526 $(M+H)^+$.

Step 3: Preparation of [2-[5-[[dimethyl(oxo)-$\lambda^6$-sulfanylidene]amino]-3-ethylsulfonyl-2-pyridyl]-1,3-benzoxazol-5-yl]-ethylimino-oxo-(trifluoromethyl)-$\lambda^6$-sulfane (compound P2

(P2)

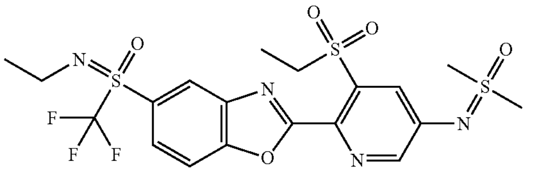

To a solution of [2-(5-bromo-3-ethylsulfonyl-2-pyridyl)-1,3-benzoxazol-5-yl]-ethylimino-oxo-(trifluoromethyl)-$\lambda^6$-sulfane (intermediate I5 prepared as described above) (0.70 g, 1.33 mmol) in 1,4-dioxane (5.0 mL) was added (dimethanesulfinylidene)amine (0.14 g, 1.46 mmol), cesium carbonate (0.87 g, 2.66 mmol) and (5-diphenylphosphanyl-9, 9-dimethyl-xanthen-4-yl)-diphenyl-phosphane (0.15 g, 0.26 mmol). The reaction mass was degassed with nitrogen for 10 min, to this was then added (1E,4E)-1,5-diphenylpenta-1,4-dien-3-one; palladium (0.12 g, 0.13 mmol). Reaction mass was refluxed at 110° C. for 3 hours under nitrogen atmosphere, then diluted with water (30 mL), extracted with ethyl acetate (3×30 mL). Combined organic layers were dried over sodium sulfate, filtered and concentrated in vacuo. The crude product was purified by combiflash (silica gel, 10% methanol in dichloromethane) to afford [2-[5-[[dimethyl(oxo)-$\lambda^6$-sulfanylidene]amino]-3-ethylsulfonyl-2-pyridyl]-1,3-benzoxazol-5-yl]-ethylimino-oxo-(trifluoromethyl)-$\lambda^6$-sulfane as a white solid. LCMS (method 1): retention time 1.07 min, 539 $(M+H)^+$. 1H NMR (400 MHz, chloroform-d) δ ppm 1.31-1.38 (m, 3H), 1.43-1.48 (m, 3H), 3.33 (s, 6H), 3.39-3.63 (m, 1H), 3.40-3.61 (m, 1H), 3.96-4.08 (m, 2H), 7.79-7.92 (m, 1H), 8.13-8.22 (m, 2H), 8.50-8.71 (m, 2H).

Example P3: Preparation of N-[5-ethylsulfonyl-6-[5-[N-ethyl-S-(trifluoromethyl)sulfonimidoyl]-1,3-benzoxazol-2-yl]-3-pyridyl]-N-methyl-acetamide (compound P3

(P3)

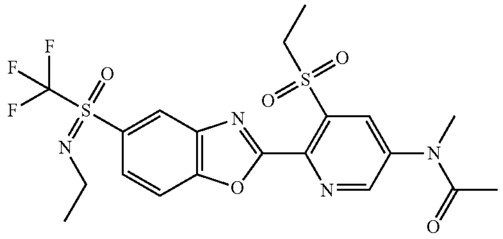

Step 1: Preparation of tert-butyl 5-bromo-3-ethylsulfanyl-pyridine-2-carboxylate (intermediate I6

(I6)

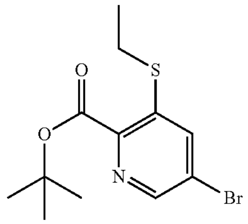

4-Dimethylaminopyridine (0.23 g, 0.19 mmol) and di-tert-butyl dicarbonate (6.31 g, 28.6 mmol) were added to a solution of 5-bromo-3-ethylsulfanyl-pyridine-2-carboxylic acid (CAS 1857366-13-2, prepared as described in WO2017084879) (5.00 g, 19.1 mmol) in acetonitrile (100 mL) with triethylamine (4.03 mL, 28.6 mmol). The reaction mixture was heated at 50° C. overnight. After cooling down to room temperature, the reaction mixture was diluted with water (80 mL) and the aqueous phase was extracted with ethyl acetate (3×100 mL). The combined organic phases were dried over sodium sulfate, filtered and concentrated in vacuo. The crude oil obtained was purified by flash chromatography over silica gel (35% ethyl acetate in cyclohexane) to afford the desired compound as a yellow oil. $^1$H NMR (400 MHz, chloroform-d) δ ppm: 1.39-1.45 (m, 3H), 1.65 (s, 9H), 2.92 (q, J=7.34 Hz, 2H), 7.75 (d, J=1.96 Hz, 1H), 8.45 (d, J=1.96 Hz, 1H).

Step 2: Preparation of tert-butyl 5-bromo-3-ethylsulfonyl-pyridine-2-carboxylate (intermediate I7

(I7)

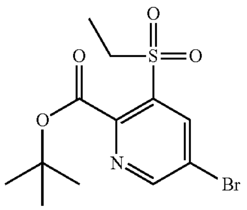

3-Chloroperbenzoic acid (2.20 g, 9.70 mmol) was added in portions to a 0° C. cooled solution of tert-butyl 5-bromo-3-ethylsulfanyl-pyridine-2-carboxylate (intermediate I6 prepared as described above) (1.50 g, 4.70 mmol) in dichloromethane (27 mL). The reaction mixture was stirred at 0° C. for 40 min, then at room temperature for 2 hours. After quenching with a saturated sodium thiosulfate solution (10 mL), and 1N sodium hydroxide (10 mL), the aqueous phase was extracted with dichloromethane (3x30 mL). The combined organic phases were dried over sodium sulfate, filtered and concentrated in vacuo. The crude material was used in the next step without further purification. $^{1}H$ NMR (400 MHz, chloroform-d) δ ppm: 1.35 (t, 3H), 1.65 (s, 9H), 3.53 (q, 2H), 8.45 (d, 1H), 8.87 (d, 1H).

Step 3: Preparation of tert-butyl 3-ethylsulfonyl-5-(methylamino)pyridine-2-carboxylate (intermediate I8

(I8)

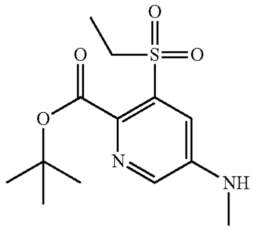

A mixture of tert-butyl 5-bromo-3-ethylsulfonyl-pyridine-2-carboxylate (intermediate I7 prepared as described above) (1.30 g, 3.70 mmol), methylamine (40% in water solution) (1.0 mL, 11.6 mmol) and copper powder (47 mg, 0.74 mmol) in tetrahydrofuran (4.0 mL) was heated at 100° C. in a sealed tube for 8 hours. After cooling down to room temperature, the reaction mixture was quenched with water (10 mL), and the aqueous phase was extracted with ethyl acetate (3x30 mL). The combined organic phases were dried over sodium sulfate, filtered and concentrated in vacuo. The crude material was used directly without purification. LCMS (method 3): retention time 1.06 min, 299 $(M-H)^-$.

$^{1}H$ NMR (400 MHz, chloroform-d) δ ppm 1.26 (t, J=7.15 Hz, 3H), 1.62 (s, 1H), 2.94 (s, 3H), 3.59 (q, J=7.46 Hz, 2H), 7.39 (s, 1H), 8.3 (br s, 1H).

Step 4: Preparation of tert-butyl 5-[acetyl(methyl)amino]-3-ethylsulfonyl-pyridine-2-carboxylate (intermediate I9

(I9)

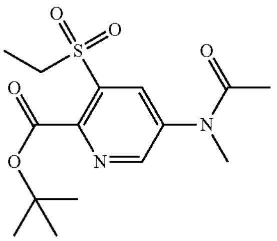

To tert-butyl 3-ethylsulfonyl-5-(methylamino)pyridine-2-carboxylate (intermediate I8 prepared as described above) (2.88 g, 9.59 mmol) was added anhydrous acetic anhydride (25 mL) and the reaction mass was heated at 60° C. for 2 h. The reaction mixture was diluted with ice water (80 mL), extracted with ethyl acetate (3x60 mL). Combined organic layers were washed with brine (30 mL), dried over sodium sulfate, filtered and concentrated in vacuo. The crude compound was co-evaporated with toluene (3x20 mL) to afford tert-butyl 5-[acetyl(methyl)amino]-3-ethylsulfonyl-pyridine-2-carboxylate as a solid. LCMS (method 1): retention time 0.90 min, 287 $(M+H)^+$.

Step 5: Preparation of 5-[acetyl(methyl)amino]-3-ethylsulfonyl-pyridine-2-carboxylic acid (intermediate I10

(I10)

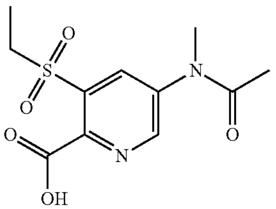

To a solution of tert-butyl 5-[acetyl(methyl)amino]-3-ethylsulfonyl-pyridine-2-carboxylate (intermediate I9 prepared as described above) (3.2 g, 9.3 mmol) in dichloromethane (20 mL) was added dropwise 2,2,2-trifluoroacetic acid (11 mL, 140 mmol) at room temperature. Reaction mass was stirred at room temperature for 16 hours, then concentrated in vacuo. The residue was co-evaporated 3x with toluene to afford 5-[acetyl(methyl)amino]-3-ethylsulfonyl-pyridine-2-carboxylic acid as an off-white solid, which was used as such for the next step. LCMS (method 1): retention time 0.14 min, 287 $(M+H)^+$. 1H NMR (400 MHz, DMSO-d6) δ ppm 1.19 (t, 3H), 2.08 (br s, 3H), 3.34 (br s, 3H), 3.50-3.60 (m, 2H), 8.29-8.36 (m, 1H), 8.91 (s, 1H).

Step 6: Preparation of 5-[acetyl(methyl)amino]-3-ethylsulfonyl-N-[2-hydroxy-5-(trifluoromethylsulfanyl)phenyl]pyridine-2-carboxamide (intermediate I11

(I11)

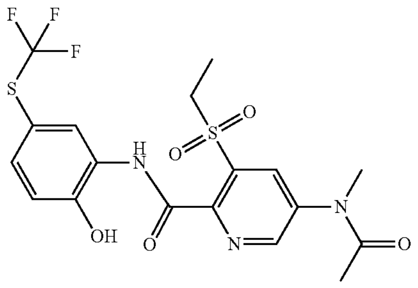

To a 0° C. cooled suspension of 5-[acetyl(methyl)amino]-3-ethylsulfonyl-pyridine-2-carboxylic acid (intermediate I10 prepared as described above) (2.7 g, 9.4 mmol) in dichloromethane (27 mL) and DMF (0.94 mL) was added oxalyl dichloride (1.7 mL, 19 mmol) dropwise via syringe. The resulting off white suspension was stirred at room temperature for 2 hours. Reaction mass was evaporated to dryness under nitrogen atmosphere to afford crude 5-[acetyl(methyl)amino]-3-ethylsulfonyl-pyridine-2-carbonyl chloride which was used as such for the next step.

To a 0° C. cooled solution of 2-amino-4-(trifluoromethylsulfanyl)phenol (CAS 228401-48-7, prepared as described in WO 2011040629) (2.4 g, 11 mmol) in tetrahydrofuran (20 mL) was added N,N-diisopropylethylamine (4.9 mL, 28 mmol), followed by addition of the freshly prepared solution of 5-[acetyl(methyl)amino]-3-ethylsulfonyl-pyridine-2-carbonyl chloride in THE (20 mL). Reaction mass was stirred for 16 hours at room temperature, then quenched with water (100 mL) and extracted with ethyl acetate (3×80 mL). Combined organic layers were washed with brine (100 mL), dried over sodium sulfate, filtered and concentrated in vacuo. The crude compound was purified using combiflash (silica-gel, 10% MeOH in dichloromethane) to afford 5-[acetyl(methyl)amino]-3-ethylsulfonyl-N-[2-hydroxy-5-(trifluoromethylsulfanyl)phenyl]pyridine-2-carboxamide. LCMS (method 1): retention time 0.99 min, 478 $(M+H)^+$.

Step 7: Preparation of 5-ethylsulfonyl-N-methyl-6-[5-(trifluoromethylsulfanyl)-1,3-benzoxazol-2-yl]pyridin-3-amine (Intermediate I12

(I12)

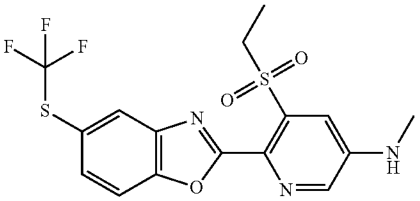

To a stirred solution of 5-[acetyl(methyl)amino]-3-ethylsulfonyl-N-[2-hydroxy-5-(trifluoromethylsulfanyl)phenyl]pyridine-2-carboxamide (intermediate I11 prepared as described above) (1.2 g, 2.9 mmol) in m-xylene (20 mL) was added 4-methylbenzenesulfonic acid hydrate (1.29 g, 7.35 mmol) at room temperature and reaction mass was heated at 160° C. for 3 h, followed by 120° C. for 16 hours. Reaction mixture was cooled to room temperature, diluted with water (50 mL) and extracted with ethyl acetate (3×50 mL). Combined organic layers were washed with brine (50 mL), dried over sodium sulfate, filtered and concentrated in vacuo. The crude compound was purification using combiflash (silica gel, 40% ethyl acetate in cyclohexane) to afford pure 5-ethylsulfonyl-N-methyl-6-[5-(trifluoromethylsulfanyl)-1,3-benzoxazol-2-yl]pyridin-3-amine. LCMS (method 1): retention time 1.09 min, 418 $(M+H)^+$. 1H NMR (400 MHz, chloroform-d) δ ppm 1.44 (t, 3H), 3.05 (s, 3H), 4.05-4.16 (m, 2H), 7.64-7.72 (m, 3H), 8.13 (s, 1H), 8.32 (d, 1H).

Step 8: Preparation of N-[5-ethylsulfonyl-6-[5-(trifluoromethylsulfanyl)-1,3-benzoxazol-2-yl]-3-pyridyl]-N-methyl-acetamide (Intermediate I13

(I13)

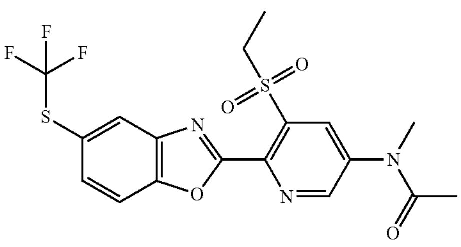

To 5-ethylsulfonyl-N-methyl-6-[5-(trifluoromethylsulfanyl)-1,3-benzoxazol-2-yl]pyridin-3-amine (intermediate I12 prepared as described above) (1.5 g, 3.6 mmol) was added anhydrous acetic anhydride (15 mL) and the reaction mass was heated at 60° C. for 2 hours. The reaction mass was diluted with ice water (50 mL), extracted with ethyl acetate (3×60 mL). Combined organic layers were washed with brine (30 mL), dried over sodium sulfate, filtered and concentrated in vacuo. The crude compound was co-evaporated with toluene (3×20 mL) to afford N-[5-ethylsulfonyl-6-[5-(trifluoromethylsulfanyl)-1,3-benzoxazol-2-yl]-3-pyridyl]-N-methyl-acetamide as an off-white solid.

LCMS (method 1): retention time 1.05 min, 460 $(M+H)^+$. 1H NMR (400 MHz, chloroform-d) δ ppm 1.47 (t, 3H), 2.25 (br s, 3H), 3.51 (s, 3H), 4.09 (q, 2H), 7.73-7.80 (m, 2H), 8.18-8.21 (m, 1H), 8.48 (d, 1H), 8.98 (br s, 1H).

Step 9: Preparation of N-[5-ethylsulfonyl-6-[5-(trifluoromethylsulfonimidoyl)-1,3-benzoxazol-2-yl]-3-pyridyl]-N-methyl-acetamide (compound P4

(P4)

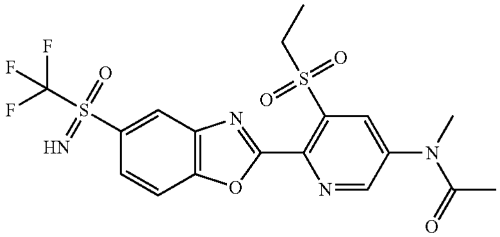

To a stirred solution of N-[5-ethylsulfonyl-6-[5-(trifluoromethylsulfanyl)-1,3-benzoxazol-2-yl]-3-pyridyl]-N-methyl-acetamide (intermediate I13 prepared as described above) (1.2 g, 2.6 mmol) in 2,2,3,3,4,4,5,5-octafluoropentan-1-ol (8.0 mL) was added ammonium carbamate (0.51 g, 6.5 mmol), followed by $PhI(OAc)_2$ (2.6 g, 7.8 mmol) at room temperature. The reaction mixture was stirred at room temperature for 8 hours, then quenched with ice cold water (30 mL), extracted with ethyl acetate (3×30 mL). Combined organic layers were washed with sodium thiosulfate solution (20 mL) and brine (20 mL), dried over sodium sulfate, filtered and concentrated in vacuo. The crude product was purified by combiflash (silica gel, 60% ethyl acetate in cyclohexane) to afford N-[5-ethylsulfonyl-6-[5-(trifluoromethylsulfonimidoyl)-1,3-benzoxazol-2-yl]-3-pyridyl]-N-methyl-acetamide.

LCMS (method 1): retention time 0.92 min, 491 $(M+H)^+$. 1H NMR (400 MHz, DMSO-d6) δ ppm 1.26-1.32 (m, 3H), 2.19 (br s, 3H), 3.45 (s, 3H), 3.93 (q, 2H), 7.11 (s, 1H), 8.25-8.31 (m, 2H), 8.56 (d, 1H), 8.63-8.65 (m, 1H), 9.15 (d, 1H).

Step 10: Preparation of N-[5-ethylsulfonyl-6-[5-[N-ethyl-S-(trifluoromethyl)sulfonimidoyl]-1,3-benzoxazol-2-yl]-3-pyridyl]-N-methyl-acetamide (compound P3

(P3)

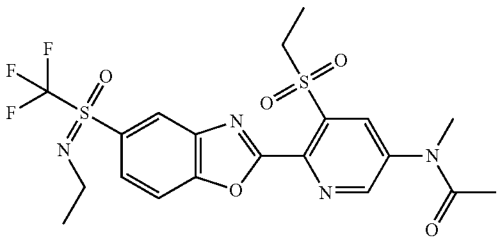

To a stirred solution of N-[5-ethylsulfonyl-6-[5-(trifluoromethylsulfonimidoyl)-1,3-benzoxazol-2-yl]-3-pyridyl]-N-methyl-acetamide (compound P4 prepared as described above) (0.11 g, 0.23 mmol) in N,N-dimethylformamide (3.0 mL) was added potassium carbonate (0.09 g, 0.70 mmol), followed by iodoethane (0.05 g, 0.35 mmol). Reaction mass was stirred at room temperature for 3 hours, then quenched with ice cold water (20 mL), extracted with ethyl acetate (3×20 mL). Combined organic layers were dried over sodium sulfate, filtered and concentrated in vacuo. The crude product was purified by combiflash (silica gel, 60% ethyl acetate in cyclohexane) to afford N-[5-ethylsulfonyl-6-[5-[N-ethyl-S-(trifluoromethyl)sulfonimidoyl]-1,3-benzoxazol-2-yl]-3-pyridyl]-N-methyl-acetamide.

LCMS (method 1): retention time 1.06 min, 519 $(M+H)^+$. 1H NMR (400 MHz, DMSO-d6) δ ppm 1.23-1.32 (m, 6H), 2.19 (br s, 3H), 3.37-3.51 (m, 5H), 3.93 (q, 2H), 8.24-8.32 (m, 2H), 8.56 (d, 1H), 8.64 (d, 1H), 9.15 (d, 1H).

Example P8: Preparation of 1-[5-ethylsulfonyl-6-[5-[N-ethyl-S-(trifluoromethyl)sulfonimidoyl]-1,3-benzoxazol-2-yl]-3-pyridyl]cyclopropanecarbonitrile (compound P8

(P8)

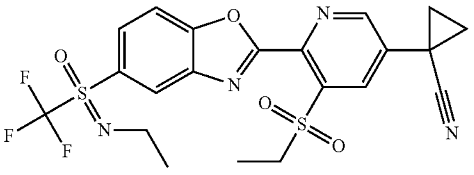

Step 1: Preparation of 5-(1-cyanocyclopropyl)-3-ethylsulfanyl-N-[2-hydroxy-5-(trifluoromethylsulfanyl)phenyl]pyridine-2-carboxamide (intermediate I14

(I14)

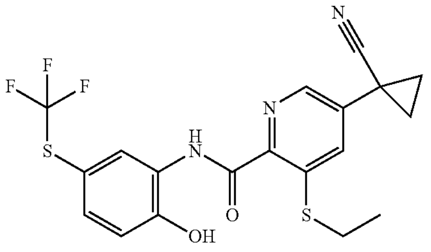

To a 0° C. cooled suspension of 5-(1-cyanocyclopropyl)-3-ethylsulfanyl-pyridine-2-carboxylic acid (CAS 2225113-77-7, prepared as described in WO 2018108726) (3.00 g, 12.1 mmol) in dichloromethane (30 mL) and DMF (1.21 mL) was added oxalyl dichloride (2.13 mL, 24.2 mmol) dropwise via syringe. The resulting off white suspension was stirred at room temperature for 2 hours. Reaction mass was evaporated to dryness under nitrogen atmosphere to afford crude 5-(1-cyanocyclopropyl)-3-ethylsulfanyl-pyridine-2-carbonyl chloride which was used as such for the next step.

To a 0° C. cooled solution of 2-amino-4-(trifluoromethylsulfanyl)phenol (CAS 228401-48-7, prepared as described in WO 2011040629) (2.8 g, 13 mmol) in tetrahydrofuran (30 mL) was added N,N-diisopropylethylamine (3.9 mL, 22 mmol), followed by addition of the freshly prepared solution of 5-(1-cyanocyclopropyl)-3-ethylsulfanyl-pyridine-2-carbonyl chloride (3.0 g, 11 mmol) in THE (50 mL).

Reaction mass was stirred for 16 hours at room temperature, then quenched with water (100 mL) and extracted with ethyl acetate (3×50 mL). Combined organic layers were washed with brine (100 mL), dried over sodium sulfate, filtered and concentrated in vacuo. The crude compound was purified using combiflash (silica-gel, 10-15% ethyl acetate in cyclohexane) to afford 5-(1-cyanocyclopropyl)-3-ethylsulfanyl-N-[2-hydroxy-5-(trifluoromethylsulfanyl)phenyl]pyridine-2-carboxamide. LCMS (method 1): retention time 1.06 min, 440 $(M+H)^+$. 1H NMR (400 MHz, DMSO-d6) δ ppm 1.32 (t, 3H), 1.74-1.85 (m, 2H), 1.85-1.93 (m, 2H), 3.04 (q, 2H), 7.06 (d, 1H), 7.33 (dd, 1H), 7.69 (d, 1H), 8.39 (d, 1H), 8.69 (d, 1H), 10.48 (s, 1H), 11.26 (s, 1H).

Step 2: Preparation of 1-[5-ethylsulfanyl-6-[5-(trifluoromethylsulfanyl)-1,3-benzoxazol-2-yl]-3-pyridyl]cyclopropanecarbonitrile (Intermediate I15

(I15)

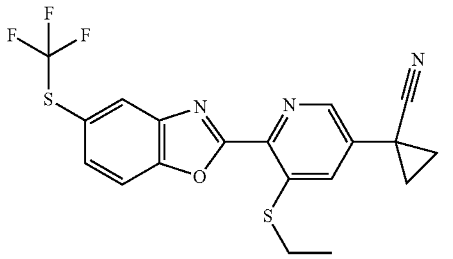

To a stirred solution of 5-(1-cyanocyclopropyl)-3-ethylsulfanyl-N-[2-hydroxy-5-(trifluoromethyl-sulfanyl)phenyl] pyridine-2-carboxamide (intermediate I14 prepared as described above) (3.10 g, 7.05 mmol) in m-xylene (30 mL) was added 4-methylbenzenesulfonic acid hydrate (1.24 g, 7.05 mmol) at room temperature and reaction mass was heated at 160° C. for 9 hours. Reaction mixture was cooled to room temperature, diluted with water (50 mL) and extracted with ethyl acetate (3×50 mL). Combined organic layers were washed with brine (50 mL), dried over sodium sulfate, filtered and concentrated in vacuo. The crude compound was purification using combiflash (silica gel, 10-15% ethyl acetate in cyclohexane) afford pure 1-[5-ethylsulfanyl-6-[5-(trifluoromethylsulfanyl)-1,3-benzoxazol-2-yl]-3-pyridyl]cyclopropanecarbonitrile. LCMS (method 1): retention time 1.14 min, 422 $(M+H)^+$. 1H NMR (400 MHz, chloroform-d) δ ppm 1.49-1.54 (m, 3H), 1.60-1.66 (m, 2H), 1.92-1.99 (m, 2H), 3.12 (q, 2H), 7.70-7.76 (m, 2H), 7.79-7.86 (m, 1H), 8.25-8.33 (m, 2H).

Step 3: Preparation of afford 1-[5-ethylsulfonyl-6-[5-(trifluoromethylsulfanyl)-1,3-benzoxazol-2-yl]-3-pyridyl]cyclopropanecarbonitrile (Intermediate I16

(I16)

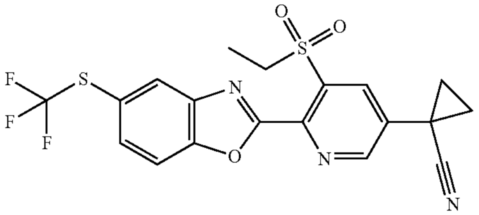

To a 0° C. cooled solution of 1-[5-ethylsulfanyl-6-[5-(trifluoromethylsulfanyl)-1,3-benzoxazol-2-yl]-3-pyridyl] cyclopropanecarbonitrile (intermediate I15 prepared as described above) (2.20 g, 5.22 mmol) in dichloromethane (44.0 mL) was added 3-chlorobenzenecarboperoxoic acid (2.57 g, 10.4 mmol). Reaction mass was allowed to come to room temperature and stirred for 4 hours, then quenched with 2M sodium hydroxide solution (70 mL) and extracted with dichloromethane (3×100 mL). Combined organic layers were dried over sodium sulfate, filtered and concentrated in vacuo. The crude product was purified by combiflash (silica gel, 40% ethyl acetate in cyclohexane) to afford 1-[5-ethylsulfonyl-6-[5-(trifluoromethylsulfanyl)-1,3-benzoxazol-2-yl]-3-pyridyl]cyclopropanecarbonitrile as a white solid.

LCMS (method 1): retention time 1.11 min, 454 $(M+H)^+$. 1H NMR (400 MHz, chloroform-d) δ ppm 1.45 (t, 3H), 1.62-1.73 (m, 2H), 1.99-2.08 (m, 2H), 4.07 (q, 2H), 7.27 (s, 1H), 7.73-7.81 (m, 2H), 8.19 (s, 1H), 8.32 (d, 1H), 9.06 (d, 1H).

Step 4: Preparation of 1-[5-ethylsulfonyl-6-[5-(trifluoromethylsulfonimidoyl)-1,3-benzoxazol-2-yl]-3-pyridyl]cyclopropanecarbonitrile (compound P7

(P7)

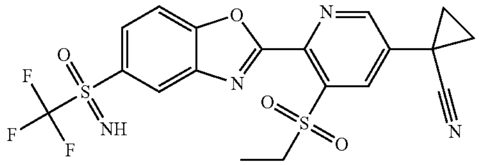

To a stirred solution of 1-[5-ethylsulfonyl-6-[5-(trifluoromethylsulfanyl)-1,3-benzoxazol-2-yl]-3-pyridyl]cyclopropanecarbonitrile (intermediate I16 prepared as described above) (1.0 g, 2.2 mmol) in 2,2,3,3,4,4,5,5-octafluoropentan-1-ol (7.0 mL) was added ammonium carbamate (0.44 g, 5.5 mmol), followed by $PhI(OAc)_2$ (2.2 g, 6.6 mmol) at room temperature. The reaction mixture was stirred at room temperature for 16 hours, then quenched with ice cold water (50 mL), extracted with ethyl acetate (3×50 mL). Combined organic layers were washed with sodium thiosulfate solution (50 mL) and brine (50 mL), dried over sodium sulfate, filtered and concentrated in vacuo. The crude product was purified by combiflash (silica gel, 30% ethyl acetate in cyclohexane) to afford 1-[5-ethylsulfonyl-6-[5-(trifluoromethylsulfonimidoyl)-1,3-benzoxazol-2-yl]-3-pyridyl]cyclopropanecarbonitrile. LCMS (method 1): retention time 1.00 min, 485 $(M+H)^+$. 1H NMR (400 MHz, DMSO-d6) δ ppm 1.23-1.33 (m, 3H), 1.91-2.08 (m, 4H), 3.95 (q, 2H), 7.12 (s, 1H), 8.25-8.33 (m, 2H), 8.43 (d, 1H), 8.66 (s, 1H), 9.04 (d, 1H).

Step 5: Preparation of 1-[5-ethylsulfonyl-6-[5-[N-ethyl-S-(trifluoromethyl)sulfonimidoyl]-1,3-benzoxazol-2-yl]-3-pyridyl]cyclopropanecarbonitrile (compound P8

(P8)

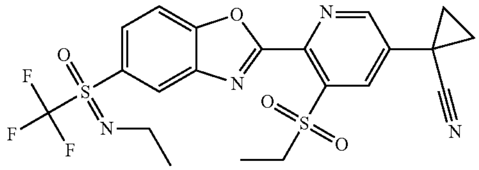

To a stirred solution of 1-[5-ethylsulfonyl-6-[5-(trifluoromethylsulfonimidoyl)-1,3-benzoxazol-2-yl]-3-pyridyl]cyclopropanecarbonitrile (compound P7 prepared as described above) (0.16 g, 0.33 mmol) in N,N-dimethylformamide (2.0 mL) was added potassium carbonate (0.13 g, 0.99 mmol), followed by iodoethane (0.07 g, 0.49 mmol). Reaction mass was stirred at room temperature for 4 hours, then quenched with ice cold water (20 mL), extracted with ethyl acetate (3×20 mL). Combined organic layers were dried over sodium sulfate, filtered and concentrated in vacuo. The crude product was purified by combiflash (silica gel, 30% ethyl acetate in cyclohexane) to afford 1-[5-ethylsulfonyl-6-[5-[N-ethyl-S-(trifluoromethyl)sulfonimidoyl]-1,3-benzoxazol-2-yl]-3-pyridyl]cyclopropanecarbonitrile as a white solid. LCMS (method 1): retention time 1.19 min, 513 $(M+H)^+$. 1H NMR (400 MHz, DMSO-d6) δ ppm 1.23-1.33 (m, 6H), 1.92-2.07 (m, 4H), 3.35-3.52 (m, 2H), 3.95 (q, 2H), 8.25-8.33 (m, 2H), 8.43 (d, 1H), 8.65 (s, 1H), 9.04 (d, 1H).

Example P20: Preparation of 1-[5-ethylsulfonyl-6-[6-[N-ethyl-S-(trifluoromethyl)sulfonimidoyl]-3-methyl-imidazo[4,5-b]pyridin-2-yl]-3-pyridyl]cyclopropanecarbonitrile (compound P20

(P20)

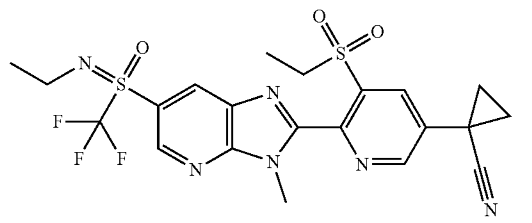

Step 1: Preparation of N-[3-amino-5-(trifluoromethylsulfanyl)-2-pyridyl]-5-(1-cyanocyclopropyl)-3-ethylsulfanyl-N-methyl-pyridine-2-carboxamide (intermediate I17

(I17)

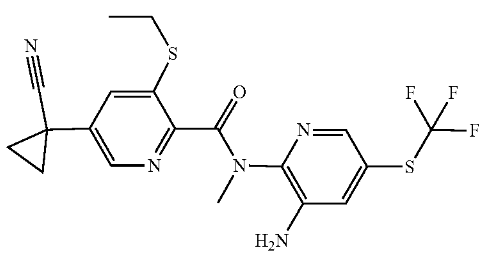

To a suspension of 5-(1-cyanocyclopropyl)-3-ethylsulfanyl-pyridine-2-carboxylic acid (CAS 2225113-77-7, prepared as described in WO 2018/108726) (3.17 g, 12.8 mmol) in dichloromethane (28.5 mL) and catalytic DMF was added oxalyl dichloride (2.05 mL, 23 mmol) dropwise via syringe at room temperature. The resulting reaction mass was stirred at room temperature for 1 hour. The reaction mass was evaporated to dryness under nitrogen atmosphere to afford crude 5-(1-cyanocyclopropyl)-3-ethylsulfanyl-pyridine-2-carbonyl chloride which was used as such for the next step.

To a 0° C. cooled solution of N2-methyl-5-(trifluoromethylsulfanyl)pyridine-2,3-diamine (CAS 1383840-73-0) (2.99 g, 13.4 mmol) in tetrahydrofuran (63.4 mL) was added triethylamine (4.13 mL, 29.4 mmol), followed by addition of the freshly prepared solution of 5-(1-cyanocyclopropyl)-3-ethylsulfanyl-pyridine-2-carbonyl chloride in tetrahydrofuran (19 mL). The reaction mixture was stirred for 2 hours at room temperature, then concentrated in vacuo. The crude compound was basified with an aqueous sodium bicarbonate solution and extracted with ethyl acetate. The combined organic layers were washed with an aqueous sodium bicarbonate solution, dried over sodium sulfate, filtered and concentrated in vacuo to afford N-[3-amino-5-(trifluoromethylsulfanyl)-2-pyridyl]-5-(1-cyanocyclopropyl)-3-ethylsulfanyl-N-methyl-pyridine-2-carboxamide. This crude material was used as such for the next step. LCMS (method 2): retention time 1.54 min, 454 $(M+H)^+$.

Step 2: Preparation of 1-[5-ethylsulfanyl-6-[3-methyl-6-(trifluoromethylsulfanyl)imidazo[4,5-b]pvridin-2-yl]-3-pyridyl]cyclopropanecarbonitrile (intermediate I18

(I18)

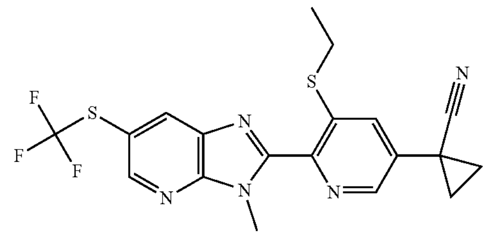

A mixture of N-[3-amino-5-(trifluoromethylsulfanyl)-2-pyridyl]-5-(1-cyanocyclopropyl)-3-ethylsulfanyl-N-methyl-pyridine-2-carboxamide (intermediate I17 prepared as described above) (6.24 g, 13.77 mmol) in acetic acid (62 mL) was heated at 130° C. for 4 hours. The reaction mixture was cooled to room temperature, concentrated in vacuo, basified with a saturated aqueous sodium bicarbonate solution and extracted with ethyl acetate. The combined organic layers were washed with a saturated aqueous sodium bicarbonate solution, dried over sodium sulfate, filtered and concentrated in vacuo. The crude compound was purified using combiflash (silica gel, 40% ethyl acetate in cyclohexane) to afford pure 1-[5-ethylsulfanyl-6-[3-methyl-6-(trifluoromethylsulfanyl)imidazo[4,5-b]pyridin-2-yl]-3-pyridyl]cyclopropanecarbonitrile. LCMS (method 1): retention time 1.19 min, 436 $(M+H)^+$. $^1$H NMR (400 MHz, $CDCl_3$) δ ppm 1.40 (t, 3H), 1.59-1.62 (m, 2H), 1.92-1.95 (m, 2H), 3.01 (q, 2H), 4.05 (s, 3H), 7.75 (s, 1H), 8.33 (s, 1H), 8.47 (s, 1H), 8.68 (s, 1H).

Step 3: Preparation of 1-[5-ethylsulfonyl-6-[3-methyl-6-(trifluoromethylsulfanyl)imidazo[4,5-b]pyridin-2-yl]-3-pyridyl]cyclopropanecarbonitrile (intermediate I19

(I19)

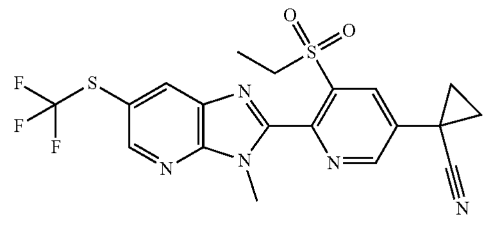

To a 0° C. cooled solution of 1-[5-ethylsulfanyl-6-[3-methyl-6-(trifluoromethylsulfanyl)imidazo[4,5-b]pyridin-2-yl]-3-pyridyl]cyclopropanecarbonitrile (intermediate I18 prepared as described above) (3.54 g, 8.13 mmol) in dichloromethane (70.0 mL) was added 3-chlorobenzenecarboperoxoic acid (4.21 g, 17.1 mmol). The reaction mixture was allowed to warm to room temperature and stirred for 2 hours, then quenched with a 2M sodium hydroxide solution and extracted with dichloromethane. The combined organic layers were dried over sodium sulfate, filtered and concentrated in vacuo. The crude product was purified by combiflash (silica gel, 40% ethyl acetate in cyclohexane) to afford 1-[5-ethylsulfonyl-6-[3-methyl-6-(trifluoromethylsulfanyl) imidazo[4,5-b]pyridin-2-yl]-3-pyridyl]cyclopropane-carbonitrile as a white solid. LCMS (method 2): retention time 1.55 min, 468 $(M+H)^+$. $^1H$ NMR (400 MHz, $CDCl_3$) δ ppm 1.38 (t, 3H), 1.67-1.69 (m, 2H), 2.01-2.07 (m, 2H), 3.86-3.93 (m, 5H), 8.26 (d, 1H), 8.38 (d, 1H), 8.72 (d, 1H), 9.05 (d, 1H).

Step 4: Preparation of 1-[5-ethylsulfonyl-6-[3-methyl-6-(trifluoromethylsulfonimidoyl)imidazo[4,5-b]pyridin-2-yl]-3-pyridyl]cyclopropanecarbonitrile (compound P21

(P21)

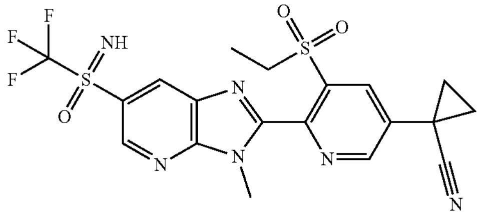

To a stirred solution of 1-[5-ethylsulfonyl-6-[3-methyl-6-(trifluoromethylsulfanyl)imidazo[4,5-b]pyridin-2-yl]-3-pyridyl]cyclopropanecarbonitrile (intermediate I19 prepared as described above) (2.44 g, 5.22 mmol) in 2,2,3,3,4,4,5,5-octafluoropentan-1-ol (25.0 mL) was added ammonium carbamate (1.25 g, 5.5 mmol), followed by (diacetoxyiodo) benzene $PhI(OAc)_2$ (4.29 g, 13.0 mmol) at room temperature. The reaction mixture was stirred at room temperature for 15 hours, then quenched with ice cold water, and extracted with ethyl acetate. The combined organic layers were washed with an aqueous sodium thiosulfate solution and brine, dried over sodium sulfate, filtered and concentrated in vacuo. The crude product was purified by combiflash (silica gel, 30% ethyl acetate in cyclohexane), followed by purification using preparative HPLC (column Atlantis T3 Prep OBD™, column length 150 mm, internal diameter 19 mm, particle size 5 μm using a mixture of acetonitrile and water containing 0.1% trifluoroacetic acid) to afford 1-[5-ethylsulfonyl-6-[3-methyl-6-(trifluoromethylsulfonimidoyl)imidazo[4,5-b]pyridin-2-yl]-3-pyridyl]cyclopropanecarbonitrile. LCMS (method 1): retention time 0.94 min, 499 $(M+H)^+$. $^1H$ NMR (400 MHz, DMSO-$d_6$) δ ppm 1.23 (t, 3H), 1.90-2.06 (m, 4H), 3.77-3.87 (m, 5H), 7.20 (br s, 1H), 8.42 (d, 1H), 8.84 (d, 1H), 9.04 (d, 1H), 9.11 (d, 1H).

Step 5: Preparation of 1-[5-ethylsulfonyl-6-[6-[N-ethyl-S-(trifluoromethyl)sulfonimidoyl]-3-methyl-imidazo[4,5-b]pyridin-2-yl]-3-pyridyl]cyclopropanecarbonitrile (compound P20

(P20)

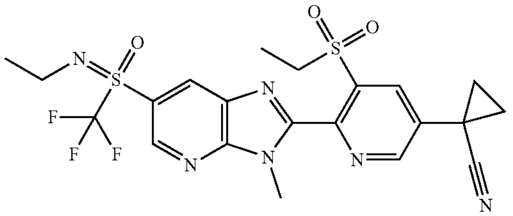

To a stirred solution of 1-[5-ethylsulfonyl-6-[3-methyl-6-(trifluoromethylsulfonimidoyl)imidazo[4,5-b]pyridin-2-yl]-3-pyridyl]cyclopropanecarbonitrile (compound P21 prepared as described above) (0.30 g, 0.60 mmol) in N,N-dimethylformamide (3.0 mL) was added potassium carbonate (0.24 g, 1.85 mmol), followed by iodoethane (0.14 g, 0.90 mmol). The reaction mixture was stirred at room temperature for 4 hours, then quenched with ice cold water, and extracted with ethyl acetate (2×25 mL). The combined organic layers were dried over sodium sulfate, filtered and concentrated in vacuo. The crude product was purified by combiflash (silica gel, 30% ethyl acetate in cyclohexane) to afford 1-[5-ethylsulfonyl-6-[6-[N-ethyl-S-(trifluoromethyl)sulfonimidoyl]-3-methyl-imidazo[4,5-b] pyridin-2-yl]-3-pyridyl]cyclopropanecarbonitrile as a white solid. LCMS (method 1): retention time 1.13 min, 527 $(M+H)^+$. $^1H$ NMR (400 MHz, $CDCl_3$) δ ppm 1.38 (dt, 6H), 1.68-1.71 (m, 2H), 2.04-2.08 (m, 2H), 3.44-3.61 (m, 2H), 3.84-3.92 (m, 5H), 8.26 (d, 1H), 8.74 (d, 1H), 9.06 (d, 1H), 9.14 (d, 1H).

Example P32: Preparation of 1-[5-ethylsulfonyl-6-[5-[N-ethyl-S-(trifluoromethyl)sulfonimidoyl]-1-methyl-benzimidazol-2-yl]-3-pyridyl]cyclopropanecarbonitrile (compound P32

(P32)

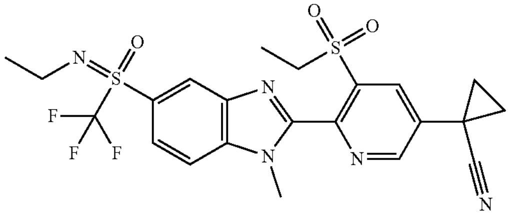

Step 1: Preparation of 1-[5-ethylsulfonyl-6-[1-methyl-5-(trifluoromethylsulfanyl)benzimidazol-2-yl]-3-pyridyl]cyclopropanecarbonitrile (intermediate I20

(I20)

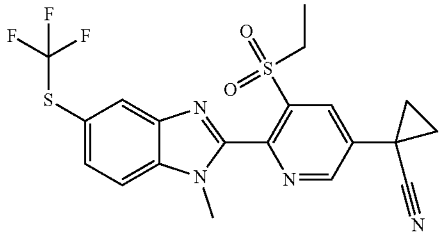

To a solution of 5-(1-cyanocyclopropyl)-3-ethylsulfonyl-pyridine-2-carboxylic acid (CAS 1879106-82-7, prepared as described in WO 2016/071214) (0.50 g, 1.78 mmol) in nitrobenzene (4 mL) was added N1-methyl-4-(trifluoromethylsulfanyl)benzene-1,2-diamine (CAS 1383840-98-9) (0.476 g, 2.14 mmol), followed by phosphoryl chloride (0.420 mL, 4.46 mmol) dropwise at room temperature. The reaction mixture was stirred at 160° C. for 6 hours followed by at 120° C. for 16 hours. After completion, the reaction mixture was quenched with an aqueous saturated sodium bicarbonate solution (50 mL), extracted with ethyl acetate (3×50 mL). The combined organic layers were washed with brine (50 mL), dried over anhydrous sodium sulfate, concentrated in vacuo. The crude product was purified by combiflash (silica gel, 35% ethyl acetate in cyclohexane) to afford 1-[5-ethylsulfonyl-6-[1-methyl-5-(trifluoromethylsulfanyl)benzimidazol-2-yl]-3-pyridyl]cyclopropanecarbonitrile as a brown solid. LCMS (method 1): Rt=1.10 min, m/z=468 $(M+H)^+$.

Step 2: Preparation of 1-[5-ethylsulfonyl-6-[1-methyl-5-(trifluoromethylsulfonimidoyl)benzimidazol-2-yl]-3-pyridyl]cyclooropanecarbonitrile (compound P33

(P33)

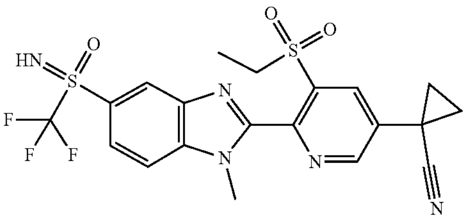

To a solution of 1-[5-ethylsulfonyl-6-[1-methyl-5-(trifluoromethylsulfanyl)benzimidazol-2-yl]-3-pyridyl]cyclopropanecarbonitrile (intermediate I20 prepared as described above) (1.00 g, 2.14 mmol) in 2,2,3,3,4,4,5,5-octafluoropentan-1-ol (10 mL) was added ammonium carbamate (0.427 g, 5.36 mmol) followed by (diacetoxyiodo)benzene (2.11 g, 6.43 mmol) at room temperature. The reaction mixture was stirred at room temperature for 16 hours, then quenched with ice cold water (50 mL), extracted with ethyl acetate (3×100 mL). The combined organic layers were washed with sodium thiosulfate solution (50 mL) followed by brine (50 mL), dried over sodium sulfate, filtered and concentrated in vacuo. The crude product was purified by combiflash (silica gel, 35% ethyl acetate in cyclohexane) to afford 1-[5-ethylsulfonyl-6-[1-methyl-5-(trifluoromethylsulfonimidoyl)benzimidazol-2-yl]-3-pyridyl]cyclopropanecarbonitrile as a white solid. LCMS (method 1): Rt=0.95 min, m/z=498 $(M+H)^+$. $^1H$ NMR (400 MHz, $CDCl_3$) δ ppm 1.38 (t, 3H), 1.62-1.74 (m, 2H), 1.99-2.08 (m, 2H), 3.66 (s, 1H), 3.85 (s, 3H), 3.85-3.94 (m, 2H), 7.67 (d, 1H), 8.16 (d, 1H), 8.24 (d, 1H), 8.64 (s, 1H), 9.06 (d, 1H).

Step 3: Preparation of 1-[5-ethylsulfonyl-6-[5-[N-ethyl-S-(trifluoromethyl)sulfonimidoyl]-1-methyl-benzimidazol-2-yl]-3-pyridyl]cyclopropanecarbonitrile (compound P32

(P32)

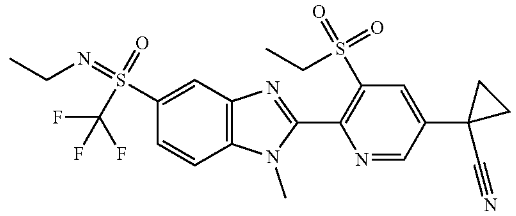

To a solution of 1-[5-ethylsulfonyl-6-[1-methyl-5-(trifluoromethylsulfonimidoyl)benzimidazol-2-yl]-3-pyridyl]cyclopropanecarbonitrile (compound P33 prepared as described above) (0.22 g, 0.442 mmol) in N,N-dimethylformamide (2.0 mL) was added potassium carbonate (0.18 g, 1.32 mmol) followed by iodoethane (0.10 g, 0.66 mmol). The reaction mass was stirred at room temperature for 16 hours, then quenched with ice cold water, extracted with ethyl acetate (2×20 mL). The combined organic layers were dried over sodium sulfate, filtered and concentrated in vacuo. The crude product was purified by combiflash (silica gel, 30% ethyl acetate in cyclohexane) to afford 1-[5-ethylsulfonyl-6-[5-[N-ethyl-S-(trifluoromethyl)sulfonimidoyl]-1-methyl-benzimidazol-2-yl]-3-pyridyl]cyclopropanecarbonitrile as a white solid. LCMS (method 1): Rt=1.10 min, m/z=526 $(M+H)^+$. $^1H$ NMR (400 MHz, $CDCl_3$) δ ppm 1.32-1.41 (m, 6H), 1.63-1.72 (m, 2H), 2.01-2.07 (m, 2H), 3.41-3.64 (m, 2H), 3.83 (s, 3H), 3.83-3.94 (m, 2H), 7.63 (d, 1H), 8.11 (d, 1H), 8.24 (d, 1H), 8.57 (s, 1H), 9.05 (d, 1H).

Example P31: Preparation of 1-[6-[5-[N-cyclopropyl-S-(trifluoromethyl)sulfonimidoyl]-1-methyl-benzimidazol-2-yl]-5-ethylsulfonyl-3-pyridyl]cyclopropanecarbonitrile (compound P31

(P31)

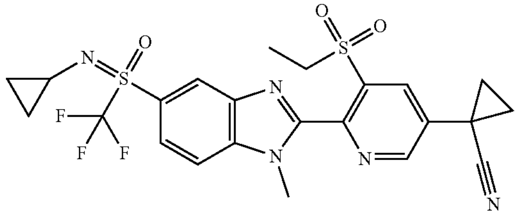

A solution of 1-[5-ethylsulfonyl-6-[1-methyl-5-(trifluoromethylsulfonimidoyl)benzimidazol-2-yl]-3-pyridyl]cyclopropanecarbonitrile (compound P33 prepared as described above) (0.19 g, 0.38 mmol), diacetoxycopper (0.104 g, 0.57 mmol) and pyridine (0.072 g, 0.91 mmol) in 1,4-dioxane (3.8 mL) was stirred under an open air condition for 5 minutes at room temperature to which cyclopropylboronic acid (0.065 g, 0.76 mmol) was added. The reaction mixture was refluxed in a pre-heated oil bath at 100° C. under air balloon for 3 hours. The reaction mixture was cooled to room temperature, diluted with ethyl acetate and washed with distilled water followed by brine solution. The organic layer was dried over anhydrous sodium sulfate, concentrated in vacuo. The crude product was purified by combiflash (silica gel, ethyl acetate in cyclohexane) to afford 1-[6-[5-[N-cyclopropyl-S-(trifluoromethyl)sulfonimidoyl]-1-methyl-benzimidazol-2-yl]-5-ethylsulfonyl-3-pyridyl]cyclopropanecarbonitrile as white solid. LCMS (method 1): Rt=1.11 min, m/z=538 $(M+H)^+$. $^1H$ NMR (400 MHz, $CDCl_3$) δ ppm 0.63-0.91 (m, 4H), 1.37 (t, 3H), 1.64-1.71 (m, 2H), 2.02-2.07 (m, 2H), 3.00 (br d, 1H), 3.80-3.94 (m, 5H), 7.62 (d, 1H), 8.07 (d, 1H), 8.24 (d, 1H), 8.54 (s, 1H), 9.05 (d, 1H).

Example P17: Preparation of N-[[2-(3-ethylsulfonyl-2-pyridyl)-1,3-benzoxazol-5-yl]-oxo-(trifluoromethyl)-$\lambda^6$-sulfanylidene]acetamide (compound P17

(P17)

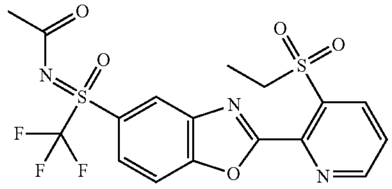

To a solution of [2-(3-ethylsulfonyl-2-pyridyl)-1,3-benzoxazol-5-yl]-imino-oxo-(trifluoromethyl)-$\lambda^6$-sulfane (compound P16, prepared in analogy to descriptions found above; LCMS (method 1): Rt=0.97 min, m/z=420 $(M+H)^+$) (50 mg, 0.119 mmol) in N,N-dimethylformamide (1.19 mL) was added N,N-diisopropylethylamine (64.9 mg, 0.477 mmol) and the mixture stirred at room temperature for 10 minutes. Acetic anhydride (50.2 mg, 0.477 mmol) was added and stirring continued at 100° C. for 16 hours. N-[[2-(3-ethylsulfonyl-2-pyridyl)-1,3-benzoxazol-5-yl]-oxo-(trifluoromethyl)-$\lambda^6$-sulfanylidene]acetamide (compound P17) was observed as indicated by LCMS analysis with incomplete conversion of the starting material. LCMS (method 1): Rt=1.00 min, m/z=462 $(M+H)^+$.

Example P15: Preparation of [[2-(3-ethylsulfonyl-2-pyridyl)-1,3-benzoxazol-5-yl]-oxo-(trifluoromethyl)-$\lambda^6$-sulfanylidene]cyanamide (compound P15

(P15)

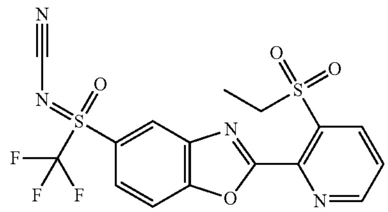

To a solution of [2-(3-ethylsulfonyl-2-pyridyl)-1,3-benzoxazol-5-yl]-imino-oxo-(trifluoromethyl)-$\lambda^6$-sulfane (compound P16, prepared in analogy to descriptions found above; LCMS (method 1): Rt=0.97 min, m/z=420 $(M+H)^+$) (300 mg, 0.715 mmol) in N,N-dimethylformamide (5 mL) was added potassium carbonate (297 mg, 2.146 mmol) at 0° C. and the mixture stirred for 10 minutes. Cyanogen bromide (2.0 equiv., 1.431 mmol) was added at 0° C., then stirring was continued at room temperature for 6 hours. After completion, the reaction mixture was quenched with ice cold water, the product extracted with ethyl acetate (2×20 mL), the combined organic layers dried over anhydrous sodium sulfate, filtered and concentrate in vacuo. The residue was purified by combiflash (silica gel, ethyl acetate in cyclohexane) to afford [[2-(3-ethylsulfonyl-2-pyridyl)-1,3-benzoxazol-5-yl]-oxo-(trifluoromethyl)-$\lambda^6$-sulfanylidene]cyanamide (compound P15) as a white solid. LCMS (method 2): Rt=1.39 min, m/z=445 $(M+H)^+$.

TABLE P

Examples of compounds of formula (I)

| Entry | IUPAC name | STRUCTURE | RT (min) | [M + H] measured | Method | mp ° C. |
|---|---|---|---|---|---|---|
| P1 | [2-[5-[[dimethyl(oxo)-$\lambda^6$-sulfanylidene]amino]-3-ethylsulfonyl-2-pyridyl]-1,3-benzoxazol-5-yl]-imino-oxo-(trifluoromethyl)-$\lambda^6$-sulfane | 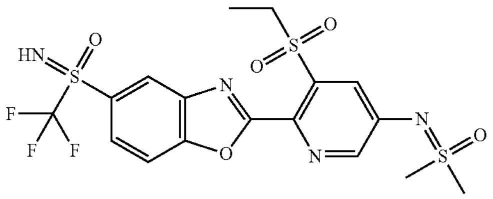 [SMILES: CCS(=O)(=O)c1cc(N=S(C)(C)=O)cnc1-c1nc2cc(S(=N)(=O)C(F)(F)F)ccc2o1] | 0.91 | 511 | 1 | 206-208 |

TABLE P-continued

Examples of compounds of formula (I)

| Entry | IUPAC name | STRUCTURE | RT (min) | [M + H] measured | Method | mp ° C. |
|---|---|---|---|---|---|---|
| P2 | [2-[5-[[dimethyl(oxo)-λ$^6$-sulfanylidene]amino]-3-ethylsulfonyl-2-pyridyl]-1,3-benzoxazol-5-yl]-ethylimino-oxo-(trifluoromethyl)-λ$^6$-sulfane | 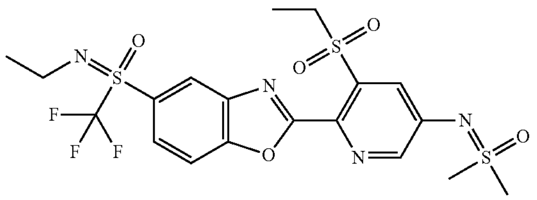 [SMILES: CCN=S(=O)(c1ccc2oc(-c3ncc(N=S(C)(C)=O)cc3S(=O)(=O)CC)nc2c1)C(F)(F)F] | 1.07 | 539 | 1 | 157-159 |
| P3 | N-[5-ethylsulfonyl-6-[5-[N-ethyl-S-(trifluoro-methyl)sulfonimidoyl]-1,3-benzoxazol-2-yl]-3-pyridyl]-N-methyl-acetamide | 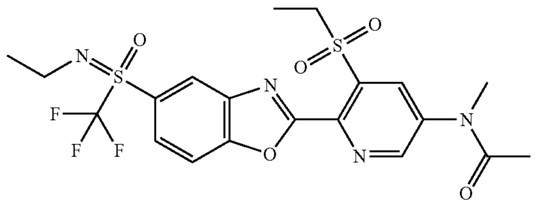 [SMILES: CCN=S(=O)(c1ccc2oc(-c3ncc(N(C)C(C)=O)cc3S(=O)(=O)CC)nc2c1)C(F)(F)F] | 1.06 | 519 | 1 | 152-154 |
| P4 | N-[5-ethylsulfonyl-6-[5-(trifluoromethyl-sulfonimidoyl)-1,3-benzoxazol-2-yl]-3-pyridyl]-N-methyl-acetamide | 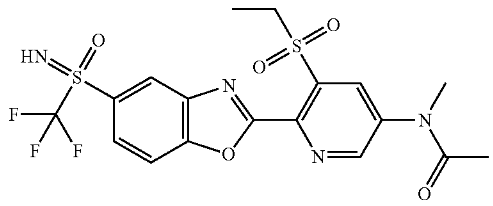 [SMILES: CCS(=O)(=O)c1cc(N(C)C(C)=O)cnc1-c1nc2cc(S(=N)(=O)C(F)(F)F)ccc2o1] | 0.92 | 491 | 1 | 190-192 |
| P5 | ethylimino-[2-[3-ethylsulfonyl-5-[3-(trifluoromethyl)pyrazol-1-yl]-2-pyridyl]-1,3-benzoxazol-5-yl]-oxo-(trifluoromethyl)-λ$^6$-sulfane | 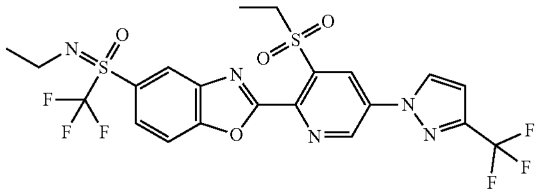 [SMILES: CCN=S(=O)(c1ccc2oc(-c3ncc(-n4ccc(C(F)(F)F)n4)cc3S(=O)(=O)CC)nc2c1)C(F)(F)F] | 1.25 | 582 | 1 | 190-192 |
| P6 | [2-[3-ethylsulfonyl-5-[3-(trifluoromethyl)pyrazol-1-yl]-2-pyridyl]-1,3-benzoxazol-5-yl]-imino-oxo-(trifluoromethyl)-λ$^6$-sulfane | 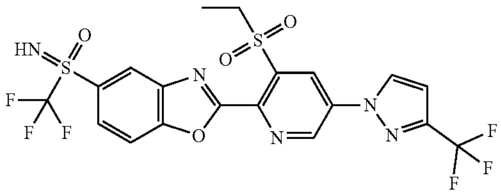 [SMILES: CCS(=O)(=O)c1cc(-n2ccc(C(F)(F)F)n2)cnc1-c1nc2cc(S(=N)(=O)C(F)(F)F)ccc2o1] | 1.12 | 554 | 1 | 188-190 |
| P7 | 1-[5-ethylsulfonyl-6-[5-(trifluoromethyl-sulfonimidoyl)-1,3-benzoxazol-2-yl]-3-pyridyl]cyclopropane-carbonitrile | 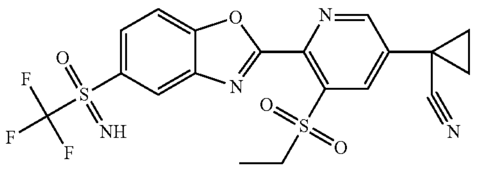 [SMILES: CCS(=O)(=O)c1cc(C2(C#N)CC2)cnc1-c1nc2cc(S(=N)(=O)C(F)(F)F)ccc2o1] | 1.00 | 485 | 1 | 226-228 |
| P8 | 1-[5-ethylsulfonyl-6-[5-[N-ethyl-S-(trifluoro-methyl)sulfonimidoyl]-1,3-benzoxazol-2-yl]-3-pyridyl]cyclopropane-carbonitrile | 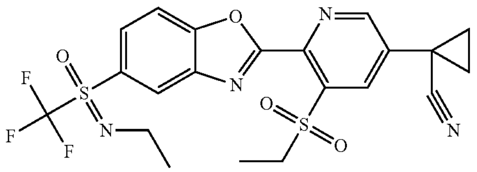 [SMILES: CCN=S(=O)(c1ccc2oc(-c3ncc(C4(C#N)CC4)cc3S(=O)(=O)CC)nc2c1)C(F)(F)F] | 1.19 | 513 | 1 | 152-154 |

TABLE P-continued

| Examples of compounds of formula (I) | | | | | | |
|---|---|---|---|---|---|---|
| Entry | IUPAC name | STRUCTURE | RT (min) | [M + H] measured | Method | mp ° C. |
| P9 | [2-[3-ethylsulfonyl-5-(2-pyridyloxy)-2-pyridyl]-1,3-benzoxazol-5-yl]-imino-oxo-(trifluoromethyl)-λ⁶-sulfane | 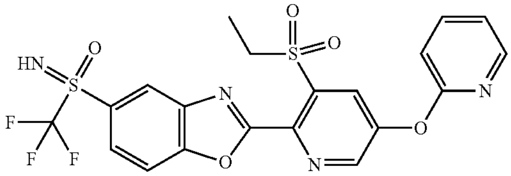 [SMILES: CCS(=O)(=O)c1cc(Oc2ccccn2)cnc1-c1nc2cc(S(=N)(=O)C(F)(F)F)ccc2o1] | 1.51 | 513 | 2 | 147-149 |
| P10 | ethylimino-[2-[3-ethylsulfonyl-5-(2-pyridyloxy)-2-pyridyl]-1,3-benzoxazol-5-yl]-oxo-(trifluoromethyl)-λ⁶-sulfane | 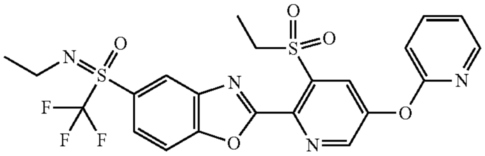 [SMILES: CCN=S(=O)(c1ccc2oc(-c3ncc(Oc4ccccn4)cc3S(=O)(=O)CC)nc2c1)C(F)(F)F] | 1.20 | 541 | 1 | 133-135 |
| P11 | [2-(5-cyclopropyl-3-ethylsulfonyl-2-pyridyl)-1,3-benzoxazol-5-yl]-ethylimino-oxo-(trifluoromethyl)-λ⁶-sulfane | 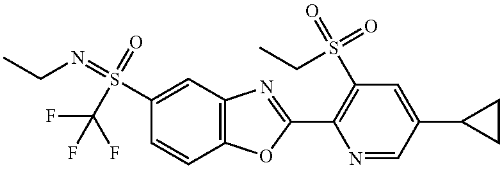 [SMILES: CCN=S(=O)(c1ccc2oc(-c3ncc(C4CC4)cc3S(=O)(=O)CC)nc2c1)C(F)(F)F] | 1.23 | 488 | 1 | 154-156 |
| P12 | [2-(5-cyclopropyl-3-ethylsulfonyl-2-pyridyl)-1,3-benzoxazol-5-yl]-imino-oxo-(trifluoromethyl)-λ⁶-sulfane | 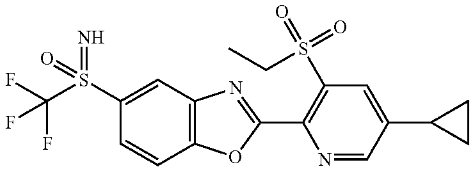 [SMILES: CCS(=O)(=O)c1cc(C2CC2)cnc1-c1nc2cc(S(=N)(=O)C(F)(F)F)ccc2o1] | 1.05 | 460 | 1 | 145-147 |
| P13 | cyclopropylimino-[2-(3-ethylsulfonyl-2-pyridyl)-1,3-benzoxazol-5-yl]-oxo-(trifluoromethyl)-λ⁶-sulfane | 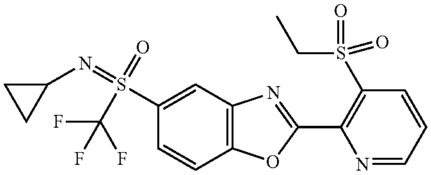 [SMILES: CCS(=O)(=O)c1cccnc1-c1nc2cc(S(=O)(=NC3CC3)C(F)(F)F)ccc2o1] | 1.12 | 460 | 1 | 124-126 |
| P14 | [2-(3-ethylsulfonyl-2-pyridyl)-1,3-benzoxazol-5-yl]-oxo-(2,2,2-trifluoroethylimino)-(trifluoromethyl)-λ⁶-sulfane | 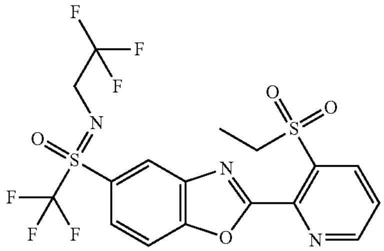 [SMILES: CCS(=O)(=O)c1cccnc1-c1nc2cc(S(=O)(=NCC(F)(F)F)C(F)(F)F)ccc2o1] | 1.53 | 502 | 2 | 130-132 |
| P15 | [[2-(3-ethylsulfonyl-2-pyridyl)-1,3-benzoxazol-5-yl]-oxo-(trifluoromethyl)-λ⁶-sulfanylidene]cyanamide | 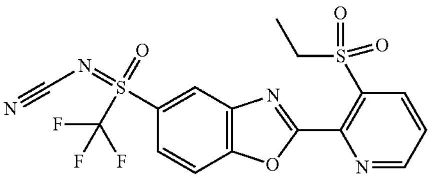 [SMILES: CCS(=O)(=O)c1cccnc1-c1nc2cc(S(=O)(=NC#N)C(F)(F)F)ccc2o1] | 1.39 | 445 | 2 | 70-72 |

TABLE P-continued

Examples of compounds of formula (I)

| Entry | IUPAC name | STRUCTURE | RT (min) | [M + H] measured | Method | mp ° C. |
|---|---|---|---|---|---|---|
| P16 | [2-(3-ethylsulfonyl-2-pyridyl)-1,3-benzoxazol-5-yl]-imino-oxo-(trifluoromethyl)-λ⁶-sulfane | 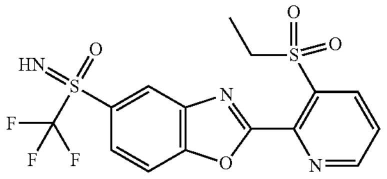 [SMILES: CCS(=O)(=O)c1cccnc1-c1nc2cc(S(=N)(=O)C(F)(F)F)ccc2o1] | 0.97 | 420 | 1 | 146-148 |
| P17 | N-[[2-(3-ethylsulfonyl-2-pyridyl)-1,3-benzoxazol-5-yl]-oxo-(trifluoromethyl)-λ⁶-sulfanylidene]acetamide | 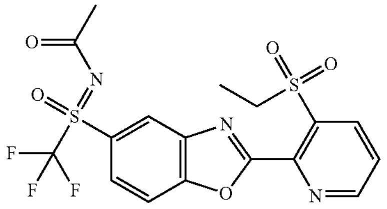 [SMILES: CCS(=O)(=O)c1cccnc1-c1nc2cc(S(=O)(=NC(C)=O)C(F)(F)F)ccc2o1] | 1.00 | 462 | 1 | 76-78 |
| P18 | [2-(3-ethylsulfonyl-2-pyridyl)-1,3-benzoxazol-5-yl]-methylimino-oxo-(trifluoromethyl)-λ⁶-sulfane | 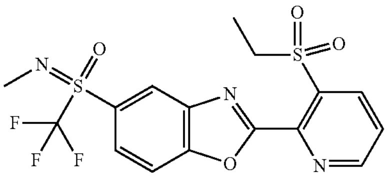 [SMILES: CCS(=O)(=O)c1cccnc1-c1nc2cc(S(=O)(=NC)C(F)(F)F)ccc2o1] | 1.06 | 434 | 1 | 118-120 |
| P19 | ethylimino-[2-(3-ethylsulfonyl-2-pyridyl)-1,3-benzoxazol-5-yl]-oxo-(trifluoromethyl)-λ⁶-sulfane | 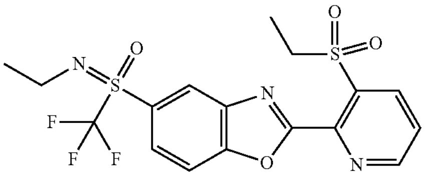 [SMILES: CCN=S(=O)(c1ccc2oc(-c3ncccc3S(=O)(=O)CC)nc2c1)C(F)(F)F] | 1.11 | 448 | 1 | 106-108 |
| P20 | 1-[5-ethylsulfonyl-6-[6-[N-ethyl-S-(trifluoromethyl)sulfonimidoyl]-3-methyl-imidazo[4,5-b]pyridin-2-yl]-3-pyridyl]cyclopropanecarbonitrile | 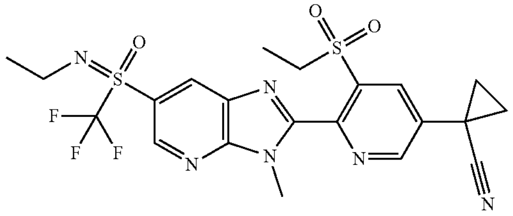 [SMILES: CCN=S(=O)(c1cnc2c(c1)nc(-c1ncc(C3(C#N)CC3)cc1S(=O)(=O)CC)n2C)C(F)(F)F] | 1.13 | 527 | 1 | 86-88 |
| P21 | 1-[5-ethylsulfonyl-6-[3-methyl-6-(trifluoromethylsulfonimidoyl)imidazo[4,5-b]pyridin-2-yl]-3-pyridyl]cyclopropanecarbonitrile | 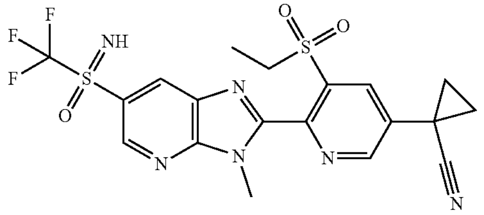 [SMILES: CCS(=O)(=O)c1cc(C2(C#N)CC2)cnc1-c1nc2cc(S(=N)(=O)C(F)(F)F)cnc2n1C] | 0.94 | 499 | 1 | 110-112 |
| P22 | ethylimino-[2-[3-ethylsulfonyl-5-(2,2,2-trifluoroethoxy)-2-pyridyl]-1,3-benzoxazol-5-yl]-oxo-(trifluoromethyl)-λ⁶-sulfane | 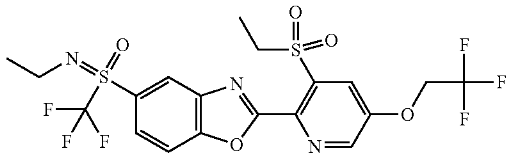 [SMILES: CCN=S(=O)(c1ccc2oc(-c3ncc(OCC(F)(F)F)cc3S(=O)(=O)CC)nc2c1)C(F)(F)F] | 1.20 | 546 | 1 | 142-144 |

TABLE P-continued

Examples of compounds of formula (I)

| Entry | IUPAC name | STRUCTURE | RT (min) | [M + H] measured | Method | mp ° C. |
|---|---|---|---|---|---|---|
| P23 | [2-[3-ethylsulfonyl-5-(2,2,2-trifluoroethoxy)-2-pyridyl]-1,3-benzoxazol-5-yl]-imino-oxo-(trifluoromethyl)-λ6-sulfane | 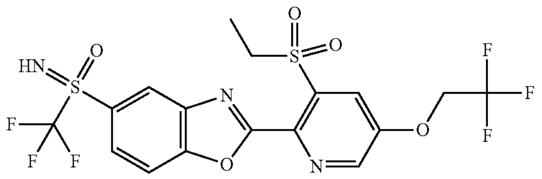 [SMILES: CCS(=O)(=O)c1cc(OCC(F)(F)F)cnc1-c1nc2cc(S(=N)(=O)C(F)(F)F)ccc2o1] | 1.51 | 518 | 2 | 178-180 |
| P24 | N-[[2-[3-ethylsulfonyl-5-(2,2,2-trifluoroethoxy)-2-pyridyl]-1,3-benzoxazol-5-yl]-oxo-(trifluoromethyl)-λ6-sulfanylidene]acetamide | 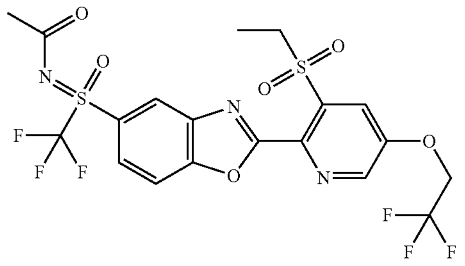 [SMILES: CCS(=O)(=O)c1cc(OCC(F)(F)F)cnc1-c1nc2cc(S(=O)(=NC(C)=O)C(F)(F)F)ccc2o1] | 1.10 | 560 | 1 | 77-79 |
| P25 | N-[[2-[3-ethylsulfonyl-5-(2-pyridyloxy)-2-pyridyl]-1,3-benzoxazol-5-yl]-oxo-(trifluoromethyl)-λ6-sulfanylidene]acetamide | 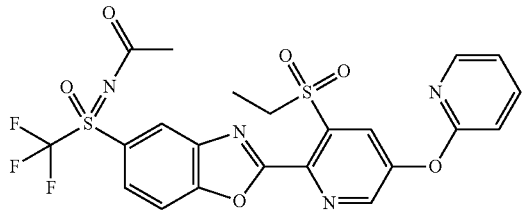 [SMILES: CCS(=O)(=O)c1cc(Oc2ccccn2)cnc1-c1nc2cc(S(=O)(=NC(C)=O)C(F)(F)F)ccc2o1] | 1.09 | 555 | 1 | 176-178 |
| P26 | [2-[5-(2,2-difluoropropoxy)-3-ethylsulfonyl-2-pyridyl]-1,3-benzoxazol-5-yl]-imino-oxo-(trifluoromethyl)-λ6-sulfane | 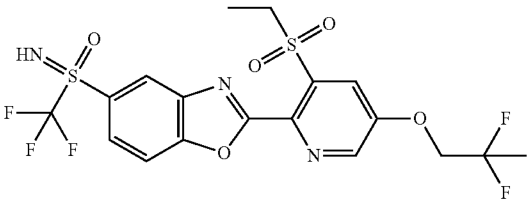 [SMILES: CCS(=O)(=O)c1cc(OCC(C)(F)F)cnc1-c1nc2cc(S(=N)(=O)C(F)(F)F)ccc2o1] | 1.05 | 514 | 1 | 183-184 |
| P27 | [2-[5-(2,2-difluoropropoxy)-3-ethylsulfonyl-2-pyridyl]-1,3-benzoxazol-5-yl]-ethylimino-oxo-(trifluoromethyl)-λ6-sulfane | 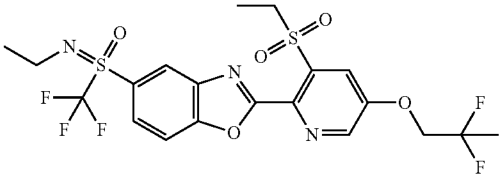 [SMILES: CCN=S(=O)(c1ccc2oc(-c3ncc(OCC(C)(F)F)cc3S(=O)(=O)CC)nc2c1)C(F)(F)F] | 1.16 | 542 | 1 | 106-108 |
| P28 | 1-[5-ethylsulfonyl-6-[5-[N-(2,2,2-trifluoroethyl)-S-(trifluoromethyl)sulfonimidoyl]-1,3-benzoxazol-2-yl]-3-pyridyl]cyclopropane-carbonitrile | 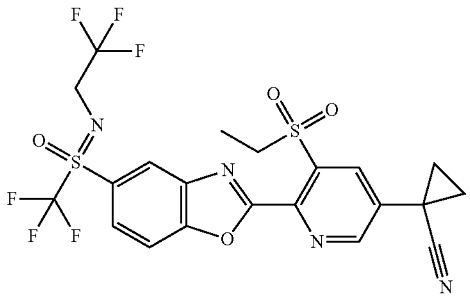 [SMILES: CCS(=O)(=O)c1cc(C2(C#N)CC2)cnc1-c1nc2cc(S(=O)(=NCC(F)(F)F)C(F)(F)F)ccc2o1] | 1.13 | 567 | 1 | 182-184 |

TABLE P-continued

Examples of compounds of formula (I)

| Entry | IUPAC name | STRUCTURE | RT (min) | [M + H] measured | Method | mp ° C. |
|---|---|---|---|---|---|---|
| P29 | 1-[5-ethylsulfonyl-6-[5-[N-methyl-S-(trifluoromethyl)sulfonimidoyl]-1,3-benzoxazol-2-yl]-3-pyridyl]cyclopropane-carbonitrile | 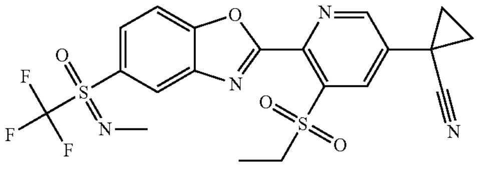 [SMILES: CCS(=O)(=O)c1cc(C2(C#N)CC2)cnc1-c1nc2cc(S(=O)(=NC)C(F)(F)F)ccc2o1] | 1.08 | 499 | 1 | 160-162 |
| P30 | 1-[6-[5-[N-cyclopropyl-S-(trifluoromethyl)sulfonimidoyl]-1,3-benzoxazol-2-yl]-5-ethylsulfonyl-3-pyridyl]cyclopropane-carbonitrile | 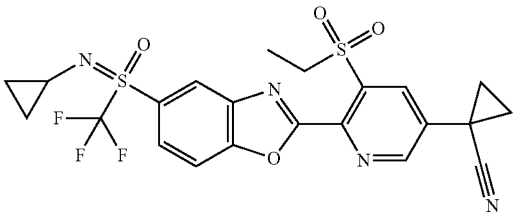 [SMILES: CCS(=O)(=O)c1cc(C2(C#N)CC2)cnc1-c1nc2cc(S(=O)(=NC3CC3)C(F)(F)F)ccc2o1] | 1.12 | 525 | 1 | 162-164 |
| P31 | 1-[6-[5-[N-cyclopropyl-S-(trifluoromethyl)sulfonimidoyl]-1-methyl-benzimidazol-2-yl]-5-ethylsulfonyl-3-pyridyl]cyclopropane-carbonitrile | 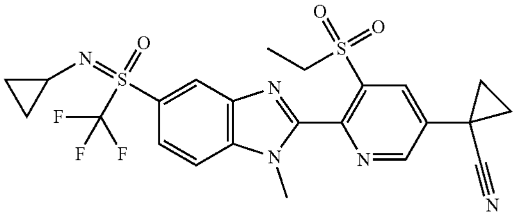 [SMILES: CCS(=O)(=O)c1cc(C2(C#N)CC2)cnc1-c1nc2cc(S(=O)(=NC3CC3)C(F)(F)F)ccc2n1C] | 1.11 | 538 | 1 | 172-174 |
| P32 | 1-[5-ethylsulfonyl-6-[5-[N-ethyl-S-(trifluoro-methyl)sulfonimidoyl]-1-methyl-benzimidazol-2-yl]-3-pyridyl]cyclopropane-carbonitrile | 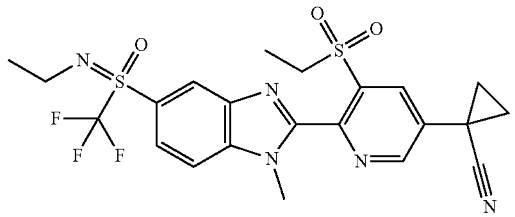 [SMILES: CCN=S(=O)(c1ccc2c(c1)nc(-c1ncc(C3(C#N)CC3)cc1S(=O)(=O)CC)n2C)C(F)(F)F] | 1.10 | 526 | 1 | 132-134 |
| P33 | 1-[5-ethylsulfonyl-6-[1-methyl-5-(trifluoromethyl-sulfonimidoyl)benzimidazol-2-yl]-3-pyridyl]cyclopropane-carbonitrile | 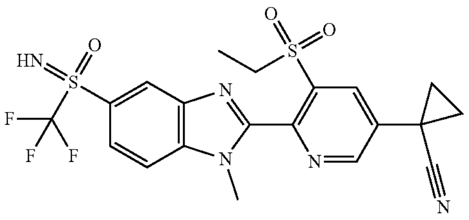 [SMILES: CCS(=O)(=O)c1cc(C2(C#N)CC2)cnc1-c1nc2cc(S(=N)(=O)C(F)(F)F)ccc2n1C] | 0.95 | 498 | 1 | 194-196 |
| P34 | 1-[5-ethylsulfonyl-6-[1-methyl-5-[N-(2,2,2-trifluoroethyl)-S-(trifluoromethyl)sulfonimidoyl]benzimidazol-2-yl]-3-pyridyl]cyclopropane-carbonitrile | 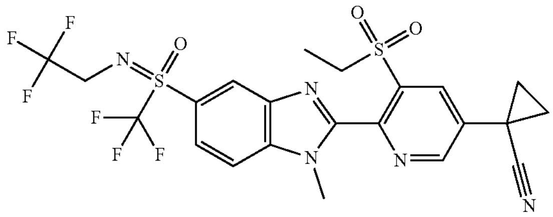 [SMILES: CCS(=O)(=O)c1cc(C2(C#N)CC2)cnc1-c1nc2cc(S(=O)(=NCC(F)(F)F)C(F)(F)F)ccc2n1C] | 1.11 | 580 | 1 | 144-146 |
| P35 | ethylimino-[2-(3-ethylsulfonyl-5-pyrimidin-2-yl-2-pyridyl)-1,3-benzoxazol-5-yl]-oxo-(trifluoromethyl)-λ$^6$-sulfane | 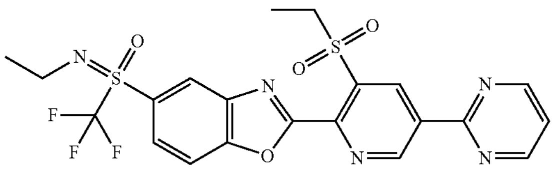 [SMILES: CCN=S(=O)(c1ccc2oc(-c3ncc(-c4ncccn4)cc3S(=O)(=O)CC)nc2c1)C(F)(F)F] | 1.18 | 526 | 1 | 96-98 |

TABLE P-continued

| Examples of compounds of formula (I) | | | | | | |
|---|---|---|---|---|---|---|
| Entry | IUPAC name | STRUCTURE | RT (min) | [M + H] measured | Method | mp ° C. |
| P36 | [2-(3-ethylsulfonyl-5-pyrimidin-2-yl-2-pyridyl)-1,3-benzoxazol-5-yl]-imino-oxo-(trifluoromethyl)-λ6-sulfane | 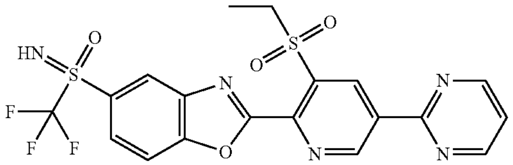 [SMILES: CCS(=O)(=O)c1cc(-c2ncccn2)cnc1-c1nc2cc(S(=N)(=O)C(F)(F)F)ccc2o1] | 1.47 | 498 | 2 | 208-210 |
| P37 | [2-[5-(3-chloropyrazol-1-yl)-3-ethylsulfonyl-2-pyridyl]-1,3-benzoxazol-5-yl]-imino-oxo-(trifluoromethyl)-λ6-sulfane | 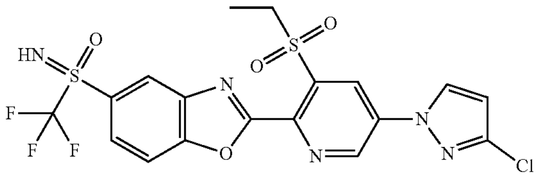 [SMILES: CCS(=O)(=O)c1cc(-n2ccc(Cl)n2)cnc1-c1nc2cc(S(=N)(=O)C(F)(F)F)ccc2o1] | 1.08 | 520/522 | 1 | 204-206 |
| P38 | [2-[5-(3-chloropyrazol-1-yl)-3-ethylsulfonyl-2-pyridyl]-1,3-benzoxazol-5-yl]-ethylimino-oxo-(trifluoromethyl)-λ6-sulfane | 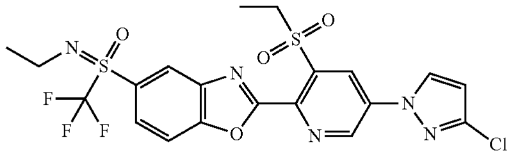 [SMILES: CCN=S(=O)(c1ccc2oc(-c3ncc(-n4ccc(Cl)n4)cc3S(=O)(=O)CC)nc2c1)C(F)(F)F] | 1.23 | 548/550 | 1 | 191-192 |
| P39 | ethylimino-[2-[3-ethylsulfonyl-6-(1,2,4-triazol-1-yl)-2-pyridyl]-1,3-benzoxazol-5-yl]-oxo-(trifluoromethyl)-λ6-sulfane | 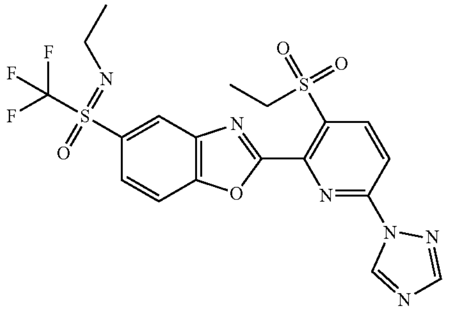 [SMILES: CCN=S(=O)(c1ccc2oc(-c3nc(-n4cncn4)ccc3S(=O)(=O)CC)nc2c1)C(F)(F)F] | 1.10 | 515 | 1 | 174-176 |
| P40 | [2-[3-ethylsulfonyl-5-[4-(trifluoromethyl)pyrimidin-2-yl]-2-pyridyl]-1,3-benzoxazol-5-yl]-imino-oxo-(trifluoromethyl)-λ6-sulfane | 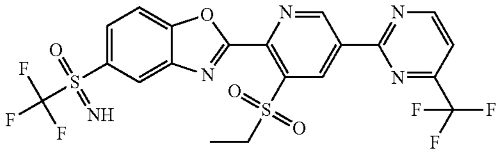 [SMILES: CCS(=O)(=O)c1cc(-c2nccc(C(F)(F)F)n2)cnc1-c1nc2cc(S(=N)(=O)C(F)(F)F)ccc2o1] | 1.11 | 566 | 1 | 177-179 |
| P41 | ethylimino-[2-[3-ethylsulfonyl-5-[4-(trifluoromethyl)pyrimidin-2-yl]-2-pyridyl]-1,3-benzoxazol-5-yl]-oxo-(trifluoromethyl)-λ6-sulfane | 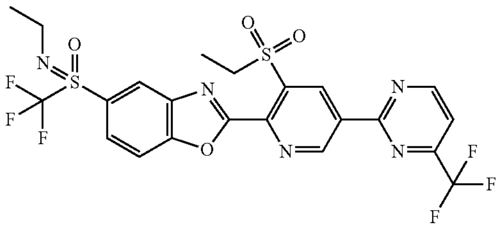 [SMILES: CCN=S(=O)(c1ccc2oc(-c3ncc(-c4nccc(C(F)(F)F)n4)cc3S(=O)(=O)CC)nc2c1)C(F)(F)F] | 1.26 | 594 | 1 | 199-201 |
| P42 | [2-[5-(5-chloropyrimidin-2-yl)-3-ethylsulfonyl-2-pyridyl]-1,3-benzoxazol-5-yl]-imino-oxo-(trifluoromethyl)-λ6-sulfane | 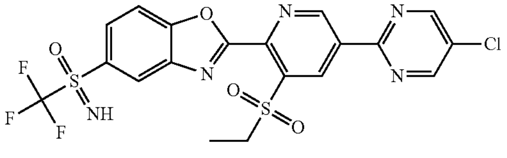 [SMILES: CCS(=O)(=O)c1cc(-c2ncc(Cl)cn2)cnc1-c1nc2cc(S(=N)(=O)C(F)(F)F)ccc2o1] | 1.10 | 532/534 | 1 | 220-222 |

TABLE P-continued

Examples of compounds of formula (I)

| Entry | IUPAC name | STRUCTURE | RT (min) | [M + H] measured | Method | mp ° C. |
|---|---|---|---|---|---|---|
| P43 | [2-[5-(5-chloropyrimidin-2-yl)-3-ethylsulfonyl-2-pyridyl]-1,3-benzoxazol-5-yl]-ethylimino-oxo-(trifluoromethyl)-λ$^6$-sulfane | 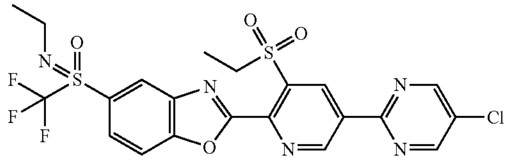 [SMILES: CCN=S(=O)(c1ccc2oc(-c3ncc(-c4ncc(Cl)cn4)cc3S(=O)(=O)CC)nc2c1)C(F)(F)F] | 1.26 | 560/562 | 1 | 162-164 |
| P44 | [2-[3-ethylsulfonyl-6-(1,2,4-triazol-1-yl)-2-pyridyl]-1-methyl-benzimidazol-5-yl]-imino-oxo-(trifluoromethyl)-λ$^6$-sulfane | 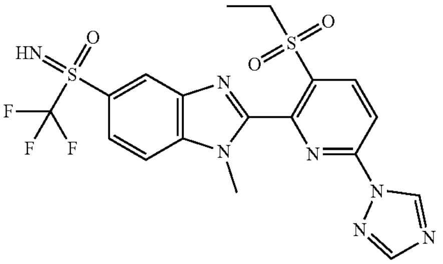 [SMILES: CCS(=O)(=O)c1ccc(-n2cncn2)nc1-c1nc2cc(S(=N)(=O)C(F)(F)F)ccc2n1C] | 0.91 | 500 | 1 | 166-168 |
| P45 | ethylimino-[2-[3-ethylsulfonyl-6-(1,2,4-triazol-1-yl)-2-pyridyl]-1-methyl-benzimidazol-5-yl]-oxo-(trifluoromethyl)-λ$^6$-sulfane | 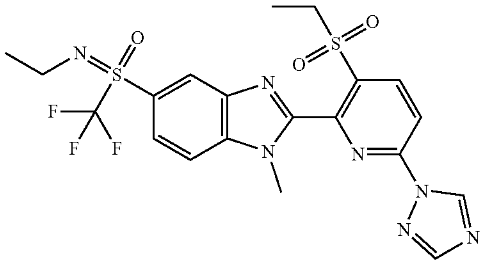 [SMILES: CCN=S(=O)(c1ccc2c(c1)nc(-c1nc(-n3cncn3)ccc1S(=O)(=O)CC)n2C)C(F)(F)F] | 1.06 | 528 | 1 | 118-120 |
| P46 | [2-[6-(3-chloro-1,2,4-triazol-1-yl)-3-ethylsulfonyl-2-pyridyl]-1-methyl-benzimidazol-5-yl]-imino-oxo-(trifluoromethyl)-λ$^6$-sulfane | 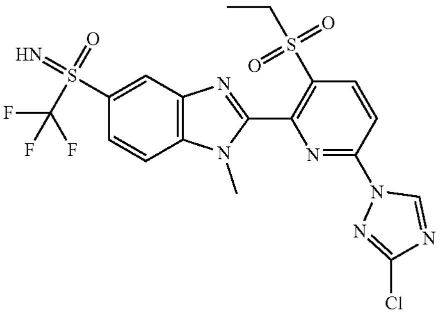 [SMILES: CCS(=O)(=O)c1ccc(-n2cnc(Cl)n2)nc1-c1nc2cc(S(=N)(=O)C(F)(F)F)ccc2n1C] | 1.01 | 534/536 | 1 | 170-172 |
| P47 | [2-[6-(3-chloro-1,2,4-triazol-1-yl)-3-ethylsulfonyl-2-pyridyl]-1-methyl-benzimidazol-5-yl]-ethylimino-oxo-(trifluoromethyl)-λ$^6$-sulfane | 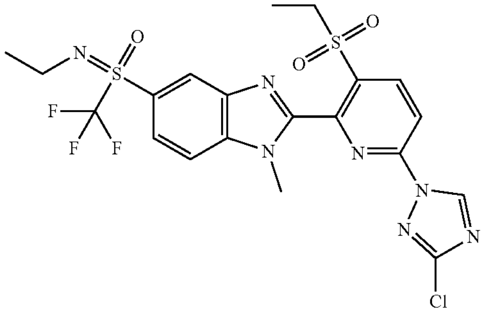 [SMILES: CCN=S(=O)(c1ccc2c(c1)nc(-c1nc(-n3cnc(Cl)n3)ccc1S(=O)(=O)CC)n2C)C(F)(F)F] | 1.16 | 562/564 | 1 | 130-132 |

TABLE P-continued

| Entry | IUPAC name | STRUCTURE | RT (min) | [M + H] measured | Method | mp ° C. |
|---|---|---|---|---|---|---|
| P48 | [2-[3-ethylsulfonyl-6-[3-(trifluoromethyl)-1,2,4-triazol-1-yl]-2-pyridyl]-1-methyl-benzimidazol-5-yl]-imino-oxo-(trifluoromethyl)-$\lambda^6$-sulfane | 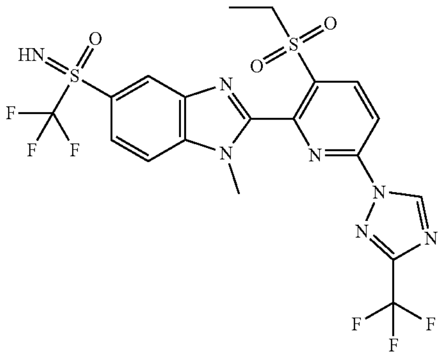 [SMILES: CCS(=O)(=O)c1ccc(-n2cnc(C(F)(F)F)n2)nc1-c1nc2cc(S(=N)(=O)C(F)(F)F)ccc2n1C] | 1.06 | 568 | 1 | 144-147 |
| P49 | ethylimino-[2-[3-ethylsulfonyl-6-[3-(trifluoromethyl)-1,2,4-triazol-1-yl]-2-pyridyl]-1-methyl-benzimidazol-5-yl]-oxo-(trifluoromethyl)-$\lambda^6$-sulfane | 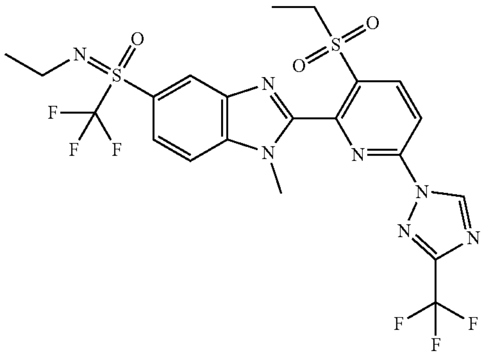 [SMILES: CCN=S(=O)(c1ccc2c(c1)nc(-c1nc(-n3cnc(C(F)(F)F)n3)ccc1S(=O)(=O)CC)n2C)C(F)(F)F] | 1.21 | 596 | 1 | 123-125 |
| P50 | [2-[3-ethylsulfonyl-5-(2-pyridyloxy)-2-pyridyl]-1-methyl-benzimidazol-5-yl]-imino-oxo-(trifluoromethyl)-$\lambda^6$-sulfane | 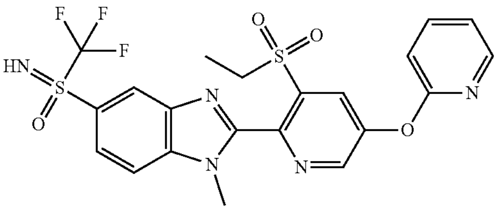 [SMILES: CCS(=O)(=O)c1cc(Oc2ccccn2)cnc1-c1nc2cc(S(=N)(=O)C(F)(F)F)ccc2n1C] | 1.00 | 524 $(M - H)^-$ | 1 | 192-194 |
| P51 | ethylimino-[2-[3-ethylsulfonyl-5-(2-pyridyloxy)-2-pyridyl]-1-methyl-benzimidazol-5-yl]-oxo-(trifluoromethyl)-$\lambda^6$-sulfane | 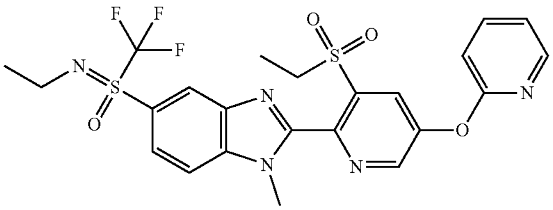 [SMILES: CCN=S(=O)(c1ccc2c(c1)nc(-c1ncc(Oc3ccccn3)cc1S(=O)(=O)CC)n2C)C(F)(F)F] | 1.15 | 554 | 1 | 74-76 |
| P52 | 2-[5-ethylsulfonyl-6-[1-methyl-5-(trifluoromethylsulfonimidoyl)benzimidazol-2-yl]-3-pyridyl]pyrimidine-5-carbonitrile | 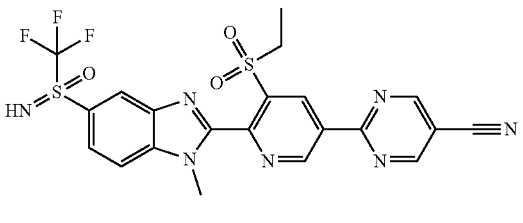 [SMILES: CCS(=O)(=O)c1cc(-c2ncc(C#N)cn2)cnc1-c1nc2cc(S(=N)(=O)C(F)(F)F)ccc2n1C] | 0.99 | 536 | 1 | — |

TABLE P-continued

| Entry | IUPAC name | STRUCTURE | RT (min) | [M + H] measured | Method | mp ° C. |
|---|---|---|---|---|---|---|
| | Examples of compounds of formula (I) | | | | | |
| P53 | 2-[5-ethylsulfonyl-6-[5-[N-ethyl-S-(trifluoro-methyl)sulfonimidoyl]-1-methyl-benzimidazol-2-yl]-3-pyridyl]pyrimidine-5-carbonitrile | 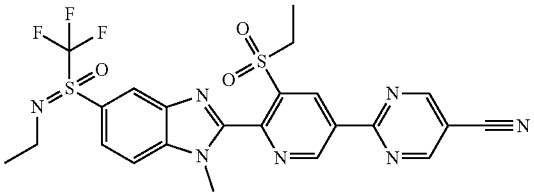 [SMILES: CCN=S(=O)(c1ccc2c(c1)nc(-c1ncc(-c3ncc(C#N)cn3)cc1S(=O)(=O)CC)n2C)C(F)(F)F] | 1.15 | 564 | 1 | — |
| P54 | [2-(3-ethylsulfonyl-6-pyrimidin-2-yl-2-pyridyl)-1,3-benzoxazol-5-yl]-imino-oxo-(trifluoromethyl)-λ$^6$-sulfane | 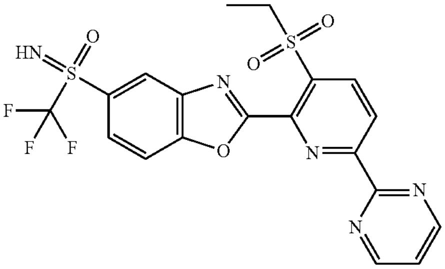 [SMILES: CCS(=O)(=O)c1ccc(-c2ncccn2)nc1-c1nc2cc(S(=N)(=O)C(F)(F)F)ccc2o1] | 0.94 | 498 | 1 | 234-236 |
| P55 | ethylimino-[2-(3-ethylsulfonyl-6-pyrimidin-2-yl-2-pyridyl)-1,3-benzoxazol-5-yl]-oxo-(trifluoromethyl)-λ$^6$-sulfane | 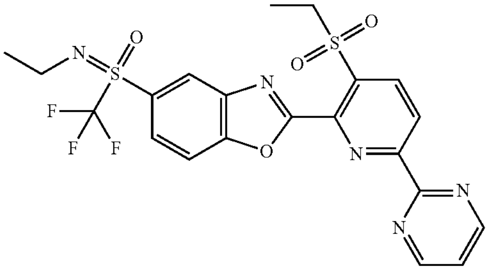 [SMILES: CCN=S(=O)(c1ccc2oc(-c3nc(-c4ncccn4)ccc3S(=O)(=O)CC)nc2c1)C(F)(F)F] | 1.08 | 526 | 1 | 201-203 |
| P56 | [2-[3-ethylsulfonyl-6-(1,2,4-triazol-1-yl)-2-pyridyl]-1,3-benzoxazol-5-yl]-imino-oxo-(trifluoromethyl)-λ$^6$-sulfane | 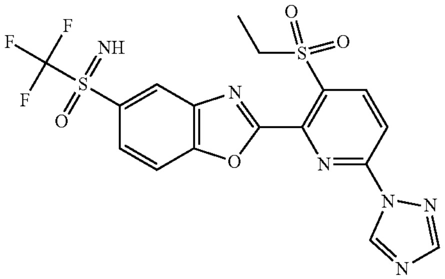 [SMILES: CCS(=O)(=O)c1ccc(-n2cncn2)nc1-c1nc2cc(S(=N)(=O)C(F)(F)F)ccc2o1] | 0.93 | 487 | 1 | 238-240 |
| P57 | 1-[5-ethylsulfonyl-6-[3-methyl-6-[N-(2,2,2-trifluoroethyl)-S-(trifluoromethyl)sulfonimidoyl]imidazo[4,5-b]pyridin-2-yl]-3-pyridyl]cyclo-propanecarbonitrile | 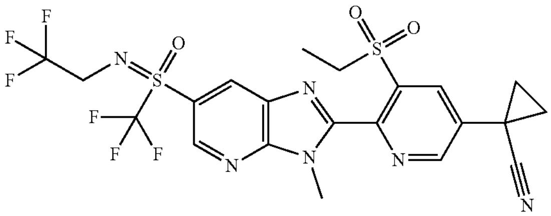 [SMILES: CCS(=O)(=O)c1cc(C2(C#N)CC2)cnc1-c1nc2cc(S(=O)(=NCC(F)(F)F)C(F)(F)F)cnc2n1C] | 1.12 | 581 | 1 | 90-101 |

TABLE P-continued

Examples of compounds of formula (I)

| Entry | IUPAC name | STRUCTURE | RT (min) | [M + H] mea-sured | Method | mp ° C. |
|---|---|---|---|---|---|---|
| P58 | 1-[6-[6-[N-cyclopropyl-S-(trifluoromethyl)sulfonimidoyl]-3-methyl-imidazo[4,5-b]pyridin-2-yl]-5-ethylsulfonyl-3-pyridyl]cyclopropane-carbonitrile | 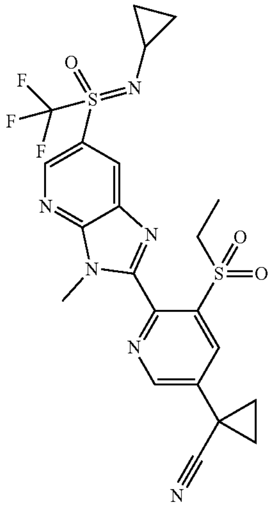 [SMILES: CCS(=O)(=O)c1cc(C2(C#N)CC2)cnc1-c1nc2cc(S(=O)(=NC3CC3)C(F)(F)F)cnc2n1C] | 1.13 | 539 | 1 | 103-105 |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organ ophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables A-1 to A-96, C-1 to C-96, E-1 to E-96, F-1 to F-96, G-1 to G-96 and H-1 to H-96 and Table P of the present invention"):

an adjuvant selected from the group of substances consisting of petroleum oils (alternative name) (628)+TX;

an insect control active substance selected from Abamectin+TX, Acequinocyl+TX, Acetamiprid+TX, Acetoprole+TX, Acrinathrin+TX, Acynonapyr+TX, Afidopyropen+TX, Afoxalaner+TX, Alanycarb+TX, Allethrin+TX, Alpha-Cypermethrin+TX, Alphamethrin+TX, Amidoflumet+TX, Aminocarb+TX, Azocyclotin+TX, Bensultap+TX, Benzoximate+TX, Benzpyrimoxan+TX, Betacyfluthrin+TX, Beta-cypermethrin+TX, Bifenazate+TX, Bifenthrin+TX, Binapacryl+TX, Bioallethrin+TX, Bioallethrin S)-cyclopentylisomer+TX, Bioresmethrin+TX, Bistrifluron+TX, Broflanilide+TX, Brofluthrinate+TX, Bromophos-ethyl+TX, Buprofezine+TX, Butocarboxim+TX, Cadusafos+TX, Carbaryl+TX, Carbosulfan+TX, Cartap+TX, CAS number: 1472050-04-6+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2249718-27-0+TX, Chlorantraniliprole+TX, Chlordane+TX, Chlorfenapyr+TX, Chloroprallethrin+TX, Chromafenozide+TX, Clenpirin+TX, Cloethocarb+TX, Clothianidin+TX, 2-chlorophenyl N-methylcarbamate (CPMC)+TX, Cyanofenphos+TX, Cyantraniliprole+TX, Cyclaniliprole+TX, Cyclobutrifluram+TX, Cycloprothrin+TX, Cycloxaprid+TX, Cycloxaprid+TX, Cyenopyrafen+TX, Cyetpyrafen+TX, Cyflumetofen+TX, Cyfluthrin+TX, Cyhalodiamide+TX, Cyhalothrin+TX, Cypermethrin+TX, Cyphenothrin+TX, Cyproflanilide+TX, Cyromazine+TX, Deltamethrin+TX, Diafenthiuron+TX, Dialifos+TX, Dibrom+TX, Dicloromezotiaz+TX, Diflovidazine+TX, Diflubenzuron+TX, dimpropyridaz+TX, Dinactin+TX, Dinocap+TX, Dinotefuran+TX, Dioxabenzofos+TX, Emamectin+TX, Empenthrin+TX, Epsilon-momfluorothrin+TX, Epsilon-metofluthrin+TX, Esfenvalerate+TX, Ethion+TX, Ethiprole+TX, Etofenprox+TX, Etoxazole+TX, Famphur+TX, Fenazaquin+TX, Fenfluthrin+TX, Fenitrothion+TX, Fenobucarb+TX, Fenothiocarb+TX, Fenoxycarb+TX, Fenpropathrin+TX, Fenpyroxymate+TX, Fensulfothion+TX, Fenthion+TX, Fentinacetate+TX, Fenvalerate+TX, Fipronil+TX, Flometoquin+TX, Flonicamid+TX, Fluacrypyrim+TX, Fluazaindolizine+TX, Fluazuron+TX, Flubendiamide+TX, Flubenzimine+TX, Flucitrinate+TX, Flucycloxuron+TX, Flucythrinate+TX, Fluensulfone+TX, Flufenerim+TX, Flufenprox+TX, Flufiprole+TX, Fluhexafon+TX, Flumethrin+TX, Fluopyram+TX, Flupentiofenox+TX, Flupyradifurone+TX, Flupyrimin+TX, Fluralaner+TX, Fluvalinate+TX, Fluxametamide+TX, Fosthiazate+TX, Gamma-Cyhalothrin+TX, Gossyplure™+TX, Guadipyr+TX, Halofenozide+TX, Halofenozide+TX, Halofenprox+TX, Heptafluthrin+TX, Hexythiazox+TX, Hydramethylnon+TX, Imicyafos+TX, Imidacloprid+TX, Imiprothrin+TX, Indoxacarb+TX, Iodomethane+TX, Iprodione+TX, Isocycloseram+TX, Isothioate+TX, Ivermectin+TX, Kappa-bifenthrin+TX, Kappa-tefluthrin+TX, Lambda-Cyhalothrin+TX, Lepimectin+TX, Lufenuron+TX, Metaflumizone+TX, Metaldehyde+TX, Metam+TX, Methomyl+TX, Methoxyfenozide+TX, Metofluthrin+TX, Metolcarb+TX, Mexacarbate+TX, Milbemectin+TX, Momfluorothrin+TX, Niclosamide+TX, Nicofluprole+TX;

Nitenpyram+TX, Nithiazine+TX, Omethoate+TX, Oxamyl+TX, Oxazosulfyl+TX, Parathion-ethyl+TX, Permethrin+TX, Phenothrin+TX, Phosphocarb+TX, Piperonylbutoxide+TX, Pirimicarb+TX, Pirimiphos-ethyl+TX, Polyhedrosis virus+TX, Prallethrin+TX, Profenofos+TX, Profenofos+TX, Profluthrin+TX, Propargite+TX, Propetamphos+TX, Propoxur+TX, Prothiophos+TX, Protrifenbute+TX, Pyflubumide+TX, Pymetrozine+TX, Pyraclofos+TX, Pyrafluprole+TX, Pyridaben+TX, Pyridalyl+TX, Pyrifluquinazon+TX, Pyrimidifen+TX, Pyrimostrobin+TX, Pyriprole+TX, Pyriproxyfen+TX, Resmethrin+TX, Sarolaner+TX, Selamectin+TX, Silafluofen+TX, Spinetoram+TX, Spinosad+TX, Spirodiclofen+TX, Spiromesifen+TX, Spiropidion+TX, Spirotetramat+TX, Sulfoxaflor+TX, Tebufenozide+TX, Tebufenpyrad+TX, Tebupirimiphos+TX, Tefluthrin+TX, Temephos+TX, Tetrachloraniliprole+TX, Tetradiphon+TX, Tetramethrin+TX, Tetramethylfluthrin+TX, Tetranactin+TX, Tetraniliprole+TX, Theta-cypermethrin+TX, Thiacloprid+TX, Thiamethoxam+TX, Thiocyclam+TX, Thiodicarb+TX, Thiofanox+TX, Thiometon+TX, Thiosultap+TX, Tioxazafen+TX, Tolfenpyrad+TX, Toxaphene+TX, Tralomethrin+TX, Transfluthrin+TX, Triazamate+TX, Triazophos+TX, Trichlorfon+TX, Trichloronate+TX, Trichlorphon+TX, Triflumezopyrim+TX, Tyclopyrazoflor+TX, Zeta-Cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, Azadirachtin+TX, *Bacillus aizawai*+TX, *Bacillus* chitinosporus AQ746 (NRRL Accession No B-21 618)+TX, *Bacillus firmus*+TX, *Bacillus* kurstaki+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. kurstaki BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria* usgae+TX, P-cymene+TX, *Plutella xylostella* Granulosis virus+TX, *Plutella xylostella* Nucleopolyhedrovirus+TX, Polyhedrosis virus+TX, *pyrethrum*+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp.;

an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX;

an anthelmintic selected from the group of substances consisting of abamectin (1)+TX, crufomate (1011)+TX, Cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX;

an avicide selected from the group of substances consisting of chloralose (127)+TX, endrin (1122)+TX, fenthion (346)+TX, pyridin-4-amine (IUPAC name) (23) and strychnine (745)+TX; a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX;

a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name)

(35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. kurstaki (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, Cryptolaemus *montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, Heterorhabditis *bacteriophora* and H. megidis (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, Neodiprion *sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, Steinernema *bibionis* (alternative name) (742)+TX, Steinernema *carpocapsae* (alternative name) (742)+TX, Steinernema *feltiae* (alternative name) (742)+TX, Steinernema *glaseri* (alternative name) (742)+TX, Steinernema riobrave (alternative name) (742)+TX, Steinernema riobravis (alternative name) (742)+TX, Steinernema scapterisci (alternative name) (742)+TX, Steinernema spp. (alternative name) (742)+TX, *Trichogramma* spp. (alternative name) (826)+TX, *Typhlodromus occidentalis* (alternative name) (844) and *Verticillium lecanii* (alternative name) (848)+TX;

a soil sterilant selected from the group of substances consisting of iodomethane (IUPAC name) (542) and methyl bromide (537)+TX;

a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX;

an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX;

an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX;

a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX; a nematicide selected from the group of substances consisting of AKD-3088 (compound code)+TX, 1,2-dibromo-3-chloropropane (IUPAC/Chemical Abstracts name)

(1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, Cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX;

a nitrification inhibitor selected from the group of substances consisting of potassium ethylxanthate [CCN] and nitrapyrin (580)+TX;

a plant activator selected from the group of substances consisting of acibenzolar (6)+TX, acibenzolar-S-methyl (6)+TX, probenazole (658) and *Reynoutria sachalinensis* extract (alternative name) (720)+TX;

a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (including alpha-bromadiolone)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX;

a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX;

an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX;

a virucide selected from the group of substances consisting of imanin (alternative name) [CCN] and ribavirin (alternative name) [CCN]+TX;

a wound protectant selected from the group of substances consisting of mercuric oxide (512)+TX, octhilinone (590) and thiophanate-methyl (802)+TX;

a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chino-methionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoatemethyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis(dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, Cryptolaemus *montrouzieri*+TX, *Cydia pomonella* GV+TX, *Dacnusa sibirica*+TX, *Diglyphus isaea*+TX, *Encarsia formosa*+TX, *Eretmocerus eremicus*+TX, Heterorhabditis *bacteriophora* and H. megidis+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, Neodiprion *sertifer* NPV and *N. lecontei* NPV+TX, *Orius* spp.+TX, *Paecilomyces fumosoroseus*+TX, *Phytoseiulus persimilis*+TX, Steinernema *bibionis*+TX, Steinernema *carpocapsae*+TX, Steinernema *feltiae*+TX, Steinernema *glaseri*+TX, Steinernema riobrave+TX, Steinernema riobravis+TX, Steinernema scapterisci+TX, Steinernema spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichloro-phenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, EI 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, and meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothio-phene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, 2-fluoro-N-(3-methoxyphenyl)-9H-purin-6-amine+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone (including alpha-bromadiolone)+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, sodium fluoroacetate+TX, thallium sulfate+TX, warfarin+TX, 2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, mercuric oxide+TX, thiophanate-methyl+TX, azaconazole+TX, bitertanol+TX, bromuconazole+TX, cyproconazole+TX, difenoconazole+TX, diniconazole+TX, epoxiconazole+TX, fenbuconazole+TX, fluquinconazole+TX, flusilazole+TX, flutriafol+TX, furametpyr+TX, hexaconazole+TX, imazalil-+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidin+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, metalaxyl-+TX, R-metalaxyl+TX, ofurace+TX, oxadixyl+TX, carbendazim+TX, debacarb+TX, fuberidazole+TX, thiabendazole+TX, chlozolinate+TX, dichlozoline+TX, myclozoline-+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb+TX, chloro-thalonil+TX, cyflufenamid+TX, cymoxanil+TX, cyclobutrifluram+TX, diclocymet+TX, diclomezine+TX, dicloran+TX, diethofencarb+TX, dimethomorph+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX, fenhexamid+TX, fosetyl-aluminium+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl] pyridine-3-carboxamide+TX, 4-(2,6-difluorophenyl)-6-methyl-5-phenyl-pyridazine-3-carbon itrile+TX, (R)-3-(difluoromethyl)-1-methyl-N-[1,1,3-trimethylindan-4-yl] pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl] carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+TX, but-3-ynyl N-[6-[[(Z)-[(1-methyltetrazol-5-yl)-phenyl-methylene]amino]oxymethyl]-2-pyridyl]carbamate+TX, methyl N-[[5-[4-(2,4-dimethylphenyl)triazol-2-yl]-2-methyl-phenyl]methyl] carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl] pyrazole-4-carboxamide+TX, 1-[2-[[1-(4-chlorophenyl) pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl) pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1,1,3-trimethylindan-4-yl) pyridine-3-carboxamide+TX, α-(1,1-dinethylethyl)-α-[4'-(trifluoromethoxy) [1,1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy] benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy] benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX, N-octyl-N'-[2-(octylamino)ethyl]ethane-1,2-diamine+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl)phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[(2-trifluoromethyl)oxetan-2-yl]phenyl]-N-methyl-formamidine+TX, N-ethyl-N'-[5-methoxy-2-methyl-4-[(2-trifuoromethyl)tetrahydrofuran-2-yl] phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3-chloro-1-methyl-but-3-enyl]-8-fluoro-quinoline-3-carboxamide+TX, N-[(1R)-1-benzyl-3,3,3-trifluoro-1-methyl-propyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1R)-1-benzyl-1,3-dimethyl-butyl]-7,8-difluoro-quinoline-3-carboxamide+TX, N-[(1S)-1-benzyl-1,3-dimethyl-butyl]-7,8-difluoro-quinoline-3-carboxamide+TX, 8-fluoro-N-[(1R)-1-[(3-fluorophenyl)methyl]-1,3-dimethyl-butyl]quinoline-3-carboxamide+TX, 8-fluoro-N-[(1S)-1-[(3-fluorophenyl) methyl]-1,3-dimethyl-butyl]quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-((1R)-1-benzyl-3-chloro-1-methyl-but-3-enyl)-8-fluoro-quinoline-3-carboxamide+TX, N-((1S)-1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N-[(Z)-methoxyiminomethyl]-4-[5-(trifluoromethyl)-1,2,4-oxadiazol-3-yl]benzamide+TX, N-[N-methoxy-C-methyl-carbonimidoyl]-4-[5-(trifluoromethyl)-1,2,4-oxadiazol-3-yl]benzamide+TX (these compounds may be prepared from the methods described in WO 2018/202428);

microbials including: *Acinetobacter*/woffii+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria* alternate+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, Azospirillum+TX, (MicroAZ®+TX, TAZO B®)+TX, *Azotobacter*+TX, *Azotobacter* chroocuccum (Azotomeal®)+TX, *Azotobacter* cysts (Bionatural Blooming Blossoms®)+TX, *Bacillus amyloliquefaciens*+TX, *Bacillus cereus*+TX, *Bacillus* chitinosporus strain CM-1+TX, *Bacillus* chitinosporus strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus* spahericus (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis*

Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis* kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis* kurstaki BMP 123 (Baritone®)+TX, *Bacillus thuringiensis* kurstaki HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROW-SWEET®+TX, Shootup®)+TX, bacteriophage of Clavipacter *michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis* cineria+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia* gladii+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea* dravisae+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium* chlorocephalum+TX, *Cladosporium* spp.+TX, *Cladosporium tenuissimum*+TX, Clonostachys *rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus* infirmo-*miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, Entomophtora *virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor* albus 620 (Muscudor®)+TX, *Muscodor roseus* strain A3-5+TX, Mycorrhizae spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces* linacinus (Biostat WP®)+TX, *Paecilomyces lilacinus* strain 251 (MeloCon WG®)+TX, *Paenibacillus polymyxa*+TX, *Pantoea agglomerans* (BlightBan $C_9$-1®)+TX, *Pantoea* spp.+TX, *Pasteuria* spp. (Econem®)+TX, *Pasteuria nishizawae*+TX, *Penicillium* aurantiogriseum+TX, *Penicillium* bil/ai (Jumpstart®+TX, TagTeam®)+TX, *Penicillium* brevicompactum+TX, *Penicillium* frequentans+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia* guilermondii+TX, *Pichia membranaefaciens*+TX, *Pichia onychis*+TX, *Pichia* stipites+TX, *Pseudomonas aeruginosa*+TX, *Pseudomonas* aureofasciens (Spot-Less Biofungicide®)+TX, *Pseudomonas cepacia*+TX, *Pseudomonas chlororaphis* (AtEze®)+TX, *Pseudomonas* corrugate+TX, *Pseudomonas fluorescens* strain A506 (BlightBan A506®)+TX, *Pseudomonas putida*+TX, *Pseudomonas* reactans+TX, *Pseudomonas* spp.+TX, *Pseudomonas syringae* (Bio-Save®)+TX, *Pseudomonas viridiflava*+TX, *Pseudomonas fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, Rhanella *aquatilis*+TX, Rhanella spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula* mucilagnosa+TX, *Rhodotorula rubra*+TX, *Saccharomyces cerevisiae*+TX, Salinococcus *roseus*+TX, *Sclerotinia* minor+TX, *Sclerotinia* minor (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera litto-*

*ralis* nucleopolyhedrovirus (Littovir®)+TX, *Sporobolomyces roseus*+TX, *Stenotrophomonas maltophilia*+TX, *Streptomyces* ahygroscopicus+TX, *Streptomyces albaduncus*+TX, *Streptomyces* exfoliates+TX, *Streptomyces galbus*+TX, *Streptomyces griseoplanus*+TX, *Streptomyces griseoviridis* (Mycostopg)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HCO+TX, RootShield®+TX, Trianum-G®)+TX, *Trichoderma harzianum* T-39 (Trichodex®)+TX, *Trichoderma* inhamatum+TX, *Trichoderma koningii*+TX, *Trichoderma* spp. LC 52 (Sentinel®)+TX, *Trichoderma* lignorum+TX, *Trichoderma longibrachiatum*+TX, *Trichoderma polysporum* (Binab T®)+TX, *Trichoderma* taxi+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, Virgibaclillus *marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden Insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, *pyrethrum*+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX, Z+TX, Z)-3+TX,8+TX,11 Tetradecatrienyl acetate+TX, (Z+TX, Z+TX, E)-7+TX,11+TX,13-Hexadecatrienal+TX, (E+TX, Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate;

Macrobials including: *Aphelinus abdominalis*+TX, *Aphidius ervi* (*Aphelinus*-System®)+TX, *Acerophagus papaya*+TX, Adalia *bipunctata* (Adalia-System®)+TX, Adalia *bipunctata* (Adaline®)+TX, Adalia *bipunctata* (Aphidalia®)+TX, *Ageniaspis citricola*+TX, *Ageniaspis fuscicollis*+TX, *Amblyseius andersoni* (Anderline®+TX, *Andersoni*-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (*Fallacis*®)+TX, *Amblyseius* swirskii (Bugline Swirskii®+TX, Swirskii-Mite®)+TX, *Amblyseius womersleyi* (WomerMite®)+TX, Amitus *hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus* benefices+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, Cephalonomia *stephanoderis*+TX, Chilocorus *nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, Cryptolaemus *montrouzieri* (Cryptobug®+TX, Cryptoline®)+TX, Cybocephalus *nipponicus*+TX, *Dacnusa sibirica*+TX, *Dacnusa sibirica* (Minusa®)+TX, *Diglyphus isaea* (Diminex®)+TX, Delphastus *catalinae* (Delphastus®)+TX, Delphastus *pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, Eretmoceris *siphonini*+TX,

*Eretmocerus californicus*+TX, *Eretmocerus eremicus* (Ercal®+TX, Eretline e®)+TX, *Eretmocerus eremicus* (Bemimix®)+TX, *Eretmocerus* hayati+TX, *Eretmocerus* mundus (Bemipar®+TX, Eretline m®)+TX, *Eretmocerus siphonini*+TX, Exochomus *quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, Goniozus *legneri*+TX, *Habrobracon hebetor*+TX, *Harmonia axyridis* (HarmoBeetle®)+TX, Heterorhabditis spp. (Lawn Patrol®)+TX, Heterorhabditis *bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, Heterorhabditis megidis (Nemasys H®+TX, BioNem H®+TX, Exhibitline hm®+TX, Larvanem-M®)+TX, *Hippodamia convergens*+TX, Hypoaspis *aculeifer* (*Aculeifer*-System®+TX, Entomite-A®)+TX, Hypoaspis *miles* (Hypoline m®+TX, Entomite-M®)+TX, Lbalia *leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, Lindorus lophanthae+TX, *Lipolexis oregmae*+TX, *Lucilia* caesar (Natufly®)+TX, *Lysiphlebus testaceipes*+TX, *Macrolophus caliginosus* (Mirical-N®+TX, Macroline c®+TX, Mirical®)+TX, Mesoseiulus *longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, Neodryinus typhlocybae+TX, *Neoseiulus californicus*+TX, *Neoseiulus cucumeris* (THRYPEX®)+TX, *Neoseiulus fallacis*+TX, Nesideocoris *tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, Phasmarhabditis *hermaphrodita* (Nemaslug®)+TX, *Phymastichus coffea*+TX, *Phytoseiulus* macropilus+TX, *Phytoseiulus persimilis* (Spidex®+TX, Phytoline p®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius* lophanthae+TX, Rodolia *cardinalis*+TX, *Rumina* decollate+TX, *Semielacher petiolatus*+TX, *Sitobion avenae* (Ervibank®)+TX, Steinernema *carpocapsae* (Nematac C®+TX, Millenium®+TX, BioNem C®+TX, NemAttack®+TX, Nemastar®+TX, Capsanem®)+TX, Steinernema *feltiae* (NemaShield®+TX, Nemasys F®+TX, BioNem F®+TX, Steinernema-System®+TX, NemAttack®+TX, Nemaplus®+TX, Exhibitline sf®+TX, Scia-rid®+TX, Entonem®)+TX, Steinernema *kraussei* (Nemasys L®+TX, BioNem L®+TX, Exhibitline srb®)+TX, Steinernema riobrave (BioVector®+TX, BioVektor®)+TX, Steinernema scapterisci (Nematac S®)+TX, Steinernema spp.+TX, Steinernematid spp. (Guardian Nematodes®)+TX, Stethorus *punctillum* (Stethorus®)+TX, *Tamarixia* radiate+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator;* other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, Microctonus *hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema* locustae (Semaspore Organic Grasshopper Control®)+TX, Sticky traps (Trapline YF®+TX, Rebell Amarillo®)+TX and Traps (Takitrapline y+b®)+TX; and a safener, such as benoxacor+TX, cloquintocet (including cloquintocet-mexyl)+TX, cyprosulfamide+TX, dichlormid+TX, fenchlorazole (including fenchlorazole-ethyl)+TX, fenclorim+TX, fluxofenim+TX, furilazole+TX, isoxadifen (including isoxadifen-ethyl)+TX, mefenpyr (including mefenpyr-diethyl)+TX, metcamifen+TX and oxabetrinil+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "*Compendium of Pesticide Common Names*", which is accessible on the internet [A. Wood; Compendium of Pesticide Common Names, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables A-1 to A-96, C-1 to C-96, E-1 to E-96, F-1 to F-96, G-1 to G-96 and H-1 to H-96 and Table P with active ingredients described above comprises a compound selected from Tables A-1 to A-96, C-1 to C-96, E-1 to E-96, F-1 to F-96, G-1 to G-96 and H-1 to H-96 and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables A-1 to A-96, C-1 to C-96, E-1 to E-96, F-1 to F-96, G-1 to G-96 and H-1 to H-96 and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables A-1 to A-96, C-1 to C-96, E-1 to E-96, F-1 to F-96, G-1 to G-96 and H-1 to H-96 and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, δ ppm, 3 ppm, 1.5 ppm, 0.8 ppm or 0.2 ppm.

Example B1: *Diabrotica balteata* (Corn Root Worm

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P2, P3, P4, P5, P6, P7, P8, P9, P10, P11, P12, P13, P14, P15, P16, P17, P18, P19, P20, P21, P22, P23, P24, P25, P26, P27, P28, P29, P30, P31, P32, P33, P34, P35, P36, P37, P38, P39, P40, P41, P42, P43, P44, P45, P46, P47, P48, P49, P50, P51, P52, P53, P54, P55, P56, P57, P58.

Example B2: *Euschistus heros* (Neotropical Brown Stink Bug

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P2, P7, P8, P9, P10, P11, P12, P16, P17, P18, P19, P20, P21, P22, P24, P25, P26, P27, P29, P31, P32, P33, P34, P35, P36, P40, P42, P50, P51, P52, P53, P58.

Example B3: *Frankliniella occidentalis* (Western Flower *Thrips*

Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P1, P2, P12, P20, P21, P26, P27, P40, P57.

Example B4: *Plutella xylostella* (Diamond Back Moth 24-well microtiter plates with artificial diet were treated with aqueous test solutions prepared from 10'000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% in at least one of the two categories (mortality or growth inhibition) at an application rate of 200 ppm: P1, P2, P3, P4, P5, P6, P7, P8, P9, P10, P11, P12, P13, P14, P15, P16, P17, P18, P19, P20, P21, P22, P23, P24, P25, P26, P27, P28, P29, P30, P31, P32, P33, P34, P35, P36, P37, P38, P40, P41, P42, P43, P44, P45, P46, P47, P48, P49, P50, P51, P52, P53, P54, P55, P56, P57, P58.

Example B5: *Myzus persicae* (Green Peach Aphid). Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P1, P3, P9, P11, P12, P13, P17, P18, P19, P20, P21, P26, P27, P44, P45, P50, P51, P52, P53, P57.

Example B6: *Bemisia tabaci* (Cotton White Fly). Feeding/Contact Activity

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm: P1, P7, P17, P33, P34, P57, P58.

Example B7: *Spodoptera littoralis* (Egyptian Cotton Leaf Worm

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P1, P2, P3, P4, P6, P7, P8, P9, P10, P11, P12, P13, P14, P16, P17, P18, P19, P20, P21, P22, P23, P24, P25, P26, P27, P28, P29, P30, P32, P33, P34, P35, P36, P37, P38, P40, P41, P42, P43, P44, P45, P46, P47, P48, P49, P50, P51, P52, P53, P54, P55, P57, P58.

Example B8: *Myzus persicae* (Green Peach Aphid). Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm: P20, P21, P32.

Example B9: *Chilo suppressalis* (Striped Rice Stemborer 24-well microtiter plates with artificial diet were treated with aqueous test solutions prepared from 10'000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, antifeedant effect, and growth inhibition is higher than the untreated sample.

For example, the following compounds resulted in at least 80% control at an application rate of 200 ppm: P57, P58.

The invention claimed is:

1. A compound of formula (I)

(I)

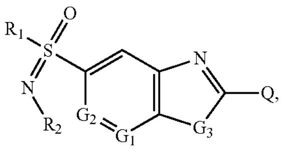

wherein $G_1$ and $G_2$ are, independently from each other, CH or N;

$G_3$ is $NCH_3$ or O;

$R_1$ is $C_1$-$C_6$alkyl or $C_1$-$C_6$haloalkyl;

$R_2$ is H, $C_1$-$C_6$alkyl, $C_1$-$C_6$cycloalkyl, $C_1$-$C_6$haloalkyl, $C(O)R_3$ or CN;

$R_3$ is $C_1$-$C_6$alkyl;

Q is a radical selected from the group consisting of formula Qa and Qb

Qa

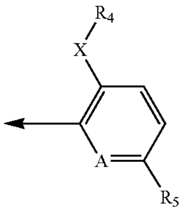

Qb

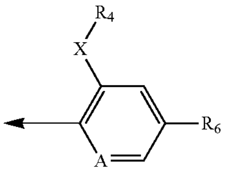

wherein the arrow denotes the point of attachment to the carbon atom of the bicyclic ring;

and wherein

A is CH or N;

X is S, SO or SO2;

$R_4$ is $C_1$-$C_4$alkyl;

$R_5$ is hydrogen or halogen; or $R_5$ is a five- to six-membered aromatic ring system, linked via a ring carbon atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system optionally contains 1, 2 or 3 ring heteroatoms selected from the group consisting of nitrogen, oxygen and sulphur, where said ring system contains no more than one ring oxygen atom and not more than one ring sulfur atom; or $R_5$ is a five-membered aromatic ring system linked via a ring nitrogen atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system contains 1, 2 or 3 ring heteroatoms selected from the group consisting of nitrogen, oxygen and sulphur, where said ring system contains at least one ring nitrogen atom but no more than one ring oxygen atom and not more than one ring sulfur atom;

$R_6$ is halogen, $C_1$-$C_6$haloalkyl, $C_3$-$C_6$cycloalkyl, $C_3$-$C_6$cycloalkyl monosubstituted by cyano, $C_3$-$C_6$alkyl monosubstituted by cyano, $C_1$-$C_6$alkoxy, $C_1$-$C_6$haloalkoxy, $C_1$-$C_6$alkoxy substituted with cyano, $—N{=}S(O)R_7R_8$, $N(R_9)C({=}O)R_{10}$, $N(R_{11})R_{12}$, or 2-pyridyloxy; or $R_6$ is a five- to six-membered aromatic ring system, linked via a ring carbon atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system optionally contains 1, 2 or 3 ring heteroatoms selected from the group consisting of nitrogen, oxygen and sulphur, where said ring system contains no more than one ring oxygen atom and not more than one ring sulfur atom; or $R_6$ is a five-membered aromatic ring system linked via a ring nitrogen atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system contains 1, 2 or 3 ring heteroatoms selected from the group consisting of nitrogen, oxygen and sulphur, where said ring system contains at least one ring nitrogen atom but no more than one ring oxygen atom and not more than one ring sulfur atom;

$R_7$ and $R_8$ are, independently from each other, $C_1$-$C_6$alkyl;

$R_9$ is H or $C_1$-$C_6$alkyl;

$R_{10}$ is $C_1$-$C_6$alkyl or $C_3$-$C_6$cycloalkyl;

$R_{11}$ and $R_{12}$ are, independently from each other, H or $C_1$-$C_6$alkyl;

or an agrochemically acceptable salt, stereoisomer, enantiomer, tautomer or N-oxide of the compound of formula I.

2. The compound of formula I according to claim 1, represented by compounds of formula I-1

(I-1)

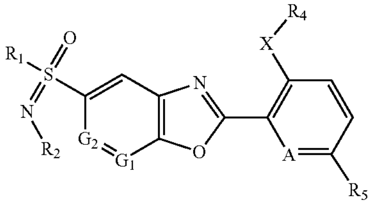

wherein $G_1$, $G_2$, $R_1$, $R_2$, A, X, $R_4$, and $R_5$, are as defined under formula I in claim 1, or an agrochemically acceptable salt, stereoisomer, enantiomer, tautomer or N-oxide thereof.

3. The compound of formula I according to claim 1, represented by compounds of formula I-2

(I-2)

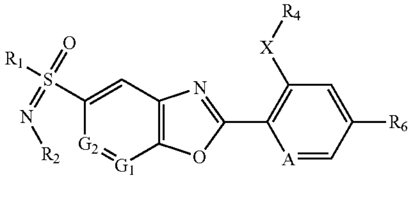

wherein $G_1$, $G_2$, $R_1$, $R_2$, A, X, $R_4$ and $R_6$ are as defined under formula I in claim 1, or an agrochemically acceptable salt, stereoisomer, enantiomer, tautomer or N-oxide thereof.

4. The compound of formula I according to claim 1, represented by compounds of formula I-3

(I-3)

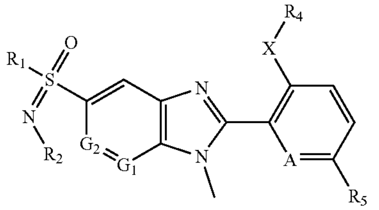

wherein $G_1$, $G_2$, $R_1$, $R_2$, A, X, $R_4$, and $R_5$, are as defined under formula I in claim 1, or an agrochemically acceptable salt, stereoisomer, enantiomer, tautomer or N-oxide thereof.

5. The compound of formula I according to claim 1, represented by compounds of formula I-4

(I-4)

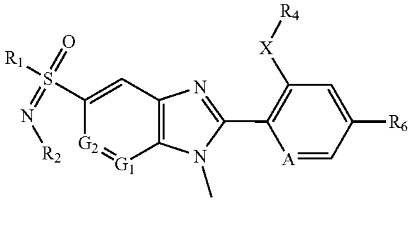

wherein herein $G_1$, $G_2$, $R_1$, $R_2$, A, X, $R_4$ and $R_6$ are as defined under formula I in claim 1, or an agrochemically acceptable salt, stereoisomer, enantiomer, tautomer or N-oxide thereof.

6. The compound of formula I according to claim 1, represented by compounds of formula I-5

(I-5)

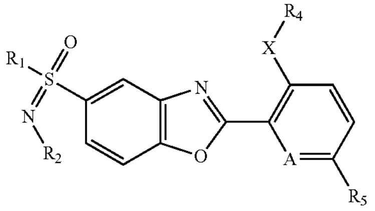

wherein $R_1$, $R_2$, A, X, $R_4$, and $R_5$, are as defined under formula I in claim 1, or an agrochemically acceptable salt, stereoisomer, enantiomer, tautomer or N-oxide thereof.

7. The compound of formula I according to claim 1, represented by compounds of formula I-6

(I-6)

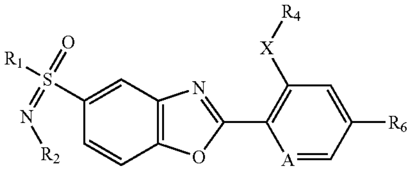

wherein $R_1$, $R_2$, A, X, $R_4$ and $R_6$ are as defined under formula I in claim 1, or an agrochemically acceptable salt, stereoisomer, enantiomer, tautomer or N-oxide thereof.

8. The compound of formula I according to claim 1, represented by compounds of formula I-7

(I-7)

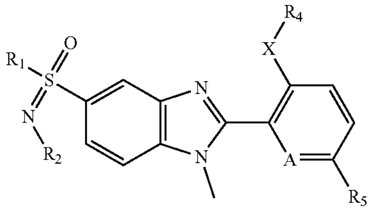

wherein $R_1$, $R_2$, A, X, $R_4$, and $R_5$, are as defined under formula I in claim 1, or an agrochemically acceptable salt, stereoisomer, enantiomer, tautomer or N-oxide thereof.

9. The compound of formula I according to claim 1, represented by compounds of formula I-8

(I-8)

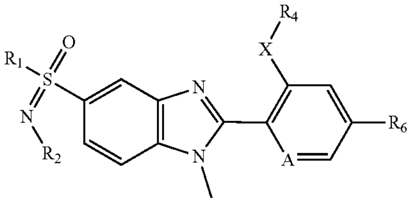

wherein $R_1$, $R_2$, A, X, $R_4$ and $R_6$ are as defined under formula I in claim 1, or an agrochemically acceptable salt, stereoisomer, enantiomer, tautomer or N-oxide thereof.

10. The compound according to claim 1, wherein:

$R_1$ is methyl or trifluoromethyl;

X is S or $SO_2$; and $R_4$ is $C_1$-$C_2$alkyl.

11. The compound of formula I according to claim 1, represented by compounds of formula I-9

(I-9)

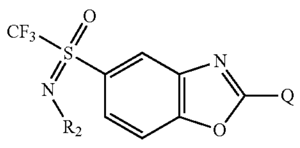

wherein Q is a radical selected from the group consisting of formula Qa1 and Qb1

Qa1

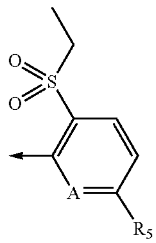

Qb1

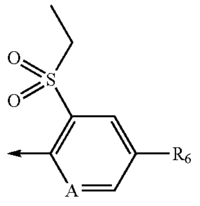

wherein the arrow denotes the point of attachment to the carbon atom of the bicyclic ring;

and wherein $R_2$, $R_5$ and $R_6$ are as defined under formula I in claim 1, or an agrochemically acceptable salt, stereoisomer, enantiomer, tautomer or N-oxide thereof.

12. The compound of formula I according to claim 1, represented by compounds of formula I-10

(I-10)

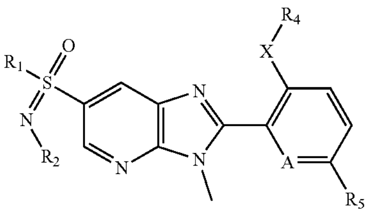

wherein $R_1$, $R_2$, A, X, $R_4$, and $R_5$, are as defined under formula I in claim 1, or an agrochemically acceptable salt, stereoisomer, enantiomer, tautomer or N-oxide thereof.

13. The compound of formula I according to claim 1, represented by compounds of formula I-11

(I-11)

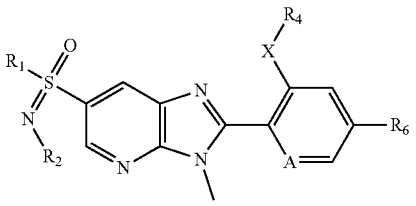

wherein $R_1$, $R_2$, A, X, $R_4$ and $R_6$ are as defined under formula I in claim 1, or an agrochemically acceptable salt, stereoisomer, enantiomer, tautomer or N-oxide thereof.

14. The compound of formula I according to claim 1, represented by compounds of formula 1-12

(I-12)

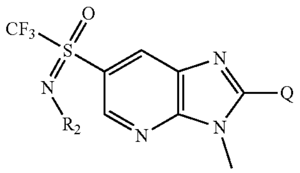

wherein $R_2$ is as defined under formula I in claim 1 and Q is a radical selected from the group consisting of formula Qa1 and Qb1

Qa1

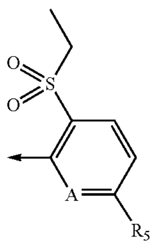

Qb1

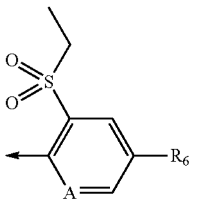

wherein the arrow denotes the point of attachment to the carbon atom of the bicyclic ring; and wherein $R_5$ and $R_6$ are as defined under formula I in claim 1, or an agrochemically acceptable salt, stereoisomer, enantiomer, tautomer or N-oxide thereof.

15. The compound of formula I according to claim 1, represented by the compounds of formula 1-13

(I-13)

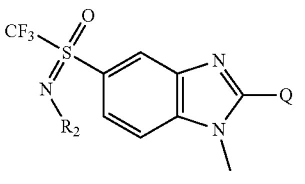

wherein $R_2$ is as defined under formula I in claim 1 and Q is a radical selected from the group consisting of formula Qa1 and Qb1

Qa1

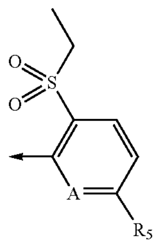

Qb1

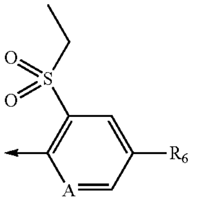

wherein the arrow denotes the point of attachment to the carbon atom of the bicyclic ring;

and wherein A, $R_5$ and $R_6$ are as defined under formula I in claim 1, or an agrochemically acceptable salt, stereoisomer, enantiomer, tautomer or N-oxide thereof.

16. The compound according claim 1, wherein:

$R_2$ is H, $C_1$-$C_4$alkyl, cyclopropyl, $C_1$-$C_4$haloalkyl, —C(O)$R_3$ or cyano;

and $R_3$ is $C_1$-$C_4$alkyl.

17. The compound according to claim 1, wherein:

$R_5$ is hydrogen, or N-linked pyrazolyl which is unsubstituted or mono-substituted by chloro, trifluoromethyl, or C-linked pyrimidinyl which is unsubstituted or mono-substituted by chloro, trifluoromethyl, or N-linked triazolyl which is unsubstituted or mono-substituted by chloro or trifluoromethyl.

18. The compound according to claim 1, wherein:

$R_6$is cyclopropyl, 1-cyanocyclopropyl, 2,2,2-trifluoroethoxy, 2,2-difluoropropoxy, 1-cyano-1-methyl-ethoxy, —N═S(O)$(CH_3)_2$, —N($CH_3$)$COCH_3$, 2-pyridyloxy, pyrimidin-2-yl, 4-trifluoromethyl-pyrimidin-2-yl, 5-cyano-pyrimidin-2-yl, 5-chloro-pyrimidin-2-yl, 3-chloro-pyrazol-1-yl, or 3-trifluoromethyl-pyrazol-1-yl.

19. The compound according to claim 1, wherein A is N.

20. The compound according to claim 1, wherein A is CH.

21. The compound of formula I according to claim 1, selected from the group consisting of:

[2-[5-[[dimethyl(oxo)-λ$^6$-sulfanylidene]amino]-3-ethylsulfonyl-2-pyridyl]-1,3-benzoxazol-5-yl]-imino-oxo-(trifluoromethyl)-λ$^6$-sulfane (compound P1);

[2-[5-[[dimethyl(oxo)-λ$^6$-sulfanylidene]amino]-3-ethylsulfonyl-2-pyridyl]-1,3-benzoxazol-5-yl]-ethylimino-oxo-(trifluoromethyl)-λ$^6$-sulfane (compound P2);

N-[5-ethylsulfonyl-6-[5-[N-ethyl-S-(trifluoromethyl) sulfonimidoyl]-1,3-benzoxazol-2-yl]-3-pyridyl]-N-methyl-acetamide (compound P3);

N-[5-ethylsulfonyl-6-[5-(trifluoromethylsulfonimidoyl)-1,3-benzoxazol-2-yl]-3-pyridyl]-N-methyl-acetamide (compound P4);

ethylimino-[2-[3-ethylsulfonyl-5-[3-(trifluoromethyl) pyrazol-1-yl]-2-pyridyl]-1,3-benzoxazol-5-yl]-oxo-(trifluoromethyl)-λ$^6$-sulfane (compound P5);

[2-[3-ethylsulfonyl-5-[3-(trifluoromethyl)pyrazol-1-yl]-2-pyridyl]-1,3-benzoxazol-5-yl]-imino-oxo-(trifluoromethyl)-λ$^6$-sulfane (compound P6);

1-[5-ethylsulfonyl-6-[5-(trifluoromethylsulfonimidoyl)-1,3-benzoxazol-2-yl]-3-pyridyl]cyclopropanecarbonitrile (compound P7);

1-[5-ethylsulfonyl-6-[5-[N-ethyl-S-(trifluoromethyl) sulfonimidoyl]-1,3-benzoxazol-2-yl]-3-pyridyl]cyclopropanecarbonitrile (compound P8);

[2-[3-ethylsulfonyl-5-(2-pyridyloxy)-2-pyridyl]-1,3-benzoxazol-5-yl]-imino-oxo-(trifluoromethyl)-λ$^6$-sulfane (compound P9); ethylimino-[2-[3-ethylsulfonyl-5-(2-pyridyloxy)-2-pyridyl]-1,3-benzoxazol-5-yl]-oxo-(trifluoromethyl)-λ$^6$-sulfane (compound P10);

[2-(5-cyclopropyl-3-ethylsulfonyl-2-pyridyl)-1,3-benzoxazol-5-yl]-ethylimino-oxo-(trifluoromethyl)-λ$^6$-sulfane (compound P11);

[2-(5-cyclopropyl-3-ethylsulfonyl-2-pyridyl)-1,3-benzoxazol-5-yl]-imino-oxo-(trifluoromethyl)-λ$^6$-sulfane (compound P12);

cyclopropylimino-[2-(3-ethylsulfonyl-2-pyridyl)-1,3-benzoxazol-5-yl]-oxo-(trifluoromethyl)-λ$^6$-sulfane (compound P13);

[2-(3-ethylsulfonyl-2-pyridyl)-1,3-benzoxazol-5-yl]-oxo-(2,2,2-trifluoroethylimino)-(trifluoromethyl)-λ$^6$-sulfane (compound P14);

[[2-(3-ethylsulfonyl-2-pyridyl)-1,3-benzoxazol-5-yl]-oxo-(trifluoromethyl)-λ$^6$-sulfanylidene]cyanamide (compound P15);

[2-(3-ethylsulfonyl-2-pyridyl)-1,3-benzoxazol-5-yl]-imino-oxo-(trifluoromethyl)-λ$^6$-sulfane (compound P16);

N-[[2-(3-ethylsulfonyl-2-pyridyl)-1,3-benzoxazol-5-yl]-oxo-(trifluoromethyl)-λ$^6$-sulfanylidene]acetamide (compound P17);

[2-(3-ethylsulfonyl-2-pyridyl)-1,3-benzoxazol-5-yl]-methylimino-oxo-(trifluoromethyl)-λ$^6$-sulfane (compound P18);

ethylimino-[2-(3-ethylsulfonyl-2-pyridyl)-1,3-benzoxazol-5-yl]-oxo-(trifluoromethyl)-λ$^6$-sulfane (compound P19);

1-[5-ethylsulfonyl-6-[6-[N-ethyl-S-(trifluoromethyl) sulfonimidoyl]-3-methyl-imidazo[4,5-b]pyridin-2-yl]-3-pyridyl]cyclopropane-carbonitrile (compound P20);

1-[5-ethylsulfonyl-6-[3-methyl-6-(trifluoromethyl-sulfonimidoyl)imidazo[4,5-b]pyridin-2-yl]-3-pyridyl]cyclopropanecarbonitrile (compound P21);

ethylimino-[2-[3-ethylsulfonyl-5-(2,2,2-trifluoroethoxy)-2-pyridyl]-1,3-benzoxazol-5-yl]-oxo-(trifluoromethyl)-λ$^6$-sulfane (compound P 22),

[2-[3-ethylsulfonyl-5-(2,2,2-trifluoroethoxy)-2-pyridyl]-1,3-benzoxazol-5-yl]-imino-oxo-(trifluoromethyl)-λ$^6$-sulfane (compound P 23), N-[[2-[3-ethylsulfonyl-5-(2,2,2-trifluoroethoxy)-2-pyridyl]-1,3-benzoxazol-5-yl]-oxo-(trifluoromethyl)-λ$^6$-sulfanylidene]acetamide (compound P 24), N-[[2-[3-ethylsulfonyl-5-(2-pyridyloxy)-2-pyridyl]-1,3-benzoxazol-5-yl]-oxo-(trifluoromethyl)-λ$^6$-sulfanylidene]acetamide (compound P 25),

[2-[5-(2,2-difluoropropoxy)-3-ethylsulfonyl-2-pyridyl]-1,3-benzoxazol-5-yl]-imino-oxo-(trifluoromethyl)-λ$^6$-sulfane (compound P 26),

[2-[5-(2,2-difluoropropoxy)-3-ethylsulfonyl-2-pyridyl]-1,3-benzoxazol-5-yl]-ethylimino-oxo-(trifluoromethyl)-λ$^6$-sulfane (compound P 27), 1-[5-ethylsulfonyl-6-[5-[N-(2,2,2-trifluoroethyl)-S-(trifluoromethyl)sulfonimidoyl]-1,3-benzoxazol-2-yl]-3-pyridyl]cyclopropanecarbonitrile (compound P 28), 1-[5-ethylsulfonyl-6-[5-[N-methyl-S-(trifluoromethyl)sulfonimidoyl]-1,3-benzoxazol-2-yl]-3-pyridyl]cyclopropanecarbonitrile (compound P 29), 1-[6-[5-[N-cyclopropyl-S-(trifluoromethyl)sulfonimidoyl]-1,3-benzoxazol-2-yl]-5-ethylsulfonyl-3-pyridyl]cyclopropanecarbonitrile (compound P 30), 1-[6-[5-[N-cyclopropyl-S-(trifluoromethyl)sulfonimidoyl]-1-methyl-benzimidazol-2-yl]-5-ethylsulfonyl-3-pyridyl]cyclopropanecarbonitrile (compound P 31), 1-[5-ethylsulfonyl-6-[5-[N-ethyl-S-(trifluoromethyl)sulfonimidoyl]-1-methyl-benzimidazol-2-yl]-3-pyridyl]cyclopropanecarbonitrile (compound P 32), 1-[5-ethylsulfonyl-6-[1-methyl-5-(trifluoromethylsulfonimidoyl)benzimidazol-2-yl]-3-pyridyl]cyclopropanecarbonitrile (compound P 33), 1-[5-ethylsulfonyl-6-[1-methyl-5-[N-(2,2,2-trifluoroethyl)-S-(trifluoromethyl)sulfonimidoyl]benzimidazol-2-yl]-3-pyridyl]cyclopropanecarbonitrile (compound P 34), ethylimino-[2-(3-ethylsulfonyl-5-pyrimidin-2-yl-2-pyridyl)-1,3-benzoxazol-5-yl]-oxo-(trifluoromethyl)-λ$^6$-sulfane (compound P 35),

[2-(3-ethylsulfonyl-5-pyrimidin-2-yl-2-pyridyl)-1,3-benzoxazol-5-yl]-imino-oxo-(trifluoromethyl)-λ$^6$-sulfane (compound P 36),

[2-[5-(3-chloropyrazol-1-yl)-3-ethylsulfonyl-2-pyridyl]-1,3-benzoxazol-5-yl]-imino-oxo-(trifluoromethyl)-λ$^6$-sulfane (compound P 37),

[2-[5-(3-chloropyrazol-1-yl)-3-ethylsulfonyl-2-pyridyl]-1,3-benzoxazol-5-yl]-ethylimino-oxo-(trifluoromethyl)-λ$^6$-sulfane (compound P 38), ethylimino-[2-[3-ethylsulfonyl-6-(1,2,4-triazol-1-yl)-2-pyridyl]-1,3-benzoxazol-5-yl]-oxo-(trifluoromethyl)-λ$^6$-sulfane (compound P 39),

[2-[3-ethylsulfonyl-5-[4-(trifluoromethyl)pyrimidin-2-yl]-2-pyridyl]-1,3-benzoxazol-5-yl]-imino-oxo-(trifluoromethyl)-λ$^6$-sulfane (compound P 40), ethylimino-[2-[3-ethylsulfonyl-5-[4-(trifluoromethyl)pyrimidin-2-yl]-2-pyridyl]-1,3-benzoxazol-5-yl]-oxo-(trifluoromethyl)-λ$^6$-sulfane (compound P 41),

[2-[5-(5-chloropyrimidin-2-yl)-3-ethylsulfonyl-2-pyridyl]-1,3-benzoxazol-5-yl]-imino-oxo-(trifluoromethyl)-λ$^6$-sulfane (compound P 42),

[2-[5-(5-chloropyrimidin-2-yl)-3-ethylsulfonyl-2-pyridyl]-1,3-benzoxazol-5-yl]-ethylimino-oxo-(trifluoromethyl)-λ$^6$-sulfane (compound P 43),

[2-[3-ethylsulfonyl-6-(1,2,4-triazol-1-yl)-2-pyridyl]-1-methyl-benzimidazol-5-yl]-imino-oxo-(trifluoromethyl)-λ$^6$-sulfane (compound P 44), ethylimino-[2-[3-ethylsulfonyl-6-(1,2,4-triazol-1-yl)-2-pyridyl]-1-methyl-benzimidazol-5-yl]-oxo-(trifluoromethyl)-λ$^6$-sulfane (compound P 45),

[2-[6-(3-chloro-1,2,4-triazol-1-yl)-$^3$-ethylsulfonyl-2-pyridyl]-1-methyl-benzimidazol-5-yl]-imino-oxo-(trifluoromethyl)-λ$^6$-sulfane (compound P 46),

[2-[6-(3-chloro-1,2,4-triazol-1-yl)-3-ethylsulfonyl-2-pyridyl]-1-methyl-benzimidazol-5-yl]-ethylimino-oxo-(trifluoromethyl)-λ$^6$-sulfane (compound P 47),

[2-[3-ethylsulfonyl-6-[3-(trifluoromethyl)-1,2,4-triazol-1-yl]-2-pyridyl]-1-methyl-benzimidazol-5-yl]-imino-oxo-(trifluoromethyl)-λ$^6$-sulfane (compound P 48), ethylimino-[2-[3-ethylsulfonyl-6-[3-(trifluoromethyl)-1,2,4-triazol-1-yl]-2-pyridyl]-1-methyl-benzimidazol-5-yl]-oxo-(trifluoromethyl)-λ$^6$-sulfane (compound P 49),

[2-[3-ethylsulfonyl-5-(2-pyridyloxy)-2-pyridyl]-1-methyl-benzimidazol-5-yl]-imino-oxo-(trifluoromethyl)-λ$^6$-sulfane (compound P 50), ethylimino-[2-[3-ethylsulfonyl-5-(2-pyridyloxy)-2-pyridyl]-1-methyl-benzimidazol-5-yl]-oxo-(trifluoromethyl)-λ$^6$-sulfane (compound P 51), 2-[5-ethylsulfonyl-6-[1-methyl-5-(trifluoromethylsulfonimidoyl)benzimidazol-2-yl]-3-pyridyl]pyrimidine-5-carbonitrile (compound P 52), 2-[5-ethylsulfonyl-6-[5-[N-ethyl-S-(trifluoromethyl)sulfonimidoyl]-1-methyl-benzimidazol-2-yl]-3-pyridyl]pyrimidine-5-carbonitrile (compound P 53),

[2-(3-ethylsulfonyl-6-pyrimidin-2-yl-2-pyridyl)-1,3-benzoxazol-5-yl]-imino-oxo-(trifluoromethyl)-λ$^6$-sulfane (compound P 54), ethylimino-[2-(3-ethylsulfonyl-6-pyrimidin-2-yl-2-pyridyl)-1,3-benzoxazol-5-yl]-oxo-(trifluoromethyl)-λ$^6$-sulfane (compound P 55),

[2-[3-ethylsulfonyl-6-(1,2,4-triazol-1-yl)-2-pyridyl]-1,3-benzoxazol-5-yl]-imino-oxo-(trifluoromethyl)-λ$^6$-sulfane (compound P 56), 1-[5-ethylsulfonyl-6-[3-methyl-6-[N-(2,2,2-trifluoroethyl)-S-(trifluoromethyl)sulfonimidoyl]imidazo[4,5-b]pyridin-2-yl]-3-pyridyl]cyclopropanecarbonitrile (compound P 57), and 1-[6-[6-[N-cyclopropyl-S-(trifluoromethyl)sulfonimidoyl]-3-methyl-imidazo[4,5-b]pyridin-2-yl]-5-ethylsulfonyl-3-pyridyl]cyclopropanecarbonitrile (compound P 58).

22. A composition comprising an insecticidally, acaricidally, nematicidally or molluscicidally effective amount of the compound of formula (I), or an agrochemically acceptable salt, stereoisomer, enantiomer, tautomer or N-oxide thereof, as defined in claim 1 and, optionally, an auxiliary or a diluent.

23. A method of combating and controlling insects, acarines, nematodes or molluscs, which comprises applying to a pest, to a locus of a pest, or to a plant susceptible to attack by a pest an insecticidally, acaricidally, nematicidally or molluscicidally effective amount of the compound of formula (I), or an agrochemically acceptable salt, stereoisomer, enantiomer, tautomer or N-oxide thereof, as defined in claim 1.

24. A method for protection of a plant propagation material from the attack by insects, acarines, nematodes or molluscs, which comprises treating the plant propagation material or the site, where the propagation material is planted, with the composition according to claim 22.

25. A method for combating and controlling insects, acarines, nematodes or molluscs, which comprises applying to a pest, to a locus of a pest, or to a plant susceptible to attack by a pest the composition according to claim 22.

26. The compound according to claim 10, wherein:

$R_1$ is trifluoromethyl;

X is $SO_2$; or $R_4$ is ethyl.

27. The compound according to claim 10, wherein:

$R_1$ is trifluoromethyl;

X is $SO_2$; and $R_4$ is ethyl.

28. The compound according to claim 16, wherein:

$R_2$ is H, cyano, methyl, ethyl, cyclopropyl, or 2,2,2-trifluoroethyl; or $R_3$ is methyl.

29. The compound according to claim 16, wherein:

$R_2$ is H, cyano, methyl, ethyl, cyclopropyl, or 2,2,2-trifluoroethyl; and $R_3$ is methyl.

* * * * *